United States Patent
Sørensen et al.

(10) Patent No.: US 11,274,092 B2
(45) Date of Patent: Mar. 15, 2022

(54) POTASSIUM CHANNEL INHIBITORS

(71) Applicant: ACESION PHARMA ApS, Copenhagen N (DK)

(72) Inventors: Ulrik Svane Sørensen, Værløse (DK); Antonio Mete, Leicestershire (GB)

(73) Assignee: ACESION PHARMA ApS, Copenhagen N (DK)

(*) Notice: Subject to any disclaimer, the term of this patent is extended or adjusted under 35 U.S.C. 154(b) by 746 days.

(21) Appl. No.: 16/078,128

(22) PCT Filed: Feb. 23, 2017

(86) PCT No.: PCT/EP2017/025033
§ 371 (c)(1),
(2) Date: Aug. 21, 2018

(87) PCT Pub. No.: WO2017/144183
PCT Pub. Date: Aug. 31, 2017

(65) Prior Publication Data
US 2021/0188804 A1 Jun. 24, 2021

(30) Foreign Application Priority Data
Feb. 24, 2016 (EP) .................................. 16020053

(51) Int. Cl.
| | | |
|---|---|---|
| *C07D 401/12* | (2006.01) | |
| *C07D 405/12* | (2006.01) | |
| *C07D 413/12* | (2006.01) | |
| *C07D 403/12* | (2006.01) | |
| *C07D 417/12* | (2006.01) | |
| *C07D 491/107* | (2006.01) | |
| *C07D 235/30* | (2006.01) | |
| *A61P 9/00* | (2006.01) | |
| *A61P 9/06* | (2006.01) | |
| *A61P 9/10* | (2006.01) | |

(52) U.S. Cl.
CPC ......... *C07D 401/12* (2013.01); *C07D 235/30* (2013.01); *C07D 403/12* (2013.01); *C07D 405/12* (2013.01); *C07D 413/12* (2013.01); *C07D 417/12* (2013.01); *C07D 491/107* (2013.01)

(58) Field of Classification Search
CPC .............. C07D 417/12; C07D 491/107; C07D 403/12; C07D 413/12; C07D 235/30; C07D 401/12; A61P 9/00; A61P 9/06; A61P 9/10
See application file for complete search history.

(56) References Cited

U.S. PATENT DOCUMENTS

2020/0216398 A1* 7/2020 Sorensen .................. A61P 9/00

FOREIGN PATENT DOCUMENTS

| WO | 2006/013210 A2 | 2/2006 |
| WO | 2006/136580 A2 | 12/2006 |
| WO | 2007/025709 A2 | 3/2007 |
| WO | 2013/104577 A1 | 7/2013 |
| WO | 2016/053855 A1 | 4/2016 |

OTHER PUBLICATIONS

Cardiac-Arrythmia-Prevention, 2021, https://www.healthline.com/health/arrhythmia/prevention#understanding.*
Cardiac-Arrythmia-Cure, 2021, https://www.okheart.com/about-us/ohh-news/can-heart-rhythm-issues-be-cured.*
International Search Report and Written Opinion of the International Search Authority dated Apr. 11, 2017 of corresponding International application No. PCT/EP2017/025033; 11 pgs.
Wulff H. et al., "Modulators of Small- and Intermediate-Conductance Calcium-Activated Potassium Channels and their Therapeutic Indications", Current Medicinal Chemistry, 2007, p. 1437-1457, vol. 14; 21 pgs.
Liegeois JF et al., "Modulation of Small Conductance Calcium-Activated Potassium (SK) Channels: a New Challenge in Medicinal Chemistry", Current Medicinal Chemistry, 2003, p. 625-647, vol. 10; 23 pgs.
Nattel S., "Calcium-activated potassium current: a novel ion channel candidate in atrial fibrillation", The Journal of Physiology, 2009 p. 1385-1386, vol. 587; 2pgs.
Jonas G. Diness et al., "Inhibition of Small-Conductance Ca2+-Activated K+ Channels Terminates and Protects Against Atrial Fibrillation", Circ Arrhythm Electrophysiol, 2010, p. 380-390, vol. 3; 11 pgs.
Jonas G. Diness et al., "Effects on Atrial Fibrillation in Aged Hypertensive Rats by Ca2+-Activated K+ Channel Inhibition", Hypertension, 2011, p. 1129-1135, vol. 57; 14 pgs.

* cited by examiner

*Primary Examiner* — Sun Jae Yoo
(74) *Attorney, Agent, or Firm* — Maier & Maier, PLLC

(57) ABSTRACT

The present invention relates to a compound of the general formula (I). The compounds of formula I are useful for treatment of a cardiac disease, disorder or condition in a mammal.

20 Claims, No Drawings

POTASSIUM CHANNEL INHIBITORS

TECHNICAL FIELD

The present invention relates to novel compounds, the use of said compounds as medicament and for the manufacture of a medicament for the treatment of a cardiac disease, disorder or condition in mammals. The invention also relates to pharmaceutical compositions comprising said novel compounds.

BACKGROUND ART

The heart is a muscle, which pumps the blood in the circulation by contracting 1-3 times per second. The heartbeat is caused by simultaneous contraction of the individual cardiac muscle cells (cardiac myocytes). The synchronization of the cellular contraction is governed by the electrical cardiac impulse (the cardiac action potential), which is generated in the pacemaker cells of the sine node and spreads rapidly over the heart through a specific conduction system.

Disturbances in the generation of the impulse and the conduction of impulse may occur either as a consequence of a disease, a drug treatment, or electrolyte imbalances. Such disturbances in the impulse are called arrhythmia or dysrhythmia and they may lead to unease, emboli, syncope or sudden death. In its simplest form, an arrhythmia covers everything different from a normal cardiac sinus rhythm. Disturbances can cover anything from simple palpitations to devastating ventricular fibrillation including bradycardia and tachycardia.

At a molecular level a group of proteins called ion channels underlie the electrical events in the heart since they are able to conduct electrical currents across the cell membrane. Different types of ion channels are thus instrumental in the generation and conduction of the cardiac action potential, in the regulation of the heart rate by the autonomic nervous system, and in the contractile process in the individual heart cells. The different types of ion channels are therefore evident targets for anti-arrhythmic cardiac drugs, and many anti-arrhythmic drugs on the market do exert their effect by interacting with ion channels.

Anti-arrhythmic drugs are usually divided into four main classes according to the so-called Singh Vaughan Williams classification: Class I compounds all inhibit the cardiac voltage-dependent sodium channel. Some Class I compounds do have additional effects influencing the cardiac action potential being the basis for a further subdivision into three subclasses:

Class IA compounds are sodium channel inhibitors such as Quinidine, Procainamide or Disopyramid, which prolong the action potential;

Class IB compounds are sodium channel inhibitors such as Lidocaine, Mexiletine, Tocainide or Phenytoine, which shorten the action potential; and Class IC compounds are sodium channel inhibitors such as Flecainide, Moricizine or Propafenone, which do not change the action potential duration.

Class I compounds interact with the sodium channel during its open or inactivated state and are dissociated from the channels during its closed state (during diastole). The rate of dissociation determines whether they show a frequency-dependent channel inhibition. Some of the class I compounds also inhibit subtypes of potassium or calcium permeable channels in addition to their sodium channel inhibiting effect.

Class II compounds are β-adrenoceptor inhibitors and include drugs like Atenolol, Metoprolol, Timolol or Propranolol. β-adrenoceptor inhibitors can be selective for cardiac β1-receptors or have affinity for β1- as well as β2-receptors. Some of the compounds also have an intrinsic β-stimulating effect.

Class III compounds are potassium channel inhibitors such as Amiodarone, Dronedarone, Sotalol, Ibutilide and Dofetilide, which prolong the action potential.

Class IV compounds are inhibitors of L-type calcium channels such as Verapamil. Small-conductance calcium-activated potassium (SK) channels belongs to the family of $Ca^{2+}$-activated $K^+$ channels. Three SK channel subtypes have been cloned: SK1, SK2 and SK3 (corresponding to KCNN1-3 using the genomic nomenclature). The activity of these channels is determined by the concentration of free intracellular calcium ($[Ca^{2+}]i$) via calmodulin that is constitutively bound to the channels. SK channels are tightly regulated by $[Ca^{2+}]i$ in the physiological range being closed at $[Ca^{2+}]i$ up to around 0.1 µM but fully activated at a $[Ca^{2+}]i$ of 1 µM. Being selective for potassium, open or active SK channels have a hyperpolarizing influence on the membrane potential of the cell. SK channels are widely expressed in the central nervous system (CNS) and in peripheral tissue, including the heart.

The hyperpolarizing action of active SK channels plays an important role in the control of firing pattern and excitability of excitable cells. SK channel inhibitors such as apamin and N-methyl bicuculline, have been demonstrated to increase excitability, whereas the SK channel opener 1-EBIO is able to reduce electrical activity. In non-excitable cells, where the amount of $Ca^{2+}$ influx via voltage-independent pathways is highly sensitive to the membrane potential, an activation of SK channels will increase the driving force, whereas an inhibitor of SK channels will have a depolarizing effect, and thus diminish the driving force for calcium.

An SK channel inhibitor is a pharmaceutical agent that impairs the conduction of potassium ions ($K^+$) through $Ca^{2+}$-activated small conductance $K^+$ channels. The impairment can be obtained by any reduction in current resulting from e.g. a direct inhibition of ion conduction to a prevention of $Ca^{2+}$ binding, that is an obligate request for channel activation, or a reduction in calcium sensitivity.

A review of SK channels and SK channel modulators may be found in Wulff H et al.: "Modulators of Small- and Intermediate-Conductance Calcium-Activated Potassium Channels and their Therapeutic Indications", Current Medicinal Chemistry 2007 14 1437-1457; and in Liegeois J-F et al.: "Modulation of small conductance calcium-activated potassium (SK) channels: a new challenge in medicinal chemistry", Current Medicinal Chemistry 2003 10 625-647.

Based on the important role of SK channels in linking $[Ca^{2+}]i$ and membrane potential, SK channels are interesting targets for developing novel therapeutic agents, and the potential of inhibitors of SK channels for use in anti-arrhythmic treatment has recently been established, see e.g. Nattel S; J. Physiol. 2009 587 1385-1386; Diness J G, Sørensen U S, Nissen J D, Al-Shahib B, Jespersen T, Grunnet M, Hansen R S; Circ. Arrhythm. Electrophysiol. 2010 3 380-90; and Diness et al; Hypertension 2011 57 1129-1135.

WO 2006/013210 describes certain 2-amino benzimidazole derivatives and their use as modulators of small-conductance calcium-activated potassium channels.

SUMMARY OF THE INVENTION

The compounds of the present invention are inhibitors or negative modulators of the small-conductance calcium activated potassium (SK) channel and have an IC50 value of below 1000 μM as demonstrated in the Automated patch clamping system described herein, and are considered potent drug candidates. Some of these compounds also have physicochemical properties suitable for a drug substance and important for making pharmaceutical formulations. Further, some of these compounds have pharmacokinetic properties making them suitable for using as pharmaceutical drugs.

In a broad aspect the present invention relates to a compound of formula (I)

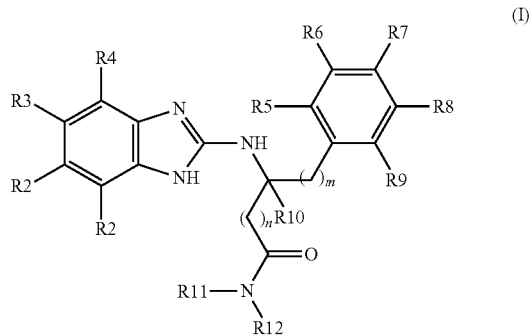

wherein
n is an integer selected from 0, 1, and 2;
m is an integer selected from 0, 1, and 2;
R1-R4 are independently a group selected from H, halogen, CN, $C_{1-6}$ alkyl, $C_{1-6}$ alkylene-OH, $C_{1-6}$ alkoxy, $C_{1-6}$ alkylene-O—$C_{1-6}$ alkyl, $C_{1-6}$ alkylene-S—$C_{1-6}$ alkyl, $C_{3-7}$cycloalkyl, and $C_{1-6}$ alkylene-NR$^a$R$^b$, wherein R$^a$ and R$^b$ are independently a group selected from H, $C_{1-6}$ alkyl, $C_{1-6}$ alkylene-OH, $C_{1-6}$ alkylene-O—$C_{1-6}$ alkyl, C(=O)—$C_{1-6}$ alkyl, C(=O)—$C_{1-6}$ alkoxy, C(=O)—$C_{1-6}$ alkyl-CN, C(=O)—$C_{1-6}$ alkyl-OH, C(=O)—$C_{1-6}$ alkylene-S—$C_{1-6}$ alkyl, C(=O)—O—$C_{1-6}$ alkylene-O—$C_{1-6}$ alkyl, C(=O)—O—$C_{1-6}$ alkyl-CN, C(=O)—O—$C_{1-6}$ alkyl-OH, C(=O)—O—$C_{1-6}$ alkylene-S—$C_{1-6}$ alkyl, C(=O)—NH$C_{1-6}$ alkyl, C(=O)—NH$C_{1-6}$ alkylene-O—$C_{1-6}$ alkyl, C(=O)—NH$C_{1-6}$ alkylene-S—$C_{1-6}$ alkyl, C(=O)—NH$C_{1-6}$ alkyl-CN, C(=O)—NH$C_{1-6}$ alkyl-OH, C(=O)—N($C_{1-6}$ alkyl)$_2$, $SO_2$—$C_{1-6}$ alkyl, $SO_2$—$C_{1-6}$ alkylene-O—$C_{1-6}$ alkyl, $SO_2$—$C_{1-6}$ alkylene-S—$C_{1-6}$ alkyl, $SO_2$—$C_{1-6}$ alkyl-CN, $SO_2$—$C_{1-6}$ alkyl-OH, and $SO_2$—$C_{1-6}$ alkyl-N($C_{1-6}$ alkyl)$_2$;
R5-R9 are independently a group selected from H, halogen, $CH_2F$, $CHF_2$, $CF_3$, CN, $C_{1-6}$ alkyl, $C_{1-6}$ alkylene-OH, OH, $C_{1-6}$ alkoxy, $C_{1-6}$ alkylene-O—$C_{1-6}$ alkyl, $C_{1-6}$ alkylene-S—$C_{1-6}$ alkyl, $C_{3-7}$cycloalkyl, C(=O)—O—$C_{1-6}$ alkyl, S—$C_{1-6}$ alkyl, $SCF_3$, $OCF_3$, $OCF_2H$, $OCFH_2$, $OC_{3-7}$cycloalkyl, $SC_{3-7}$cycloalkyl;
R10 is a group selected from H and $C_{1-6}$ alkyl, $C_{1-6}$ alkyl substituted with 1 to 3 Fluorine atoms, $C_{3-4}$cycloalkyl;
R11 is a group selected from $C_{1-6}$ alkylene-OH; $C_{1-6}$ alkylene-O—$C_{1-6}$ alkyl, wherein $C_{1-6}$ alkylene is optionally substituted with a phenyl, and wherein $C_{1-6}$ alkyl is optionally substituted with a halogen, such as F; $C_{1-6}$ alkylene-S—$C_{1-6}$ alkyl; $C_{1-6}$ alkylene-CN; $C_{1-6}$ alkylene-C(=O)—O—$C_{1-6}$ alkyl; $C_{1-6}$ alkylene-O—C(=O)—NH—$C_{1-6}$ alkyl; $C_{1-6}$ alkylene-NH—C(=O)—$C_{1-6}$ alkylene-O—$C_{1-6}$ alkyl; $C_{1-6}$ alkylene-NH—$SO_2$—$C_{1-6}$ alkyl; $C_{1-6}$ alkylene-NH—$SO_2$—$C_{1-6}$ alkylene-phenyl, wherein the phenyl is optionally substituted with a group selected from $C_{1-6}$ alkyl; $C_{1-6}$ alkylene-NR$^c$R$^d$, wherein R$^c$ and R$^d$ are independently a group selected from H and $C_{1-6}$ alkyl; $C_{1-6}$ alkylene-C(=O)—NR$^e$R$^f$, wherein R$^e$ and R$^f$ are independently a group selected from H and $C_{1-6}$ alkyl; a heterocyclyl, optionally substituted with a group selected from $C_{1-6}$ alkyl, OH, and $C_{1-6}$ alkylene-OH; $C_{1-6}$ alkylene-R$^g$, wherein R$^g$ is a heteroaryl, optionally substituted with a group selected from $C_{1-6}$ alkyl, OH, and $C_{1-6}$ alkylene-OH; $C_{1-6}$ alkylene-R$^h$, wherein R$^h$ is a heterocyclyl, optionally substituted with a group selected from $C_{1-6}$ alkyl, OH, and $C_{1-6}$ alkylene-OH; $C_{1-6}$ alkylene-R$^j$, wherein R$^j$ is a $C_{3-7}$ cycloalkyl, optionally substituted with a group selected from $C_{1-6}$ alkyl, OH, and $C_{1-6}$ alkylene-OH; and $C_{1-6}$ alkylene-R$^k$, wherein R$^k$ is a phenyl, optionally substituted with a group selected from $C_{1-6}$ alkyl, OH, and $C_{1-6}$ alkylene-OH; R12 is a group selected from H, $C_{1-6}$ alkyl, $C_{1-6}$ alkylene-OH, $C_{1-6}$ alkylene-O—$C_{1-6}$ alkyl, $C_{1-6}$ alkylene-S—$C_{1-6}$ alkyl, $C_{1-6}$ alkylene-CN, and $C_{1-6}$ alkylene-$CF_3$; or
R11 and R12 together with the nitrogen to which R11 and R12 are linked form a monocyclic or bicyclic 3-10 membered aliphatic heterocycle containing the nitrogen to which R11 and R12 are linked and optionally one or more heteroatoms selected from O, S, and N, wherein the monocyclic or bicyclic heterocycle is optionally substituted with a group selected from $C_{1-6}$ alkyl; oxo; OH; $C_{1-6}$ alkylene-OH; C(=O)—$C_{1-6}$ alkyl; C(=O)—O—$C_{1-6}$ alkyl; $SO_2$—$C_{1-6}$ alkyl; NR$^k$R$^l$, wherein R$^k$ and R$^l$ are independently a group selected from H and $C_{1-6}$ alkyl; and $C_{1-6}$ alkylene-NR$^m$R$^n$, wherein R$^m$ and R$^n$ are independently a group selected from H and $C_{1-6}$ alkyl; or
a pharmaceutically acceptable salt thereof.

In a further aspect the present invention relates to a compound of formula (I)

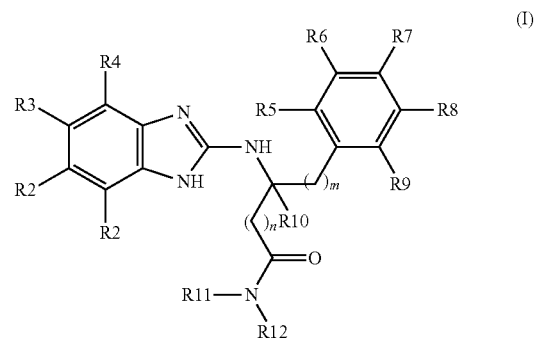

wherein
n is an integer selected from 0, 1, and 2;
m is an integer selected from 0, 1, and 2;
R1-R4 are independently a group selected from H, halogen, CN, $C_{1-6}$ alkyl, $C_{1-6}$ alkylene-OH, $C_{1-6}$ alkoxy, $C_{1-6}$ alkylene-O—$C_{1-6}$ alkyl, $C_{1-6}$ alkylene-S—$C_{1-6}$ alkyl, $C_{3-7}$cycloalkyl, and $C_{1-6}$ alkylene-NR$^a$R$^b$, wherein R$^a$ and R$^b$ are independently a group selected from H, $C_{1-6}$ alkyl, $C_{1-6}$ alkylene-OH, $C_{1-6}$ alkylene-O—$C_{1-6}$ alkyl, C(=O)—$C_{1-6}$ alkyl, C(=O)—$C_{1-6}$ alkoxy, C(=O)—$C_{1-6}$ alkyl-CN, C(=O)—$C_{1-6}$ alkyl-OH, C(=O)—$C_{1-6}$ alkylene-S—$C_{1-6}$ alkyl, C(=O)—O—$C_{1-6}$ alkylene-O—$C_{1-6}$ alkyl, C(=O)—O—$C_{1-6}$ alkyl-CN, C(=O)—O—$C_{1-6}$ alkyl-OH, C(=O)—O—$C_{1-6}$ alkylene-S—$C_{1-6}$ alkyl, C(=O)—NH$C_{1-6}$ alkyl, C(=O)—NH$C_{1-6}$ alkylene-O—$C_{1-6}$ alkyl, C(=O)—NH$C_{1-6}$ alkylene-S—$C_{1-6}$ alkyl, C(=O)—NH$C_{1-6}$ alkyl-CN, C(=O)—NH$C_{1-6}$ alkyl-OH, C(=O)—N($C_{1-6}$ alkyl)$_2$, $SO_2$—$C_{1-6}$ alkyl, $SO_2$—$C_{1-6}$ alkylene-O—$C_{1-6}$ alkyl, $SO_2$—

$C_{1-6}$ alkylene-S—$C_{1-6}$ alkyl, $SO_2$—$C_{1-6}$ alkyl-CN, $SO_2$—$C_{1-6}$ alkyl-OH, and $SO_2$—$C_{1-6}$ alkyl-N($C_{1-6}$ alkyl)$_2$;

R5-R9 are independently a group selected from H, halogen, $CH_2F$, $CHF_2$, $CF_3$, CN, $C_{1-6}$ alkyl, $C_{1-6}$ alkylene-OH, OH, $C_{1-6}$ alkoxy, $C_{1-6}$ alkylene-O—$C_{1-6}$ alkyl, $C_{1-6}$ alkylene-S—$C_{1-6}$ alkyl, $C_{3-7}$cycloalkyl, C(=O)—O—$C_{1-6}$ alkyl, S—$C_{1-6}$ alkyl, $C_{1-6}$ alkoxy, $SCF_3$, $OCF_3$, $OCF_2H$, $OCFH_2$, $OC_{3-7}$cycloalkyl, $SC_{3-7}$cycloalkyl;

R10 is a group selected from H and $C_{1-6}$ alkyl, $C_{1-6}$ alkyl substituted with 1 to 3 Fluorine atoms, $C_{3-4}$ cycloalkyl;

R11 is a group selected from $C_{1-6}$ alkylene-OH; $C_{1-6}$ alkylene-O—$C_{1-6}$ alkyl; $C_{1-6}$ alkylene-S—$C_{1-6}$ alkyl; $C_{1-6}$ alkylene-CN; $C_{1-6}$ alkylene-C(=O)—O—$C_{1-6}$ alkyl; $C_{1-6}$ alkylene-O—C(=O)—NH—$C_{1-6}$ alkyl; $C_{1-6}$ alkylene-NH—C(=O)—$C_{1-6}$ alkylene-O—$C_{1-6}$ alkyl; $C_{1-6}$ alkylene-NH—$SO_2$—$C_{1-6}$ alkyl; $C_{1-6}$ alkylene-NH—$SO_2$—$C_{1-6}$ alkylene-phenyl, wherein the phenyl is optionally substituted with a group selected from $C_{1-6}$ alkyl; $C_{1-6}$ alkylene-NR$^c$R$^d$, wherein R$^c$ and R$^d$ are independently a group selected from H and $C_{1-6}$ alkyl; $C_{1-6}$ alkylene-C(=O)—NR$^e$R$^f$, wherein R$^e$ and R$^f$ are independently a group selected from H and $C_{1-6}$ alkyl; a heterocyclyl, optionally substituted with a group selected from $C_{1-6}$ alkyl, OH, and $C_{1-6}$ alkylene-OH; $C_{1-6}$ alkylene-R$^g$, wherein R$^g$ is a heteroaryl, optionally substituted with a group selected from $C_{1-6}$ alkyl, OH, and $C_{1-6}$ alkylene-OH; $C_{1-6}$ alkylene-R$^h$, wherein R$^h$ is a heterocyclyl, optionally substituted with a group selected from $C_{1-6}$ alkyl, OH, and $C_{1-6}$ alkylene-OH; $C_{1-6}$ alkylene-R$^j$, wherein R$^j$ is a $C_{3-7}$ cycloalkyl, optionally substituted with a group selected from $C_{1-6}$ alkyl, OH, and $C_{1-6}$ alkylene-OH; and $C_{1-6}$ alkylene-R$^k$, wherein R$^k$ is a phenyl, optionally substituted with a group selected from $C_{1-6}$ alkyl, OH, and $C_{1-6}$ alkylene-OH;

R12 is a group selected from H, $C_{1-6}$ alkyl, $C_{1-6}$ alkylene-OH, $C_{1-6}$ alkylene-O—$C_{1-6}$ alkyl, $C_{1-6}$ alkylene-S—$C_{1-6}$ alkyl, $C_{1-6}$ alkylene-CN, and $C_{1-6}$ alkylene-$CF_3$; or R11 and R12 together with the nitrogen to which R11 and R12 are linked form a monocyclic or bicyclic 3-10 membered aliphatic heterocycle containing the nitrogen to which R11 and R12 are linked and optionally one or more heteroatoms selected from O, S, and N, wherein the monocyclic or bicyclic heterocycle is optionally substituted with a group selected from $C_{1-6}$ alkyl; oxo; OH; $C_{1-6}$ alkylene-OH; C(=O)—$C_{1-6}$ alkyl; C(=O)—O—$C_{1-6}$ alkyl; $SO_2$—$C_{1-6}$ alkyl; NR$^k$R$^l$, wherein R$^k$ and R$^l$ are independently a group selected from H and $C_{1-6}$ alkyl; and $C_{1-6}$ alkylene-NR$^m$R$^n$, wherein R$^m$ and R$^n$ are independently a group selected from H and $C_{1-6}$ alkyl; or a pharmaceutically acceptable salt thereof.

In one embodiment m is 0.

In a further embodiment n is 0. In another embodiment n is 1.

In a further embodiment R1 is selected from H and $C_{1-6}$ alkyl-OH. Typically, R1 is selected from H, $CH_2OH$, and $CH_2CH_2OH$.

In a further embodiment R2 is selected from H and $C_{1-6}$ alkyl-NR$^a$R$^b$, wherein R$^a$ and R$^b$ are independently selected from H, $C_{1-6}$ alkyl, $C_{1-6}$ alkyl-OH, $C_{1-6}$ alkoxy, C(=O)—$C_{1-6}$ alkyl, C(=O)—$C_{1-6}$ alkoxy, C(=O)—O—$C_{1-6}$ alkyl, C(=O)—NH$C_{1-6}$ alkyl, C(=O)—N($C_{1-6}$ alkyl)$_2$, and $SO_2$—$C_{1-6}$alkyl. Typically, R2 is selected from H and $C_{1-6}$ alkyl-NR$^a$R$^b$, wherein R$^a$ and R$^b$ are independently selected from H and C(=O)—O—$C_{1-6}$ alkyl. For instance, R2 is selected from H and $CH_2$—NH—C(=O)—O—$CH_2CH_3$.

In a further embodiment R3 is selected from H and $C_{1-6}$ alkyl-NR$^a$R$^b$, wherein R$^a$ and R$^b$ are independently selected from H, $C_{1-6}$ alkyl, $C_{1-6}$ alkyl-OH, $C_{1-6}$ alkoxy, C(=O)—$C_{1-6}$ alkyl, C(=O)—$C_{1-6}$ alkoxy, C(=O)—O—$C_{1-6}$ alkyl, C(=O)—NHC$_{1-6}$ alkyl, C(=O)—N($C_{1-6}$ alkyl)$_2$, and $SO_2$—$C_{1-6}$alkyl. Typically, R3 is selected from H and $C_{1-6}$ alkyl-NR$^a$R$^b$, wherein R$^a$ and R$^b$ are independently selected from H and C(=O)—O—$C_{1-6}$ alkyl. For instance, R3 is selected from H and $CH_2$—NH—C(=O)—O—$CH_2CH_3$.

In a further embodiment R4 is selected from H and $C_{1-6}$ alkyl-OH. Typically, R4 is selected from H, $CH_2OH$, and $CH_2CH_2OH$.

In a further embodiment R5 is selected from H.

In a further embodiment R6 is selected from H, halogen, $CF_3$, and $C_{1-6}$ alkyl. Typically, R6 is selected from H, Cl, $CF_3$, $CH_3$ and $CH_2CH_3$.

In a further embodiment R7 is selected from H, halogen, and $C_{1-6}$ alkyl. Typically, R7 is selected from H, F, Cl, and $CH_3$.

In a further embodiment R8 is selected from H, halogen, $CF_3$, and $C_{1-6}$ alkyl. Typically, R8 is selected from H, Cl, $CF_3$, $CH_3$ and $CH_2CH_3$.

In a further embodiment R9 is selected from H.

In a further embodiment R10 is selected from H.

In a further embodiment wherein R11 is selected from $C_{1-6}$ alkylene-OH, $C_{1-6}$ alkylene-O—$C_{1-6}$ alkyl, $C_{1-6}$ alkylene-S—$C_{1-6}$ alkyl, $C_{1-6}$ alkylene-CN, $C_{1-6}$ alkylene-C(=O)—O—$C_{1-6}$ alkyl, $C_{1-6}$ alkylene-O—C(=O)—NH—$C_{1-6}$ alkyl, $C_{1-6}$ alkylene-NH—C(=O)—$C_{1-6}$ alkylene-O—$C_{1-6}$ alkyl, $C_{1-6}$ alkylene-NH—$SO_2$—$C_{1-6}$ alkyl, $C_{1-6}$ alkylene-NH—$SO_2$—$C_{1-6}$ alkylene-phenyl; $C_{1-6}$ alkylene-NR$^c$R$^d$, wherein R$^c$ and R$^d$, are independently selected from H and $C_{1-6}$ alkyl; $C_{1-6}$ alkylene-C(=O)NR$^e$R$^f$, wherein R$^e$ and R$^f$ are independently selected from H and $C_{1-6}$ alkyl; a heterocyclyl; $C_{1-6}$ alkylene-R$^g$, wherein R$^g$ is a heteroaryl, optionally substituted with a group selected from $C_{1-6}$ alkyl; $C_{1-6}$ alkylene-R$^h$, wherein R$^h$ is a heterocyclyl. Typically, R11 is selected from $C_{1-4}$ alkylene-OH, $C_{1-3}$ alkylene-O—$CH_3$, $C_{1-3}$ alkylene-S—$CH_3$, $C_{1-3}$ alkylene-CN, $C_{1-3}$ alkylene-C(=O)—O—$C_{1-3}$ alkyl, $C_{1-3}$ alkylene-O—C(=O)—NH—$C_{1-3}$ alkyl, $C_{1-3}$ alkylene-NH—C(=O)—$C_{1-3}$ alkylene-O—$C_{1-2}$ alkyl, $C_{1-3}$ alkylene-NH—$SO_2$—$C_{1-3}$ alkyl, $C_{1-3}$ alkylene-NH—$SO_2$—$C_{1-3}$ alkylene-phenyl; $C_{1-4}$ alkylene-NR$^c$R$^d$, wherein R$^c$ and R$^d$, are independently selected from H and $CH_3$; $C_{1-3}$ alkylene-C(=O)—NR$^e$R$^f$, wherein R$^e$ and R$^f$ are independently selected from H and $CH_3$; a heterocyclyl selected from a monocyclic 4-5 membered aliphatic heterocycle containing one heteroatom selected from O; $C_{1-3}$ alkylene-R$^g$, wherein R$^g$ is a heteroaryl selected from a monocyclic aromatic ring system containing one or two heteroatoms selected from O and N, optionally substituted with a group selected from $CH_3$; $C_{1-3}$ alkylene-R$^h$, wherein R$^h$ is a heterocyclyl selected from a monocyclic 4-6 membered aliphatic heterocycle containing one or two heteroatoms selected from O and N. For instance, R11 is selected from $CH(CH_3)_2$—OH, $CH_2CH_2OH$, $CH_2CH_2CH_2OH$, $CH_2CH_2OCH_3$, $CH_2CH_2SCH_3$, $CH_2CN$, $CH_2COOCH_3$, $CH_2COOCH_2CH_3$, $CH(CH_3)COOCH_3$, $CH_2CH_2$—O—CO—NH—$CH_2CH_3$, $CH_2CH_2$—NH—CO—$CH_2$—O—$CH_3$, $CH_2CH_2$—NH—$SO_2$—$CH_2CH_3$, $CH_2CH_2$—NH—$SO_2$—$CH_2$Phenyl, $CH_2CH_2NH_2$, $CH_2CH_2CH_2NH_2$, $(CH_2)_4NH_2$, $(CH_2)_3N(CH_3)_2$, $(CH_2)_4N(CH_3)_2$, $CH_2CH_2NHCH_3$, $CH_2CH_2N(CH_3)_2$, $CH_2CON(CH_3)_2$, $CH_2CONH_2$, oxetanyl, tetrahydrofuranyl, $CH_2$-oxazolyl, $CH_2$-imidazolyl substituted with one $CH_3$, $CH_2$-oxetanyl, $CH_2$-tetrahydrofuranyl, $CH_2CH_2$-piperazinyl.

In a further embodiment R12 is selected from H and $C_{1-6}$ alkyl. Typically, R12 is selected from H, $CH_3$ and $CH_2CH_3$.

In another embodiment R11 and R12 together with the nitrogen to which R11 and R12 are linked forms a mono or bicyclic 3-7 membered aliphatic heterocycle containing the nitrogen to which R11 and R12 are linked selected from aziridinyl, oxaziridinyl, azetidinyl, diazetidinyl, pyrrolidinyl, imidazolidinyl, pyrazolidinyl, oxazolidinyl, isoxazolidinyl, thiazolidinyl, isothiazolidinyl, morpholinyl, piperidinyl, piperazinyl, and 2-oxa-6-azaspiro[3.3]-heptanyl, optionally substituted with a group selected from $C_{1-6}$ alkyl, oxo, OH, $C_{1-6}$ alkylene-OH, C(=O)—$C_{1-6}$ alkyl, C(=O)—O—$C_{1-6}$ alkyl, $SO_2$—$C_{1-6}$ alkyl, $NR^kR^l$, wherein $R^k$ and $R^l$ are independently selected from H and $C_{1-6}$ alkyl; $C_{1-6}$ alkylene-$NR'''R''$, wherein $R'''$ and $R''$ are independently selected from H and $C_{1-6}$ alkyl. Typically, R11 and R12 together with the nitrogen to which R11 and R12 are linked forms a mono or bicyclic 3-7 membered aliphatic heterocycle containing the nitrogen to which R11 and R12 are linked selected from aziridinyl, pyrrolidinyl, morpholinyl, piperidinyl, piperazinyl, and 2-oxa-6-azaspiro[3.3]-heptanyl optionally substituted with a group selected from $C_{1-6}$ alkyl, oxo, OH, $C_{1-6}$ alkylene —OH, C(=O)—$C_{1-6}$ alkyl, C(=O)—O—$C_{1-6}$ alkyl, $SO_2$—$C_{1-6}$ alkyl, $NR^kR^l$, wherein $R^k$ and $R^l$ are independently selected from H and $C_{1-6}$ alkyl; $C_{1-6}$ alkylene-$NR'''R''$, wherein $R'''$ and $R''$ are independently selected from H and $C_{1-6}$ alkyl. In particular, R11 and R12 together with the nitrogen to which R11 and R12 are linked forms a mono or bicyclic 3-7 membered aliphatic heterocycle containing the nitrogen to which R11 and R12 are linked selected from aziridinyl optionally substituted with a group selected from OH, $C_{1-3}$ alkylene-OH and $NR^kR^l$, wherein $R^k$ and $R^l$ are independently selected from H and $C_{1-3}$ alkyl; pyrrolidinyl optionally substituted with a group selected from OH; morpholinyl; piperidinyl optionally substituted with a group selected from OH; piperazinyl optionally substituted with a group selected from $C_{1-6}$ alkyl, oxo, C(=O)—$C_{1-3}$ alkyl, C(=O)—O—$C_{1-3}$ alkyl, $SO_2$—$C_{1-4}$ alkyl, $C_{1-4}$ alkylene-$NR'''R''$, wherein $R'''$ and $R''$ are independently selected from H and $C_{1-3}$ alkyl; and 2-oxa-6-azaspiro[3.3]-heptanyl. For instance, R11 and R12 together with the nitrogen to which R11 and R12 are linked forms a mono or bicyclic 3-7 membered aliphatic heterocycle containing the nitrogen to which R11 and R12 are linked selected from aziridinyl optionally substituted with a group selected from OH, $CH_2$—OH and $N(CH_3)_2$; pyrrolidinyl optionally substituted with a group selected from OH; morpholinyl; piperidinyl optionally substituted with a group selected from OH; piperazinyl optionally substituted with a group selected from $CH_3$, oxo, C(=O)—$CH_3$, C(=O)—O—$CH_3$, $SO_2$—CH$(CH_3)_2$, $CH_2CH_2$—$N(CH_3)_2$; and 2-oxa-6-azaspiro[3.3]-heptanyl.

In a further embodiment a compound of the present invention is selected from:

3-[(1H-1,3-benzodiazol-2-yl)amino]-N-[2-(methylsulfanyl)ethyl]-3-[3-(trifluoromethyl)phenyl]propanamide, 3-[(1H-1,3-benzodiazol-2-yl)amino]-N-[2-(dimethylamino)ethyl]-N-methyl-3-[3-(trifluoromethyl)phenyl]propanamide, 3-[(1H-1,3-benzodiazol-2-yl)amino]-N-(2-ethanesulfonamidoethyl)-3-[3-(trifluoromethyl)phenyl]propanamide, 3-[(1H-1,3-benzodiazol-2-yl)amino]-N-(2-hydroxy-2-methylpropyl)-3-[3-(trifluoromethyl)phenyl]propanamide, (−) 3-[(1H-1,3-benzodiazol-2-yl)amino]-N-(2-hydroxy-2-methylpropyl)-3-[3-(trifluoromethyl)phenyl]propanamide, (+) 3-[(1H-1,3-benzodiazol-2-yl)amino]-N-(2-hydroxy-2-methylpropyl)-3-[3-(trifluoromethyl)phenyl]propanamide, 3-[(1H-1,3-benzodiazol-2-yl)amino]-1-(4-hydroxypiperidin-1-yl)-3-[3-(trifluoromethyl)phenyl]propan-1-one, 3-[(1H-1,3-benzodiazol-2-yl)amino]-1-(3-hydroxyazetidin-1-yl)-3-[3-(trifluoromethyl)phenyl]propan-1-one, 3-[(1H-1,3-benzodiazol-2-yl)amino]-N-(oxetan-3-ylmethyl)-3-[3-(trifluoromethyl)phenyl]propanamide, 3-[(1H-1,3-benzodiazol-2-yl)amino]-N-(oxolan-2-ylmethyl)-3-[3-(trifluoromethyl)phenyl]propanamide, 3-[(1H-1,3-benzodiazol-2-yl)amino]-N-[(3S)-oxolan-3-yl]-3-[3-(trifluoromethyl)phenyl]propanamide, 3-[(1H-1,3-benzodiazol-2-yl)amino]-N-(oxetan-3-yl)-3-[3-(trifluoromethyl)phenyl]propanamide, 4-{3-[(1H-1,3-benzodiazol-2-yl)amino]-3-[3-(trifluoromethyl)phenyl]propanoyl}-1-methylpiperazin-2-one, 3-[(1H-1,3-benzodiazol-2-yl)amino]-N-[2-(phenylmethanesulfonamido)ethyl]-3-[3-(trifluoromethyl)phenyl]propanamide, 3-[(1H-1,3-benzodiazol-2-yl)amino]-1-[(3R)-3-hydroxypiperidin-1-yl]-3-[3-(trifluoromethyl)phenyl]propan-1-one, 3-[(1H-1,3-benzodiazol-2-yl)amino]-1-[(3R)-3-hydroxypyrrolidin-1-yl]-3-[3-(trifluoromethyl)phenyl]propan-1-one, 3-[(1H-1,3-benzodiazol-2-yl)amino]-1-[(3S)-3-hydroxypyrrolidin-1-yl]-3-[3-(trifluoromethyl)phenyl]propan-1-one, 3-[(1H-1,3-benzodiazol-2-yl)amino]-N-(3-hydroxypropyl)-3-[3-(trifluoromethyl)phenyl]propanamide, 3-[(1H-1,3-benzodiazol-2-yl)amino]-N-(3-hydroxypropyl)-N-methyl-3-[3-(trifluoromethyl)phenyl]propanamide, (−) 3-[(1H-1,3-benzodiazol-2-yl)amino]-N-(3-hydroxypropyl)-N-methyl-3-[3-(trifluoromethyl)phenyl]propanamide, (+) 3-[(1H-1,3-benzodiazol-2-yl)amino]-N-(3-hydroxypropyl)-N-methyl-3-[3-(trifluoromethyl)phenyl]propanamide, 3-[(1H-1,3-benzodiazol-2-yl)amino]-N-[(1,3-oxazol-2-yl)methyl]-3-[3-(trifluoromethyl)phenyl]propanamide, 3-[(1H-1,3-benzodiazol-2-yl)amino]-N-[(1-methyl-1H-imidazol-2-yl)methyl]-3-[3-(trifluoromethyl)phenyl]propanamide, 3-[(1H-1,3-benzodiazol-2-yl)amino]-3-(3-chloro-4-methylphenyl)-N-ethyl-N-(2-hydroxyethyl)propanamide, 3-[(1H-1,3-benzodiazol-2-yl)amino]-N-(cyanomethyl)-3-[3-(trifluoromethyl)phenyl]propanamide, 3-[(1H-1,3-benzodiazol-2-yl)amino]-N-[(dimethylcarbamoyl)methyl]-3-[3-(trifluoromethyl)phenyl]propanamide, Ethyl 2-{3-[(1H-1,3-benzodiazol-2-yl)amino]-3-[3-(trifluoromethyl)phenyl]propanamido}acetate, N-(2-aminoethyl)-2-[(1H-1,3-benzodiazol-2-yl)amino]-2-[3-(trifluoromethyl)phenyl]acetamide, 2-[(1H-1,3-benzodiazol-2-yl)amino]-N-[2-(dimethylamino)ethyl]-N-methyl-2-[3-(trifluoromethyl)phenyl]acetamide, 2-[(1H-1,3-benzodiazol-2-yl)amino]-1-(piperazin-1-yl)-2-[3-(trifluoromethyl)phenyl]ethan-1-one, 2-[(1H-1,3-benzodiazol-2-yl)amino]-1-(4-methylpiperazin-1-yl)-2-[3-(trifluoromethyl)phenyl]ethan-1-one, (−)2-[(1H-1,3-benzodiazol-2-yl)amino]-1-(4-methylpiperazin-1-yl)-2-[3-(trifluoromethyl)phenyl]ethan-1-one, (+)2-[(1H-1,3-benzodiazol-2-yl)amino]-1-(4-methylpiperazin-1-yl)-2-[3-(trifluoromethyl)phenyl]ethan-1-one, 2-[(1H-1,3-benzodiazol-2-yl)amino]-1-[3-(dimethylamino)azetidin-1-yl]-2-[3-(trifluoromethyl)phenyl]ethan-1-one, 2-[(1H-1,3-benzodiazol-2-yl)amino]-1-(pyrrolidin-1-yl)-2-[3-(trifluoromethyl)phenyl]ethan-1-one, 2-[(1H-1,3-benzodiazol-2-yl)amino]-N-(2-hydroxyethyl)-N-methyl-2-[3-(trifluoromethyl)phenyl]acetamide, 2-[(1H-1,3-benzodiazol-2-yl)amino]-1-(piperidin-1-yl)-2-[3-(trifluoromethyl)phenyl]ethan-1-one, 2-[(1H-1,3-benzodiazol-2-yl)amino]-1-(morpholin-4-yl)-2-[3-(trifluoromethyl)phenyl]ethan-1-one, 2-[(1H-1,3-benzodiazol-2-yl)amino]-1-[4-(propane-2-sulfonyl)piperazin-1-yl]-2-[3-(trifluoromethyl)phenyl]ethan-1-one, 1-(azetidin-1-yl)-2-[(1H-1,3-benzodiazol-2-yl)amino]-2-[3-(trifluoromethyl)phenyl]ethan-1-one, (+)1-(azetidin-1-yl)-2-[(1H-1,3-benzodiazol-2-yl)amino]-2-[3-(trifluoromethyl)phenyl]ethan-1-one, 1-(azetidin-1-yl)-2-[(1H-1,3-benzodiazol-2-yl)amino]-2-[3-(trifluoromethyl)phenyl]ethan-1-one, 2-[(1H-1,3-benzodiazol-2-yl)amino]-N-(oxetan-3-yl)-2-[3-(trifluoromethyl)phenyl]acetamide, 2-[(1H-1,3-benzodiazol-2-yl)amino]-1-{2-oxa-6-azaspiro[3.3]heptan-6-yl}-2-[3-(trifluoromethyl)phenyl]ethan-1-one, 4-{2-[(1H-1,3-benzodiazol-2-yl)amino]-2-[3-(trifluoromethyl)phenyl]acetyl}-1,1-dimethylpiperazin-1-ium, 2-[(1H-1,3-benzodiazol-2-yl)amino]-N-ethyl-N-(2-hydroxyethyl)-2-[3-(trifluoromethyl)phenyl]acetamide, (−)2-[(1H-1,3-benzodiazol-2-yl)amino]-N-ethyl-N-(2-hydroxyethyl)-2-[3-(trifluoromethyl)phenyl]acetamide, (+)2-[(1H-1,3-benzodiazol-2-yl)amino]-N-ethyl-N-(2-hydroxyethyl)-2-[3-(trifluoromethyl)phenyl]acetamide, 3-[(1H-1,3-benzodiazol-2-yl)amino]-N-ethyl-3-(4-fluoro-3-methylphenyl)-N-(2-hydroxyethyl)propanamide, (−)3-[(1H-1,3-benzodiazol-2-yl)amino]-N-ethyl-3-(4-fluoro-3-methylphenyl)-N-(2-hydroxyethyl)propanamide, (+)3-[(1H-1,3-benzodiazol-2-yl)amino]-N-ethyl-3-(4-fluoro-3-methylphenyl)-N-(2-hydroxyethyl)propanamide, 3-[(1H-1,3-benzodiazol-2-yl)amino]-3-(4-chloro-3-methylphenyl)-N-ethyl-N-(2-hydroxyethyl)propanamide, (−)3-[(1H-1,3-benzodiazol-2-yl)amino]-3-(4-chloro-3-methylphenyl)-N-ethyl-N-(2-hydroxyethyl)propanamide, (+)3-[(1H-1,3-benzodiazol-2-yl)amino]-3-(4-chloro-3-methylphenyl)-N-ethyl-N-(2-hydroxyethyl)propanamide, 3-[(1H-1,3-benzodiazol-2-yl)amino]-N-ethyl-N-(2-hydroxyethyl)-3-[3-(trifluoromethyl)phenyl]propanamide, (−)3-[(1H-1,3-benzodiazol-2-yl)amino]-N-ethyl-N-(2-hydroxyethyl)-3-[3-(trifluoromethyl)phenyl]propanamide, 3-[(1H-1,3-benzodiazol-2-yl)amino]-N-ethyl-N-(2-hydroxyethyl)-3-[3-(trifluoromethyl)phenyl]propanamide, 3-[(1H-1,3-benzodiazol-2-yl)amino]-N-(2-methoxyethyl)-3-[3-(trifluoromethyl)phenyl]propanamide, (−)3-[(1H-1,3-benzodiazol-2-yl)amino]-N-(2-methoxyethyl)-3-[3-(trifluoromethyl)phenyl]propanamide, (+)3-[(1H-1,3-benzodiazol-2-yl)amino]-N-(2-methoxyethyl)-3-[3-(trifluoromethyl)phenyl]propanamide, 3-[(1H-1,3-benzodiazol-2-yl)amino]-N-(2-methoxyethyl)-N-methyl-3-[3-(trifluoromethyl)phenyl]propanamide, 3-[(1H-1,3-benzodiazol-2-yl)amino]-N-methyl-N-[2-(methylamino)ethyl]-3-[3-(trifluoromethyl)phenyl]propanamide, 3-[(1H-1,3-benzodiazol-2-yl)amino]-N-[2-(dimethylamino)ethyl]-N-ethyl-3-[3-(trifluoromethyl)phenyl]propanamide, Methyl (2R)-2-{3-[(1H-1,3-benzodiazol-2-yl)amino]-3-[3-(trifluoromethyl)phenyl]propanamido}propanoate, Methyl 2-{3-[(1H-1,3-benzodiazol-2-yl)amino]-N-ethyl-3-[3-(trifluoromethyl)phenyl]propanamido}acetate, Ethyl 2-{3-[(1H-1,3-benzodiazol-2-yl)amino]-N-ethyl-3-[3-(trifluoromethyl)phenyl]propanamido}acetate, N-ethyl-N-(2-hydroxyethyl)-3-{[4-(hydroxymethyl)-1H-1,3-benzodiazol-2-yl]amino}-3-[3-(trifluoromethyl)phenyl]propanamide, N-(cyanomethyl)-3-{[4-(hydroxymethyl)-1H-1,3-benzodiazol-2-yl]amino}-N-methyl-3-[3-(trifluoromethyl)phenyl]propanamide, N-(cyanomethyl)-3-{[4-(2-hydroxyethyl)-1H-1,3-benzodiazol-2-yl]amino}-N-methyl-3-[3-(trifluoromethyl)phenyl]propanamide, N-(cyanomethyl)-N-ethyl-3-{[4-(2-hydroxyethyl)-1H-1,3-benzodiazol-2-yl]amino}-3-[3-(trifluoromethyl)phenyl]propanamide, N-(cyanomethyl)-N-ethyl-3-{[4-(hydroxymethyl)-1H-1,3-benzodiazol-2-yl]amino}-3-[3-(trifluoromethyl)phenyl]propanamide, N-(carbamoylmethyl)-N-ethyl-3-{[4-(hydroxymethyl)-1H-1,3-benzodiazol-2-yl]amino}-3-[3-(trifluoromethyl)phenyl]propanamide, 3-[(1H-1,3-benzodiazol-2-yl)amino]-N-(cyanomethyl)-N-ethyl-3-[3-(trifluoromethyl)phenyl]propanamide, 3-[(1H-1,3-benzodiazol-2-yl)amino]-N-(cyanomethyl)-N-methyl-3-[3-(trifluoromethyl)phenyl]propanamide, (−)3-[(1H-1,3-benzodiazol-2-yl)amino]-N-(cyanomethyl)-N-methyl-3-[3-(trifluoromethyl)phenyl]propanamide, (+)3-[(1H-1,3-benzodiazol-2-yl)amino]-N-(cyanomethyl)-N-methyl-3-[3-(trifluoromethyl)phenyl]propanamide, Methyl 2-{3-[(1H-1,3-benzodiazol-2-yl)amino]-N-methyl-3-[3-(trifluoromethyl)phenyl]propanamido}acetate, (−)Methyl 2-{3-[(1H-1,3-benzodiazol-2-yl)amino]-N-methyl-3-[3-(trifluoromethyl)phenyl]propanamido}acetate, (+)Methyl 2-{3-[(1H-1,3-benzodiazol-2-yl)amino]-N-methyl-3-[3-(trifluoromethyl)phenyl]propanamido}acetate, N-ethyl-3-{[4-(hydroxymethyl)-1H-1,3-benzodiazol-2-yl]amino}-N-[2-(methylsulfanyl)ethyl]-3-[3-(trifluoromethyl)phenyl]propanamide, Methyl 2-{3-[(1H-1,3-benzodiazol-2-yl)amino]-3-[3-(trifluoromethyl)phenyl]propanamido}acetate, (−)Methyl 2-{3-[(1H-1,3-benzodiazol-2-yl)amino]-3-[3-(trifluoromethyl)phenyl]propanamido}acetate, (+)Methyl 2-{3-[(1H-1,3-benzodiazol-2-yl)amino]-3-[3-(trifluoromethyl)phenyl]propanamido}acetate, 3-[(1H-1,3-benzodiazol-2-yl)amino]-N-(carbamoylmethyl)-N-methyl-3-[3-(trifluoromethyl)phenyl]propanamide, Methyl 4-{2-[(1H-1,3-benzodiazol-2-yl)amino]-2-[3-(trifluoromethyl)phenyl]acetyl}piperazine-1-carboxylate, 3-[(1H-1,3-benzodiazol-2-yl)amino]-N-[2-(2-methoxyacetamido)ethyl]-3-[3-(trifluoromethyl)phenyl]propanamide, 2-{3-[(1H-1,3-benzodiazol-2-yl)amino]-3-[3-(trifluoromethyl)phenyl]propanamido}ethyl N-ethylcarbamate, 2-[(1H-1,3-benzodiazol-2-yl)amino]-N-ethyl-N-(2-hydroxyethyl)-3-[3-(trifluoromethyl)phenyl]propanamide, 3-[(1H-1,3-benzodiazol-2-yl)amino]-N-ethyl-3-(3-ethyl-4-fluorophenyl)-N-(2-hydroxyethyl)propanamide, (−)3-[(1H-1,3-benzodiazol-2-yl)amino]-N-ethyl-3-(3-ethyl-4-fluorophenyl)-N-(2-hydroxyethyl)propanamide, (+)3-[(1H-1,3-benzodiazol-2-yl)amino]-N-ethyl-3-(3-ethyl-4-fluorophenyl)-N-(2-hydroxyethyl)propanamide, and ethyl N-{[2-({2-[ethyl(2-hydroxyethyl)carbamoyl]-1-[3-(trifluoromethyl)phenyl]ethyl}amino)-1H-1,3-benzodiazol-5-yl]methyl}carbamate;

or a pharmaceutically acceptable salt thereof.

In a further embodiment a compound of the present invention is selected from:

3-[(1H-1,3-benzodiazol-2-yl)amino]-N-[2-(trifluoromethoxy)ethyl]-3-[3-(trifluoromethyl)phenyl]propanamide, (+)-3-[(1H-1,3-benzodiazol-2-yl)amino]-N-[2-(trifluoromethoxy)ethyl]-3-[3-(trifluoromethyl)phenyl]propanamide,
(−)-3-[(1H-1,3-benzodiazol-2-yl)amino]-N-[2-(trifluoromethoxy)ethyl]-3-[3-(trifluoromethyl)phenyl]propanamide,
3-[(1H-1,3-benzodiazol-2-yl)amino]-N-[2-(2,2,2-trifluoroethoxy)ethyl]-3-[3-(trifluoromethyl)phenyl]propanamide,
(+)-3-[(1H-1,3-benzodiazol-2-yl)amino]-N-[2-(2,2,2-trifluoroethoxy)ethyl]-3-[3-(trifluoromethyl)phenyl]propanamide,
(−)-3-[(1H-1,3-benzodiazol-2-yl)amino]-N-[2-(2,2,2-trifluoroethoxy)ethyl]-3-[3-(trifluoromethyl)phenyl]propanamide,
3-[(1H-1,3-benzodiazol-2-yl)amino]-N-[(1R)-2-methoxy-1-phenylethyl]-3-[3-(trifluoromethyl)phenyl]propanamide,
(+)-3-[(1H-1,3-benzodiazol-2-yl)amino]-N-[(1R)-2-methoxy-1-phenylethyl]-3-[3-(trifluoromethyl)phenyl]propanamide,
(−)-3-[(1H-1,3-benzodiazol-2-yl)amino]-N-[(1R)-2-methoxy-1-phenylethyl]-3-[3-(trifluoromethyl)phenyl]propanamide,
3-[(1H-1,3-benzodiazol-2-yl)amino]-N-[(1R)-2-methoxy-1-phenylethyl]-3-{3-[(trifluoromethyl)sulfanyl]phenyl}propanamide,
(+)-3-[(1H-1,3-benzodiazol-2-yl)amino]-N-[(1R)-2-methoxy-1-phenylethyl]-3-{3-[(trifluoromethyl)sulfanyl]phenyl}propanamide,
(−)-3-[(1H-1,3-benzodiazol-2-yl)amino]-N-[(1R)-2-methoxy-1-phenylethyl]-3-{3-[(trifluoromethyl)sulfanyl]phenyl}propanamide,
3-[(1H-1,3-benzodiazol-2-yl)amino]-N-(1,2-oxazol-3-ylmethyl)-3-[3-(trifluoromethyl)phenyl]propanamide,
3-[(1H-1,3-benzodiazol-2-yl)amino]-N-(1,3-benzoxazol-2-ylmethyl)-3-[3-(trifluoromethyl)phenyl]propanamide,
3-[(1H-1,3-benzodiazol-2-yl)amino]-N-(1-methoxypropan-2-yl)-3-[3-(trifluoromethyl)phenyl]propanamide,
3-[(1H-1,3-benzodiazol-2-yl)amino]-N-[2-(dimethyl-1,2-oxazol-4-yl)ethyl]-3-[3-(trifluoromethyl)phenyl]propanamide,
3-[(1H-1,3-benzodiazol-2-yl)amino]-N-(1,3-thiazol-2-ylmethyl)-3-[3-(trifluoromethyl)phenyl]propanamide,
3-[(1H-1,3-benzodiazol-2-yl)amino]-N-[1-(6-methylpyridin-2-yl)ethyl]-3-[3-(trifluoromethyl)phenyl]propanamide,
3-[(1H-1,3-benzodiazol-2-yl)amino]-N-[(2-methyl-1,3-thiazol-5-yl)methyl]-3-[3-(trifluoromethyl)phenyl]propanamide,
3-[(1H-1,3-benzodiazol-2-yl)amino]-N-(pyrimidin-5-ylmethyl)-3-[3-(trifluoromethyl)phenyl]propanamide,
3-[(1H-1,3-benzodiazol-2-yl)amino]-N-[(2-methylpyridin-4-yl)methyl]-3-[3-(trifluoromethyl)phenyl]propanamide,
3-[(1H-1,3-benzodiazol-2-yl)amino]-3-(4-fluoro-3,5-dimethylphenyl)-N-(2-methoxyethyl)propanamide,
3-[(1H-1,3-benzodiazol-2-yl)amino]-N-[2-(trifluoromethoxy)ethyl]-3-{3-[(trifluoromethyl)sulfanyl]phenyl}propanamide,
3-[(1H-1,3-benzodiazol-2-yl)amino]-N-(2-methoxyethyl)-3-{3-[(trifluoromethyl)sulfanyl]phenyl}propanamide,
3-[(1H-1,3-benzodiazol-2-yl)amino]-N-[2-(trifluoromethoxy)ethyl]-3-[3-(trifluoromethoxy)phenyl]propanamide,
3-[(1H-1,3-benzodiazol-2-yl)amino]-N-(2-methoxyethyl)-3-[3-(trifluoromethoxy)phenyl]propanamide,
3-[(1H-1,3-benzodiazol-2-yl)amino]-N-(cyanomethyl)-3-[3-(trifluoromethoxy)phenyl]propanamide,
3-[(1H-1,3-benzodiazol-2-yl)amino]-N-(cyanomethyl)-3-(4-fluoro-3,5-dimethylphenyl)propanamide,
3-[(1H-1,3-benzodiazol-2-yl)amino]-3-[3-(cyclobutylsulfanyl)phenyl]-N-(2-methoxyethyl)propanamide,
3-[(1H-1,3-benzodiazol-2-yl)amino]-N-(1,2-oxazol-3-ylmethyl)-3-[3-(trifluoromethoxy)phenyl]propanamide,
3-[(1H-1,3-benzodiazol-2-yl)amino]-N-(1,3-benzoxazol-2-ylmethyl)-3-{3-[(trifluoromethyl)sulfanyl]phenyl}propanamide,
3-[(1H-1,3-benzodiazol-2-yl)amino]-N-(1,3-benzoxazol-2-ylmethyl)-3-[3-(trifluoromethoxy)phenyl]propanamide,
3-[(5-fluoro-1H-1,3-benzodiazol-2-yl)amino]-N-(2-methoxyethyl)-3-[3-(trifluoromethyl)phenyl]butanamide,
3-[(1H-1,3-benzodiazol-2-yl)amino]-N-(2-methoxyethyl)-3-[3-(methylsulfanyl)phenyl]propanamide,
3-[(4-methoxy-1H-1,3-benzodiazol-2-yl)amino]-N-(2-methoxyethyl)-3-[3-(trifluoromethyl)phenyl]propanamide,
3-{[4-(hydroxymethyl)-1H-1,3-benzodiazol-2-yl]amino}-N-[2-(trifluoromethoxy)ethyl]-3-[3-(trifluoromethyl)phenyl]propanamide,
3-[(5,6-difluoro-1H-1,3-benzodiazol-2-yl)amino]-N-(2-methoxyethyl)-3-[3-(trifluoromethyl)phenyl]propanamide, and
3-[(5-fluoro-4-methyl-1H-1,3-benzodiazol-2-yl)amino]-N-(2-methoxyethyl)-3-[3-(trifluoromethyl)phenyl]propanamide;
or
a pharmaceutically acceptable salt thereof.

In a further aspect the present invention relates to a compound of the present invention, for instance according to any one of the above embodiments, for use as a medicine.

In a further aspect the present invention relates to a pharmaceutical composition comprises a compound of the present invention, for instance according to any one of the above embodiments, and optionally a pharmaceutically acceptable additive, such as a carrier or excipient.

In a further aspect the present invention relates to a compound of the present invention, for instance according to any one of the above embodiments, for use in a method for treating a cardiac disease, disorder or condition in a mammal, such as a human. In an embodiment, for use in a method for treating the cardiac disease, disorder or condition wherein the disease, disorder or condition is associated with an abnormal rhythm of the heart or variant and exercise induced angina. In another embodiment, for use in a method for treating the cardiac disease, disorder or condition selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, and bradyarrhythmias.

In a further aspect the present invention relates to a method for treatment of a cardiac disease, disorder or condition in a mammal, such as a human, wherein a therapeutically effective amount of at least one compound of the present invention is administered to a mammal in need of said treatment. In a further embodiment said cardiac disease, disorder or condition in a mammal is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, and bradyarrhythmias.

In a still further aspect the present invention relates to a process of preparing a compound of formula I or a pharmaceutically acceptable salt or solvate thereof comprising the steps:

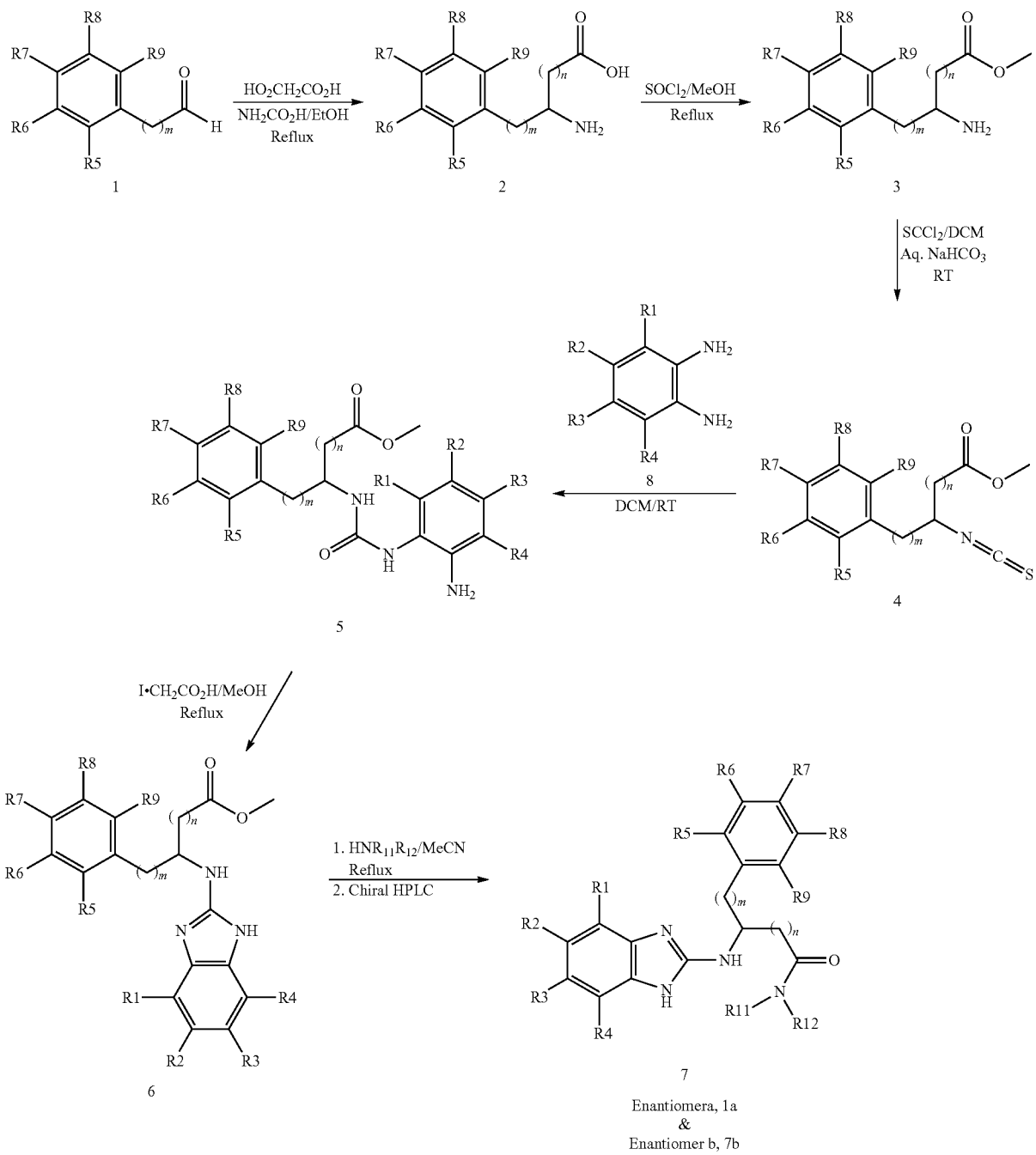

Wherein a) an aldehyde of formula (1) is converted to the β-amino acid of formula (2), such as reaction of (2) with malonic acid derivatives under the influence of ammonium salts (e.g. ammonium formate) followed by subsequent decarboxylation upon heating;

b) the β-amino acid (2) is converted to the ester derivative (3) by reaction with an alcohol (e.g. methanol, ethanol) under the influence of a strong acid (e.g. hydrochloric acid, sulphuric acid) or by first activation to the acid chloride with reagents, such a thionyl chloride, and then reaction with an alcohol;

c) the β-amino ester (3) is converted to the isothiocyanate derivative (4) by reaction with thiophosgene in a suitable solvent (e.g. dichloromethane) under the influence of a base (e.g. sodium hydrogen carbonate)

d) the isothiocyanates (4) is reacted with a benzene-1,2-diamine derivative (8) in a suitable solvent (e.g. dichloromethane) to afford the thiourea products (5);

e) the thiourea derivative (5) is converted to 2-aminobenzimidazole derivative (6) by a ring forming reaction that occurs under the influence of iodoacetic acid and heating in a suitable solvent (such as methanol or acetonitrile), or the cyclisation of (5) to afford (6) done under the influence of mercury salts (e.g. mercuric oxide) with heating in a suitable solvent (e.g. acetonitrile);

f) the 2-aminobenzimidazole ester derivative (6) is reacted with an amine NHR11R12 in a suitable solvent (e.g. acetonitrile) to heating (up to reflux) or to irradiation with microwaves (with heating) to afford the amide derivatives (7);

g) optionally, if the 2-aminobenzimidazole derivative (7) is a racemic mixture, it is separated into the two enantiomers (7a) and (7b), such as by chromatography using a chiral stationary phase, e.g. a normal-phase or reverse phase chromatography, using a suitable organic solvent (e.g. chloroform, dichloromethane, ethanol, ethyl acetate, methanol, or ethanol, or mixtures thereof, sometimes with additives, such as ammonia, triethylamine, trifluoroacetic acid, acetic acid) as eluent.

DETAILED DESCRIPTION OF THE INVENTION

In a broad aspect the present invention relates to a compound of formula (I)

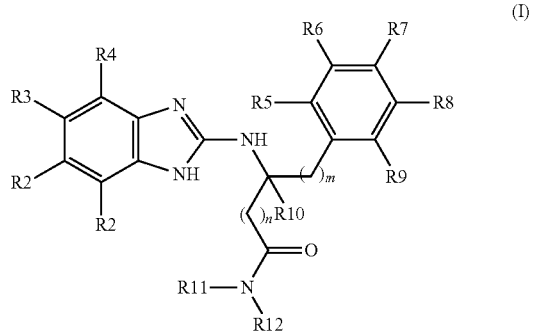

wherein n is an integer selected from 0, 1, and 2;

m is an integer selected from 0, 1, and 2;

R1-R4 are independently a group selected from H, halogen, CN, $C_{1-6}$ alkyl, $C_{1-6}$ alkylene-OH, $C_{1-6}$ alkoxy, $C_{1-6}$ alkylene-O—$C_{1-6}$ alkyl, $C_{1-6}$ alkylene-S—$C_{1-6}$ alkyl, $C_{3-7}$ cycloalkyl, and $C_{1-6}$ alkylene-NR$^a$R$^b$, wherein R$^a$ and R$^b$ are independently a group selected from H, $C_{1-6}$ alkyl, $C_{1-6}$ alkylene-OH, $C_{1-6}$ alkylene-O—$C_{1-6}$ alkyl, C(=O)—$C_{1-6}$ alkyl, C(=O)—$C_{1-6}$ alkoxy, C(=O)—$C_{1-6}$ alkyl-CN, C(=O)—$C_{1-6}$ alkyl-OH, C(=O)—$C_{1-6}$ alkylene-S—$C_{1-6}$ alkyl, C(=O)—O—$C_{1-6}$ alkylene-O—$C_{1-6}$ alkyl, C(=O)—O—$C_{1-6}$ alkyl-CN, C(=O)—O—$C_{1-6}$ alkyl-OH, C(=O)—O—$C_{1-6}$ alkylene-S—$C_{1-6}$ alkyl, C(=O)—NHC$_{1-6}$ alkyl, C(=O)—NHC$_{1-6}$ alkylene-O—$C_{1-6}$ alkyl, C(=O)—NHC$_{1-6}$ alkylene-S—$C_{1-6}$ alkyl, C(=O)—NHC$_{1-6}$ alkyl-CN, C(=O)—NHC$_{1-6}$ alkyl-OH, C(=O)—N($C_{1-6}$ alkyl)$_2$, SO$_2$—$C_{1-6}$ alkyl, SO$_2$—$C_{1-6}$ alkylene-O—$C_{1-6}$ alkyl, SO$_2$—$C_{1-6}$ alkylene-S—$C_{1-6}$ alkyl, SO$_2$—$C_{1-6}$ alkyl-CN, SO$_2$—$C_{1-6}$ alkyl-OH, and SO$_2$—$C_{1-6}$alkyl-N($C_{1-6}$alkyl)$_2$;

R5-R9 are independently a group selected from H, halogen, CH$_2$F, CHF$_2$, CF$_3$, CN, $C_{1-6}$ alkyl, $C_{1-6}$ alkylene-OH, OH, $C_{1-6}$ alkoxy, $C_{1-6}$ alkylene-O—$C_{1-6}$ alkyl, $C_{1-6}$ alkylene-S—$C_{1-6}$ alkyl, $C_{3-7}$cycloalkyl, C(=O)—$C_{1-6}$ alkoxy, S—$C_{1-6}$ alkyl, SCF$_3$, OCF$_3$, OCF$_2$H, OCFH$_2$, OC$_{3-7}$ cycloalkyl, SC$_{3-7}$cycloalkyl;

R10 is a group selected from H and $C_{1-6}$ alkyl, $C_{1-6}$ alkyl substituted with 1 to 3 Fluorine atoms, $C_{3-4}$cycloalkyl;

R11 is a group selected from $C_{1-6}$ alkylene-OH; $C_{1-6}$ alkylene-O—$C_{1-6}$ alkyl; $C_{1-6}$ alkylene-S—$C_{1-6}$ alkyl; $C_{1-6}$ alkylene-CN; $C_{1-6}$ alkylene-C(=O)—O—$C_{1-6}$ alkyl; $C_{1-6}$ alkylene-O—C(=O)—NH—$C_{1-6}$ alkyl; $C_{1-6}$ alkylene-NH—C(=O)—$C_{1-6}$ alkylene-O—$C_{1-6}$ alkyl; $C_{1-6}$ alkylene-NH—SO$_2$—$C_{1-6}$ alkyl; $C_{1-6}$ alkylene-NH—SO$_2$—$C_{1-6}$ alkylene-phenyl, wherein the phenyl is optionally substituted with a group selected from $C_{1-6}$ alkyl; $C_{1-6}$ alkylene-NR$^c$R$^d$, wherein R$^c$ and R$^d$ are independently a group selected from H and $C_{1-6}$ alkyl; $C_{1-6}$ alkylene-C(=O)—NR$^e$R$^f$, wherein R$^e$ and R$^f$ are independently a group selected from H and $C_{1-6}$ alkyl; a heterocyclyl, optionally substituted with a group selected from $C_{1-6}$ alkyl, OH, and $C_{1-6}$ alkylene-OH; $C_{1-6}$ alkylene-R$^g$, wherein R$^g$ is a heteroaryl, optionally substituted with a group selected from $C_{1-6}$ alkyl, OH, and $C_{1-6}$ alkylene-OH; $C_{1-6}$ alkylene-R$^h$, wherein R$^h$ is a heterocyclyl, optionally substituted with a group selected from $C_{1-6}$ alkyl, OH, and $C_{1-6}$ alkylene-OH; $C_{1-6}$ alkylene-R$^j$, wherein R$^j$ is a $C_{3-7}$ cycloalkyl, optionally substituted with a group selected from $C_{1-6}$ alkyl, OH, and $C_{1-6}$ alkylene-OH; and $C_{1-6}$ alkylene-R$^k$, wherein R$^k$ is a phenyl, optionally substituted with a group selected from $C_{1-6}$ alkyl, OH, and $C_{1-6}$ alkylene-OH;

R12 is a group selected from H, $C_{1-6}$ alkyl, $C_{1-6}$ alkylene-OH, $C_{1-6}$ alkylene-O—$C_{1-6}$ alkyl, $C_{1-6}$ alkylene-S—$C_{1-6}$ alkyl, $C_{1-6}$ alkylene-CN, and $C_{1-6}$ alkylene-CF$_3$; or R11 and R12 together with the nitrogen to which R11 and R12 are linked form a monocyclic or bicyclic 3-10 membered aliphatic heterocycle containing the nitrogen to which R11 and R12 are linked and optionally one or more heteroatoms selected from O, S, and N, wherein the monocyclic or bicyclic heterocycle is optionally substituted with a group selected from $C_{1-6}$ alkyl; oxo; OH; $C_{1-6}$ alkylene-OH; C(=O)—$C_{1-6}$ alkyl; C(=O)—O—$C_{1-6}$ alkyl; SO$_2$—$C_{1-6}$ alkyl; NR$^k$R$^l$, wherein R$^k$ and R$^l$ are independently a group selected from H and $C_{1-6}$ alkyl; and $C_{1-6}$ alkylene-NR$^m$R$^n$, wherein R$^m$ and R$^n$ are independently a group selected from H and $C_{1-6}$ alkyl; or a pharmaceutically acceptable salt thereof.

In one embodiment m is 0. In another embodiment m is 1.

In a further embodiment n is 0. In another embodiment n is 1.

In a still further embodiment m is 0 and n is 0. In a further embodiment m is 0 and n is 1.

In a further embodiment R1 is a group selected from H.

In a further embodiment R1 is a group selected from H and halogen.

In a further embodiment R1 is a group selected from H, halogen and $C_{1-6}$ alkyl.

In a further embodiment R1 is a group selected from H, halogen, CN, $C_{1-6}$ alkyl, $C_{1-6}$ alkylene-OH, $C_{1-6}$ alkoxy, $C_{1-6}$ alkylene-O—$C_{1-6}$ alkyl, $C_{1-6}$ alkylene-S—$C_{1-6}$ alkyl, $C_{3-7}$cycloalkyl.

In a further embodiment R1 is a group selected from $C_{1-6}$ alkyl, and $C_{1-6}$ alkoxy.

In a further embodiment R1 is a group selected from CH$_3$, and OCH$_3$.

In a further embodiment R1 is a group selected from H and $C_{1-6}$ alkylene-OH. Typically, R1 is a group selected from H, CH$_2$OH, and CH$_2$CH$_2$OH.

In a further embodiment R1 is a group selected from H, halogen and $C_{1-6}$ alkylene-NR$^a$R$^b$, wherein R$^a$ and R$^b$ are independently a group selected from H, $C_{1-6}$ alkyl, $C_{1-6}$ alkylene-OH, $C_{1-6}$ alkylene-O—$C_{1-6}$ alkyl.

In a further embodiment R1 is a group selected from H, halogen and $C_{1-6}$ alkylene-NR$^a$R$^b$, wherein R$^a$ and R$^b$ are independently a group selected from H, C(=O)—C$_{1-6}$alkyl, C(=O)—C$_{1-6}$alkyl-CN, C(=O)—C$_{1-6}$ alkyl-OH, C(=O)—C$_{1-6}$ alkylene-S—C$_{1-6}$ alkyl.

In a further embodiment R1 is a group selected from H, halogen and C$_{1-6}$ alkylene-NR$^a$R$^b$, wherein R$^a$ and R$^b$ are independently a group selected from H, C(=O)—C$_{1-6}$ alkoxy, C(=O)—O—C$_{1-6}$ alkylene-O—C$_{1-6}$ alkyl, C(=O)—O—C$_{1-6}$alkyl-CN, C(=O)—O—C$_{1-6}$alkyl-OH, C(=O)—O—C$_{1-6}$ alkylene-S—C$_{1-6}$ alkyl.

In a further embodiment R1 is a group selected from H, halogen and C$_{1-6}$ alkylene-NR$^a$R$^b$, wherein R$^a$ and R$^b$ are independently a group selected from H, C(=O)—NHC$_{1-6}$ alkyl, C(=O)—NHC$_{1-6}$ alkylene-O—C$_{1-6}$ alkyl, C(=O)—NHC$_{1-6}$ alkylene-S—C$_{1-6}$ alkyl, C(=O)—NHC$_{1-6}$ alkyl-CN, C(=O)—NHC$_{1-6}$ alkyl-OH, C(=O)—N(C$_{1-6}$ alkyl)$_2$.

In a further embodiment R1 is a group selected from H, halogen and C$_{1-6}$ alkylene-NR$^a$R$^b$, wherein R$^a$ and R$^b$ are independently a group selected from H, SO$_2$—C$_{1-6}$alkyl, SO$_2$—C$_{1-6}$ alkylene-O—C$_{1-6}$ alkyl, SO$_2$—C$_{1-6}$ alkylene-S—C$_{1-6}$ alkyl, SO$_2$—C$_{1-6}$ alkyl-CN, SO$_2$—C$_{1-6}$ alkyl-OH, and SO$_2$—C$_{1-6}$alkyl-N(C$_{1-6}$ alkyl)$_2$.

In a further embodiment R2 is selected from H.

In a further embodiment R2 is a group selected from H and halogen.

In a further embodiment R2 is a group selected from F.

In a further embodiment R2 is a group selected from H, halogen and C$_{1-6}$ alkyl.

In a further embodiment R2 is a group selected from H, halogen, CN, C$_{1-6}$ alkyl, C$_{1-6}$ alkylene-OH, C$_{1-6}$ alkoxy, C$_{1-6}$ alkylene-O—C$_{1-6}$ alkyl, C$_{1-6}$ alkylene-S—C$_{1-6}$ alkyl, C$_{3-7}$cycloalkyl.

In a further embodiment R2 is a group selected from H, halogen and C$_{1-6}$ alkylene-NR$^a$R$^b$, wherein R$^a$ and R$^b$ are independently a group selected from H, C$_{1-6}$ alkyl, C$_{1-6}$ alkylene-OH, C$_{1-6}$ alkylene-O—C$_{1-6}$ alkyl.

In a further embodiment R2 is a group selected from H, halogen and C$_{1-6}$ alkylene-NR$^a$R$^b$, wherein R$^a$ and R$^b$ are independently a group selected from H, C(=O)—C$_{1-6}$alkyl, C(=O)—C$_{1-6}$alkyl-CN, C(=O)—C$_{1-6}$ alkyl-OH, C(=O)—C$_{1-6}$ alkylene-S—C$_{1-6}$ alkyl.

In a further embodiment R2 is a group selected from H, halogen and C$_{1-6}$ alkylene-NR$^a$R$^b$, wherein R$^a$ and R$^b$ are independently a group selected from H, C(=O)—C$_{1-6}$ alkoxy, C(=O)—O—C$_{1-6}$ alkylene-O—C$_{1-6}$ alkyl, C(=O)—O—C$_{1-6}$ alkyl-C N, C(=O)—O—C$_{1-6}$ alkyl-OH, C(=O)—O—C$_{1-6}$ alkylene-S—C$_{1-6}$ alkyl.

In a further embodiment R2 is a group selected from H, halogen and C$_{1-6}$ alkylene-NR$^a$R$^b$, wherein R$^a$ and R$^b$ are independently a group selected from H, C(=O)—NHC$_{1-6}$ alkyl, C(=O)—NHC$_{1-6}$ alkylene-O—C$_{1-6}$ alkyl, C(=O)—NHC$_{1-6}$ alkylene-S—C$_{1-6}$ alkyl, C(=O)—NHC$_{1-6}$ alkyl-CN, C(=O)—NHC$_{1-6}$ alkyl-OH, C(=O)—N(C$_{1-6}$ alkyl)$_2$.

In a further embodiment R2 is a group selected from H, halogen and C$_{1-6}$ alkylene-NR$^a$R$^b$, wherein R$^a$ and R$^b$ are independently a group selected from H, SO$_2$—C$_{1-6}$alkyl, SO$_2$—C$_{1-6}$ alkylene-O—C$_{1-6}$ alkyl, SO$_2$—C$_{1-6}$ alkylene-S—C$_{1-6}$ alkyl, SO$_2$—C$_{1-6}$ alkyl-CN, SO$_2$—C$_{1-6}$ alkyl-OH, and SO$_2$—C$_{1-6}$alkyl-N(C$_{1-6}$ alkyl)$_2$.

In a further embodiment R2 is a group selected from H and C$_{1-6}$ alkyl-NR$^a$R$^b$, wherein R$^a$ and R$^b$ are independently a group selected from H, C$_{1-6}$ alkyl, C$_{1-6}$ alkyl-OH, C$_{1-6}$ alkoxy, C(=O)C$_{1-6}$ alkyl, C(=O)—C$_{1-6}$ alkoxy, C(=O)—NHC$_{1-6}$ alkyl, C(=O)—N(C$_{1-6}$ alkyl)$_2$, and SO$_2$—C$_{1-6}$ alkyl. Typically, R2 is a group selected from H and C$_{1-6}$ alkyl-NR$^a$R$^b$, wherein R$^a$ and R$^b$ are independently selected from H and C(=O)—C$_{1-6}$ alkoxy. For instance, R2 is a group selected from H and CH$_2$—NH—C(=O)—O—CH$_2$CH$_3$.

In a further embodiment R3 is selected from H.

In a further embodiment R3 is a group selected from H and halogen.

In a further embodiment R3 is a group selected from F.

In a further embodiment R3 is a group selected from H, halogen and C$_{1-6}$ alkyl.

In a further embodiment R3 is a group selected from H, halogen, CN, C$_{1-6}$ alkyl, C$_{1-6}$ alkylene-OH, C$_{1-6}$ alkoxy, C$_{1-6}$ alkylene-O—C$_{1-6}$ alkyl, C$_{1-6}$ alkylene-S—C$_{1-6}$ alkyl, C$_{3-7}$cycloalkyl.

In a further embodiment R3 is a group selected from H, halogen and C$_{1-6}$ alkylene-NR$^a$R$^b$, wherein R$^a$ and R$^b$ are independently a group selected from H, C$_{1-6}$ alkyl, C$_{1-6}$ alkylene-OH, C$_{1-6}$ alkylene-O—C$_{1-6}$ alkyl.

In a further embodiment R3 is a group selected from H, halogen and C$_{1-6}$ alkylene-NR$^a$R$^b$, wherein R$^a$ and R$^b$ are independently a group selected from H, C(=O)—C$_{1-6}$alkyl, C(=O)—C$_{1-6}$alkyl-CN, C(=O)—C$_{1-6}$ alkyl-OH, C(=O)—C$_{1-6}$ alkylene-S—C$_{1-6}$ alkyl.

In a further embodiment R3 is a group selected from H, halogen and C$_{1-6}$ alkylene-NR$^a$R$^b$, wherein R$^a$ and R$^b$ are independently a group selected from H, C(=O)—C$_{1-6}$alkoxy, C(=O)—O—C$_{1-6}$ alkylene-O—C$_{1-6}$ alkyl, C(=O)—O—C$_{1-6}$ alkyl-CN, C(=O)—O—C$_{1-6}$ alkyl-OH, C(=O)—O—C$_{1-6}$ alkylene-S—C$_{1-6}$ alkyl.

In a further embodiment R3 is a group selected from H, halogen and C$_{1-6}$ alkylene-NR$^a$R$^b$, wherein R$^a$ and R$^b$ are independently a group selected from H, C(=O)—NHC$_{1-6}$ alkyl, C(=O)—NHC$_{1-6}$ alkylene-O—C$_{1-6}$ alkyl, C(=O)—NHC$_{1-6}$ alkylene-S—C$_{1-6}$ alkyl, C(=O)—NHC$_{1-6}$ alkyl-CN, C(=O)—NHC$_{1-6}$ alkyl-OH, C(=O)—N(C$_{1-6}$ alkyl)$_2$.

In a further embodiment R3 is a group selected from H, halogen and C$_{1-6}$ alkylene-NR$^a$R$^b$, wherein R$^a$ and R$^b$ are independently a group selected from H, SO$_2$—C$_{1-6}$alkyl, SO$_2$—C$_{1-6}$ alkylene-O—C$_{1-6}$ alkyl, SO$_2$—C$_{1-6}$ alkylene-S—C$_{1-6}$ alkyl, SO$_2$—C$_{1-6}$ alkyl-CN, SO$_2$—C$_{1-6}$ alkyl-OH, and SO$_2$—C$_{1-6}$alkyl-N(C$_{1-6}$ alkyl)$_2$.

In a further embodiment R3 is a group selected from H and C$_{1-6}$ alkyl-NR$^a$R$^b$, wherein R$^a$ and R$^b$ are independently a group selected from H, C$_{1-6}$ alkyl, C$_{1-6}$ alkyl-OH, C$_{1-6}$ alkoxy, C(=O)C$_{1-6}$ alkyl, C(=O)—C$_{1-6}$ alkoxy, C(=O)—NHC$_{1-6}$ alkyl, C(=O)—N(C$_{1-6}$ alkyl)$_2$, and SO$_2$—C$_{1-6}$ alkyl. Typically, R3 is a group selected from H and C$_{1-6}$ alkyl-NR$^a$R$^b$, wherein R$^a$ and R$^b$ are independently a group selected from H and C(=O)—C$_{1-6}$ alkoxy. For instance, R3 is a group selected from H and CH$_2$—NH—C(=O)—O—CH$_2$CH$_3$.

In a further embodiment R4 is selected from H.

In a further embodiment R4 is a group selected from H and halogen.

In a further embodiment R4 is a group selected from H, halogen and C$_{1-6}$ alkyl.

In a further embodiment R4 is a group selected from H, halogen, CN, C$_{1-6}$ alkyl, C$_{1-6}$ alkylene-OH, C$_{1-6}$ alkoxy, C$_{1-6}$ alkylene-O—C$_{1-6}$ alkyl, C$_{1-6}$ alkylene-S—C$_{1-6}$ alkyl, C$_{3-7}$cycloalkyl.

In a further embodiment R4 is a group selected from H and C$_{1-6}$ alkylene-OH. Typically, R4 is a group selected from H, CH$_2$OH, and CH$_2$CH$_2$OH.

In a further embodiment R4 is a group selected selected from H, halogen and C$_{1-6}$ alkylene-NR$^a$R$^b$, wherein R$^a$ and R$^b$ are independently a group selected from H, C$_{1-6}$ alkyl, C$_{1-6}$ alkylene-OH, C$_{1-6}$ alkylene-O—C$_{1-6}$ alkyl.

In a further embodiment R4 is a group selected from H, halogen and $C_{1-6}$ alkylene-$NR^aR^b$, wherein $R^a$ and $R^b$ are independently a group selected from H, C(=O)—$C_{1-6}$alkyl, C(=O)—$C_{1-6}$alkyl-CN, C(=O)—$C_{1-6}$ alkyl-OH, C(=O)—$C_{1-6}$ alkylene-S—$C_{1-6}$ alkyl.

In a further embodiment R4 is a group selected from H, halogen and $C_{1-6}$ alkylene-$NR^aR^b$, wherein $R^a$ and $R^b$ are independently a group selected from H, C(=O)—$C_{1-6}$ alkoxy, C(=O)—O—$C_{1-6}$ alkylene-O—$C_{1-6}$ alkyl, C(=O)—O—$C_{1-6}$ alkyl-CN, C(=O)—O—$C_{1-6}$ alkyl-OH, C(=O)—O—$C_{1-6}$ alkylene-S—$C_{1-6}$ alkyl.

In a further embodiment R4 is a group selected from H, halogen and $C_{1-6}$ alkylene-$NR^aR^b$, wherein $R^a$ and $R^b$ are independently a group selected from H, C(=O)—$NHC_{1-6}$alkyl, C(=O)—$NHC_{1-6}$ alkylene-O—$C_{1-6}$ alkyl, C(=O)—$NHC_{1-6}$ alkylene-S—$C_{1-6}$ alkyl, C(=O)—$NHC_{1-6}$ alkyl-CN, C(=O)—$NHC_{1-6}$ alkyl-OH, C(=O)—N($C_{1-6}$ alkyl)$_2$.

In a further embodiment R4 is a group selected from H, halogen and $C_{1-6}$ alkylene-$NR^aR^b$, wherein $R^a$ and $R^b$ are independently a group selected from H, $SO_2$—$C_{1-6}$alkyl, $SO_2$—$C_{1-6}$ alkylene-O—$C_{1-6}$ alkyl, $SO_2$—$C_{1-6}$ alkylene-S—$C_{1-6}$ alkyl, $SO_2$—$C_{1-6}$ alkyl-CN, $SO_2$—$C_{1-6}$ alkyl-OH, and $SO_2$—$C_{1-6}$alkyl-N($C_{1-6}$ alkyl)$_2$.

It is to be understood that further embodiments concerns any combination of R1-R4 as described above, for instance in an embodiment R1-R4 are all H, or in another embodiment three of R1-R4 are H and one is selected from a group as defined above for any one of R1-R4 except H. For instance, R2-R4 are all H and R1 is $C_{1-6}$ alkylene-OH. In a further embodiment R1, R3, and R4 are all H and R2 is a group selected from $C_{1-6}$ alkyl-$NR^aR^b$, wherein $R^a$ and $R^b$ are independently a group selected from H and C(=O)—$C_{1-6}$ alkoxy.

In a further embodiment R5 is selected from H.

In a further embodiment R5 is a group selected from halogen, $CH_2F$, $CHF_2$, $CF_3$, $SCF_3$, $OCF_3$, $OCF_2H$, $OCFH_2$, and $C_{1-6}$ alkyl.

In a further embodiment R5 is a group selected from CN, $C_{1-6}$ alkyl, $C_{1-6}$ alkylene-OH, OH, $C_{1-6}$ alkoxy, and S—$C_{1-6}$ alkyl.

In a further embodiment R5 is a group selected from $C_{1-6}$ alkylene-O—$C_{1-6}$ alkyl, $C_{1-6}$ alkylene-S—$C_{1-6}$ alkyl, $C_{3-7}$cycloalkyl, C(=O)—$C_{1-6}$ alkoxy, $OC_{3-7}$cycloalkyl, and $SC_{3-7}$cycloalkyl.

In a further embodiment R6 is a group selected from H, halogen, $CH_2F$, $CHF_2$, $CF_3$, $SCF_3$, $OCF_3$, $OCF_2H$, $OCFH_2$, and $C_{1-6}$ alkyl.

In a further embodiment R6 is a group selected from H, halogen, $CF_3$, and $C_{1-6}$ alkyl.

In a further embodiment R6 is a group selected from halogen, $CF_3$, and $C_{1-6}$ alkyl.

In a further embodiment R6 is a group selected from CN, $C_{1-6}$ alkyl, $C_{1-6}$ alkylene-OH, OH, $C_{1-6}$ alkoxy, and S—$C_{1-6}$ alkyl.

In a further embodiment R6 is a group selected from $OCF_3$, $SCF_3$, $SC_{1-6}$ alkyl, $SC_{3-7}$cycloalkyl, such as $OCF_3$, $SCF_3$, $SCH_3$, S-cyclobutyl.

In a further embodiment R6 is a group selected from $C_{1-6}$ alkylene-O—$C_{1-6}$ alkyl, $C_{1-6}$ alkylene-S—$C_{1-6}$ alkyl, $C_{3-7}$cycloalkyl, C(=O)—$C_{1-6}$ alkoxy, $OC_{3-7}$cycloalkyl, and $SC_{3-7}$cycloalkyl.

Typically, R6 is selected from H, Cl, $CF_3$, $CH_3$ and $CH_2CH_3$.

In a further embodiment R7 is selected from H.

In a further embodiment R7 is a group selected from H, halogen, $CH_2F$, $CHF_2$, $CF_3$, $SCF_3$, $OCF_3$, $OCF_2H$, $OCFH_2$, and $C_{1-6}$ alkyl.

In a further embodiment R7 is a group selected from H, halogen, $CF_3$, and $C_{1-6}$ alkyl.

In a further embodiment R7 is a group selected from H, halogen, and $C_{1-6}$ alkyl.

In a further embodiment R7 is a group selected from halogen, and $C_{1-6}$ alkyl.

In a further embodiment R7 is a group selected from halogen, $CF_3$, and $C_{1-6}$ alkyl.

In a further embodiment R7 is a group selected from CN, $C_{1-6}$ alkyl, $C_{1-6}$ alkylene-OH, OH, $C_{1-6}$ alkoxy, and S—$C_{1-6}$ alkyl.

In a further embodiment R7 is a group selected from $C_{1-6}$ alkylene-O—$C_{1-6}$ alkyl, $C_{1-6}$ alkylene-S—$C_{1-6}$ alkyl, $C_{3-7}$cycloalkyl, C(=O)—$C_{1-6}$ alkoxy, $OC_{3-7}$cycloalkyl, and $SC_{3-7}$cycloalkyl.

Typically, R7 is a group selected from H, F, Cl, and $CH_3$.

In a further embodiment R8 is selected from H.

In a further embodiment R8 is a group selected from H, halogen, $CH_2F$, $CHF_2$, $CF_3$, $SCF_3$, $OCF_3$, $OCF_2H$, $OCFH_2$, and $C_{1-6}$ alkyl.

In a further embodiment R8 is a group selected from H, halogen, $CF_3$, and $C_{1-6}$ alkyl.

In a further embodiment R8 is a group selected from halogen, $CF_3$ and $C_{1-6}$ alkyl.

In a further embodiment R8 is a group selected from halogen, $CF_3$, and $C_{1-6}$ alkyl.

In a further embodiment R8 is a group selected from CN, $C_{1-6}$ alkyl, $C_{1-6}$ alkylene-OH, OH, $C_{1-6}$ alkoxy, and S—$C_{1-6}$ alkyl.

In a further embodiment R8 is a group selected from $C_{1-6}$ alkylene-O—$C_{1-6}$ alkyl, $C_{1-6}$ alkylene-S—$C_{1-6}$ alkyl, $C_{3-7}$cycloalkyl, C(=O)—$C_{1-6}$ alkoxy, $OC_{3-7}$cycloalkyl, and $SC_{3-7}$cycloalkyl.

Typically, R8 is a group selected from H, Cl, $CF_3$, $CH_3$ and $CH_2CH_3$.

In a further embodiment R9 is selected from H.

In a further embodiment R9 is a group selected from halogen, $CH_2F$, $CHF_2$, $CF_3$, $SCF_3$, $OCF_3$, $OCF_2H$, $OCFH_2$, and $C_{1-6}$ alkyl.

In a further embodiment R9 is a group selected from CN, $C_{1-6}$ alkyl, $C_{1-6}$ alkylene-OH, OH, $C_{1-6}$ alkoxy, and S—$C_{1-6}$ alkyl.

In a further embodiment R9 is a group selected from $C_{1-6}$ alkylene-O—$C_{1-6}$ alkyl, $C_{1-6}$ alkylene-S—$C_{1-6}$ alkyl, $C_{3-7}$cycloalkyl, C(=O)—$C_{1-6}$ alkoxy, $OC_{3-7}$cycloalkyl, and $SC_{3-7}$cycloalkyl.

It is to be understood that further embodiments concerns any combination of R5-R9 as described above, for instance four of R5-R9 are H and one is selected from a group as defined above for any one of R5-R9 except H. For instance, R5, R7-R9 are all H and R6 is a group selected from halogen, $CF_3$, and $C_{1-6}$ alkyl. In a further embodiment R5, R8, and R9 are all H and R6 and R7 are independently a group selected from halogen, and $C_{1-6}$ alkyl.

In a further embodiment R10 is selected from H.

In a further embodiment R10 is a group selected from H and $C_{1-6}$ alkyl.

In a further embodiment R10 is selected from $CH_3$.

In a further embodiment R10 is a group selected from H, cyclopropyl and cyclobutyl.

In a further embodiment R10 is a group selected from H and $C_{1-6}$ alkyl substituted with a fluorine atom, such as 1 to 3 fluorine atoms.

In a further embodiment R11 is a group selected from $C_{1-6}$ alkylene-OH, $C_{1-6}$ alkylene-O—$C_{1-6}$ alkyl, $C_{1-6}$ alkylene-S—$C_{1-6}$ alkyl, and $C_{1-6}$ alkylene-CN. In particular R11 is a group selected from $C_{1-4}$ alkylene-OH, $C_{1-3}$ alkylene-O—

CH$_3$, C$_{1-3}$ alkylene-S—CH$_3$, C$_{1-3}$ alkylene-CN. Typically, R11 is a group selected from CH(CH$_3$)$_2$—OH, CH$_2$CH$_2$OH, CH$_2$CH$_2$CH$_2$OH, CH$_2$CH$_2$OCH$_3$, CH$_2$CH$_2$SCH$_3$, and CH$_2$CN.

In a further embodiment R11 is a group selected from C$_{1-3}$ alkylene-O—CH$_3$, such as CH$_2$CH$_2$OCH$_3$.

In a further embodiment R11 is a group selected from C$_{1-3}$ alkylene-CN, such as CH$_2$CN.

In a further embodiment R11 is a group selected from C$_{1-6}$ alkylene-O—C$_{1-6}$ alkyl wherein C$_{1-6}$ alkylene is substituted with a phenyl, and C$_{1-6}$ alkylene-O—C$_{1-6}$ alkyl wherein C$_{1-6}$ alkyl is substituted with a halogen.

In a further embodiment R11 is a group selected from C$_{1-3}$ alkylene-O—C$_{1-3}$ alkyl wherein C$_{1-3}$ alkylene is substituted with one phenyl, and C$_{1-3}$ alkylene-O—C$_{1-3}$ alkyl wherein C$_{1-3}$ alkyl is substituted with a F.

In a further embodiment R11 is a group selected from CH$_2$CH$_2$CH$_2$OCH$_3$, CH(CH$_3$)CH$_2$OCH$_3$, CH(Ph)CH$_2$OCH$_3$, CH$_2$CH$_2$OCF$_3$, and CH$_2$CH$_2$OCH$_2$CF$_3$.

In a further embodiment R11 is a group selected from C$_{1-6}$ alkylene-C(=O)—O—C$_{1-6}$ alkyl, and C$_{1-6}$ alkylene-O—C(=O)—NH—C$_{1-6}$ alkyl. In particular R11 is a group selected from C$_{1-3}$ alkylene-C(=O)—O—C$_{1-3}$ alkyl, and C$_{1-3}$ alkylene-O—C(=O)—NH—C$_{1-3}$ alkyl. Typically, R11 is a group selected from CH$_2$COOCH$_3$, CH$_2$COOCH$_2$CH$_3$, CH(CH$_3$)COOCH$_3$, and CH$_2$CH$_2$—O—CO—NHCH$_2$CH$_3$.

In a further embodiment R11 is a group selected from C$_{1-6}$ alkylene-NH—C(=O)—C$_{1-6}$ alkylene-O—C$_{1-6}$ alkyl, C$_{1-6}$ alkylene-NH—SO$_2$—C$_{1-6}$ alkyl, C$_{1-6}$ alkylene-NH—SO$_2$—C$_{1-6}$ alkylene-phenyl. In particular R11 is a group selected from C$_{1-3}$ alkylene-NH—C(=O)—C$_{1-3}$ alkylene-O—C$_{1-2}$ alkyl, C$_{1-3}$ alkylene-NH—SO$_2$—C$_{1-3}$ alkyl, and C$_{1-3}$ alkylene-NH—SO$_2$—C$_{1-3}$ alkylene-phenyl. Typically, R11 is a group selected from CH$_2$CH$_2$—NH—CO—CH$_2$—O—CH$_3$, CH$_2$CH$_2$—NH—SO$_2$—CH$_2$CH$_3$, and CH$_2$CH$_2$—NH—SO$_2$—CH$_2$Phenyl.

In a further embodiment R11 is a group selected from C$_{1-6}$ alkylene-NR$^c$R$^d$, wherein R$^c$ and R$^d$, are independently selected from H and C$_{1-6}$ alkyl; C$_{1-6}$ alkylene-C(=O)—NR$^e$R$^f$, wherein R$^e$ and R$^f$ are independently selected from H and C$_{1-6}$ alkyl. In particular R11 is a group selected from C$_{1-4}$ alkylene-NR$^c$R$^d$, wherein R$^c$ and R$^d$, are independently selected from H and CH$_3$; C$_{1-3}$ alkylene-C(=O)—NR$^e$R$^f$, wherein R$^e$ and R$^f$ are independently selected from H and CH$_3$. Typically, R11 is a group selected from CH$_2$CH$_2$NH$_2$, CH$_2$CH$_2$CH$_2$NH$_2$, (CH$_2$)$_4$NH$_2$, (CH$_2$)$_3$N(CH$_3$)$_2$, (CH$_2$)$_4$N(CH$_3$)$_2$, CH$_2$CH$_2$NHCH$_3$, CH$_2$CH$_2$N(CH$_3$)$_2$, CH$_2$CON(CH$_3$)$_2$, and CH$_2$CONH$_2$.

In a further embodiment R11 is a group selected from a heterocyclyl; C$_{1-6}$ alkylene-R$^g$, wherein R$^g$ is a heteroaryl, optionally substituted with a group selected from C$_{1-6}$ alkyl; C$_{1-6}$ alkylene-R$^h$, wherein R$^h$ is a heterocyclyl. In particular R11 is a group selected from a heterocyclyl selected from a monocyclic 4-5 membered aliphatic heterocycle containing one heteroatom selected from O; C$_{1-3}$ alkylene-R$^g$, wherein R$^g$ is a heteroaryl selected from a monocyclic aromatic ring system containing one or two heteroatoms selected from O and N, optionally substituted with a group selected from CH$_3$; C$_{1-3}$ alkylene-R$^h$, wherein R$^h$ is a heterocyclyl selected from a monocyclic 4-6 membered aliphatic heterocycle containing one or two heteroatoms selected from O and N. Typically, R11 is a group selected from oxetanyl, tetrahydrofuranyl, CH$_2$-oxazolyl, CH$_2$-imidazolyl substituted with one CH$_3$, CH$_2$-oxetanyl, CH$_2$-tetrahydrofuranyl, and CH$_2$CH$_2$-piperazinyl.

In a further embodiment R11 is a group selected from C$_{1-3}$ alkylene-R$^g$, wherein R$^g$ is a heteroaryl selected from a monocyclic aromatic ring system containing 1-3 heteroatoms selected from O, S and N, optionally substituted with a group selected from CH$_3$.

In a further embodiment R11 is a group selected from C$_{1-3}$ alkylene-R$^g$, wherein R$^g$ is a heteroaryl selected from a bicyclic aromatic ring system containing one or two heteroatoms selected from O and N, optionally substituted with a group selected from CH$_3$.

In a further embodiment R11 is a group selected from CH$_2$-oxazolyl substituted with one CH$_3$, CH$_2$CH$_2$-oxazolyl substituted with two CH$_3$, CH$_2$-thiazolyl, CH$_2$-thiazolyl substituted with one CH$_3$, CH(CH$_3$)-pyridinyl, CH(CH$_3$)-pyridinyl substituted with one CH$_3$, CH$_2$-pyridinyl substituted with one CH$_3$, CH$_2$-pyrazolyl substituted with one CH$_3$, CH$_2$-1,2,4-triazolyl substituted with one CH$_3$, CH$_2$-1,3,4-oxadiazolyl substituted with one CH$_3$, CH$_2$CH$_2$-pyrimidinyl, CH$_2$-pyrimidinyl, and CH$_2$-benzoxazolyl.

In a further embodiment R11 is a group selected from a heterocyclyl, optionally substituted with a group selected from C$_{1-6}$ alkyl, OH, and C$_{1-6}$ alkylene-OH.

In a further embodiment R11 is a group selected from C$_{1-6}$ alkylene-R$^g$, wherein R$^g$ is a heteroaryl, optionally substituted with a group selected from C$_{1-6}$ alkyl, OH, and C$_{1-6}$ alkylene-OH.

In a further embodiment R11 is a group selected from a C$_{1-6}$ alkylene-R$^h$, wherein R$^h$ is a heterocyclyl, optionally substituted with a group selected from C$_{1-6}$ alkyl, OH, and C$_{1-6}$ alkylene-OH.

In a further embodiment R11 is a group selected from a C$_{1-6}$ alkylene-R$^j$, wherein R$^j$ is a C$_{3-7}$ cycloalkyl, optionally substituted with a group selected from C$_{1-6}$ alkyl, OH, and C$_{1-6}$ alkylene-OH.

In a further embodiment R11 is a group selected from a C$_{1-6}$ alkylene-R$^k$, wherein R$^k$ is a phenyl, optionally substituted with a group selected from C$_{1-6}$ alkyl, OH, and C$_{1-6}$ alkylene-OH.

In a further embodiment R11 is a group selected from C$_{1-6}$ alkylene-OH, C$_{1-6}$ alkylene-OC$_{1-6}$ alkyl, C$_{1-6}$ alkylene-S—C$_{1-6}$ alkyl, C$_{1-6}$ alkylene-CN, C$_{1-6}$ alkylene-C(=O)—O—C$_{1-6}$ alkyl, C$_{1-6}$ alkylene-O—C(=O)—NH—C$_{1-6}$ alkyl, C$_{1-6}$ alkylene-NH—C(=O)—C$_{1-6}$ alkylene-O—C$_{1-6}$ alkyl, C$_{1-6}$ alkylene-NH—SO$_2$—C$_{1-6}$ alkyl, C$_{1-6}$ alkylene-NH—SO$_2$—C$_{1-6}$ alkylene-phenyl; C$_{1-6}$ alkylene-NR$^c$R$^d$, wherein R$^c$ and R$^d$, are independently selected from H and C$_{1-6}$ alkyl; C$_{1-6}$ alkylene-C(=O)NR$^e$R$^f$, wherein R$^e$ and R$^f$ are independently selected from H and C$_{1-6}$ alkyl; a heterocyclyl; C$_{1-6}$ alkylene-R$^g$, wherein R$^g$ is a heteroaryl, optionally substituted with a group selected from C$_{1-6}$ alkyl; C$_{1-6}$ alkylene-R$^h$, wherein R$^h$ is a heterocyclyl. Typically, R11 is a group selected from C$_{1-4}$ alkylene-OH, C$_{1-3}$ alkylene-O—CH$_3$, C$_{1-3}$ alkylene-S—CH$_3$, C$_{1-3}$ alkylene-CN, C$_{1-3}$ alkylene-C(=O)—O—C$_{1-3}$ alkyl, C$_{1-3}$ alkylene-O—C(=O)—NH—C$_{1-3}$ alkyl, C$_{1-3}$ alkylene-NH—C(=O)—C$_{1-3}$ alkylene-O—C$_{1-2}$ alkyl, C$_{1-3}$ alkylene-NH—SO$_2$—C$_{1-3}$ alkyl, C$_{1-3}$ alkylene-NH—SO$_2$—C$_{1-3}$ alkylene-phenyl; C$_{1-4}$ alkylene-NR$^c$R$^d$, wherein R$^c$ and R$^d$, are independently selected from H and CH$_3$; C$_{1-3}$ alkylene-C(=O)—NR$^e$R$^f$, wherein R$^e$ and R$^f$ are independently selected from H and CH$_3$; a heterocyclyl selected from a monocyclic 4-5 membered aliphatic heterocycle containing one heteroatom selected from O; C$_{1-3}$ alkylene-R$^g$, wherein R$^g$ is a heteroaryl selected from a monocyclic aromatic ring system containing one or two heteroatoms selected from O and N, optionally substituted with a group selected from CH$_3$; C$_{1-3}$ alkylene-R$^h$, wherein R$^h$ is a heterocyclyl selected from a monocyclic 4-6 membered aliphatic heterocycle containing one or two heteroatoms selected from O and N. For instance, R11 is a group selected from $CH(CH_3)_2$—OH, $CH_2CH_2OH$, $CH_2CH_2CH_2OH$, $CH_2CH_2OCH_3$, $CH_2CH_2SCH_3$, $CH_2CN$, $CH_2COOCH_3$, $CH_2COOCH_2CH_3$, $CH(CH_3)COOCH_3$, $CH_2CH_2$—O—CO—NH—$CH_2CH_3$, $CH_2CH_2$—NH—CO—O—$CH_3$, $CH_2CH_2$—NH—$SO_2$—$CH_2CH_3$, $CH_2CH_2$—NH—$SO_2$—$CH_2$Phenyl, $CH_2CH_2NH_2$, $CH_2CH_2CH_2NH_2$, $(CH_2)_4NH_2$, $(CH_2)_3N(CH_3)_2$, $(CH_2)_4N(CH_3)_2$, $CH_2CH_2NHCH_3$, $CH_2CH_2N(CH_3)_2$, $CH_2CON(CH_3)_2$, $CH_2CONH_2$, oxetanyl, tetrahydrofuranyl, $CH_2$-oxazolyl, $CH_2$-imidazolyl substituted with one $CH_3$, $CH_2$-oxetanyl, $CH_2$-tetrahydrofuranyl, $CH_2CH_2$-piperazinyl.

In a further embodiment R12 is a group selected from H, $C_{1-4}$ alkyl, and $C_{1-4}$ alkylene-OH.

In a further embodiment R12 is a group selected from $C_{1-4}$ alkylene-O—$C_{1-4}$ alkyl, $C_{1-4}$ alkylene-S—$C_{1-4}$ alkyl, $C_{1-4}$ alkylene-CN, and $C_{1-4}$ alkylene-$CF_3$.

In a further embodiment R12 is a group selected from H and $C_{1-6}$ alkyl. In particular R12 is a group selected from H and $C_{1-4}$ alkyl. In an embodiment R12 is selected from H. In another embodiment R12 is selected from $C_{1-4}$ alkyl, such as $C_{1-3}$ alkyl. Typically, R12 is a group selected from H, $CH_3$ and $CH_2CH_3$.

In another embodiment R11 and R12 together with the nitrogen to which R11 and R12 are linked form a monocyclic or bicyclic 3-7 membered aliphatic heterocycle containing the nitrogen to which R11 and R12 are linked and optionally one or more heteroatoms selected from O, S, and N, wherein the monocyclic or bicyclic heterocycle is optionally substituted with a group selected from $C_{1-6}$ alkyl; oxo; OH; $C_{1-6}$ alkylene-OH; C(=O)—$C_{1-6}$ alkyl; C(=O)—O—$C_{1-6}$ alkyl; $SO_2$—$C_{1-6}$ alkyl; $NR^kR^l$, wherein $R^k$ and $R^l$ are independently a group selected from H and $C_{1-6}$ alkyl; and $C_{1-6}$ alkylene-$NR'''R''$, wherein $R'''$ and $R''$ are independently a group selected from H and $C_{1-6}$ alkyl.

In a further embodiment R11 and R12 together with the nitrogen to which R11 and R12 are linked form a monocyclic 4-6 membered aliphatic heterocycle containing the nitrogen to which R11 and R12 are linked and optionally one or more heteroatoms selected from O, S, and N, wherein the monocyclic heterocycle is optionally substituted with a group selected from $C_{1-6}$ alkyl; oxo; OH; $C_{1-6}$ alkylene-OH; C(=O)—$C_{1-6}$ alkyl; C(=O)—O—$C_{1-6}$ alkyl; $SO_2$—$C_{1-6}$ alkyl; $NR^kR^l$, wherein $R^k$ and $R^l$ are independently a group selected from H and $C_{1-6}$ alkyl; and $C_{1-6}$ alkylene-$NR_mR''$, wherein $R'''$ and $R''$ are independently a group selected from H and $C_{1-6}$ alkyl.

In a further embodiment R11 and R12 together with the nitrogen to which R11 and R12 are linked form a monocyclic 4-6 membered aliphatic heterocycle containing the nitrogen to which R11 and R12 are linked and optionally one heteroatom selected from O and N, wherein the monocyclic heterocycle is optionally substituted with a group selected from $C_{1-6}$ alkyl; oxo; OH; $C_{1-6}$ alkylene-OH; C(=O)—$C_{1-6}$ alkyl; C(=O)—O—$C_{1-6}$ alkyl; $SO_2$—$C_{1-6}$ alkyl; $NR^kR^l$, wherein $R^k$ and $R^l$ are independently a group selected from H and $C_{1-6}$ alkyl; and $C_{1-6}$ alkylene-$NR'''R''$, wherein $R'''$ and $R''$ are independently a group selected from H and $C_{1-6}$ alkyl.

In a further embodiment R11 and R12 together with the nitrogen to which R11 and R12 are linked form a monocyclic 4-6 membered aliphatic heterocycle containing the nitrogen to which R11 and R12 are linked and optionally one heteroatom selected from O and N, wherein the monocyclic heterocycle is optionally substituted with a group selected from $C_{1-6}$ alkyl, OH, and C(=O)—O—$C_{1-6}$ alkyl.

In a further embodiment R11 and R12 together with the nitrogen to which R11 and R12 are linked form a monocyclic 4-6 membered aliphatic heterocycle containing the nitrogen to which R11 and R12 are linked form a monocyclic 4-6 membered aliphatic heterocycle containing the nitrogen to which R11 and R12 are linked, wherein the monocyclic heterocycle is optionally substituted with a group selected from $C_{1-6}$ alkyl, OH, and C(=O)—O—$C_{1-6}$ alkyl. In particular R11 and R12 together with the nitrogen to which R11 and R12 are linked form a monocyclic 4-6 membered aliphatic heterocycle containing the nitrogen to which R11 and R12 are linked selected from azetidinyl, pyrrolidinyl and piperidinyl. Such azetidinyl, pyrrolidinyl or piperidinyl is optionally substituted with one OH.

In a further embodiment R11 and R12 together with the nitrogen to which R11 and R12 are linked form a bicyclic 7 membered aliphatic heterocycle containing the nitrogen to which R11 and R12 are linked and optionally one heteroatoms selected from O, wherein the bicyclic heterocycle is optionally substituted with a group selected from $C_{1-6}$ alkyl; oxo; OH; $C_{1-6}$ alkylene-OH; C(=O)—$C_{1-6}$ alkyl; C(=O)—O—$C_{1-6}$ alkyl; $SO_2$—$C_{1-6}$ alkyl; $NR^kR^l$, wherein $R^k$ and $R^l$ are independently a group selected from H and $C_{1-6}$ alkyl; and $C_{1-6}$ alkylene-$NR'''R''$, wherein $R'''$ and $R''$ are independently a group selected from H and $C_{1-6}$ alkyl. In one embodiment R11 and R12 together with the nitrogen to which R11 and R12 are linked form a bicyclic 7 membered aliphatic heterocycle containing the nitrogen to which R11 and R12 are linked and optionally one heteroatom selected from O. In another embodiment R11 and R12 together with the nitrogen to which R11 and R12 are linked form a bicyclic 7 membered aliphatic heterocycle containing the nitrogen to which R11 and R12 are linked and one heteroatom selected from O.

In another embodiment R11 and R12 together with the nitrogen to which R11 and R12 are linked forms a mono or bicyclic 3-7 membered aliphatic heterocycle containing the nitrogen to which R11 and R12 are linked selected from aziridinyl, oxaziridinyl, azetidinyl, diazetidinyl, pyrrolidinyl, imidazolidinyl, pyrazolidinyl, oxazolidinyl, isoxazolidinyl, thiazolidinyl, isothiazolidinyl, morpholinyl, piperidinyl, piperazinyl, and 2-oxa-6-azaspiro[3.3]-heptanyl, optionally substituted with a group selected from $C_{1-6}$ alkyl, oxo, OH, $C_{1-6}$ alkylene-OH, C(=O)—$C_{1-6}$ alkyl, C(=O)—O—$C_{1-6}$ alkyl, $SO_2$—$C_{1-6}$ alkyl, $NR^kR^l$, wherein $R^k$ and $R^l$ are independently selected from H and $C_{1-6}$ alkyl; $C_{1-6}$ alkylene-$NR'''R''$, wherein $R'''$ and $R''$ are independently selected from H and $C_{1-6}$ alkyl.

Typically, R11 and R12 together with the nitrogen to which R11 and R12 are linked forms a mono or bicyclic 3-7 membered aliphatic heterocycle containing the nitrogen to which R11 and R12 are linked selected from aziridinyl, pyrrolidinyl, morpholinyl, piperidinyl, piperazinyl, and 2-oxa-6-azaspiro[3.3]-heptanyl optionally substituted with a group selected from $C_{1-6}$ alkyl, oxo, OH, $C_{1-6}$ alkylene —OH, C(=O)—$C_{1-6}$ alkyl, C(=O)—O—$C_{1-6}$ alkyl, $SO_2$—$C_{1-6}$ alkyl, $NR^kR^l$, wherein $R^k$ and $R^l$ are independently selected from H and $C_{1-6}$ alkyl; $C_{1-6}$ alkylene-$NR'''R''$, wherein $R'''$ and $R''$ are independently selected from H and $C_{1-6}$ alkyl. In particular, R11 and R12 together with the nitrogen to which R11 and R12 are linked forms a mono or bicyclic 3-7 membered aliphatic heterocycle containing the nitrogen to which R11 and R12 are linked selected from aziridinyl optionally substituted with a group selected from OH, $C_{1-3}$ alkylene-OH and $NR^kR^l$, wherein $R^k$ and $R^l$ are independently selected from H and $C_{1-3}$ alkyl; pyrrolidinyl optionally substituted with a group selected from OH; morpholinyl; piperidinyl optionally substituted with a group selected from OH; piperazinyl optionally substituted with a group selected from $C_{1-6}$ alkyl, oxo, C(=O)$C_{1-3}$ alkyl, C(=O)—O—$C_{1-3}$ alkyl, $SO_2$—$C_{1-4}$ alkyl, $C_{1-4}$ alkylene-NR'''R'', wherein R''' and R'' are independently selected from H and $C_{1-3}$ alkyl; and 2-oxa-6-azaspiro[3.3]-heptanyl. For instance, R11 and R12 together with the nitrogen to which R11 and R12 are linked forms a mono or bicyclic 3-7 membered aliphatic heterocycle containing the nitrogen to which R11 and R12 are linked selected from aziridinyl optionally substituted with a group selected from OH, $CH_2$—OH and N($CH_3$)$_2$; pyrrolidinyl optionally substituted with a group selected from OH; morpholinyl; piperidinyl optionally substituted with a group selected from OH; piperazinyl optionally substituted with a group, such as one or two, selected from $CH_3$, oxo, C(=O)—$CH_3$, C(=O)—O—$CH_3$, $SO_2$—CH($CH_3$)$_2$, $CH_2CH_2$—N($CH_3$)$_2$; and 2-oxa-6-azaspiro[3.3]-heptanyl.

In another embodiment R11 and R12 together with the nitrogen to which R11 and R12 are linked forms a mono or bicyclic 3-7 membered aliphatic heterocycle containing the nitrogen to which R11 and R12 are linked selected from piperidinyl substituted with a group selected from OH; azetidinyl; and azetidinyl substituted with a group selected from OH.

In a further embodiment a compound of the present invention is selected from:

3-[(1H-1,3-benzodiazol-2-yl)amino]-N-[2-(methylsulfanyl)ethyl]-3-[3-(trifluoromethyl)phenyl]propanamide, 3-[(1H-1,3-benzodiazol-2-yl)amino]-N-[2-(dimethylamino)ethyl]-N-methyl-3-[3-(trifluoromethyl)phenyl]propanamide, 3-[(1H-1,3-benzodiazol-2-yl)amino]-N-(2-ethanesulfonamidoethyl)-3-[3-(trifluoromethyl)phenyl]propanamide, 3-[(1H-1,3-benzodiazol-2-yl)amino]-N-(2-hydroxy-2-methylpropyl)-3-[3-(trifluoromethyl)phenyl]propanamide, (−) 3-[(1H-1,3-benzodiazol-2-yl)amino]-N-(2-hydroxy-2-methylpropyl)-3-[3-(trifluoromethyl)phenyl]propanamide, (+) 3-[(1H-1,3-benzodiazol-2-yl)amino]-N-(2-hydroxy-2-methylpropyl)-3-[3-(trifluoromethyl)phenyl]propanamide, 3-[(1H-1,3-benzodiazol-2-yl)amino]-1-(4-hydroxypiperidin-1-yl)-3-[3-(trifluoromethyl)phenyl]propan-1-one, 3-[(1H-1,3-benzodiazol-2-yl)amino]-1-(3-hydroxyazetidin-1-yl)-3-[3-(trifluoromethyl)phenyl]propan-1-one, 3-[(1H-1,3-benzodiazol-2-yl)amino]-N-(oxetan-3-ylmethyl)-3-[3-(trifluoromethyl)phenyl]propanamide, 3-[(1H-1,3-benzodiazol-2-yl)amino]-N-(oxolan-2-ylmethyl)-3-[3-(trifluoromethyl)phenyl]propanamide, 3-[(1H-1,3-benzodiazol-2-yl)amino]-N-[(3S)-oxolan-3-yl]-3-[3-(trifluoromethyl)phenyl]propanamide, 3-[(1H-1,3-benzodiazol-2-yl)amino]-N-(oxetan-3-yl)-3-[3-(trifluoromethyl)phenyl]propanamide, 4-{3-[(1H-1,3-benzodiazol-2-yl)amino]-3-[3-(trifluoromethyl)phenyl]propanoyl}-1-methylpiperazin-2-one, 3-[(1H-1,3-benzodiazol-2-yl)amino]-N-[2-(phenylmethanesulfonamido)ethyl]-3-[3-(trifluoromethyl)phenyl]propanamide, 3-[(1H-1,3-benzodiazol-2-yl)amino]-1-[(3R)-3-hydroxypiperidin-1-yl]-3-[3-(trifluoromethyl)phenyl]propan-1-one, 3-[(1H-1,3-benzodiazol-2-yl)amino]-1-[(3R)-3-hydroxypyrrolidin-1-yl]-3-[3-(trifluoromethyl)phenyl]propan-1-one, 3-[(1H-1,3-benzodiazol-2-yl)amino]-1-[(3S)-3-hydroxypyrrolidin-1-yl]-3-[3-(trifluoromethyl)phenyl]propan-1-one, 3-[(1H-1,3-benzodiazol-2-yl)amino]-N-(3-hydroxypropyl)-3-[3-(trifluoromethyl)phenyl]propanamide, 3-[(1H-1,3-benzodiazol-2-yl)amino]-N-(3-hydroxypropyl)-N-methyl-3-[3-(trifluoromethyl)phenyl]propanamide, (−) 3-[(1H-1,3-benzodiazol-2-yl)amino]-N-(3-hydroxypropyl)-N-methyl-3-[3-(trifluoromethyl)phenyl]propanamide, (+) 3-[(1H-1,3-benzodiazol-2-yl)amino]-N-(3-hydroxypropyl)-N-methyl-3-[3-(trifluoromethyl)phenyl]propanamide, 3-[(1H-1,3-benzodiazol-2-yl)amino]-N-[(1,3-oxazol-2-yl)methyl]-3-[3-(trifluoromethyl)phenyl]propanamide, 3-[(1H-1,3-benzodiazol-2-yl)amino]-N-[(1-methyl-1H-imidazol-2-yl)methyl]-3-[3-(trifluoromethyl)phenyl]propanamide, 3-[(1H-1,3-benzodiazol-2-yl)amino]-3-(3-chloro-4-methylphenyl)-N-ethyl-N-(2-hydroxyethyl)propanamide, 3-[(1H-1,3-benzodiazol-2-yl)amino]-N-(cyanomethyl)-3-[3-(trifluoromethyl)phenyl]propanamide, 3-[(1H-1,3-benzodiazol-2-yl)amino]-N-[(dimethylcarbamoyl)methyl]-3-[3-(trifluoromethyl)phenyl]propanamide, Ethyl 2-{3-[(1H-1,3-benzodiazol-2-yl)amino]-3-[3-(trifluoromethyl)phenyl]propanamido}acetate, N-(2-aminoethyl)-2-[(1H-1,3-benzodiazol-2-yl)amino]-2-[3-(trifluoromethyl)phenyl]acetamide, 2-[(1H-1,3-benzodiazol-2-yl)amino]-N-[2-(dimethylamino)ethyl]-N-methyl-2-[3-(trifluoromethyl)phenyl]acetamide, 2-[(1H-1,3-benzodiazol-2-yl)amino]-1-(piperazin-1-yl)-2-[3-(trifluoromethyl)phenyl]ethan-1-one, 2-[(1H-1,3-benzodiazol-2-yl)amino]-1-(4-methylpiperazin-1-yl)-2-[3-(trifluoromethyl)phenyl]ethan-1-one, (−)2-[(1H-1,3-benzodiazol-2-yl)amino]-1-(4-methylpiperazin-1-yl)-2-[3-(trifluoromethyl)phenyl]ethan-1-one, (+)2-[(1H-1,3-benzodiazol-2-yl)amino]-1-(4-methylpiperazin-1-yl)-2-[3-(trifluoromethyl)phenyl]ethan-1-one, 2-[(1H-1,3-benzodiazol-2-yl)amino]-1-[3-(dimethylamino)azetidin-1-yl]-2-[3-(trifluoromethyl)phenyl]ethan-1-one, 2-[(1H-1,3-benzodiazol-2-yl)amino]-1-(pyrrolidin-1-yl)-2-[3-(trifluoromethyl)phenyl]ethan-1-one, 2-[(1H-1,3-benzodiazol-2-yl)amino]-N-(2-hydroxyethyl)-N-methyl-2-[3-(trifluoromethyl)phenyl]acetamide, 2-[(1H-1,3-benzodiazol-2-yl)amino]-1-(piperidin-1-yl)-2-[3-(trifluoromethyl)phenyl]ethan-1-one, 2-[(1H-1,3-benzodiazol-2-yl)amino]-1-(morpholin-4-yl)-2-[3-(trifluoromethyl)phenyl]ethan-1-one, 2-[(1H-1,3-benzodiazol-2-yl)amino]-1-[4-(propane-2-sulfonyl)piperazin-1-yl]-2-[3-(trifluoromethyl)phenyl]ethan-1-one, 1-(azetidin-1-yl)-2-[(1H-1,3-benzodiazol-2-yl)amino]-2-[3-(trifluoromethyl)phenyl]ethan-1-one, (+)1-(azetidin-1-yl)-2-[(1H-1,3-benzodiazol-2-yl)amino]-2-[3-(trifluoromethyl)phenyl]ethan-1-one, 1-(azetidin-1-yl)-2-[(1H-1,3-benzodiazol-2-yl)amino]-2-[3-(trifluoromethyl)phenyl]ethan-1-one, 2-[(1H-1,3-benzodiazol-2-yl)amino]-N-(oxetan-3-yl)-2-[3-(trifluoromethyl)phenyl]acetamide, 2-[(1H-1,3-benzodiazol-2-yl)amino]-1-{2-oxa-6-azaspiro[3.3]heptan-6-yl}-2-[3-(trifluoromethyl)phenyl]ethan-1-one, 4-{2-[(1H-1,3-benzodiazol-2-yl)amino]-2-[3-(trifluoromethyl)phenyl]acetyl}-1,1-dimethylpiperazin-1-ium, 2-[(1H-1,3-benzodiazol-2-yl)amino]-N-ethyl-N-(2-hydroxyethyl)-2-[3-(trifluoromethyl)phenyl]acetamide, (−)2-[(1H-1,3-benzodiazol-2-yl)amino]-N-ethyl-N-(2-hydroxyethyl)-2-[3-(trifluoromethyl)phenyl]acetamide, (+)2-[(1H-1,3-benzodiazol-2-yl)amino]-N-ethyl-N-(2-hydroxyethyl)-2-[3-(trifluoromethyl)phenyl]acetamide,
3-[(1H-1,3-benzodiazol-2-yl)amino]-N-ethyl-3-(4-fluoro-3-methylphenyl)-N-(2-hydroxyethyl)propanamide,
(−)3-[(1H-1,3-benzodiazol-2-yl)amino]-N-ethyl-3-(4-fluoro-3-methylphenyl)-N-(2-hydroxyethyl)propanamide,
(+)3-[(1H-1,3-benzodiazol-2-yl)amino]-N-ethyl-3-(4-fluoro-3-methylphenyl)-N-(2-hydroxyethyl)propanamide,
3-[(1H-1,3-benzodiazol-2-yl)amino]-3-(4-chloro-3-methylphenyl)-N-ethyl-N-(2-hydroxyethyl)propanamide,
(−)3-[(1H-1,3-benzodiazol-2-yl)amino]-3-(4-chloro-3-methylphenyl)-N-ethyl-N-(2-hydroxyethyl)propanamide,
(+)3-[(1H-1,3-benzodiazol-2-yl)amino]-3-(4-chloro-3-methylphenyl)-N-ethyl-N-(2-hydroxyethyl)propanamide,
3-[(1H-1,3-benzodiazol-2-yl)amino]-N-ethyl-N-(2-hydroxyethyl)-3-[3-(trifluoromethyl)phenyl]propanamide,
(−)3-[(1H-1,3-benzodiazol-2-yl)amino]-N-ethyl-N-(2-hydroxyethyl)-3-[3-(trifluoromethyl)phenyl]propanamide,
3-[(1H-1,3-benzodiazol-2-yl)amino]-N-ethyl-N-(2-hydroxyethyl)-3-[3-(trifluoromethyl)phenyl]propanamide,
3-[(1H-1,3-benzodiazol-2-yl)amino]-N-(2-methoxyethyl)-3-[3-(trifluoromethyl)phenyl]propanamide,
(−)3-[(1H-1,3-benzodiazol-2-yl)amino]-N-(2-methoxyethyl)-3-[3-(trifluoromethyl)phenyl]propanamide,
(+)3-[(1H-1,3-benzodiazol-2-yl)amino]-N-(2-methoxyethyl)-3-[3-(trifluoromethyl)phenyl]propanamide,
3-[(1H-1,3-benzodiazol-2-yl)amino]-N-(2-methoxyethyl)-N-methyl-3-[3-(trifluoromethyl)phenyl]propanamide,
3-[(1H-1,3-benzodiazol-2-yl)amino]-N-methyl-N-[2-(methylamino)ethyl]-3-[3-(trifluoromethyl)phenyl]propanamide,
3-[(1H-1,3-benzodiazol-2-yl)amino]-N-[2-(dimethylamino)ethyl]-N-ethyl-3-[3-(trifluoromethyl)phenyl]propanamide,
Methyl (2R)-2-{3-[(1H-1,3-benzodiazol-2-yl)amino]-3-[3-(trifluoromethyl)phenyl]propanamido}propanoate,
Methyl 2-{3-[(1H-1,3-benzodiazol-2-yl)amino]-N-ethyl-3-[3-(trifluoromethyl)phenyl]propanamido}acetate,
Ethyl 2-{3-[(1H-1,3-benzodiazol-2-yl)amino]-N-ethyl-3-[3-(trifluoromethyl)phenyl]propanamido}acetate,
N-ethyl-N-(2-hydroxyethyl)-3-{[4-(hydroxymethyl)-1H-1,3-benzodiazol-2-yl]amino}-3-[3-(trifluoromethyl)phenyl]propanamide,
N-(cyanomethyl)-3-{[4-(hydroxymethyl)-1H-1,3-benzodiazol-2-yl]amino}-N-methyl-3-[3-(trifluoromethyl)phenyl]propanamide,
N-(cyanomethyl)-3-{[4-(2-hydroxyethyl)-1H-1,3-benzodiazol-2-yl]amino}-N-methyl-3-[3-(trifluoromethyl)phenyl]propanamide,
N-(cyanomethyl)-N-ethyl-3-{[4-(2-hydroxyethyl)-1H-1,3-benzodiazol-2-yl]amino}-3-[3-(trifluoromethyl)phenyl]propanamide,
N-(cyanomethyl)-N-ethyl-3-{[4-(hydroxymethyl)-1H-1,3-benzodiazol-2-yl]amino}-3-[3-(trifluoromethyl)phenyl]propanamide,
N-(carbamoylmethyl)-N-ethyl-3-{[4-(hydroxymethyl)-1H-1,3-benzodiazol-2-yl]amino}-3-[3-(trifluoromethyl)phenyl]propanamide,
3-[(1H-1,3-benzodiazol-2-yl)amino]-N-(cyanomethyl)-N-ethyl-3-[3-(trifluoromethyl)phenyl]propanamide,
3-[(1H-1,3-benzodiazol-2-yl)amino]-N-(cyanomethyl)-N-methyl-3-[3-(trifluoromethyl)phenyl]propanamide,
(−)3-[(1H-1,3-benzodiazol-2-yl)amino]-N-(cyanomethyl)-N-methyl-3-[3-(trifluoromethyl)phenyl]propanamide,
(+)3-[(1H-1,3-benzodiazol-2-yl)amino]-N-(cyanomethyl)-N-methyl-3-[3-(trifluoromethyl)phenyl]propanamide,
Methyl 2-{3-[(1H-1,3-benzodiazol-2-yl)amino]-N-methyl-3-[3-(trifluoromethyl)phenyl]propanamido}acetate,
(−)Methyl 2-{3-[(1H-1,3-benzodiazol-2-yl)amino]-N-methyl-3-[3-(trifluoromethyl)phenyl]propanamido}acetate,
(+)Methyl 2-{3-[(1H-1,3-benzodiazol-2-yl)amino]-N-methyl-3-[3-(trifluoromethyl)phenyl]propanamido}acetate,
N-ethyl-3-{[4-(hydroxymethyl)-1H-1,3-benzodiazol-2-yl]amino}-N-[2-(methylsulfanyl)ethyl]-3-[3-(trifluoromethyl)phenyl]propanamide,
Methyl 2-{3-[(1H-1,3-benzodiazol-2-yl)amino]-3-[3-(trifluoromethyl)phenyl]propanamido}acetate,
(−)Methyl 2-{3-[(1H-1,3-benzodiazol-2-yl)amino]-3-[3-(trifluoromethyl)phenyl]propanamido}acetate,
(+)Methyl 2-{3-[(1H-1,3-benzodiazol-2-yl)amino]-3-[3-(trifluoromethyl)phenyl]propanamido}acetate,
3-[(1H-1,3-benzodiazol-2-yl)amino]-N-(carbamoylmethyl)-N-methyl-3-[3-(trifluoromethyl)phenyl]propanamide,
Methyl 4-{2-[(1H-1,3-benzodiazol-2-yl)amino]-2-[3-(trifluoromethyl)phenyl]acetyl}piperazine-1-carboxylate,
3-[(1H-1,3-benzodiazol-2-yl)amino]-N-[2-(2-methoxyacetamido)ethyl]-3-[3-(trifluoromethyl)phenyl]propanamide,
2-{3-[(1H-1,3-benzodiazol-2-yl)amino]-3-[3-(trifluoromethyl)phenyl]propanamido}ethyl N-ethylcarbamate,
2-[(1H-1,3-benzodiazol-2-yl)amino]-N-ethyl-N-(2-hydroxyethyl)-3-[3-(trifluoromethyl)phenyl]propanamide,
3-[(1H-1,3-benzodiazol-2-yl)amino]-N-ethyl-3-(3-ethyl-4-fluorophenyl)-N-(2-hydroxyethyl)propanamide,
(−)-3-[(1H-1,3-benzodiazol-2-yl)amino]-N-ethyl-3-(3-ethyl-4-fluorophenyl)-N-(2-hydroxyethyl)propanamide,
(+)-3-[(1H-1,3-benzodiazol-2-yl)amino]-N-ethyl-3-(3-ethyl-4-fluorophenyl)-N-(2-hydroxyethyl)propanamide, and
ethyl N-{[2-({2-[ethyl(2-hydroxyethyl)carbamoyl]-1-[3-(trifluoromethyl)phenyl]ethyl}amino)-1H-1,3-benzodiazol-5-yl]methyl}carbamate;
or
a pharmaceutically acceptable salt thereof.

In a further embodiment a compound of the present invention is selected from:
3-[(1H-1,3-benzodiazol-2-yl)amino]-N-[2-(trifluoromethoxy)ethyl]-3-[3-(trifluoromethyl)phenyl]propanamide,
(+)-3-[(1H-1,3-benzodiazol-2-yl)amino]-N-[2-(trifluoromethoxy)ethyl]-3-[3-(trifluoromethyl)phenyl]propanamide,
(−)-3-[(1H-1,3-benzodiazol-2-yl)amino]-N-[2-(trifluoromethoxy)ethyl]-3-[3-(trifluoromethyl)phenyl]propanamide,
3-[(1H-1,3-benzodiazol-2-yl)amino]-N-[2-(2,2,2-trifluoroethoxy)ethyl]-3-[3-(trifluoromethyl)phenyl]propanamide,
(+)-3-[(1H-1,3-benzodiazol-2-yl)amino]-N-[2-(2,2,2-trifluoroethoxy)ethyl]-3-[3-(trifluoromethyl)phenyl]propanamide,
(−)-3-[(1H-1,3-benzodiazol-2-yl)amino]-N-[2-(2,2,2-trifluoroethoxy)ethyl]-3-[3-(trifluoromethyl)phenyl]propanamide,
3-[(1H-1,3-benzodiazol-2-yl)amino]-N-[(1R)-2-methoxy-1-phenylethyl]-3-[3-(trifluoromethyl)phenyl]propanamide,
(+)-3-[(1H-1,3-benzodiazol-2-yl)amino]-N-[(1R)-2-methoxy-1-phenylethyl]-3-[3-(trifluoromethyl)phenyl]propanamide,
(−)-3-[(1H-1,3-benzodiazol-2-yl)amino]-N-[(1R)-2-methoxy-1-phenylethyl]-3-[3-(trifluoromethyl)phenyl]propanamide, 3-[(1H-1,3-benzodiazol-2-yl)amino]-N-[(1R)-2-methoxy-1-phenylethyl]-3-{3-[(trifluoromethyl)sulfanyl]phenyl}propanamide, (+)-3-[(1H-1,3-benzodiazol-2-yl)amino]-N-[(1R)-2-methoxy-1-phenylethyl]-3-{3-[(trifluoromethyl)sulfanyl]phenyl}propanamide, (−)-3-[(1H-1,3-benzodiazol-2-yl)amino]-N-[(1R)-2-methoxy-1-phenylethyl]-3-{3-[(trifluoromethyl)sulfanyl]phenyl}propanamide, 3-[(1H-1,3-benzodiazol-2-yl)amino]-N-(1,2-oxazol-3-ylmethyl)-3-[3-(trifluoromethyl)phenyl]propanamide, 3-[(1H-1,3-benzodiazol-2-yl)amino]-N-(1,3-benzoxazol-2-ylmethyl)-3-[3-(trifluoromethyl)phenyl]propanamide, 3-[(1H-1,3-benzodiazol-2-yl)amino]-N-(1-methoxypropan-2-yl)-3-[3-(trifluoromethyl)phenyl]propanamide, 3-[(1H-1,3-benzodiazol-2-yl)amino]-N-[2-(dimethyl-1,2-oxazol-4-yl)ethyl]-3-[3-(trifluoromethyl)phenyl]propanamide, 3-[(1H-1,3-benzodiazol-2-yl)amino]-N-(1,3-thiazol-2-ylmethyl)-3-[3-(trifluoromethyl)phenyl]propanamide, 3-[(1H-1,3-benzodiazol-2-yl)amino]-N-[1-(6-methylpyridin-2-yl)ethyl]-3-[3-(trifluoromethyl)phenyl]propanamide, 3-[(1H-1,3-benzodiazol-2-yl)amino]-N-[(2-methyl-1,3-thiazol-5-yl)methyl]-3-[3-(trifluoromethyl)phenyl]propanamide, 3-[(1H-1,3-benzodiazol-2-yl)amino]-N-(pyrimidin-5-ylmethyl)-3-[3-(trifluoromethyl)phenyl]propanamide, 3-[(1H-1,3-benzodiazol-2-yl)amino]-N-[(2-methylpyridin-4-yl)methyl]-3-[3-(trifluoromethyl)phenyl]propanamide, 3-[(1H-1,3-benzodiazol-2-yl)amino]-3-(4-fluoro-3,5-dimethylphenyl)-N-(2-methoxyethyl)propanamide, 3-[(1H-1,3-benzodiazol-2-yl)amino]-N-[2-(trifluoromethoxy)ethyl]-3-{3-[(trifluoromethyl)sulfanyl]phenyl}propanamide, 3-[(1H-1,3-benzodiazol-2-yl)amino]-N-(2-methoxyethyl)-3-{3-[(trifluoromethyl)sulfanyl]phenyl}propanamide, 3-[(1H-1,3-benzodiazol-2-yl)amino]-N-[2-(trifluoromethoxy)ethyl]-3-[3-(trifluoromethoxy)phenyl]propanamide, 3-[(1H-1,3-benzodiazol-2-yl)amino]-N-(2-methoxyethyl)-3-[3-(trifluoromethoxy)phenyl]propanamide, 3-[(1H-1,3-benzodiazol-2-yl)amino]-N-(cyanomethyl)-3-[3-(trifluoromethoxy)phenyl]propanamide, 3-[(1H-1,3-benzodiazol-2-yl)amino]-N-(cyanomethyl)-3-(4-fluoro-3,5-dimethylphenyl)propanamide, 3-[(1H-1,3-benzodiazol-2-yl)amino]-3-[3-(cyclobutylsulfanyl)phenyl]-N-(2-methoxyethyl)propanamide, 3-[(1H-1,3-benzodiazol-2-yl)amino]-N-(1,2-oxazol-3-ylmethyl)-3-[3-(trifluoromethoxy)phenyl]propanamide, 3-[(1H-1,3-benzodiazol-2-yl)amino]-N-(1,3-benzoxazol-2-ylmethyl)-3-{3-[(trifluoromethyl)sulfanyl]phenyl}propanamide, 3-[(1H-1,3-benzodiazol-2-yl)amino]-N-(1,3-benzoxazol-2-ylmethyl)-3-[3-(trifluoromethoxy)phenyl]propanamide, 3-[(5-fluoro-1H-1,3-benzodiazol-2-yl)amino]-N-(2-methoxyethyl)-3-[3-(trifluoromethyl)phenyl]butanamide, 3-[(1H-1,3-benzodiazol-2-yl)amino]-N-(2-methoxyethyl)-3-[3-(methylsulfanyl)phenyl]propanamide, 3-[(4-methoxy-1H-1,3-benzodiazol-2-yl)amino]-N-(2-methoxyethyl)-3-[3-(trifluoromethyl)phenyl]propanamide, 3-{[4-(hydroxymethyl)-1H-1,3-benzodiazol-2-yl]amino}-N-[2-(trifluoromethoxy)ethyl]-3-[3-(trifluoromethyl)phenyl]propanamide, 3-[(5,6-difluoro-1H-1,3-benzodiazol-2-yl)amino]-N-(2-methoxyethyl)-3-[3-(trifluoromethyl)phenyl]propanamide, and 3-[(5-fluoro-4-methyl-1H-1,3-benzodiazol-2-yl)amino]-N-(2-methoxyethyl)-3-[3-(trifluoromethyl)phenyl]propanamide;

or a pharmaceutically acceptable salt thereof.

In a further aspect the present invention relates to a compound of the present invention, for instance according to any one of the above embodiments, for use as a medicine.

In a further aspect the present invention relates to a pharmaceutical composition comprises a compound of the present invention, for instance according to any one of the above embodiments, and optionally a pharmaceutically acceptable additive, such as carrier or excipient.

In a further aspect the present invention relates to a compound of the present invention, for instance according to any one of the above embodiments, for use in a method for treating a cardiac disease, disorder or condition in a mammal, such as a human. In an embodiment, for use in a method for treating the cardiac disease, disorder or condition wherein the disease, disorder or condition is associated with an abnormal rhythm of the heart or variant and exercise induced angina. In another embodiment, for use in a method for treating the cardiac disease, disorder or condition selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, and bradyarrhythmias.

In a further aspect the present invention relates to a method for treatment of a cardiac disease, disorder or condition in a mammal, such as a human, wherein a therapeutically effective amount of at least one compound of the present invention is administered to a mammal in need of said treatment. In a further embodiment said cardiac disease, disorder or condition in a mammal is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, and bradyarrhythmias.

Cardiac Diseases

In the context of this invention a cardiac disease, disorder or condition is any cardiac disease, disorder or condition, including, but not limited to, an abnormal rhythm of the heart or variant and exercise induced angina.

In a more specific embodiment the cardiac disease, disorder or condition is any disease, disorder or condition associated with an abnormal rhythm of the heart or variant and exercise induced angina.

In a more specific embodiment the cardiac disease, disorder or condition is any disease, disorder or condition associated with an abnormal rhythm of the heart.

In a more specific embodiment the cardiac disease, disorder or condition associated with an abnormal rhythm of the heart is selected from cardiac arrhythmia, atrial arrhythmia, ventricular arrhythmia, atrial fibrillation, ventricular fibrillation, tachyarrhythmia, atrial tachyarrhythmia, ventricular tachyarrhythmia, and bradyarrhythmias.

In another embodiment a cardiac disease, disorder or condition of the invention is an abnormal rhythm caused by myocardial ischaemia, myocardial infarction, cardiac hypertrophy, or cardiomyopathy.

In another embodiment a cardiac disease, disorder or condition of the invention is an abnormal rhythm arising after cardiac surgery or a cardiac ablation procedure.

In a further specific embodiment the cardiac disease, disorder or condition associated with an abnormal rhythm of the heart is a cardiac arrhythmia caused by a genetic disease.

In a still further preferred embodiment the cardiac disease, disorder or condition associated with an abnormal rhythm of the heart is cardiac arrhythmia.

In a preferred embodiment the cardiac disease, disorder or condition associated with an abnormal rhythm of the heart is atrial fibrillation.

In a particular embodiment the compound of formula (I) of the present invention is useful for treatment of atrial fibrillation by acute cardioversion to normal sinus rhythm.

In another particular embodiment the compound of formula (I) of the present invention is useful for treatment of atrial fibrillation by maintaining normal sinus rhythm and avoiding or reducing the occurrence of new episodes of atrial fibrillation.

Pharmacological Treatment of Atrial Fibrillation

In the context of this invention, and as understood by a person skilled in the art, treatment of atrial fibrillation is acute cardioversion or maintenance of sinus rhythm or both. Acute conversion is defined as application of compound that has the ability to convert atrial fibrillation to a normal cardiac sinus rhythm. Normal sinus rhythm is defined as regular stable heart beating at frequencies between 40 and 100 beats at rest in adults with normal regular p-wave on a standard 12-lead electrocardiogram. Maintenance of sinus rhythm is defined as the ability for a compound to preserve a normal stable sinus rhythm over time with no relapse to atrial fibrillation or the ability of a compound to significantly reduced the incidence of relapse from atrial fibrillation to normal sinus rhythm compared to non-treated controls.

Description of General Process

Scheme 1 summarises one of the synthetic approaches that can be used to prepare compounds of general formula (I).

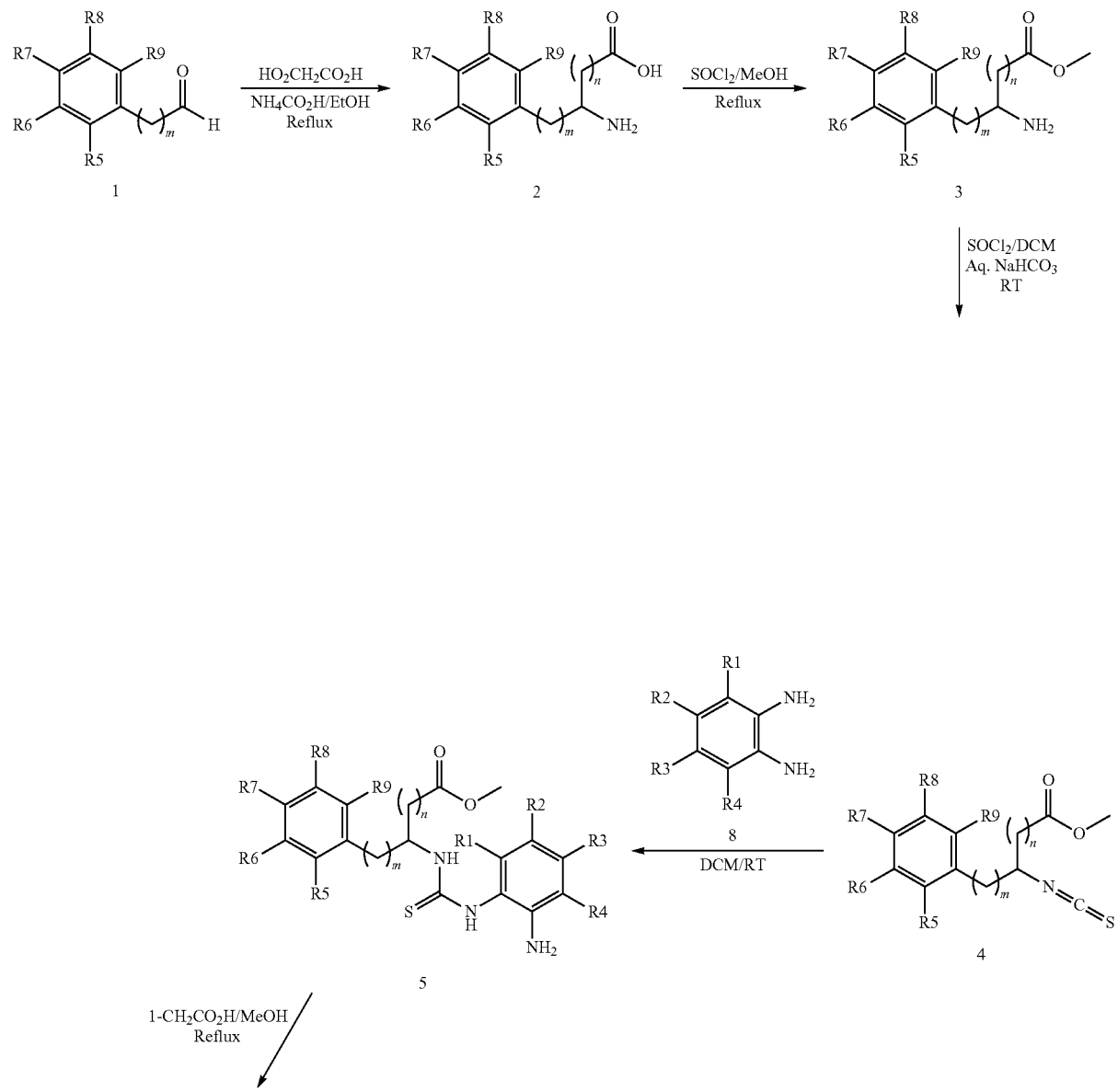

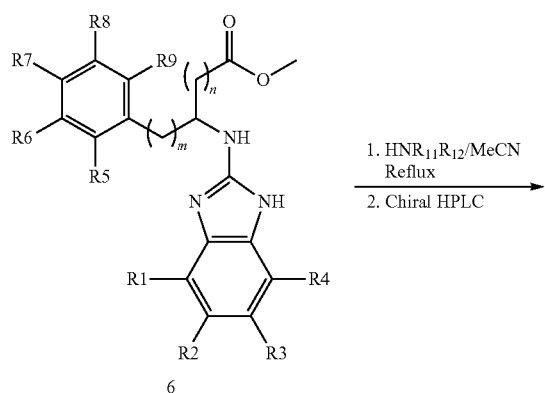

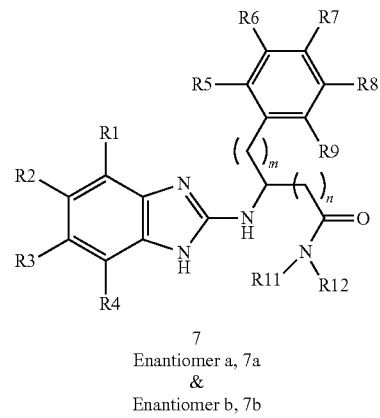

6

7
Enantiomer a, 7a
&
Enantiomer b, 7b

A large number of aldehydes (1) are commercially available or can be readily prepared by many routes described in the literature. The aldehydes (1) can be converted to the β-amino acids (2) by a wide range of methods, such as reaction of (2) with malonic acid derivatives under the influence of ammonium salts (e.g. ammonium formate) followed by subsequent decarboxylation upon heating. In addition, a large number of β-amino acids (2) and derivatives (such as their esters and amides) are also available from commercial sources. The β-amino acids (2) can be converted to their ester derivatives (3) by reaction with an alcohol (e.g. methanol, ethanol) under the influence of a strong acid (e.g. hydrochloric acid, sulphuric acid) or by first activation to the acid chloride with reagents, such a thionyl chloride, and then reaction with an alcohol. There are many other well-established methods for converting acids to esters described in the literature. The β-amino esters (3) can be converted to the isothiocyanate derivatives (4) by reaction with thiophosgene in a suitable solvent (e.g. dichloromethane) under the influence of a base (e.g. sodium hydrogen carbonate). The isothiocyanates (4) can react with a wide range of benzene-1,2-diamine derivatives (8) in a suitable solvent (e.g. dichloromethane) to afford the thiourea products (5). A wide range of benzene-1,2-diamine derivatives (8) are available commercially or can be readily prepared by well-established methods described in the literature (e.g. by nitration and subsequent reduction of commercial substituted benzene starting materials). The thiourea derivatives (5) can be converted to 2-aminobenzimidazole derivatives (6) by a ring forming reaction that occurs under the influence of iodoacetic acid and heating in a suitable solvent (such as methanol or acetonitrile). The cyclisation of (5) to afford (6) can also occur under the influence of mercury salts (e.g. mercuric oxide) with heating in a suitable solvent (e.g. acetonitrile). The 2-aminobenzimidazole ester derivatives (6) can react with a wide range of commercial amines to afford the amide derivatives (7). This reaction can be performed by subjecting a mixture of (6) and the amine in a suitable solvent (e.g. acetonitrile) to heating (up to reflux) or to irradiation with microwaves (with heating). The 2-aminobenzimidazole derivatives (7) can be a racemic mixture, which can be separated into the two enantiomers (7a) and (7b) by a range of methods, including chromatography using a chiral stationary phase. This can be normal-phase or reverse phase chromatography, which uses suitable solvent mixtures as eluent (e.g. chloroform, dichloromethane, ethanol, ethyl acetate, methanol, ethanol) sometimes with additives (e.g. ammonia, triethylamine, trifluoroacetic acid, acetic acid).

The process described above is applicable to prepare compounds of general formula (1) in which m=0, 1 or 2 by starting with the appropriate starting aldehyde (1). A large number of aldehydes (1) (m=0, 1, 2) are available commercially or can be readily prepared by many well-established methods described in the literature.

Compounds of general formula (I) in which n=0 can also be made by the general process described above, by starting with an α-amino acid (2) (n=0). A large number of α-amino acids are available commercially or can be readily prepared by many well-established methods described in the literature.

The process is suitable for a wide range of derivatives bearing a variety of R1 to R9 groups. In some cases the R1 to R9 groups may need to carry a chemical protecting group (e.g. when R1 to R9 bear substituents such as: OH, —NH$_2$, NHR, —SH, —CO$_2$H etc). The protecting groups can be removed by a suitable de-protection step.

The skilled person will understand that it may be necessary to adjust or change the order of steps in the processes described above, and such change of order is encompassed by the aspects of the process as described above in the reaction schemes and accompanying description of the process steps.

Furthermore the skilled person will understand that the processes described above and hereinafter the functional groups of intermediate compounds may need to be protected by protecting group.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g., t-butyldimethylsilyl, t-butyldiphenylsilyl or trimethylsilyl), AcO (acetoxy), TBS (t-butyldimethylsilyl), TMS (trimethylsilyl), PMB (p-methoxybenzyl), and tetrahydropyranyl. Suitable protecting groups for carboxylic acid include (C1-C6)-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbony 1 (Teoc). Suitable protecting groups for S include S—C(=N)NH$_2$, TIPS (Triisopropylsilane).

The protection and deprotection of functional groups may take place before or after any reaction in the above mentioned processes.

Furthermore the skilled person will appreciate that, in order to obtain compounds of the invention in an alternative, and on some occasions, more convenient, manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The compound of formula (I) have at least one asymmetric center, and may have further asymmetric centres and it is intended that any optical isomers (i.e. enantiomers or diastereomers), in the form of separated, pure or partially purified optical isomers and any mixtures thereof including racemic mixtures, i.e. a mixture of stereoisomers, are included within the scope of the invention. In particular, the carbon atom of formula (I) wherein the 4 valence bonds are linked to R10, NH, $(C)_n$, and $(C)_m$ and is an asymmetric centre giving rise to two optical isomers, an R form and an S form. In one embodiment, the compounds of the present invention have the S form. In another embodiment, the compounds of the present invention have the R form. In a further embodiment, the compounds of the present invention are a racemic mixture.

In this context is understood that when specifying the enantiomeric form, then the compound is in enantiomeric excess, e.g. essentially in a pure, mono-enantiomeric form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography of an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

In a still further embodiment the compound I is on free form. In one embodiment the free form is an anhydrate. In another embodiment the free form is a solvate, such as a hydrate.

In a further embodiment the compound is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "free form" as used herein means a compound of formula (I) which is a free base or free acid, as the case may be, and which is not in any salt form.

The term "$C_{1-x}$ alkyl" as used herein means an alkyl group containing 1 to x carbon atoms, e.g. $C_{1-3}$, $C_{1-4}$, $C_{1-5}$ or $C_{1-6}$, such as methyl, ethyl, propyl, butyl, pentyl or hexyl, and also includes branched $C_{3-6}$ alkyl, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl. When $C_{1-x}$ alkyl, such as $C_{1-6}$ alkyl, is substituted with a group, such as halogen, such as a F, it means that such F, e.g. 3 F are attached to one carbon ($CF_3$) or two carbons ($CF_2$—CF) or even three carbons (CF—CF—CF).

The term "$C_{1-x}$ alkylene" as used herein means an alkylene group containing 1 to x carbon atoms, e.g. $C_{1-3}$, $C_{1-4}$, $C_{1-5}$ or $C_{1-6}$, such as methylene, ethylene, propylene, butylene, pentylene or hexylene, and also includes branched $C_{3-6}$ alkylene, such as isopropylene, isobutylene, tert-butylene, isopentylene, 3-methylbutylene, 2,2-dimethylpropylene, n-hexylene, 2-methylpentylene, 2,2-dimethylbutylene, 2,3-dimethylbutylene.

The term "$C_{1-x}$ alkoxy" or "O—$C_{1-x}$alkyl" (used interchangeable) as used herein means one oxygen atom covalently linked to an alkyl group containing 1 to x carbon atoms, e.g. $C_{1-5}$ or $C_{1-6}$, such as methoxy, ethoxy, n-propoxy, iso-propoxy, n-butyloxy, n-pentyloxy, or n-hexyloxy.

The term "$C_{3-7}$ cycloalkyl" as used herein means a cyclic alkyl group containing 3-7 carbon atoms, such as cyclopropyl, cyclobutyl, cyclopentyl, cyclohexyl, cycloheptyl, and 1-methylcyclopropyl.

The term "Oxo" as used herein means an oxygen atom with double bonds, also indicated as =O.

The term "CN" as used herein means a nitril (C and N linked by triple bond).

The term "C(=O)" as used herein means a carbonyl group.

When "$C_{1-6}$ alkyl" or "$C_{1-6}$ alkylene" is linked to another group or atom, such as in $C_{1-6}$ alkylene-OH, $C_{1-6}$ alkylene-CN, $C_{1-6}$ alkylene-$CF_3$, $C_{1-6}$ alkylene-O—$C_{1-6}$ alkyl, $C_{1-6}$ alkylene-S—$C_{1-6}$ alkyl, $C_{1-6}$ alkylene-$NR^aR^b$, C(=O)—$C_{1-6}$ alkyl, C(=O)—$C_{1-6}$alkoxy, C(=O)—$C_{1-6}$alkyl-CN, C(=O)$C_{1-6}$ alkyl-OH, C(=O)—$C_{1-6}$ alkylene-S—$C_{1-6}$ alkyl, C(=O)—O—$C_{1-6}$ alkylene-O—$C_{1-6}$ alkyl, C(=O)—O—$C_{1-6}$ alkyl-CN, C(=O)—O—$C_{1-6}$ alkyl-OH, C(=O)—O—$C_{1-6}$ alkylene-S—$C_{1-6}$ alkyl, C(=O)—NH$C_{1-6}$ alkyl, C(=O)—NH$C_{1-6}$ alkylene-O—$C_{1-6}$ alkyl, C(=O)—NH$C_{1-6}$ alkylene-S—$C_{1-6}$ alkyl, C(=O)—NH$C_{1-6}$ alkyl-CN, C(=O)—NH$C_{1-6}$ alkyl-OH, C(=O)—N($C_{1-6}$ alkyl)$_2$, $SO_2$—$C_{1-6}$ alkyl, $SO_2$—$C_{1-6}$ alkylene-O—$C_{1-6}$ alkyl, $SO_2$—$C_{1-6}$ alkylene-S—$C_{1-6}$ alkyl, $SO_2$—$C_{1-6}$ alkyl-CN, $SO_2$—$C_{1-6}$ alkyl-OH, $SO_2$—$C_{1-6}$alkyl-N($C_{1-6}$alkyl)$_2$, S—$C_{1-6}$ alkyl, O$C_{3-7}$cycloalkyl, S$C_{3-7}$ cycloalkyl, $C_{1-6}$ alkylene-C(=O)—O—$C_{1-6}$ alkyl, $C_{1-6}$ alkylene-O—C(=O)—NH—$C_{1-6}$ alkyl, $C_{1-6}$ alkylene-NH—C(=O)—$C_{1-6}$ alkylene-O—$C_{1-6}$ alkyl, $C_{1-6}$ alkylene-NH—$SO_2$—$C_{1-6}$ alkyl, $C_{1-6}$ alkylene-NH—$SO_2$—$C_{1-6}$ alkylene-phenyl, $C_{1-6}$ alkylene-$NR^cR^d$, $C_{1-6}$ alkylene-C(=O)—$NR^eR^f$, $C_{1-6}$ alkylene-$R^g$, $C_{1-6}$ alkylene-$R^h$, $C_{1-6}$ alkylene-$R^j$, it means that one such group or atom may be linked covalently to any one of the carbon atoms of the $C_{1-6}$ alkyl or $C_{1-6}$ alkylene.

The term "halogen" as used herein means an atom selected from Chloro (Cl), Fluoro (F), Iodo (I) and Bromo (Br).

The term "a heteroaryl" as used herein means a mono or bicyclic aromatic ring system containing one or more heteroatoms, such as 1-10, e.g. 1-6, selected from O, S, and N, including but not limited to oxazolyl, oxadiazolyl, thiophenyl, thiadiazolyl, thiazolyl, pyridyl, pyrimidinyl, pyridonyl, pyrimidonyl, quinolinyl, azaquionolyl, isoquinolinyl, azaisoquinolyl, quinazolinyl, azaquinazolinyl, bensozazoyl, azabensoxazoyl, bensothiazoyl, or azabensothiazoyl.

The term "a heterocyclyl" as used herein means a mono or bicyclic 3-10 membered aliphatic heterocycle containing one or more heteroatoms, such as 1-7, e.g. 1-5, selected from O, S, and N, including but not limited to aziridinyl, oxaziridinyl, azetidinyl, diazetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, tetrahydropyranyl, tetrahydrothipyranyl, piperidonyl, or 2-oxa-6-azaspiro[3.3]-heptanyl.

The term "a five or six membered heteroaromatic ring" as used herein means one five membered heteroaromatic ring or one six membered heteroaromatic ring. The five membered heteroaromatic ring contains 5 ring atoms of which one to four are heteroatoms selected from N, O, and S. The six membered heteroaromatic ring contains 6 ring atoms of which one to five are heteroatoms selected from N, O and S. Examples include thiophene, furan, pyran, pyrrole, imidazole, pyrazole, isothiazole, isooxazole, pyridine, pyrazine, pyrimidine and pyridazine. When such heteroaromatic rings are substituents they are termed thiophenyl, furanyl, pyranyl, pyrrolyl, imidazolyl, pyrazolyl, isothiazolyl, isooxazolyl, pyridinyl, pyrazinyl, pyrimidinyl and pyridazinyl. Also included are oxazoyl, thiazoyl, thiadiazoyl, oxadiazoyl, and pyridonyl.

When "R11 and R12 together with the nitrogen to which R11 and R12 are linked form a monocyclic or bicyclic 3-10 membered aliphatic heterocycle containing the nitrogen to which R11 and R12 are linked and optionally one or more heteroatoms selected from O, S, and N" is substituted with a group selected from $C_{1-6}$ alkyl; oxo; OH; $C_{1-6}$ alkylene-OH; C(=O)—$C_{1-6}$ alkyl; C(=O)—O—$C_{1-6}$ alkyl; $SO_2$—$C_{1-6}$ alkyl; $NR^kR^l$, wherein $R^k$ and $R^l$ are independently a group selected from H and $C_{1-6}$ alkyl; and $C_{1-6}$ alkylene-$NR'''R''$, wherein $R'''$ and $R''$ are independently a group selected from H and $C_{1-6}$ alkyl; such group, e.g. one or two groups, may be linked to any member of the aliphatic heterocycle, such as any carbon atom, O, S, or N, as long as such substitution does not provide an unstable heterocycle.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular a human being, but it may also include animals, such as dogs, cats, cows, sheep and pigs.

The term "a therapeutically effective amount" of a compound of formula (I) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (I) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compound as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Experimental Procedures

Automated Patch Clamping

Automated whole cell patch-clamp recordings were performed using a QPatch 16 HT system and single-hole Qplates (Biolin Scientific, Sophion, Denmark) on HEK-293 cells stably expressing the human SK3 channel ($hK_{Ca}2.3$). Cells were cultured and prepared for experiments using normal cell culturing procedures. A total of 4-5 million cells were used per experiment. The Qpatch automatically generates giga sealing, whole-cell formation, compound application and recording of current. $hK_{Ca}2.3$ currents were recorded in symmetrical $K^+$ solutions, with an intracellular solution consisting of in mM: KCl 108; KOH/EGTA (ethylene glycol-bis(2-aminoethylether)-N,N,N',N'-tetraacetic acid) 31.25/10; $CaCl_2$ 8.1; $MgCl_2$ 1.2; HEPES (2-[4-(2-hydroxyethyl)piperazin-1-yl]ethanesulfonic acid) 10; KOH 15, pH adjusted to pH=7.2 with HCl. The free calcium concentration was calculated to 400 nM. The extracellular solution consisted of in mM: KCl 150; $CaCl_2$) 0.1; $MgCl_2$ 3; HEPES 10; Glucose 10, pH=7.4 with KOH. The cells were held at 0 mV and $hK_{Ca}2.3$ currents were elicited by a linear voltage ramp from 80 mV to +80 mV (200 ms in duration) applied every 5th second. The compound application protocol consisted of 12 recording periods lasting from 50-200 s: 1) Baseline recordings in extracellular solution; 2) Application of the positive control N-methyl bicuculline (100 µM), which is characterized by full efficacy, fast on- and off-rate; 3-4) Wash-out; 5-9) Increasing concentrations of test compound to establish an IC50 value; 10-11) Wash-out; 12) positive control with compound NS8593 (N-[(1R)-1,2,3,4-tetrahydro-1-naphthalenyl]-1H-benzimidazol-2-amine) (1 µM). Data were sampled at 10 kHz, 4th order Bessel filter, cut-off frequency 3 kHz. Currents were compensated for run-down. Potency was quantified as the concentration needed to inhibit half of the SK channel activity and reported as an IC50 value. All effects of compounds of the present invention as tested were normalized to the observed inhibitory effect of N-methyl bicuculline.

Results

The examples described are potent inhibitors of the SK3 channel and have shown the following $IC_{50}$ in the Automated patch clamping assay described above:

Examples: 1, 6, 8, 9, 10, 17, 17a, 17b, 18, 20, 21, 22, 23, 27, 29, 30, 31, 32, 34, 34a, 34b, 38, 38a, 39a, 39b, 40a, 41, 41a, 41b, 42, 42a, 42b, 43, 46, 47, 48, 54, 55, 56, 56a, 56b, 57, 57a, 57b, 58, 59, 59a, 59b, 61, 63, 65, 65a, 65b, 67, 67a, 67b, 68, 68a, 68b, 69a, 69b, 70a, 70b, 71, 72, 73, 74, 75, 76, 77, 78, 79, 80, 81, 82, 83, 84, 85, 86, 87, 88, 89, 90, 91, 92, 93, and 94 all have an $IC_{50}$ below 10 µM.

Examples: 2, 3, 4a, 4b, 5, 7, 11, 12, 13, 14, 15, 16, 19, 24, 25, 26, 27a, 28, 33, 35, 36, 37, 38b, 40b, 44, 45, 49, 50, 51, 52, 53, 60, 62, 64, 66, 95 and 96 all have an $IC_{50}$ above 10 µM and below 100 µM.

Materials and Methods

Commercial reagents were used without further purification unless otherwise stated. Analytical TLC was performed on silica gel 60-F254 (Merck) with detection by fluorescence and by immersion in a KMnO$_4$ solution [KMnO$_4$ solution recipe: Dissolve 1.5 g KMnO$_4$, 10 g K$_2$CO$_3$, and 1.25 mL 10% NaOH in 200 mL of water] followed by charring. Purification of compound was carried out by column chromatography on silica gel (60-120 mesh, Swambe Chemicals, India). NMR spectra such as $^1$H, $^{13}$C and 2D COSY were recorded with Bruker AV 400 MHz spectrometer (400 MHz for $^1$H, 100 MHz for $^{13}$C) at ambient temperature by using deuterated DMSO-d6, CDCl$_3$, or CD$_3$OD as a solvent for NMR. Chemical shifts are reported in δ parts per million (ppm). ESI-MS was recorded on Agilent LC1200 series MS single quadrupole 6130 mass spectrometer.

Abbreviations Used in Experimental Section

BOP=(Benzotriazol-1-yloxy)tris(dimethylamino)phosphonium hexafluorophosphate

PyBOP=(Benzotriazol-1-yloxy)tripyrrolidinophosphonium hexafluorophosphate

EDC.HCl=N-(3-Dimethylaminopropyl)-N'-ethylcarbodiimide hydrochloride

HBTU=N,N,N',N'-Tetramethyl-O-(1H-benzotriazol-1-yl) uronium hexafluorophosphate

Grace Flash Chromatography System

The Grace REVELERIS® Prep Purification System was used to perform sample purification by flash chromatography, using Flash Cartridges pre-packed with silica:
Columns Used:
 Hi-Purit Flash Columns Silica (Normal Phase);
 12 g, 60 A, max pressure 350 psi (24 bar),
 24 g, 60 A, max pressure 350 psi (24 bar),
 40 g, 60 A, max pressure 350 psi (24 bar),
 80 g, 60 A, max pressure 350 psi (24 bar).
 Solvents: Hexane, EtOAc, CHCl$_3$ and MeOH.

Example 1: 3-[(1H-1,3-benzodiazol-2-yl)amino]-N-[2-(methylsulfanyl)ethyl]-3-[3-(trifluoromethyl)phenyl]propanamide

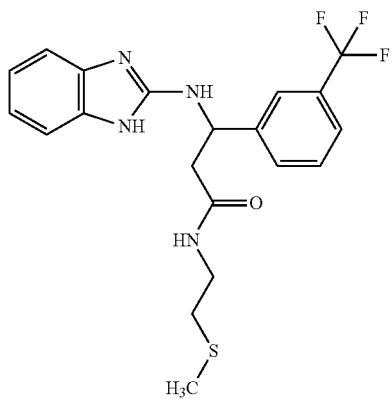

Step 1: Preparation of 3-amino-3-[3-(trifluoromethyl)phenyl]propanoic acid

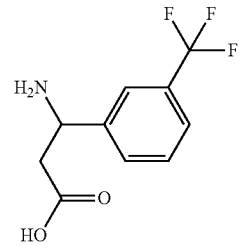 [SMILES: NC(CC(=O)O)c1cccc(C(F)(F)F)c1]

A mixture of malonic acid (298.82 g, 2872 mmol), ammonium formate (362.14 g, 5743 mmol) and 3-(trifluoromethyl)benzaldehyde (500 g, 2873 mmol) in ethanol (1000 mL) was refluxed for 12 h. The reaction mixture was evaporated to remove ethanol and the residue was triturated with acetone (2500 mL). The solid was filtered and dried to afford 3-amino-3-[3-(trifluoromethyl)phenyl]propanoic acid (255 g) as white solid.

$^1$H NMR (400 MHz, AcOH-d$_4$) δ 7.87-7.81 (m, 2H), 7.74 (d, 1H, J=7.6 Hz), 7.66-7.62 (m, 1H), 4.98 (br. S, 1H), 3.36 (dd, 1H, J=16.0, 8.0 Hz), 3.13 (dd, 1H, J=17.6, 5.6 Hz);

MS: m/z 234 (M+1).

Step 2: Preparation of Methyl 3-amino-3-[3-(trifluoromethyl)phenyl]propanoate hydrochloride

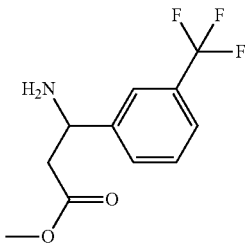 [SMILES: COC(=O)CC(N)c1cccc(C(F)(F)F)c1]

To a suspension of 3-amino-3-[3-(trifluoromethyl)phenyl]propanoic acid (from Step 1) (75 g, 322 mmol) in methanol (150 mL) cooled to 0° C. was added thionyl chloride (46.65 mL, 644 mmol) and the mixture was then warmed to ambient temperature and refluxed for 20 h. The reaction mixture was evaporated to dryness to afford the hydrochloride salt of methyl 3-amino-3-[3-(trifluoromethyl)phenyl]propanoate (55 g) as an off-white solid.

$^1$H NMR (400 MHz, DMSO-d$_6$) δ 7.87 (s, 1H), 7.77 (d, 2H, J=8.0 Hz), 7.67 (t, 1H, J=7.6 Hz), 4.74 (t, 1H, J=8.0 Hz), 3.55 (s, 3H), 3.14 (dd, 1H, J=16.8, 8.0 Hz), 3.04 (dd, 1H, J=16.8, 8.0 Hz);

MS: m/z 247.8 (M+1).

Step 3: Preparation of Methyl 3-isothiocyanato-3-[3-(trifluoromethyl)phenyl]propanoate

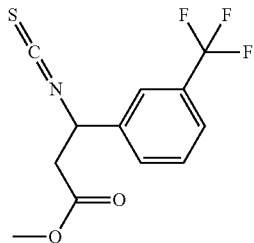 [SMILES: COC(=O)CC(N=C=S)c1cccc(C(F)(F)F)c1]

To a suspension of methyl 3-amino-3-[3-(trifluoromethyl)phenyl]propanoate hydrochloride (from Step 2) (65 g, 230 mmol) in dichloromethane cooled at 0° C. was added thiophosgene (35.4 mL, d=1.5, 461 mmol) followed by 10% aqueous sodium bicarbonate solution (150 mL). The reaction mixture was then stirred at ambient temperature. After 1 h, the reaction mixture was diluted with 10% aqueous sodium bicarbonate solution (75 mL) and extracted with dichloromethane (3×250 mL). The combined organic extracts were dried over anhydrous sodium sulphate and evaporated to dryness to afford methyl 3-isothiocyanato-3-[3-(trifluoromethyl)phenyl]propanoate (60 g) as a red gum.

$^1$H NMR (400 MHz, CDCl$_3$) δ 7.65-7.54 (m, 4H), 5.38 (q, 1H, J=8.0 Hz), 3.77 (s, 3H), 3.02 (dd, 1H, J=8.0, 8.8 Hz), 2.86 (dd, 1H, J=16.0, 5.2 Hz);

MS: m/z 289.1 (M+).

Step 4: Preparation of Methyl 3-{[(2-aminophenyl)carbamothioyl]amino}-3-[3-(trifluoromethyl)phenyl]propanoate

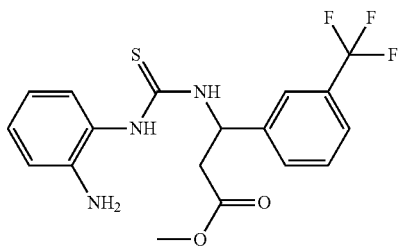 [SMILES: COC(=O)CC(NC(=S)Nc1ccccc1N)c1cccc(C(F)(F)F)c1]

A mixture of methyl 3-isothiocyanato-3-[3-(trifluoromethyl)phenyl]propanoate (from Step 3) (60 g, 207 mmol) and 1,2-phenylene diamine (22.43 g, 207 mmol) in dichloromethane (200 mL) was stirred at ambient temperature for 12 h. The reaction mixture was concentrated to afford a crude product (85 g) as a brownish gum, which was purified by silica gel (60-120 mesh) column chromatography eluting with 7% methanol in chloroform to afford methyl 3-{[(2-aminophenyl)carbamothioyl]amino}-3-[3-(trifluoromethyl)phenyl]propanoate (55 g) as a brownish gum.

$^1$H NMR (400 MHz, DMSO-d$_6$) δ 7.45-7.31 (m, 4H), 6.78-6.71 (m, 2H), 6.53 (d, 1H, J=7.6 Hz), 6.34 (t, 1H, J=7.6 Hz), 5.69 (bs, 1H), 3.28 (s, 3H), 2.83 (dd, 1H, J=16.0, 8.0 Hz), 2.70 (dd, 1H, J=16.0, 6.4 Hz);

MS: m/z 398 (M+1).

Step 5: Preparation of Methyl 3-[(1H-1,3-benzodiazol-2-yl)amino]-3-[3-(trifluoromethyl)phenyl] propanoate

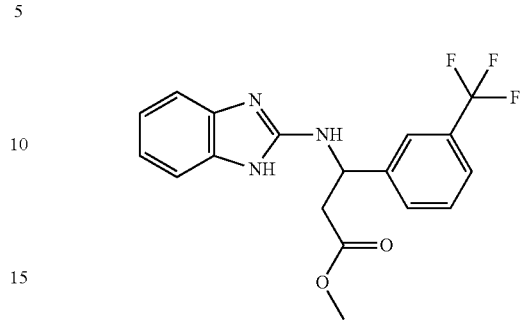

To a solution of methyl 3-{[(2-aminophenyl)carbamothioyl]amino}-3-[3-(trifluoromethyl)phenyl] propanoate (from Step 4) (55 g, 134 mmol) in methanol (550 mL) was added iodoacetic acid (32.19 g, 174 mmol) and the mixture was refluxed for 2 h. The reaction mixture was evaporated to afford the crude product (90 g) which was purified by silica gel (60-120 mesh) column chromatography using 7% methanol in chloroform as eluent to afford methyl 3-[(1H-1,3-benzodiazol-2-yl)amino]-3-[3-(trifluoromethyl)phenyl] propanoate (37 g) as an off-white solid.

$^1$H NMR (400 MHz, MeOH-d$_4$) δ 7.83-7.78 (m, 2H), 7.71-7.64 (m, 2H), 7.42-7.39 (m, 2H), 7.32-7.30 (m, 2H), 5.39 (bs, 1H), 3.70 (s, 3H), 3.14 (d, 2H, J=8.0 Hz);

MS: m/z 364.0 (M+1).

Example 1, Step 6: 3-[(1H-1,3-benzodiazol-2-yl)amino]-N-[2-(methylsulfanyl)ethyl]-3-[3-(trifluoromethyl)phenyl]propanamide

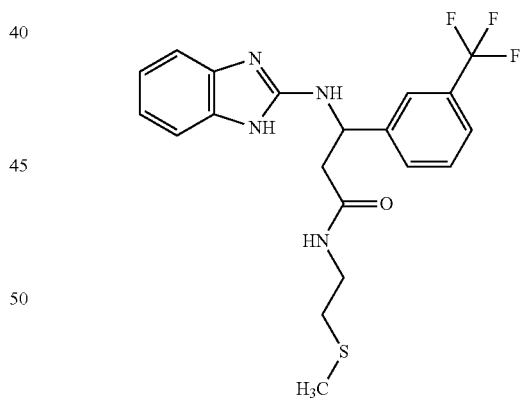

A suspension of methyl 3-[(1H-1,3-benzodiazol-2-yl)amino]-3-[3-(trifluoromethyl)phenyl] propanoate (from Step 5) (0.36 g, 0.994 mmol) and 2-(methylsulfanyl)ethan-1-amine (0.253 g, 2.479 mmol) in acetonitrile was irradiated with microwaves at 140° C. for 1 hr. The crude product was purified by silica gel (60-120 mesh) column chromatography using 3% methanol in chloroform as eluent to afford the desired product 3-[(1H-1,3-benzodiazol-2-yl)amino]-N-(2-ethanesulfonamidoethyl)-3-[3-(trifluoromethyl)phenyl]propanamide (0.075 g) as an off-white solid.

$^1$H NMR (400 MHz, DMSO-d$_6$): δ 10.87 (s, 1H), 8.09 (t, 1H, J=5.68 Hz), 7.78 (s, 1H), 7.72 (d, 1H, J=7.36 Hz), 7.58-7.51 (m, 2H), 7.40 (d, 1H, J=9.20 Hz), 7.10 (d, 2H, J=8.88 Hz), 6.85 (s, 2H), 5.40-5.34 (dd, 1H, J=7.2, 15.56 Hz), 3.19-3.14 (dd, 2H, J=6.44, 12.12 Hz), 2.77-2.71 (dd, 1H, J=7.04, 14.36 Hz), 2.680 (dd, 1H, J=7.62, 14.28 Hz), 2.36 (t, 2H, J=6.92 Hz), 1.98 (s, 3H);

MS: m/z 423.2 (M+1).

The above general microwave method described for the preparation of Example 1 (Step 6) was used in the preparation of the following examples.

Example 2: 3-[(1H-1,3-benzodiazol-2-yl)amino]-N-[2-(dimethylamino)ethyl]-N-methyl-3-[3-(trifluoromethyl)phenyl]propanamide Prepared by the method described for Example 1 (Step 6) but using [2-(dimethylamino)ethyl](methyl)amine in place of 2-(methylsulfanyl)ethan-1-amine.

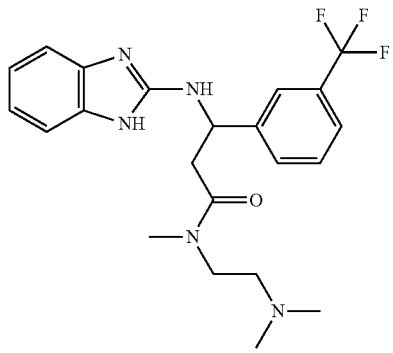 [SMILES: CN(C)CCN(C)C(=O)CC(Nc1nc2ccccc2[nH]1)c1cccc(C(F)(F)F)c1]

$^1$H NMR (400 MHz, DMSO-d$_6$): δ 7.81 (s, 1H), 7.75 (s, 1H), 7.55 (dd, 2H, J=8.0, 15.0 Hz), 7.34 (dd, 2H, J=9.2, 26.6 Hz) 7.27 (d, 2H, J=9.20 Hz), 7.09 (t, 2H, J=4.40 Hz), 6.84 (s, 2H), 5.39 (d, 1H, J=3.60 Hz), 3.39-3.29 (m, 1H), 3.12-3.04 (m, 1H), 2.92-2.77 (m, 3H), 2.33-2.24 (m, 2H), 2.14 (s, 3H), 2.10 (s, 3H);

MS: m/z 434.2 (M+1).

Example 3: 3-[(1H-1,3-benzodiazol-2-yl)amino]-N-(2-ethanesulfonamidoethyl)-3-[3-(trifluoromethyl)phenyl]propanamide Prepared by the method described for Example 1 (Step 6) but using N-(2-aminoethyl)ethane-1-sulfonamide in place of 2-(methylsulfanyl)ethan-1-amine.

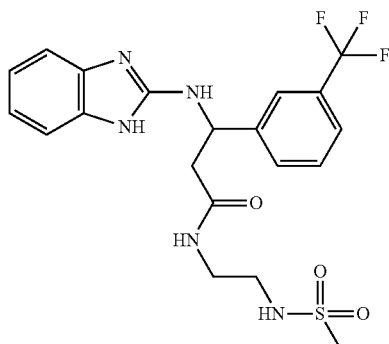

$^1$H NMR (400 MHz, DMSO-d$_6$ & D$_2$O)) δ 7.89 (s, 1H), 7.82 (d, J=7.64 Hz, 1H), 7.70-7.62 (m, 2H), 7.40-7.38 (m, 2H), 7.24-7.22 (m, 2H), 5.44 (q, J=8.8 Hz, 1H), 3.17-3.05 (m, 2H), 2.96-2.81 (m, 6H), 1.14 (t, J=7.32, 3H);

MS: m/z 484.2 (M+1).

Example 4: 3-[(1H-1,3-benzodiazol-2-yl)amino]-N-(2-hydroxy-2-methylpropyl)-3-[3-(trifluoromethyl)phenyl]propanamide Prepared by the method described for Example 1 (Step 6) but using 1-amino-2-methylpropan-2-ol in place of 2-(methylsulfanyl)ethan-1-amine.

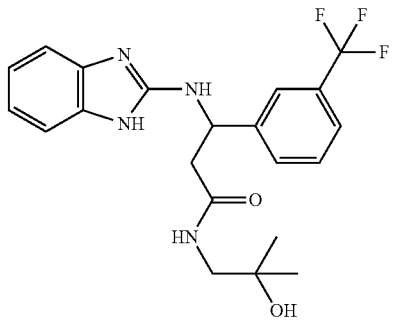 [SMILES: CC(C)(O)CNC(=O)CC(Nc1nc2ccccc2[nH]1)c1cccc(C(F)(F)F)c1]

$^1$H NMR (400 MHz, DMSO-d$_6$ & D$_2$O): 7.77-7.71 (m, 2H), 7.55 (dd, 2H, J=9.24, 16.8 Hz), 7.1 (d, 2H, 7.56 Hz), 6.88 (m, 2H), 5.36 (dd, 1H, J=6.52, 15.04 Hz), 3.33-2.94 (m, 2H), 2.80-2.71 (m, 2H), 0.88 (s, 3H), 0.86 (s, 3H);

MS: m/z 421.2 (M+1).

The enantiomers of the above example were separated by chiral chromatography. Column: Chiral Phenomenex lux Cellulose-2 (250×4.6) mm 5 u; Mobile Phase 'A': Hexane: Ethanol (80:20); Flow: 1.0 ml/min.

Example 4a: (−) 3-[(1H-1,3-benzodiazol-2-yl)amino]-N-(2-hydroxy-2-methylpropyl)-3-[3-(trifluoromethyl)phenyl]propanamide The (−) enantiomer was the first to elute off the column.
$^1$H NMR (400 MHz, DMSO-d$_6$): δ 10.86 (bs, 1H), 7.80 (t, 2H, J=9.60 Hz), 7.73 (d, 1H, J=7.20 Hz), 7.56-7.50 (m, 2H), 7.40 (d, 1H, J=6.80 Hz), 7.09 (t, 2H, J=4.80 Hz), 6.84 (bs, 2H), 5.39-5.33 (dd, 1H, J=6.8, 15.2 Hz), 4.34 (s, 1H), 3.00-2.89 (m, 2H), 2.80-2.67 (m, 2H), 0.87 (s, 3H), 0.85 (s, 3H);

MS: m/z 421.2 (M+1).

Example 4b: (+) 3-[(1H-1,3-benzodiazol-2-yl)amino]-N-(2-hydroxy-2-methylpropyl)-3-[3-(trifluoromethyl)phenyl]propanamide The (+) enantiomer was the second to elute off the column.
$^1$H NMR (400 MHz, DMSO-d$_6$): δ 10.88 (s, 1H), 7.83-7.72 (m, 3H), 7.55-7.51 (m, 2H), 7.42 (bs, 1H), 7.10 (d, 2H, J=8.68 Hz), 6.85 (bs, 2H), 5.38 (t, 1H, J=7.8 Hz), 4.36 (s, 1H), 3.01-2.89 (m, 2H), 2.79-2.67 (m, 2H), 0.87 (s, 3H), 0.86 (s, 3H);

MS: m/z 421.2 (M+1).

Example 5: 3-[(1H-1,3-benzodiazol-2-yl)amino]-1-(4-hydroxypiperidin-1-yl)-3-[3-(trifluoromethyl)phenyl]propan-1-one Prepared by the method described for Example 1 (Step 6) but using piperidin-4-ol in place of 2-(methylsulfanyl)ethan-1-amine.

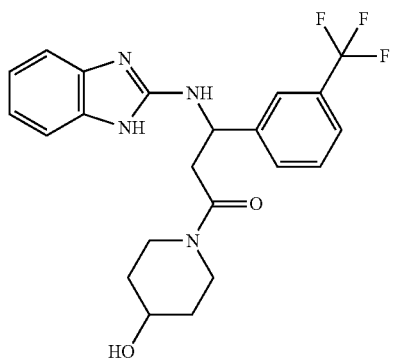 [SMILES: O=C(CC(Nc1nc2ccccc2[nH]1)c1cccc(C(F)(F)F)c1)N1CCC(O)CC1]

¹H NMR (400 MHz, DMSO-d₆): δ 7.83 (s, 1H), 7.76 (d, 1H, J=6.60 Hz), 7.57 (t, 2H, J=7.64 Hz), 7.12 (t, 2H, J=4.24 Hz), 6.88 (bs, 2H), 5.39 (d, 2H, J=6.68 Hz), 4.72 (dd, 1H, J=3.7, 7.6 Hz), 3.15-3.08 (m, 2H), 2.99-2.97 (m, 2H), 2.85-2.84 (m, 2H), 1.61 (bs, 2H), 1.20-1.14 (m, 3H);

MS: m/z 433.2 (M+1).

Example 6: 3-[(1H-1,3-benzodiazol-2-yl)amino]-1-(3-hydroxyazetidin-1-yl)-3-[3-(trifluoromethyl)phenyl]propan-1-one Prepared by the method described for Example 1 (Step 6) but using azetidin-3-ol in place of 2-(methylsulfanyl)ethan-1-amine.

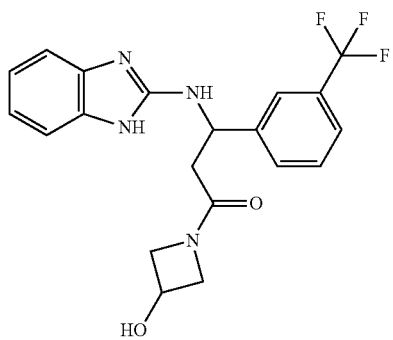 [SMILES: O=C(CC(Nc1nc2ccccc2[nH]1)c1cccc(C(F)(F)F)c1)N1CC(O)C1]

¹H NMR (400 MHz, DMSO-d₆): δ 7.88 (d, 1H, J=12.32 Hz), 7.81 (t, 1H, J=8.64 Hz), 7.71-7.63 (m, 2H), 7.38 (m, 2H), 7.24 (m, 2H), 5.75 (m, 1H), 5.39-5.37 (m, 3H), 4.42 (m, 1H), 4.31-4.22 (m, 1H), 4.03-3.97 (m, 1H), 3.88-3.55 (m, 2H), 2.89-2.67 (m, 2H);

MS: m/z 405.2 (M+1).

Example 7: 3-[(1H-1,3-benzodiazol-2-yl)amino]-N-(oxetan-3-ylmethyl)-3-[3-(trifluoromethyl)phenyl]propanamide Prepared by the method described for Example 1 (Step 6) but using oxetan-3-ylmethanamine in place of 2-(methylsulfanyl)ethan-1-amine

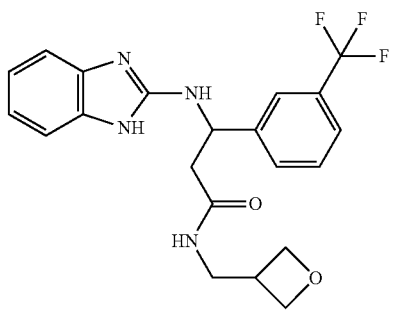 [SMILES: O=C(CC(Nc1nc2ccccc2[nH]1)c1cccc(C(F)(F)F)c1)NCC1COC1]

¹H NMR (400 MHz, DMSO-d₆): δ 10.86 (s, 1H), 8.06 (t, 1H, J=5.56 Hz), 7.78 (s, 1H), 7.71 (d, 1H, J=7.08 Hz), 7.58-7.52 (m, 2H), 7.40 (d, 1H, J=8.32 Hz), 7.11 (d, 2H, J=1.44 Hz), 6.84 (bs, 2H), 5.37 (t, 1H, J=7.76 Hz), 4.42 (dd, 2H, J=6.16, 7.60 Hz), 4.10 (t, 2H, J=5.96 Hz), 3.29-3.20 (m, 2H), 2.85 (t, 1H, J=7.40 Hz), 2.76-2.63 (m, 2H);

MS: m/z 419.2 (M+1).

Example 8: 3-[(1H-1,3-benzodiazol-2-yl)amino]-N-(oxolan-2-ylmethyl)-3-[3-(trifluoromethyl)phenyl]propanamide Prepared by the method described for Example 1 (Step 6) but using oxolan-2-ylmethanamine in place of 2-(methylsulfanyl)ethan-1-amine.

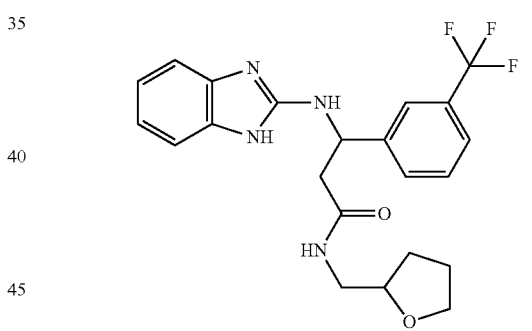

¹H NMR (400 MHz, DMSO-d₆): δ 10.83 (d, 1H, J=13.60 Hz), 8.00 (d, 1H, J=4.80 Hz), 7.76 (t, 2H, J=22.80 Hz), 7.56 (dd, 2H, J=8.0, 16.8 Hz), 7.38 (d, 1H, J=6.00 Hz), 7.09 (d, 2H, J=7.60 Hz), 6.88-6.79 (m, 2H), 5.37 (m, 1H), 3.65 (d, 2H, J=4.00 Hz), 3.57 (d, 2H, J=32.00 Hz), 3.13-2.98 (m, 2H), 2.80-2.64 (m, 2H), 1.67 (d, 2H, J=6.8 Hz), 1.28-1.23 (t, 1H, J=11.6 Hz);

MS: m/z 433.2 (M+1).

Example 9: 3-[(1H-1,3-benzodiazol-2-yl)amino]-N-[(3S)-oxolan-3-yl]-3-[3-(trifluoromethyl)phenyl]propanamide Prepared by the method described for Example 1 (Step 6) but using (3S)-oxolan-3-amine in place of 2-(methylsulfanyl)ethan-1-amine.

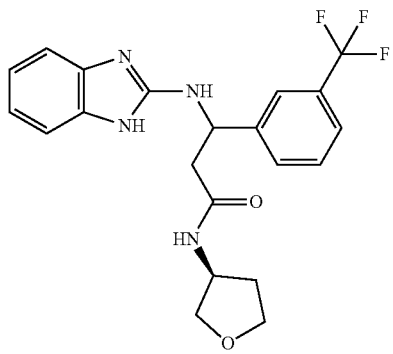 [SMILES: O=C(CC(Nc1nc2ccccc2[nH]1)c1cccc(C(F)(F)F)c1)N[C@H]1CCOC1]

¹H-NMR (400 MHz, DMSO-d₆): δ 10.1 (s, 1H), 8.17 (d, 1H, J=6.68 Hz), 7.77 (s, 1H), 7.73 (d, 1H, J=6.76 Hz), 7.59-7.53 (m, 3H), 7.22 (t, 2H, J=4.16 Hz), 6.88 (s, 2H), 5.39-5.34 (dd, 1H, J=6.84, 15.2 Hz), 4.15 (t, 1H, J=2.92 Hz), 3.67-3.57 (m, 3H), 3.25-3.19 (m, 1H), 2.77-2.62 (m, 2H), 2.01-1.92 (m, 1H), 1.57-1.49 (m, 1H);

MS: m/z 419.2 (M+1).

Example 10: 3-[(1H-1,3-benzodiazol-2-yl)amino]-N-(oxetan-3-yl)-3-[3-(trifluoromethyl)phenyl]propanamide Prepared by the method described for Example 1 (Step 6) but using oxetan-3-amine in place of 2-(methylsulfanyl)ethan-1-amine.

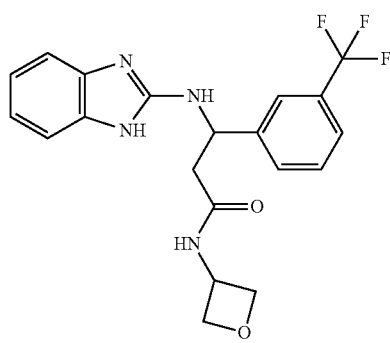 [SMILES: O=C(CC(Nc1nc2ccccc2[nH]1)c1cccc(C(F)(F)F)c1)NC1COC1]

¹H NMR (400 MHz, DMSO-d₆): δ 10.86 (s, 1H), 8.70 (d, 1H, J=6.40 Hz), 7.78 (s, 1H), 7.72 (d, 1H, J=7.20 Hz), 7.57 (dd, 2H, J=8.0, 10.0 Hz), 7.42 (d, 1H, J=6.00 Hz), 7.11-7.08 (m, 2H), 6.85-6.83 (dd, 2H, J=2.80, 5.60 Hz), 5.38 (d, 1H, J=5.60 Hz), 4.72-4.59 (m, 3H), 4.30 (t, 1H, J=6.00 Hz), 4.22 (t, 1H, J=6.00 Hz), 2.79-2.65 (m, 2H);

MS: m/z 405.2 (M+1).

Example 11: 4-{3-[(1H-1,3-benzodiazol-2-yl)amino]-3-[3-(trifluoromethyl)phenyl]propanoyl}-1-methylpiperazin-2-one Prepared by the method described for Example 1 (Step 6) but using 1-methylpiperazin-2-one in place of 2-(methylsulfanyl)ethan-1-amine.

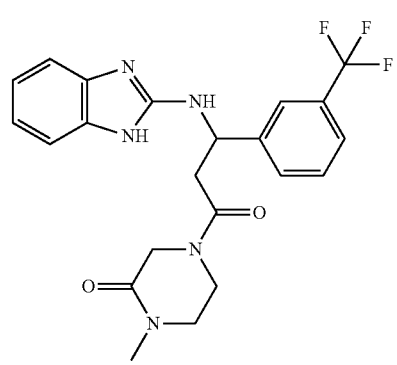 [SMILES: CN1CCN(C(=O)CC(Nc2nc3ccccc3[nH]2)c2cccc(C(F)(F)F)c2)CC1=O]

¹H NMR (400 MHz, Acetic acid-d₄) δ 7.87 (dd, 2H, J=5.2, 23.2 Hz), 7.66 (d, 1H, J=7.6 Hz), 7.6 (t, 1H, J=8 Hz) 7.40 (dd, 2H, J=3.2, 6 Hz), 7.26-7.24 (m, 2H), 5.63-5.54 (m, 1H), 4.44-4.19 (m, 2H), 3.97-3.78 (m, 2H), 3.66-3.35 (m, 3H), 3.15-3.08 (m, 1H), 2.99 (s, 3H);

MS: m/z 446.2 (M+1).

Example 12: 3-[(1H-1,3-benzodiazol-2-yl)amino]-N-[2-(phenylmethanesulfonamido)ethyl]-3-[3-(trifluoromethyl)phenyl]propanamide Prepared by the method described for Example 1 (Step 6) but using N-(2-aminoethyl)-1-phenyl-methanesulfonamide in place of 2-(methylsulfanyl)ethan-1-amine.

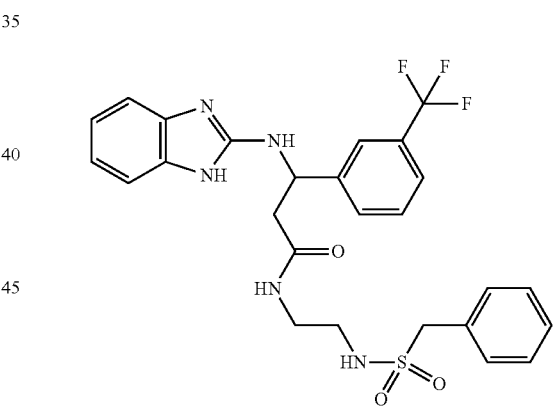

¹H NMR (400 MHz, MeOH-d₄) δ 7.81 (s, 1H), 7.75 (d, 1H, J=7.32 Hz), 7.69-7.62 (m, 2H), 7.40-7.29 (m, 9H), 5.38 (t, 1H, J=6.56 Hz), 4.29 (s, 2H), 3.24-3.15 (m, 2H), 2.97-2.92 (m, 4H);

MS: m/z 546.2 (M+1).

Example 13: 3-[(1H-1,3-benzodiazol-2-yl)amino]-1-[(3R)-3-hydroxypiperidin-1-yl]-3-[3-(trifluoromethyl)phenyl]propan-1-one Prepared by the method described for Example 1 (Step 6) but using (3R)-piperidin-3-ol in place of 2-(methylsulfanyl)ethan-1-amine.

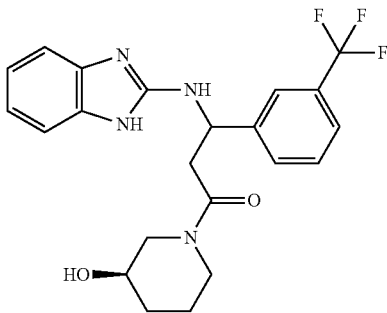 [SMILES: O=C(CC(Nc1nc2ccccc2[nH]1)c1cccc(C(F)(F)F)c1)N1CCC[C@@H](O)C1]

¹H NMR (400 MHz AcOH-d₄): δ 7.89 (s, 1H), 7.85 (d, 1H, J=7.60 Hz), 7.66 (d, 1H, J=7.60 Hz), 7.60 (t, 1H, J=7.60 Hz), 7.42-7.40 (m, 2H), 7.27-7.25 (m, 2H), 5.61 (m, 1H), 4.02-3.86 (m, 1H), 3.80-3.70 (m, 1H), 3.68-3.44 (m, 4H), 3.34-3.29 (m, 1H), 3.14-3.07 (m, 1H), 1.93-1.72 (m, 2H), 1.45-1.43 (m, 1H);

MS: m/z 433.2 (M+1).

Example 14: 3-[(1H-1,3-benzodiazol-2-yl)amino]-1-[(3R)-3-hydroxypyrrolidin-1-yl]-3-[3-(trifluoromethyl)phenyl]propan-1-one; trifluoroacetic acid Prepared by the method described for Example 1 (Step 6) but using (3R)-pyrrolidin-3-ol in place of 2-(methylsulfanyl)ethan-1-amine.

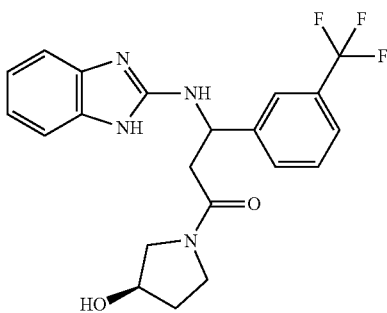 [SMILES: O=C(CC(Nc1nc2ccccc2[nH]1)c1cccc(C(F)(F)F)c1)N1CC[C@@H](O)C1]

¹H NMR (400 MHz, DMSO-d₆): δ 12.85 (bs, 2H), 9.52 (t, 1H, J=8.80 Hz), 7.89 (s, 1H), 7.82 (d, 1H, J=6.88 Hz), 7.71-7.63 (m, 2H), 7.40 (dd, 2H, J=3.20, 5.84 Hz), 7.25 (dd, 2H, J=3.16, 5.84 Hz), 5.44-5.43 (m, 1H), 4.96 (bs, 1H), 4.31-4.24 (m, 1H), 3.54-3.48 (m, 2H), 3.39-3.32 (m, 2H), 3.28-2.91 (m, 2H), 1.84-1.74 (m, 2H);

MS: m/z 419.2 (M+1).

Example 15: 3-[(1H-1,3-benzodiazol-2-yl)amino]-1-[(3S)-3-hydroxypyrrolidin-1-yl]-3-[3-(trifluoromethyl)phenyl]propan-1-one; trifluoroacetic acid Prepared by the method described for Example 1 (Step 6) but using (3S)-pyrrolidin-3-ol in place of 2-(methylsulfanyl)ethan-1-amine.

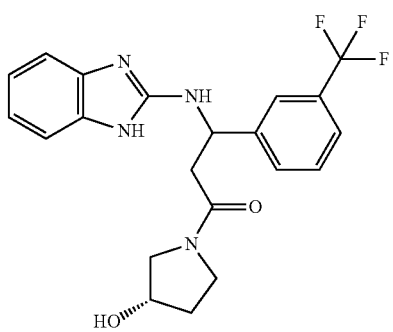 [SMILES: O=C(CC(Nc1nc2ccccc2[nH]1)c1cccc(C(F)(F)F)c1)N1CC[C@H](O)C1]

¹H NMR (400 MHz, DMSO-d₆): δ 12.85 (bs, 2H), 9.52 (t, 1H, J=8.80), 7.88 (s, 1H), 7.81 (d, 1H, J=7.60 Hz), 7.70-7.62 (m, 2H), 7.40-7.37 (m, 2H), 7.26-7.23 (m, 2H), 5.45-5.40 (m, 1H), 4.98 (bs, 1H), 4.30-4.23 (m, 1H), 3.53-3.48 (m, 2H), 3.31-3.23 (m, 2H), 3.12-2.94 (m, 2H), 1.90-1.73 (m, 2H);

MS: m/z 419.2 (M+1).

Example 16: 3-[(1H-1,3-benzodiazol-2-yl)amino]-N-(3-hydroxypropyl)-3-[3-(trifluoromethyl)phenyl]propanamide Prepared by the method described for Example 1 (Step 6) but using 3-aminopropan-1-ol in place of 2-(methylsulfanyl)ethan-1-amine.

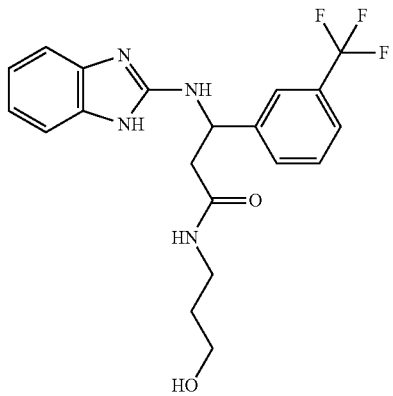 [SMILES: O=C(CC(Nc1nc2ccccc2[nH]1)c1cccc(C(F)(F)F)c1)NCCCO]

¹H NMR (400 MHz DMSO-d₆): δ 10.85 (s, 1H), 7.89 (t, 1H, J=5.20 Hz), 7.76 (s, 1H), 7.70 (d, 1H, J=7.20), 7.55 (m, 2H), 7.38 (d, 1H, J=8.80 Hz), 7.08 (d, 2H, J=8.80 Hz), 6.83 (bs, 2H), 5.35 (m, 1H,), 4.34 (t, 1H, J=4.80 Hz), 3.26 (q, 2H, J=6.00, 11.60 Hz), 3.02 (q, 2H, J=6.40, 13.20 Hz), 2.74-2.60 (m, 2H), 1.41 (m, 2H);

MS: m/z 407.2 (M+1).

Example 17: 3-[(1H-1,3-benzodiazol-2-yl)amino]-N-(3-hydroxypropyl)-N-methyl-3-[3-(trifluoromethyl)phenyl]propanamide Prepared by the method described for Example 1 (Step 6) but using 3-(methylamino)propan-1-ol in place of 2-(methylsulfanyl)ethan-1-amine.

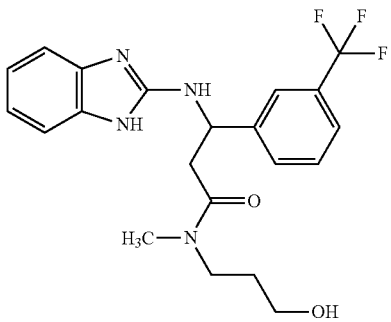 [SMILES: CN(CCCO)C(=O)CC(Nc1nc2ccccc2[nH]1)c1cccc(C(F)(F)F)c1]

¹H NMR (400 MHz, MeOH-d₄): δ 7.83 (s, 1H), 7.77 (d, 1H, J=6.80), 7.56 (t, 2H, J=6.64 Hz), 7.21 (dd, 2H, J=3.16, 5.80 Hz), 7.01 (dd, 2H, J=3.16, 5.76 Hz), 5.44 (t, 1H, J=5.32 Hz), 3.59-3.54 (m, 1H), 3.50-3.37 (m, 3H), 3.27-3.15 (m, 1H), 2.97 (s, 3H), 2.88 (s, 1H), 1.76-1.62 (m, 2H);

MS: m/z 421.2 (M+1).

The above product was resolved by normal phase HPLC (Condition: Chiral Phenomenex lux cellulose-2 (250×4.6) mm 5μ/Hexane: 20 mM ammonia in EtOH (70:30)/flow rate: 1.0 ml/min) to obtain the two enantiomers.

Example 17a: (−) 3-[(1H-1,3-benzodiazol-2-yl) amino]-N-(3-hydroxypropyl)-N-methyl-3-[3-(trifluoromethyl)phenyl]propanamide The (−) enantiomer was the first to elute off the column.

¹H NMR (400 MHz, MeOH-d₄): δ 7.82 (s, 1H), 7.76 (d, 1H, J=6.80 Hz), 7.56-7.53 (m, 2H), 7.18 (m, 2H), 6.98 (m, 2H), 5.46-5.42 (m, 1H), 3.56-3.53 (m, 1H), 3.45-3.38 (m, 3H), 3.25-3.13 (m, 1H), 2.95 (s, 3H), 2.86 (s, 1H), 1.73-1.62 (m, 2H);

MS: m/z 421.2 (M+1); $[\alpha]_D^{27.6}$=(−)17.23° (MeOH, c=0.65).

Example 17b: (+) 3-[(1H-1,3-benzodiazol-2-yl) amino]-N-(3-hydroxypropyl)-N-methyl-3-[3-(trifluoromethyl)phenyl]propanamide The (+) enantiomer was the second off the column.

¹H NMR (400 MHz, MeOH-d₄): δ 7.82 (s, 1H), 7.76 (d, 1H, J=6.40 Hz), 7.58-7.52 (m, 2H), 7.20 (m, 2H), 7.00 (m, 2H), 5.46-5.42 (m, 1H), 3.56-3.53 (m, 1H), 3.45-3.38 (m, 3H), 3.25-3.9 (m, 1H), 2.95 (s, 3H), 2.86 (s, 1H), 1.73-1.66 (m, 2H);

MS: m/z 421.2 (M+1); $[\alpha]_D^{27.8}$=(+)14.75 (MeOH, c=0.70)

Example 18: 3-[(1H-1,3-benzodiazol-2-yl)amino]-N-[(1,3-oxazol-2-yl)methyl]-3-[3-(trifluoromethyl) phenyl]propanamide Prepared by the method described for Example 1 (Step 6) but using 1,3-oxazol-2-ylmethanamine in place of 2-(methylsulfanyl)ethan-1-amine.

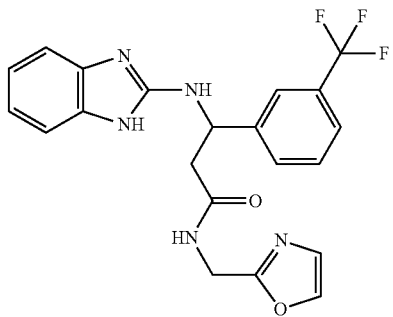 [SMILES: O=C(CC(Nc1nc2ccccc2[nH]1)c1cccc(C(F)(F)F)c1)NCc1ncco1]

¹H NMR (400 MHz, DMSO-d₆): δ 10.83 (s, 1H), 8.62 (t, 1H, J=5.60 Hz), 7.94 (s, 1H), 7.84 (s, 1H), 7.72 (d, 1H, J=7.20 Hz), 7.58-7.51 (m, 2H), 7.37 (d, 1H, J=8.80 Hz), 7.10 (d, 3H, J=8.40 Hz), 6.87-6.82 (m, 2H), 5.40 (t, 1H, J=8.80), 4.32 (d, 2H, J=5.60 Hz), 2.85-2.74 (m, 2H);

MS: m/z 430.2 (M+1).

Example 19: 3-[(1H-1,3-benzodiazol-2-yl)amino]-N-[(1-methyl-1H-imidazol-2-yl)methyl]-3-[3-(trifluoromethyl)phenyl]propanamide Prepared by the method described for Example 1 (Step 6) but using (1-methyl-1H-imidazol-2-yl)methanamine in place of 2-(methylsulfanyl)ethan-1-amine.

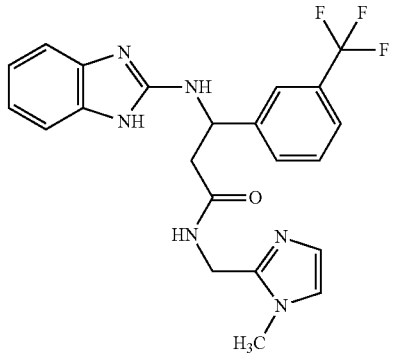 [SMILES: Cn1ccnc1CNC(=O)CC(Nc1nc2ccccc2[nH]1)c1cccc(C(F)(F)F)c1]

¹H NMR (400 MHz, DMSO-d₆ and D₂O): δ 7.85 (s, 1H), 7.76 (d, 1H, J=7.60 Hz), 7.69 (d, 1H, J=7.60 Hz), 7.63 (t, 1H, J=8.00 Hz), 7.58 (s, 1H), 7.52 (s, 1H), 7.40-7.38 (m, 2H), 7.25-7.23 (m, 2H), 5.40 (q, 1H, J=8.00 Hz), 4.86-4.49 (m, 2H), 3.65 (s, 3H), 3.00 (d, 2H, J=7.20 Hz);

MS: m/z 443.2 (M+1).

Example 20: 3-[(1H-1,3-benzodiazol-2-yl)amino]-3-(3-chloro-4-methylphenyl)-N-ethyl-N-(2-hydroxyethyl)propanamide Prepared by the method described for Example 1 (Step 1 to Step 6) but using 3-chloro-4-methylbenzaldehyde in place of 3-(trifluoromethyl)benzaldehyde in Step 1 and 2-(ethylamino)ethan-1-ol in place of 2-(methylsulfanyl)ethan-1-amine in Step 6.

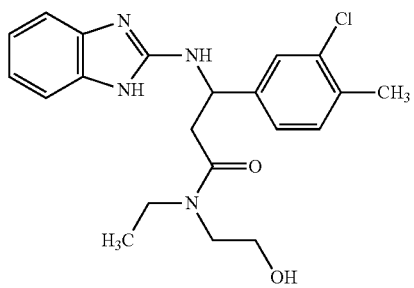 [SMILES: CCN(CCO)C(=O)CC(Nc1nc2ccccc2[nH]1)c1ccc(C)c(Cl)c1]

¹H NMR (400 MHz, MeOH-d₄): δ 7.48 (s, 1H), 7.32 (d, 1H, J=8.00 Hz), 7.25 (d, 1H, J=7.92 Hz), 7.19-7.16 (m, 2H), 6.97-6.94 (m, 2H), 5.30 (dd, 1H, J=5.88, 10.84 Hz), 3.67 (t, 1H, J=5.52 Hz), 3.59 (t, 1H, J=6.12 Hz), 3.42-3.38 (m, 4H), 3.21-3.15 (m, 1H), 2.97-2.89 (m, 1H), 2.33 (s, 3H), 1.07 (dt, 3H, J=7.08 Hz);

MS: m/z 401.2 (M+1).

Example 21: 3-[(1H-1,3-benzodiazol-2-yl)amino]-N-(cyanomethyl)-3-[3-(trifluoromethyl)phenyl]propanamide Prepared by the method described for Example 1 (Step 6) but using 2-aminoacetonitrile in place of 2-(methylsulfanyl)ethan-1-amine.

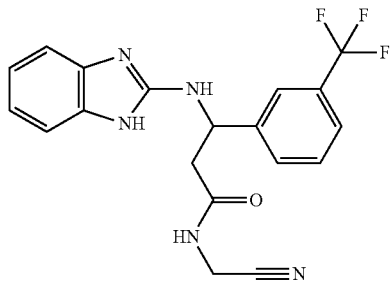 [SMILES: N#CCNC(=O)CC(Nc1nc2ccccc2[nH]1)c1cccc(C(F)(F)F)c1]

¹H NMR (400 MHz, DMSO-d₆) δ 9.64 (bs, 1H, exchangeable), 8.80 (t, 1H, J=5.68 Hz, exchangeable), 7.86 (s, 1H), 7.77 (d, 1H, J=7.4 Hz), 7.69 (d, 1H, J=7.68 Hz), 7.65-7.61 (m, 1H), 7.39-7.37 (m, 2H), 7.25-7.22 (m, 2H), 5.41 (q, 1H, J=7.48 Hz), 4.13 (d, 2H, J=5.52 Hz), 2.96 (d, 2H, J=6.92 Hz);

MS: m/z 388.2 (M+1).

Example 22: 3-[(1H-1,3-benzodiazol-2-yl)amino]-N-[(dimethylcarbamoyl)methyl]-3-[3-(trifluoromethyl)phenyl]propanamide Prepared by the method described for Example 1 (Step 6) but using 2-amino-N,N-dimethylacetamide in place of 2-(methylsulfanyl)ethan-1-amine.

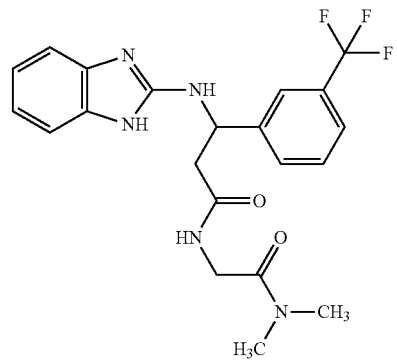 [SMILES: CN(C)C(=O)CNC(=O)CC(Nc1nc2ccccc2[nH]1)c1cccc(C(F)(F)F)c1]

¹H NMR (400 MHz, DMSO-d₆) δ 11.15 (bs, 1H), 8.07 (t, 1H, J=5.2 Hz), 7.82 (s, 1H), 7.74 (d, 1H, J=7.2 Hz), 7.59-7.52 (m, 2H), 7.13 (t, 2H, J=4.4 Hz), 6.89 (s, 2H), 5.36 (q, 1H, J=7.6 Hz), 3.89 (d, 2H, J=5.2 Hz), 2.88 (s, 3H), 2.81 (s, 3H), 2.78-2.72 (m, 2H);

MS: m/z 434.2 (M+1).

Example 23: Ethyl 2-{3-[(1H-1,3-benzodiazol-2-yl)amino]-3-[3-(trifluoromethyl)phenyl]propanamido}acetate; hydrochloric acid Prepared by the method described for Example 1 (Step 6) but using ethyl 2-aminoacetate in place of 2-(methylsulfanyl)ethan-1-amine.

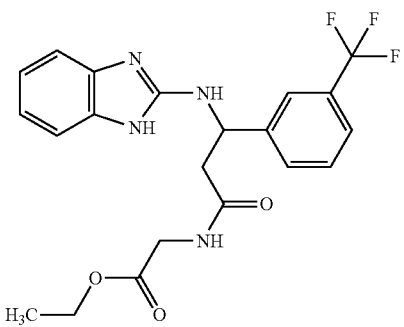 [SMILES: CCOC(=O)CNC(=O)CC(Nc1nc2ccccc2[nH]1)c1cccc(C(F)(F)F)c1]

A solution of 3-[(1H-1,3-benzodiazol-2-yl)amino]-N-(cyanomethyl)-3-[3-(trifluoromethyl)phenyl]propanamide (Example 21) (0.25 g, 0.64 mmol) in ethanol (50 mL) at −5° C. was purged with gaseous HCl for 30 min. The solution was allowed to warm to ambient temperature and stirred for 12 h. The reaction mixture was evaporated to afford the title product (0.075 g) as off white solid, as a hydrochloride salt.

¹H NMR (400 MHz, DMSO-d₆) δ 12.84 (bs, 2H, exchangeable), 9.78 (bs, 1H, exchangeable), 8.57 (t, 1H, J=5.92 Hz, exchangeable), 7.90 (s, 1H), 7.82 (d, 1H, J=7.52 Hz), 7.69-7.61 (m, 2H), 7.39-7.37 (m, 2H), 7.23-7.21 (m, 2H), 5.44 (dd, 1H, J=8.36, 14.2 Hz), 4.02 (q, 2H, J=7.08 Hz), 3.80 (d, 2H, J=6.20 Hz), 3.01 (dd, 1H, J=8.48, 15.52 Hz), 2.90 (dd, 1H, J=5.32, 15.56 Hz), 1.11 (t, 3H, J=7.12 Hz);

MS: m/z 435.2 (M+1).

Example 24: N-(2-aminoethyl)-2-[(1H-1,3-benzodiazol-2-yl)amino]-2-[3-(trifluoromethyl)phenyl]acetamide

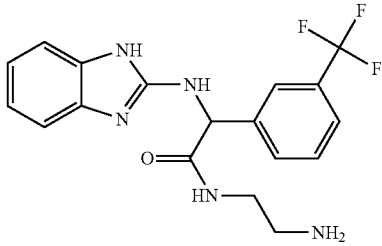

Step 1: Methyl 2-amino-2-[3-(trifluoromethyl)phenyl]acetate hydrochloride salt

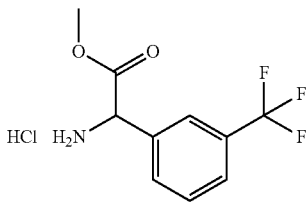 [SMILES: Cl ; COC(=O)C(N)c1cccc(C(F)(F)F)c1]

To a well stirred solution of commercially available 2-amino-2-(3-(trifluoromethyl)phenyl)acetic acid (7 g, 32 mmol) in methanol (70 mL) was added thionyl chloride (4.6 mL, 64 mmol) at 0° C. and refluxed for 16 h. The reaction mixture was concentrated. The residue was washed with diethyl ether (3×100 mL) to afford the title compound as hydrochloride salt (7 g).

$^1$H NMR (400 MHz, DMSO-$d_6$) δ 9.32 (s, 3H, exchangeable), 7.98 (s, 1H), 7.98-7.80 (m, 2H), 7.71 (t, 1H, J=7.6 Hz), 5.48 (d, 1H, J=4.40 Hz), 3.71 (s, 3H);
MS: m/z 234.0 (M+1).

Step 2: Methyl 2-[(1H-1,3-benzodiazol-2-yl)amino]-2-[3-(trifluoromethyl)phenyl]acetate

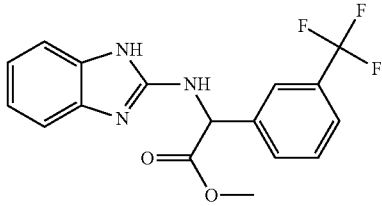 [SMILES: COC(=O)C(Nc1nc2ccccc2[nH]1)c1cccc(C(F)(F)F)c1]

A mixture of methyl 2-amino-2-[3-(trifluoromethyl)phenyl]acetate (from Step 1) (10 g, 66 mmol) and 2-chloro-1H-1,3-benzodiazole (15.3 g, 66 mmol) in acetonitrile (160 mL) was irradiated in a microwave oven at 145° C. for 3 h. The crude product was purified by column chromatography on silica gel (1:0.03 chloroform/methanol) to give the desired product as an off-white solid (12 g).

$^1$H NMR (400 MHz, DMSO-$d_6$) δ 10.75 (s, 1H), 7.90 (s, 1H), 7.84 (d, 1H, J=7.68 Hz), 7.79 (d, 1H, J=7.60 Hz), 7.73 (d, 1H, J=7.64 Hz), 7.66 (t, 1H, J=7.72 Hz), 7.18 (d, 2H, J=8.36 Hz), 6.90 (s, 2H), 5.78 (d, 1H, J=7.80 Hz), 3.67 (s, 3H);
MS: m/z 350.0 (M+1).

Example 24, Step 3: N-(2-aminoethyl)-2-[(1H-1,3-benzodiazol-2-yl)amino]-2-[3-(trifluoromethyl)phenyl]acetamide

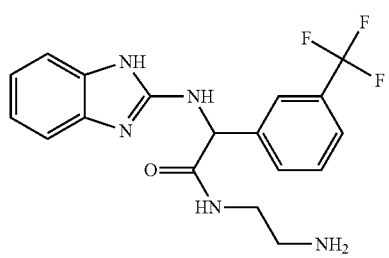 [SMILES: NCCNC(=O)C(Nc1nc2ccccc2[nH]1)c1cccc(C(F)(F)F)c1]

A mixture of methyl 2-[(1H-1,3-benzodiazol-2-yl)amino]-2-[3-(trifluoromethyl)phenyl]acetate (form Step 2) (1 mmol) and ethane-1,2-diamine (1 mmol) in acetonitrile (3 mL) was irradiated in a microwave oven at 130° C. for 3 h. The crude product was purified by silica gel (60-120 mesh) column chromatography using 15% methanol in chloroform as eluent to afford the title product (0.05 g) as an off-white solid;

1H NMR (400 MHz, DMSO-$d_6$ & $D_2O$): δ 7.87 (s, 1H), 7.80 (d, J=7.68 Hz, 1H), 7.62 (dd, 2H, J=7.64, 18.32 Hz), 7.16 (t, 2H, J=4.00 Hz), 6.89 (dd, 2H, J=3.16, 5.76 Hz), 5.59 (s, 1H), 3.13 (dd, 1H, J=6.44, 13.10 Hz), 3.00 (dd, 1H, J=6.72, 13.02 Hz), 2.54 (dd, 2H, J=13.44, 16.44 Hz);
MS: m/z 378.2 (M+1).

Example 25: 2-[(1H-1,3-benzodiazol-2-yl)amino]-N-[2-(dimethylamino)ethyl]-N-methyl-2-[3-(trifluoromethyl)phenyl]acetamide Prepared by the method described for Example 24 (Step 3) but using [2-(dimethylamino)ethyl](methyl)amine in place of ethane-1,2-diamine.

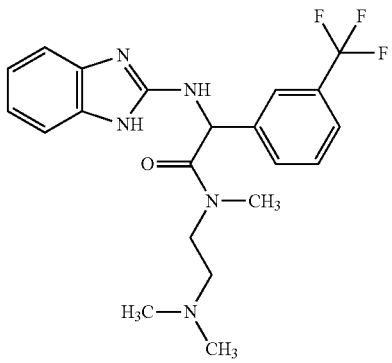 [SMILES: CN(C)CCN(C)C(=O)C(Nc1nc2ccccc2[nH]1)c1cccc(C(F)(F)F)c1]

$^1$H NMR (400 MHz, DMSO-$d_6$): δ 10.53 (s, 1H), 7.83 (dd, 2H, J=8.6, 20.4 Hz), 7.65 (dd, 2H, J=6.2, 18.96 Hz), 7.41 (m, 1H), 7.17 (d, 2H, J=8.40 Hz), 6.88 (s, 2H), 6.10 (m, 1H), 3.67 (m, 1H), 3.23 (t, 1H, J=6.76 Hz), 3.01-2.90 (m, 3H), 2.34-2.18 (m, 2H), 2.12 (d, 6H, J=5.28 Hz);
MS: m/z 420.2 (M+1).

Example 26: 2-[(1H-1,3-benzodiazol-2-yl)amino]-1-(piperazin-1-yl)-2-[3-(trifluoromethyl)phenyl]ethan-1-one Prepared by the method described for Example 24 (Step 3) but using piperazine in place of ethane-1,2-diamine.

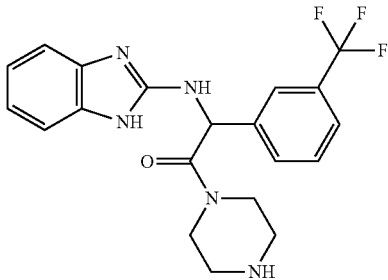 [SMILES: O=C(C(Nc1nc2ccccc2[nH]1)c1cccc(C(F)(F)F)c1)N1CCNCC1]

$^1$H NMR (400 MHz, DMSO-d$_6$ & D$_2$O) δ 7.87 (s, 1H), 7.82 (d, 1H, J=7.52 Hz), 7.68-7.59 (m, 2H), 7.15 (d, 2H, J=7.60 Hz), 6.86 (bs, 2H), 6.11 (d, 1H, J=8.48 Hz), 3.57-3.39 (m, 4H), 2.63-2.56 (m, 2H), 2.33-2.22 (m, 2H);
MS: m/z 404.2 (M+1).

Example 27: 2-[(1H-1,3-benzodiazol-2-yl)amino]-1-(4-methylpiperazin-1-yl)-2-[3-(trifluoromethyl)phenyl]ethan-1-one Prepared by the method described for Example 24 (Step 3) but using 1-methylpiperazine in place of ethane-1,2-diamine.

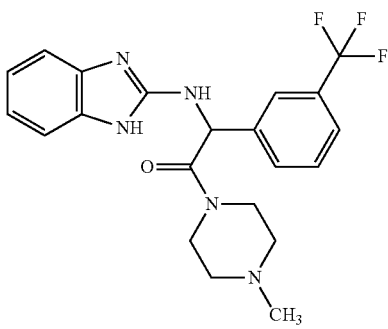 [SMILES: CN1CCN(C(=O)C(Nc2nc3ccccc3[nH]2)c2cccc(C(F)(F)F)c2)CC1]

$^1$H NMR (400 MHz, DMSO-d$_6$) δ 10.54 (s, 1H), 7.86 (d, 2H, J=11.44 Hz), 7.68 (d, 1H, J=7.40 Hz), 7.62 (t, 1H, J=7.52 Hz), 7.44 (d, 1H, J=8.44 Hz), 7.16 (d, 2H, J=7.40 Hz), 6.92-6.84 (m, 2H), 6.13 (d, 1H, J=8.44 Hz), 3.64-3.47 (m, 4H), 2.33-2.30 (m, 2H), 2.10 (s, 4H), 1.84-1.82 (m, 1H);
LCMS: m/z 418.2 (M+1).

The above product was resolved into its two enantiomers by normal phase HPLC (Condition: Chiral Pak AD-H (250× 4.6) mm 5μ/Hexane:Ethanol (70:30)/flow rate: 1.0 ml/min).

Example 27a: (−)2-[(1H-1,3-benzodiazol-2-yl)amino]-1-(4-methylpiperazin-1-yl)-2-[3-(trifluoromethyl)phenyl]ethan-1-one The (−) isomer was the first to elute off the column.
$^1$H NMR (400 MHz, DMSO-d$_6$) δ 10.54 (s, 1H), 7.85 (d, 2H, J=12.20 Hz), 7.68 (d, 1H, J=7.40 Hz), 7.63 (t, 1H, J=7.60 Hz), 7.46 (d, 1H, J=8.52 Hz), 7.16 (d, 2H, J=8.88 Hz), 6.88 (bs, 2H), 6.13 (d, 1H, J=8.56 Hz), 3.67-3.43 (m, 4H), 2.33-2.30 (m, 2H), 2.10 (s, 4H), 1.84-1.82 (m, 1H);
MS: m/z 418.2 (M+1); $[\alpha]_D^{26.7}$=(−)138.00° (MeOH, c=0.1).

Example 27b: (+)2-[(1H-1,3-benzodiazol-2-yl)amino]-1-(4-methylpiperazin-1-yl)-2-[3-(trifluoromethyl)phenyl]ethan-1-one The (+) isomer was the second to elute off the column.
$^1$H NMR (400 MHz, DMSO-d$_6$) δ 10.54 (s, 1H), 7.85 (d, 2H, J=11.96 Hz), 7.68 (d, 1H, J=7.84 Hz), 7.62 (t, 1H, J=7.64 Hz), 7.44 (d, 1H, J=8.52 Hz), 7.16 (d, 2H, J=8.44 Hz), 6.92-6.84 (m, 2H), 6.13 (d, 1H, J=8.56 Hz), 3.64-3.47 (m, 4H), 2.33-2.30 (m, 2H), 2.10 (s, 4H), 1.84-1.82 (m, 1H);
MS: m/z 418.2 (M+1); $[\alpha]_D^{26.6}$=(+)137.00° (MeOH, c=0.1).

Example 28: 2-[(1H-1,3-benzodiazol-2-yl)amino]-1-[3-(dimethylamino)azetidin-1-yl]-2-[3-(trifluoromethyl)phenyl]ethan-1-one; hydrochloric acid Prepared by the method described for Example 24 (Step 3) but using N,N-dimethylazetidin-3-amine in place of ethane-1,2-diamine.

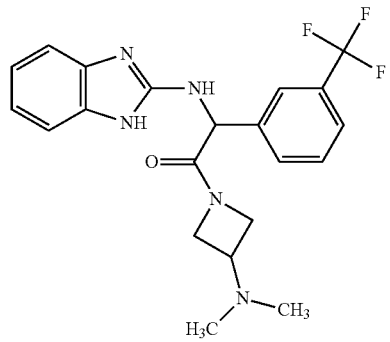 [SMILES: CN(C)C1CN(C(=O)C(Nc2nc3ccccc3[nH]2)c2cccc(C(F)(F)F)c2)C1]

1H NMR (400 MHz, DMSO-d$_6$): δ 11.40 (d, 1H, J=69.84 Hz), 9.93 (s, 1H), 7.95 (t, 2H, J=9.60 Hz), 7.80 (t, 1H, J=6.08 Hz), 7.73 (t, 1H, J=7.00 Hz), 7.46 (t, 2H, J=3.24 Hz), 7.24 (d, 2H, J=12.84 Hz), 6.21-6.15 (m, 1H), 4.93 (d, 2H, J=7.00 Hz), 4.29-4.10 (m, 4H), 2.77 (s, 3H), 2.68 (s, 3H);
MS: m/z 418.2 (M+1).

Example 29: 2-[(1H-1,3-benzodiazol-2-yl)amino]-1-(pyrrolidin-1-yl)-2-[3-(trifluoromethyl)phenyl]ethan-1-one Prepared by the method described for Example 24 (Step 3) but using pyrrolidine in place of ethane-1,2-diamine. The product was purified by silica gel (60-120 mesh) column chromatography using 3% methanol in chloroform as eluent.

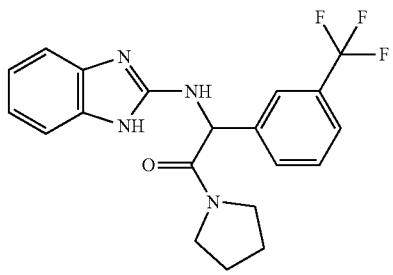 [SMILES: O=C(C(Nc1nc2ccccc2[nH]1)c1cccc(C(F)(F)F)c1)N1CCCC1]

¹H NMR (400 MHz, DMSO-d₆) δ 7.87 (s, 1H), 7.81 (d, 2H, J=7.56 Hz), 7.67 (d, 1H, J=7.8 Hz), 7.61 (t, 1H, J=7.6 Hz), 7.16 (t, 2H, J=4.16 Hz), 6.89 (bs, 1H), 5.87 (d, 1H, J=8.36 Hz), 3.84-3.82 (m, 1H), 3.40-3.20 (m, 3H), 1.88-1.68 (m, 4H);

MS: m/z 389.2 (M+1).

Example 30: 2-[(1H-1,3-benzodiazol-2-yl)amino]-N-(2-hydroxyethyl)-N-methyl-2-[3-(trifluoromethyl)phenyl]acetamide Prepared by the method described for Example 29 but using 2-(methylamino)ethan-1-ol in place of pyrrolidine.

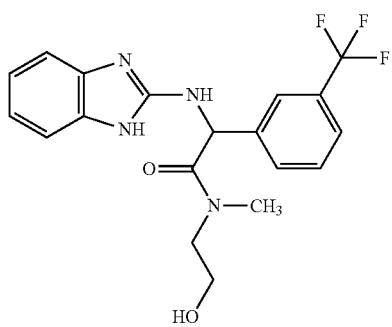 [SMILES: CN(CCO)C(=O)C(Nc1nc2ccccc2[nH]1)c1cccc(C(F)(F)F)c1]

¹H NMR (400 MHz, DMSO-d₆): δ 10.54 (s, 1H), 7.83 (dd, 2H, J=7.04 Hz), 7.67 (d, 1H, J=7.60 Hz), 7.62 (t, 1H, J=7.56 Hz), 7.51-7.38 (m, 1H), 7.16 (d, 2H, J=5.16 Hz), 6.88 (s, 2H), 6.18-6.05 (m, 1H), 5.27 (s, 1H), 4.68 (d, 1H, J=4.76 Hz), 3.64 (d, 1H, J=9.48 Hz), 3.46 (t, 2H, J=2.80 Hz), 3.07 (s, 3H);

MS: m/z 393.2 (M+1).

Example 31: 2-[(1H-1,3-benzodiazol-2-yl)amino]-1-(piperidin-1-yl)-2-[3-(trifluoromethyl)phenyl]ethan-1-one Prepared by the method described for Example 29 but using piperidine in place of pyrrolidine.

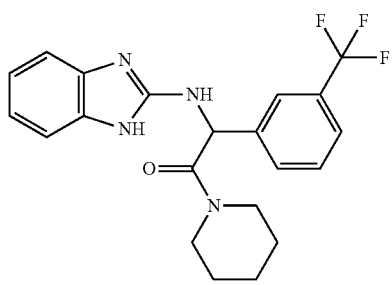 [SMILES: O=C(C(Nc1nc2ccccc2[nH]1)c1cccc(C(F)(F)F)c1)N1CCCCC1]

¹H NMR (400 MHz, DMSO-d₆) δ 10.57 (s, 1H), 7.86 (s, 1H), 7.84 (d, 1H, J=7.44 Hz), 7.67 (d, 1H, J=7.44 Hz), 7.62 (t, 1H, J=7.56 Hz), 7.42 (d, 1H, J=7.00 Hz), 7.16 (d, 2H, J=8.84 Hz), 6.88 (s, 2H), 6.11 (d, 1H, J=8.44 Hz), 3.60 (m, 1H), 3.52 (m, 2H), 1.47 (m, 5H), 1.24 (m, 2H);

MS: m/z 403.2 (M+1).

Example 32: 2-[(1H-1,3-benzodiazol-2-yl)amino]-1-(morpholin-4-yl)-2-[3-(trifluoromethyl)phenyl]ethan-1-one Prepared by the method described for Example 29 but using morpholine in place of pyrrolidine.

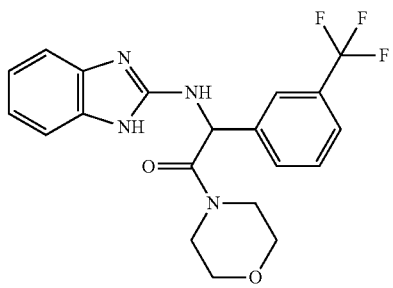 [SMILES: O=C(C(Nc1nc2ccccc2[nH]1)c1cccc(C(F)(F)F)c1)N1CCOCC1]

¹H NMR (400 MHz, DMSO-d₆) δ 10.58 (s, 1H), 7.89 (s, 1H), 7.83 (d, 1H, J=7.52 Hz), 7.68 (d, 1H, J=7.76 Hz), 7.62 (t, 1H, J=7.76 Hz), 7.53 (d, 1H, J=8.60 Hz), 7.16 (d, 2H, J=7.40 Hz), 6.92-6.85 (m, 2H), 6.14 (d, 1H, J=8.56 Hz), 3.77-3.73 (m, 1H), 3.57-3.45 (m, 6H), 3.28-3.24 (m, 1H);

MS: m/z 405.2 (M+1).

Example 33: 2-[(1H-1,3-benzodiazol-2-yl)amino]-1-[4-(propane-2-sulfonyl)piperazin-1-yl]-2-[3-(trifluoromethyl)phenyl]ethan-1-one Prepared by the method described for Example 29 but using 1-(propane-2-sulfonyl)piperazine in place of pyrrolidine.

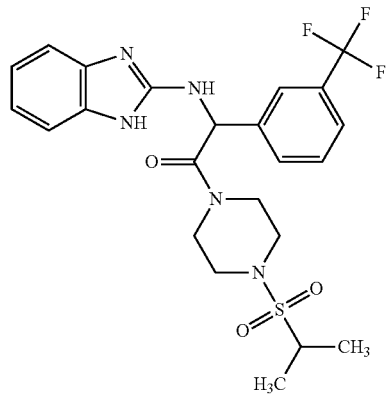 [SMILES: CC(C)S(=O)(=O)N1CCN(C(=O)C(Nc2nc3ccccc3[nH]2)c2cccc(C(F)(F)F)c2)CC1]

1H NMR (400 MHz, DMSO-d₆): δ 10.57 (s, 1H), 7.9 (s, 1H), 7.85 (d, 1H, J=7.48 Hz), 7.70 (d, 1H, J=7.52 Hz), 7.64 (t, 1H, J=7.56 Hz), 7.55 (d, 1H, J=7.04 Hz), 7.17 (d, 2H, J=7.84 Hz), 6.89 (dd, 2H, J=7.96, 12.50 Hz), 6.16 (d, 1H, J=8.48 Hz), 3.83 (s, 1H), 3.65 (s, 1H), 3.51 (m, 1H), 3.22 (m, 1H), 3.08 (d, 2H, J=10.92 Hz), 2.81 (s, 1H), 2.74 (s, 6H);

MS: m/z 511.2 (M+1).

Example 34: 1-(azetidin-1-yl)-2-[(1H-1,3-benzodiazol-2-yl)amino]-2-[3-(trifluoromethyl)phenyl]ethan-1-one Prepared by the method described for Example 29 but using azetidine in place of pyrrolidine.

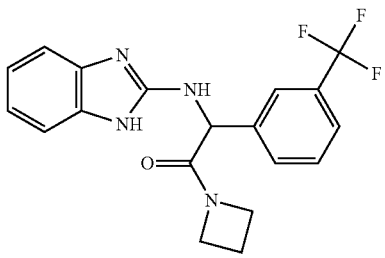 [SMILES: O=C(C(Nc1nc2ccccc2[nH]1)c1cccc(C(F)(F)F)c1)N1CCC1]

¹H NMR (400 MHz, DMSO-d₆) δ 10.52 (s, 1H), 7.86 (s, 1H), 7.80 (d, 1H, J=7.88 Hz), 7.67 (d, 1H, J=7.44 Hz), 7.62 (t, 1H, J=7.56 Hz), 7.51 (d, 1H, J=7.92 Hz), 7.15 (d, 2H, J=7.56 Hz), 6.89 (t, 2H, J=12.48 Hz), 5.65 (d, 1H, J=8.24 Hz), 4.53 (q, 1H, J=9.00 Hz), 4.05 (q, 1H, J=9.24 Hz), 3.95 (q, 1H, J=9.08 Hz), 3.83 (q, 1H, J=9.36 Hz), 2.27-2.18 (m, 2H);

MS: m/z 375.2 (M+1).

The above product was resolved into its two enantiomers by normal phase HPLC (Condition: Chiral Pak IA (250×4.6) mm 5µ/0.1% Diethylamine in Hexane: Ethanol (70:30)/flow rate: 1.0 ml/min). The products obtained from the chiral HPLC separation were concentrated, dissolved in ether, a saturated solution of hydrogen chloride in ether (2 mL) was added. The solid formed was filtered, washed with ether, dried to afford the two isomers as hydrochloride salts.

Example 34a: (+)1-(azetidin-1-yl)-2-[(1H-1,3-benzodiazol-2-yl)amino]-2-[3-(trifluoromethyl)phenyl]ethan-1-one; hydrochloric acid The (+) isomer was the first to elute off the column and was isolated as an off-white solid.

¹H NMR (400 MHz, DMSO-d₆) δ 12.82 (bs, 2H), 9.83 (bs, 1H), 7.95 (s, 1H), 7.90 (d, 1H, J=7.72 Hz), 7.78 (d, 1H, J=7.44 Hz), 7.70 (t, 1H, J=7.72), 7.44 (dd, 2H, J=5.76, 3.16 Hz), 7.24 (dd, 2H, J=5.84, 3.16 Hz), 5.96 (d, 1H, J=8.52 Hz), 4.57 (q, 1H, J=8.76 Hz), 4.00 (q, 1H, J=9.68 Hz), 3.87 (q, 2H, J=8.92 Hz), 2.29-2.16 (m, 2H);

MS: m/z 375.2 (M+1); $[\alpha]_D^{24.4}$=(+)143.478° (MeOH, c=0.115).

Example 34b: 1-(azetidin-1-yl)-2-[(1H-1,3-benzodiazol-2-yl)amino]-2-[3-(trifluoromethyl)phenyl]ethan-1-one; hydrochloric acid The (−) isomer was the second to elute off the column and was isolated as an off-white solid.

¹H NMR (400 MHz, DMSO-d₆) δ 12.85 (bs, 2H), 9.83 (bs, 1H), 7.95 (s, 1H), 7.91 (d, 1H, J=7.60 Hz), 7.77 (d, 1H, J=7.84 Hz), 7.70 (t, 1H, J=7.80), 7.44 (m, 2H), 7.25 (m, 2H), 6.00 (d, 1H, J=7.32 Hz), 4.58 (q, 1H, J=9.04 Hz), 4.00 (q, 1H, J=9.60 Hz), 3.88 (q, 2H, J=8.96 Hz), 2.23 (m, 2H);

MS: m/z 375.2 (M+1); $[\alpha]_D^{24.5}$=(−)155.00° (MeOH, c=0.100).

Example 35: 2-[(1H-1,3-benzodiazol-2-yl)amino]-N-(oxetan-3-yl)-2-[3-(trifluoromethyl)phenyl]acetamide Prepared by the method described for Example 29 but using oxetan-3-amine in place of pyrrolidine.

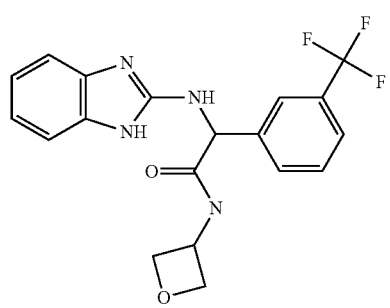 [SMILES: O=C(NC1COC1)C(Nc1nc2ccccc2[nH]1)c1cccc(C(F)(F)F)c1]

¹H NMR (400 MHz, DMSO-d₆) δ 10.48 (s, 1H), 9.34 (d, 1H, J=6.40 Hz), 7.88 (s, 1H), 7.81 (d, 1H, J=7.60 Hz), 7.63 (m, 2H), 7.53 (d, 1H, J=8.80 Hz), 7.14 (dd, 2H, J=19.20, 7.20 Hz), 6.91-6.87 (m, 2H), 5.71 (d, 1H, J=8.40 Hz), 4.70-4.65 (m, 3H), 4.45 (t, 1H, J=5.60 Hz), 4.32 (t, 1H, J=6.00 Hz);

MS: m/z 391.2 (M+1).

Example 36: 2-[(1H-1,3-benzodiazol-2-yl)amino]-1-{2-oxa-6-azaspiro[3.3]heptan-6-yl}-2-[3-(trifluoromethyl)phenyl]ethan-1-one Prepared by the method described for Example 29 but using 2-oxa-6-azaspiro[3.3]heptane in place of pyrrolidine.

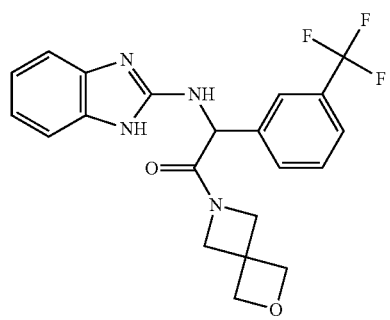 [SMILES: O=C(C(Nc1nc2ccccc2[nH]1)c1cccc(C(F)(F)F)c1)N1CC2(COC2)C1]

¹H NMR (400 MHz, DMSO-d₆) δ 10.53 (s, 1H), 7.84 (s, 1H), 7.79 (d, 1H, J=7.52 Hz), 7.67 (d, 1H, J=7.40 Hz), 7.61 (t, 1H, J=7.60 Hz), 7.53 (d, 1H, J=8.12 Hz), 7.15 (t, 2H, J=6.56 Hz), 6.92-6.85 (m, 2H), 5.63 (d, 1H, J=8.12 Hz), 4.76, (d, 1H, J=9.32 Hz), 4.71 (d, 1H, J=6.76 Hz), 4.66 (d, 1H, J=6.76 Hz), 4.62 (s, 2H), 4.25 (d, 1H, J=9.32 Hz), 4.13 (d, 1H, J=10.36 Hz), 4.03 (d, 1H, J=10.44 Hz);

MS: m/z 417.2 (M+1).

Example 37: 4-{2-[(1H-1,3-benzodiazol-2-yl)amino]-2-[3-(trifluoromethyl)phenyl]acetyl}-1,1-dimethylpiperazin-1-ium iodide Prepared by the method described for Example 29 but using 1,1-dimethylpiperazin-1-ium iodide in place of pyrrolidine.

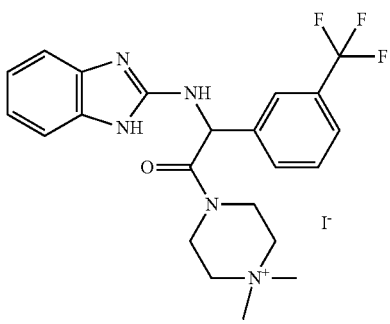 [SMILES: C[N+]1(C)CCN(C(=O)C(Nc2nc3ccccc3[nH]2)c2cccc(C(F)(F)F)c2)CC1 ; [I-]]

1H NMR (400 MHz, DMSO-d₆): δ 12.8 (s, 2H), 7.95 (s, 1H), 7.85 (d, 1H, J=7.68 Hz), 7.81 (d, 1H, J=7.80 Hz), 7.73 (t, 1H, J=8.16 Hz), 7.47-7.45 (m, 2H), 7.25 (d, 2H, J=2.88 Hz), 6.30 (d, 1H, J=8.80 Hz), 4.20 (d, 1H, J=15.00 Hz), 4.20 (d, 1H, J=15.00 Hz), 3.71-3.60 (m, 3H), 3.48-3.36 (m, 3H), 3.16 (d, 6H, J=8.84 Hz);

MS: m/z 432.2 (M+).

Example 38: 2-[(1H-1,3-benzodiazol-2-yl)amino]-N-ethyl-N-(2-hydroxyethyl)-2-[3-(trifluoromethyl)phenyl]acetamide Prepared by the method described for Example 29 but using 2-(ethylamino)ethan-1-ol in place of pyrrolidine.

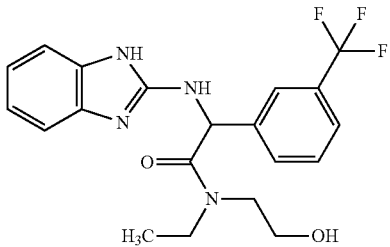

¹H NMR (400 MHz, Acetic acid-d₄): δ 10.53 (s, 1H), 8.04-7.96 (m, 3H), 7.77 (d, 1H, J=4.80 Hz), 7.63 (t, 1H, J=8.00 Hz), 7.17 (s, 2H), 6.90 (s, 2H), 4.30 (m, 1H), 3.93 (m, 1H), 3.6-3.3 (m, 4H), 3.2-3.1 (m, 2H), 1.10 (t, 3H);

MS: m/z 407.2 (M+1).

The above product was resolved into its two enantiomers by HPLC (Column: Phenomenex Lux C-4 (250×4.6) mm 5 u, Mobile Phase 'A': Hexane: 20 mM Ammonia in ETOH (95:05); Flow: 1.0 ml/min.).

Example 38a: (−)-2-[(1H-1,3-benzodiazol-2-yl)amino]-N-ethyl-N-(2-hydroxyethyl)-2-[3-(trifluoromethyl)phenyl]acetamide The (−) isomer was the first to elute off the column.

¹H NMR (400 MHz, DMSO-d₆) δ 10.5 (s, 1H), 7.84 (d, 2H, J=12.28 Hz), 7.69-7.61 (m, 2H), 7.43 (d, 1H, J=13.48 Hz), 7.17 (d, 2H, J=7.88 Hz), 6.88 (s, 2H), 5.32 (d, 1H, J=7.80 Hz), 4.63 (s, 1H), 3.57-3.48 (m, 4H), 3.21-3.16 (m, 1H), 0.99 (m, 4H);

MS: m/z 407.2 (M+1); $[\alpha]_D^{27.2}$=−96.5 (MeOH, c=0.20)

Example 38b: (+)-2-[(1H-1,3-benzodiazol-2-yl)amino]-N-ethyl-N-(2-hydroxyethyl)-2-[3-(trifluoromethyl)phenyl]acetamide The (+) isomer was the second to elute off the column.

H NMR (400 MHz, DMSO-d₆) δ 10.50 (s, 1H), 7.84 (d, 2H, J=13.52 Hz), 7.69 (d, 1H, J=7.72 Hz), 7.63 (t, 1H, J=7.64 Hz), 7.48-7.44 (m, 1H), 7.17 (d, 2H, J=5.92 Hz), 6.15-6.06 (m, 2H), 5.32 (d, 1H, J=7.64 Hz), 4.6 (s, 1H), 3.62-3.47 (m, 4H), 3.22-3.00 (m, 1H), 1.05-0.94 (m, 4H);

MS: m/z 407.2 (M+1); $[\alpha]_D^{27.0}$=+105. (MeOH, c=0.20).

Example 39: 3-[(1H-1,3-benzodiazol-2-yl)amino]-N-ethyl-3-(4-fluoro-3-methylphenyl)-N-(2-hydroxyethyl)propanamide

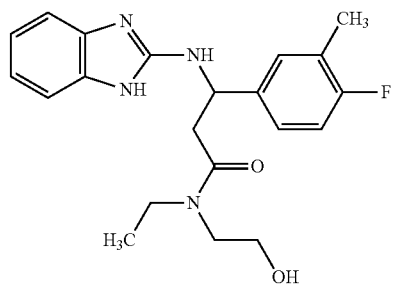 [SMILES: CCN(CCO)C(=O)CC(Nc1nc2ccccc2[nH]1)c1ccc(F)c(C)c1]

To a solution of methyl 3-[(1H-1,3-benzodiazol-2-yl)amino]-3-(4-fluoro-3-methylphenyl)propanoate [prepared by the method described for methyl 3-[(1H-1,3-benzodiazol-2-yl)amino]-3-[3-(trifluoromethyl)phenyl]propanoate, (Example 1 Steps 1 to 5), but using 4-fluoro-3-methylbenzaldehyde in place of 3-(trifluoromethyl)benzaldehyde], (1.25 g, 4 mmol) in acetonitrile (25 mL), 2-(ethylamino)ethan-1-ol (0.85 g) was added and the reaction mixture was irradiated at 80° C. in a microwave reactor for 2 h. The solvent was evaporated in vacuum to afford the crude product (2.0 g) which was purified by silica gel (230-400 mesh) column chromatography using 4% methanol in chloroform as eluent to afford 3-[(1H-1,3-benzodiazol-2-yl)amino]-N-ethyl-3-(4-fluoro-3-methylphenyl)-N-(2-hydroxyethyl)propanamide (0.8 g) as an off-white solid.

¹H NMR (400 MHz, DMSO-d₆) δ 10.81 (s, 1H), 7.34-7.27 (m, 2H), 7.15 (t, J=8.4 Hz, 1H), 7.10-7.04 (m, 3H), 6.83 (s, 2H), 5.26-5.24 (m, 1H), 4.9 (s, 0.5H), 4.62 (t, J=5.6 Hz, 0.5H), 3.46 (t, J=5.2 Hz, 1H), 3.39-3.21 (m, 5H), 3.04-2.96 (m, 1H), 2.78-2.72 (m, 1H), 2.19 (s, 3H), 1.02 (t, J=6.8 Hz, 1.3H), 0.92 (t, J=7.2 Hz, 1.7H);

MS: m/z 385.2 (M+1).

The above compound was resolved into its two enantiomers using chiral SFC. [Resolution Method: Lux C1, Mobile Phase: 20 mM Ammonia in IPA, Flow: 4 ml/min.]

Example 39a: (−)-3-[(1H-1,3-benzodiazol-2-yl)amino]-N-ethyl-3-(4-fluoro-3-methylphenyl)-N-(2-hydroxyethyl)propanamide The (−) enantiomer was the first to elute off the column.

¹H NMR (400 MHz, Acetic acid-d₄) δ 7.60-7.34 (m, 4H), 7.23-7.21 (m, 2H), 7.05-7.00 (t, J=8.8, 1H), 5.44-5.23 (m, 1H), 3.84-3.76 (m, 1H), 3.72 (t, J=5.6 Hz, 1H), 3.58-3.34 (m, 5H), 3.02-2.94 (m, 1H), 2.11 (s, 3H), 1.14 (t, J=7.2 Hz, 1.3H), 0.99 (t, J=14.4 Hz, 1.7H); MS: m/z 385.2 (M+1); $[\alpha]_D^{24.8}$=−32.00° (MeOH, c=0.2).

Example 39b: (+)3-[(1H-1,3-benzodiazol-2-yl)amino]-N-ethyl-3-(4-fluoro-3-methylphenyl)-N-(2-hydroxyethyl)propanamide The (+) enantiomer was the second to elute off the column.
$^1$H NMR (400 MHz, AcOH-d$_4$) δ 7.43-7.32 (m, 4H), 7.23-7.21 (m, 2H), 7.03 (t, J=9.2, 1H), 5.45-5.42 (m, 1H), 3.83-3.79 (m, 1H), 3.72 (t, J=6.0 Hz, 1H), 3.58-3.37 (m, 5H), 3.02-2.94 (m, 1H), 2.27 (s, 3H), 1.15 (t, J=7.2 Hz, 1.2H), 1.01 (t, J=6.8 Hz, 1.7H);
MS: m/z 385.2 (M+1); $[\alpha]_D^{24.9}$=+25.40° (MeOH, c=0.2).

Example 40: 3-[(1H-1,3-benzodiazol-2-yl)amino]-3-(4-chloro-3-methylphenyl)-N-ethyl-N-(2-hydroxyethyl)propanamide

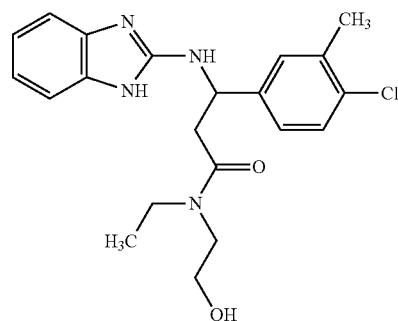 [SMILES: CCN(CCO)C(=O)CC(Nc1nc2ccccc2[nH]1)c1ccc(Cl)c(C)c1]

To a solution of methyl 3-[(1H-1,3-benzodiazol-2-yl)amino]-3-(4-chloro-3-methylphenyl)propanoate [prepared by the method described for methyl 3-[(1H-1,3-benzodiazol-2-yl)amino]-3-[3-(trifluoromethyl)phenyl]propanoate, (Example 1 Steps 1 to 5), but using 4-chloro-3-methylbenzaldehyde in place of 3-(trifluoromethyl)benzaldehyde], (1.6 g, 5 mmol) in acetonitrile (30 mL), 2-(ethylamino)ethan-1-ol (1.03 g) was added and the reaction mixture was irradiated at 100° C. in a microwave reactor for 2 h. The solvent was evaporated in vacuum to afford the crude product (2.5 g) which was purified by silica gel (230-400 mesh) column chromatography using 5% methanol in chloroform as an eluent to afford the title compound (0.4 g) as an off-white solid.
$^1$H NMR (400 MHz, AcOH-d$_4$) δ 7.47 (d, J=10.8 Hz, 1H), 7.40-7.37 (m, 2H), 7.35-7.31 (m, 2H), 7.24-7.21 (m, 2H), 5.44-5.42 (m, 1H), 3.79-3.77 (m, 1H), 3.74 (m, 1H), 3.58-3.38 (m, 5H), 3.03-2.95 (m, 1H), 2.37 (s, 3H), 1.15 (t, J=7.2 Hz, 1.4H), 1.01 (t, J=6.8 Hz, 1.6H);
MS: m/z 401.2 (M+1).
The above product was resolved by chiral SFC into its two enantiomers. Resolution Method: [YMC Cellulose C, Mobile Phase: 20 mM Ammonia in Methanol, Flow rate: 3 ml/min.]

Example 40a: (−)3-[(1H-1,3-benzodiazol-2-yl)amino]-3-(4-chloro-3-methylphenyl)-N-ethyl-N-(2-hydroxyethyl)propanamide The (−) enantiomer was the first to elute off the column.
$^1$H NMR (400 MHz, AcOH-d$_4$) δ 7.47 (d, J=9.96 Hz, 1H), 7.41-7.33 (m, 4H), 7.25-7.23 (m, 2H), 5.46-5.44 (m, 1H), 3.85-3.81 (m, 1H), 3.74 (t, J=5.8 Hz, 1H), 3.60-3.36 (m, 5H), 3.04-2.96 (m, 1H), 2.37 (s, 3H), 1.16 (t, J=6.88 Hz, 1.2H), 1.03 (t, J=7.08 Hz, 1.8H);
MS: m/z 401.2 (M+1); $[\alpha]_D^{25.0}$=−52.00° (MeOH, c=0.2)

Example 40b: (+)3-[(1H-1,3-benzodiazol-2-yl)amino]-3-(4-chloro-3-methylphenyl)-N-ethyl-N-(2-hydroxyethyl)propanamide The (+) enantiomer was the second to elute off the column.
$^1$H NMR (400 MHz, AcOH-d$_4$) δ 7.47 (d, J=10.4 Hz, 1H), 7.40-7.30 (m, 4H), 7.24-7.21 (m, 2H), 5.45-5.42 (m, 1H), 3.84-3.77 (m, 1H), 3.72 (t, J=6.0 Hz, 1H), 3.58-3.36 (m, 5H), 3.03-2.95 (m, 1H), 2.37 (s, 3H), 1.15 (t, J=7.2 Hz, 1.2H), 1.01 (t, J=7.2 Hz, 1.8H);
MS: m/z 401.2 (M+1); $[\alpha]_D^{25.0}$=+55.10° (MeOH, c=0.2).

Example 41: Preparation of 3-[(1H-1,3-benzodiazol-2-yl)amino]-N-ethyl-N-(2-hydroxy-ethyl)-3-[3-(trifluoromethyl)phenyl]propanamide

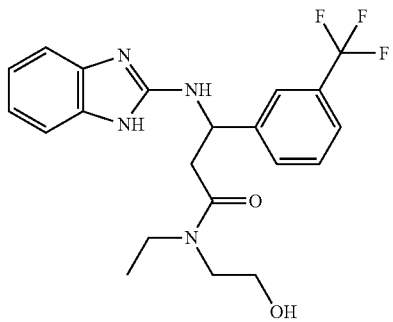 [SMILES: CCN(CCO)C(=O)CC(Nc1nc2ccccc2[nH]1)c1cccc(C(F)(F)F)c1]

The title compound was prepared by the method described for Example 42 but using 2-(ethylamino)ethan-1-ol in place of 2-methoxyethan-1-amine.
$^1$H NMR (400 MHz, MeOH-d$_4$): δ 7.82 (s, 1H), 7.76 (d, 1H, J=6.80 Hz), 7.57-7.51 (m, 2H), 7.20-7.17 (m, 2H), 6.98-6.95 (m, 2H), 5.44 (dd, 1H, J=6.0, 12.0 Hz), 3.67 (t, 1H, J=5.60 Hz), 3.58 (t, 1H, J=5.60 Hz), 3.43-3.34 (m, 4H), 3.28-3.16 (m, 1H), 3.02-2.95 (m, 1H), 1.11-1.01 (tt, 3H, J=7.2 Hz,).
MS: m/z 421 (M+1)
The above product was resolved into its two enantiomers by chiral SFC.
Method: Column: YMC Cellulose C; Mobile Phase: 20 mM Ammonia in Methanol; Flow: 3.0 mL/Min.

Example 41a: (−)3-[(1H-1,3-benzodiazol-2-yl)amino]-N-ethyl-N-(2-hydroxyethyl)-3-[3-(trifluoromethyl)phenyl]propanamide The (−) enantiomer was the first to elute off the column.
$^1$H NMR (400 MHz, MeOH-d$_4$): δ 7.81 (s, 1H), 7.76 (d, 1H, J=7.20 Hz), 7.57-7.51 (m, 2H), 7.20-7.16 (m, 2H), 6.98-6.95 (m, 2H), 5.46 (dd, 1H, J=6.0, 12.0 Hz), 3.66 (t, 1H, J=5.60 Hz), 3.58 (t, 1H, J=6.00 Hz), 3.44-3.36 (m, 4H), 3.25-3.14 (m, 1H), 3.02-2.95 (m, 1H), 1.10-1.04 (tt, 3H, J=7.2 Hz);

MS: m/z 421 (M+1); $[\alpha]_D^{25}$=−18.0 (MeOH, c=0.272).

Example 41b: Preparation of 3-[(1H-1,3-benzodiazol-2-yl)amino]-N-ethyl-N-(2-hydroxyethyl)-3-[3-(trifluoromethyl)phenyl]propanamide The (+) enantiomer was the second to elute off the column.

$^1$H NMR (400 MHz, MeOH-d$_4$): δ 7.81 (s, 1H), 7.76 (d, 1H, J=6.80 Hz), 7.56-7.51 (m, 2H), 7.19-7.16 (m, 2H), 6.97-6.94 (m, 2H), 5.44 (dd, 1H, J=6.0, 12.0 Hz), 3.66 (t, 1H, J=5.60 Hz), 3.57 (t, 1H, J=6.00 Hz), 3.42-3.36 (m, 4H), 3.31-3.15 (m, 1H), 3.02-2.95 (m, 1H), 1.10-1.04 (tt, 3H, J=7.2 Hz);

MS: m/z 421 (M+1); $[\alpha]_D^{25.1}$=+15.5 (MeOH, c=0.238).

Example 42: Preparation of 3-[(1H-1,3-benzodiazol-2-yl)amino]-N-(2-methoxyethyl)-3-[3-(trifluoromethyl)phenyl]propanamide

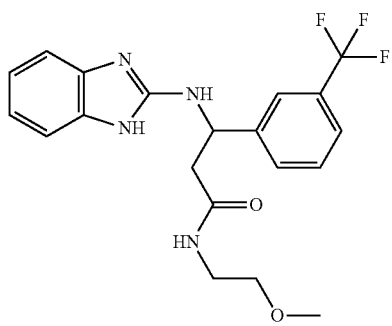 [SMILES: COCCNC(=O)CC(Nc1nc2ccccc2[nH]1)c1cccc(C(F)(F)F)c1]

To a solution of methyl 3-[(1H-1,3-benzodiazol-2-yl)amino]-3-[3-(trifluoromethyl)phenyl] propanoate (from Example 1 Step 5), (1.5 g, 4 mmol) in acetonitrile (15 mL) was added 2-methoxyethan-1-amine (0.75 g, 10 mmol) and the reaction mixture was heated at 70° C. After 5 h, the reaction mixture was diluted with water (25 mL) and extracted with dichloromethane (3×50 mL). The combined organic extracts were dried over anhydrous sodium sulphate and evaporated to afford the crude product (2 g), which was purified by silica gel (60-120 mesh) column chromatography using 8% methanol in chloroform as eluent to afford 3-[(1H-1,3-benzodiazol-2-yl)amino]-N-(2-methoxyethyl)-3-[3-(trifluoromethyl)phenyl]propanamide (1 g) as an off-white solid.

$^1$H NMR (400 MHz, Acetic acid-d$_4$): δ 7.79 (s, 1H), 7.73 (d, 1H, J=7.20 Hz), 7.58-7.51 (m, 2H), 7.20-7.17 (dd, 2H, J=2.8, 6.0 Hz), 6.96 (dd, 2H, J=4.0, 7.2 Hz), 5.36 (t, 1H, J=6.80 Hz), 3.31-3.26 (m, 4H), 3.24 (s, 3H), 2.89-2.77 (m, 2H);

MS: m/z 407 (M+1).

The above product was resolved into its two isomers by chiral SFC. Method: Column: YMC Cellulose C; Mobile Phase 'A': 20 mM Ammonia in Methanol; Flow: 1.0 ml/min.

Example 42a: (−)3-[(1H-1,3-benzodiazol-2-yl)amino]-N-(2-methoxyethyl)-3-[3-(trifluoromethyl)phenyl]propanamide The (−) enantiomer was the first to elute off the column.

$^1$H NMR (400 MHz, Acetic acid-d$_4$): δ 7.86 (s, 1H), 7.81 (d, 1H, J=7.60 Hz), 7.65 (d, 1H, J=7.6 Hz), 7.59 (t, 1H, J=7.6 Hz), 7.41-7.39 (m, 2H), 7.24-7.22 (m, 2H), 5.53 (dd, 1H, J=5.2, 9.6 Hz), 3.47-3.34 (m, 4H), 3.26 (s, 3H), 3.21-3.14 (m, 1H), 3.04-2.99 (m, 1H);

MS: m/z 407 (M+1); $[\alpha]_D^{25.4}$=−39.5 (MeOH, c=0.22).

Example 42b: (+)3-[(1H-1,3-benzodiazol-2-yl)amino]-N-(2-methoxyethyl)-3-[3-(trifluoromethyl)phenyl]propanamide The (+) enantiomer was the second to elute off the column.

$^1$H NMR (400 MHz, Acetic acid-d$_4$): δ 7.86 (s, 1H), 7.81 (d, 1H, J=7.60 Hz), 7.66 (d, 1H, J=8.0 Hz), 7.60 (t, 1H, J=7.60 Hz), 7.41 (dd, 2H, J=3.2, 6.0 Hz), 7.23 (dd, 2H, J=2.8, 5.6 Hz), 5.54 (dd, 1H, J=5.2, 9.6 Hz), 3.46-3.41 (m, 1H), 3.47-3.41 (m, 3H), 3.26 (s, 3H), 3.18 (dd, 1H, J=10.0, 14.8 Hz), 3.0 (dd, 1H, J=5.2, 14.4 Hz);

MS: m/z 407 (M+1); $[\alpha]_D^{25.5}$=+33.5 (MeOH, c=0.24).

Example 43: 3-[(1H-1,3-benzodiazol-2-yl)amino]-N-(2-methoxyethyl)-N-methyl-3-[3-(trifluoromethyl)phenyl]propanamide

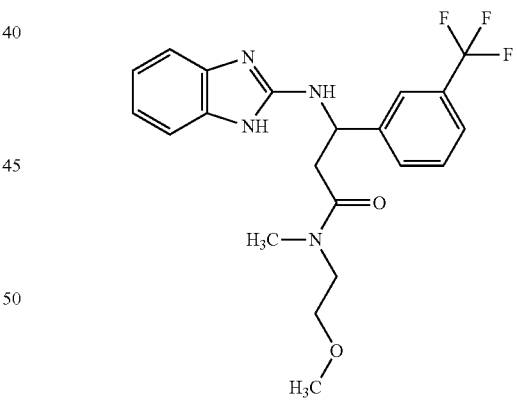

To a solution of compound (from Example 1 Step 5), (0.20 g, 0.55 mmol) in acetonitrile (4 mL) was added 2-methoxy-N-methylethan-1-amine (0.12 g, 1.37 mmol) at ambient temperature and then refluxed for 4 h. The reaction mixture was diluted with water (25 mL) and extracted with dichloromethane (3×25 mL). The combined organic extracts were dried over anhydrous sodium sulphate and evaporated to afford a crude product (0.22 g) which was purified by preparative HPLC to afford the title compound (0.052 g) as a colorless gum.

¹H NMR (400 MHz, MeOH-d₄) δ 7.84 (d, 1H, J=8.28 Hz), 7.78 (bs, 1H), 7.68-7.64 (m, 2H), 7.40-7.37 (m, 2H), 7.31-7.29 (m, 2H), 5.42-5.40 (m, 1H), 3.59-3.47 (m, 4H), 3.32-3.31 (m, 2H), 3.28-3.19 (m, 3H), 2.94 (s, 3H);

MS: m/z 421.2 (M+1).

Example 44: 3-[(1H-1,3-benzodiazol-2-yl)amino]-N-methyl-N-[2-(methylamino)ethyl]-3-[3-(trifluoromethyl)phenyl]propanamide Prepared by the method described for Example 43 but using methyl[2-(methylamino)ethyl]amine in place of 2-methoxy-N-methylethan-1-amine.

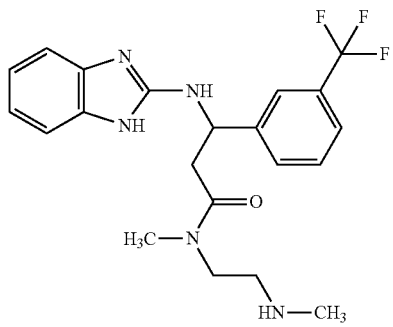 [SMILES: CNCCN(C)C(=O)CC(Nc1nc2ccccc2[nH]1)c1cccc(C(F)(F)F)c1]

¹H NMR (400 MHz, MeOH-d₄) δ 7.84 (s, 1H), 7.80 (d, 1H, J=7.6 Hz), 7.70-7.62 (m, 2H), 7.39-7.35 (m, 2H), 7.31-7.28 (m, 2H), 5.44-5.41 (m, 1H), 3.81-3.70 (m, 1H), 3.64-3.55 (m, 1H), 3.21-3.13 (m, 4H), 3.06 (s, 3H), 2.70 (s, 3H);

MS: m/z 420.2 (M+1).

Example 45: 3-[(1H-1,3-benzodiazol-2-yl)amino]-N-[2-(dimethylamino)ethyl]-N-ethyl-3-[3-(trifluoromethyl)phenyl]propanamide Prepared by the method described for Example 43 but using [2-(dimethylamino)ethyl](ethyl)amine in place of 2-methoxy-N-methylethan-1-amine.

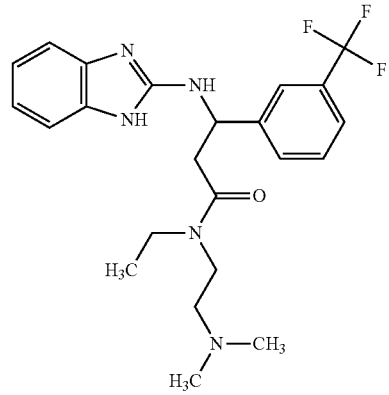 [SMILES: CCN(CCN(C)C)C(=O)CC(Nc1nc2ccccc2[nH]1)c1cccc(C(F)(F)F)c1]

¹H NMR (400 MHz, MeOH-d₄) δ 7.86 (s, 1H), 7.81 (d, 1H, J=7.36 Hz), 7.70-7.63 (m, 2H), 7.40-7.37 (m, 2H), 7.32-7.29 (m, 2H), 5.47 (dd, 1H, J=8.48, 4.20 Hz), 3.81-3.70 (m, 1H), 3.70-3.60 (m, 1H), 3.43 (dd, 2H, J=13.88, 6.84 Hz), 3.29-3.24 (m, 2H), 3.14-3.08 (m, 2H), 2.93 (s, 6H), 1.18 (t, 3H, J=7.08 Hz);

MS: m/z 448.2 (M+1).

Example 46: Methyl (2R)-2-{3-[(1H-1,3-benzodiazol-2-yl)amino]-3-[3-(trifluoromethyl)phenyl]propanamido}propanoate

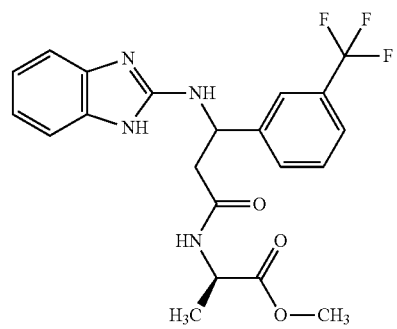 [SMILES: COC(=O)[C@@H](C)NC(=O)CC(Nc1nc2ccccc2[nH]1)c1cccc(C(F)(F)F)c1]

Step 1: 3-{[(tert-butoxy)carbonyl]amino}-3-[3-(trifluoromethyl)phenyl]propanoic acid

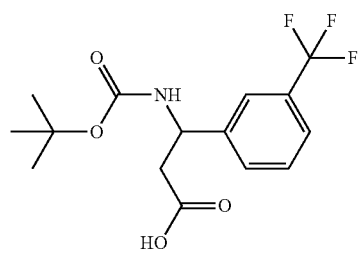 [SMILES: CC(C)(C)OC(=O)NC(CC(=O)O)c1cccc(C(F)(F)F)c1]

To a solution of 3-amino-3-(3-(trifluoromethyl)phenyl) propanoic acid (from Example 1 Step 1), (5 g, 21 mmol) in t-butanol (20 mL) was added 2N NaOH solution (0.85 g, 21 mmol) at 0° C. followed by di-tert-butyl dicarbonate (5.6 g, 26 mmol). The reaction mixture was stirred at ambient temperature for 18 h. The reaction mixture was evaporated to remove t-butanol. The aqueous phase was acidified (pH 4) with 1.5N HCl, extracted with dichloromethane (3×50 mL). The combined organic extracts were dried over anhydrous sodium sulphate and evaporated to afford 3-{[(tert-butoxy) carbonyl]amino}-3-[3-(trifluoromethyl)phenyl]propanoic acid as a colorless gum (3.5 g).

¹H NMR (400 MHz, MeOH-d₄) δ 7.66-7.50 (m, 4H), 5.08 (s, 1H), 3.13 (q, 2H, J=5.20 Hz), 1.42 (s, 9H).

Step 2: Methyl (2S)-2-(3-{[(tert-butoxy)carbonyl]amino}-3-[3-(trifluoromethyl)phenyl]propanamido)propanoate

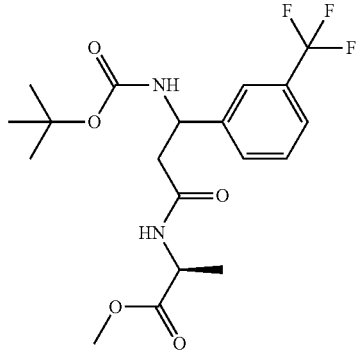 [SMILES: COC(=O)[C@H](C)NC(=O)CC(NC(=O)OC(C)(C)C)c1cccc(C(F)(F)F)c1]

To a suspension of 3-{[(tert-butoxy)carbonyl]amino}-3-[3-(trifluoromethyl)phenyl]propanoic acid (from Step 1), (0.5 g, 2.0 mmol), BOP (0.628 g, 2.0 mmol) and N,N-diisopropylethylamine (0.969 g, 8.0 mmol) in tetrahydrofuran (15 mL) at 0° C. was added methyl (2S)-2-aminopropanoate (1.29 mL, 5.0 mmol) and allowed to warm to ambient temperature and stirred for 12 h.

The reaction mixture was poured into crushed ice water (50 ml) with stirring and the precipitate thus formed was filtered and dried under vacuum to afford the title product (0.3 g) as off white solid.

$^1$H NMR (400 MHz, MeOH-d$_4$): δ 7.65-7.55 (m, 4H), 5.09 (s, 1H), 4.36 (t, 1H, J=6.80 Hz), 3.58 (s, 3H), 2.68-2.67 (m, 2H), 1.43-1.38 (m, 12H);

MS: m/z 419.2 (M+1).

Step 3: Preparation of Methyl (2S)-2-{3-amino-3-[3-(trifluoromethyl)phenyl]propanamido}propanoate

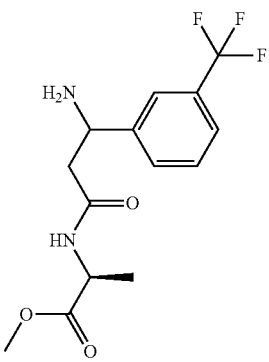 [SMILES: COC(=O)[C@H](C)NC(=O)CC(N)c1cccc(C(F)(F)F)c1]

To a solution of methyl (2S)-2-(3-{[(tert-butoxy)carbonyl]amino}-3-[3-(trifluoromethyl)phenyl]propanamido)propanoate (from Step 2), (0.3 g, 0.717 mmol) in dichloromethane (15 mL) at −5° C. was added trifluoroacetic acid (0.122 mL, 3.5 mmol), allowed to warm to ambient temperature and stirred for 12 h. The reaction mixture was evaporated to afford the title compound (0.228 g) as off white solid.

MS: m/z 319.2 (M+1).

Step 4: Preparation Methyl (2S)-2-{3-isothiocyanato-3-[3-(trifluoromethyl)phenyl]propanamido}propanoate

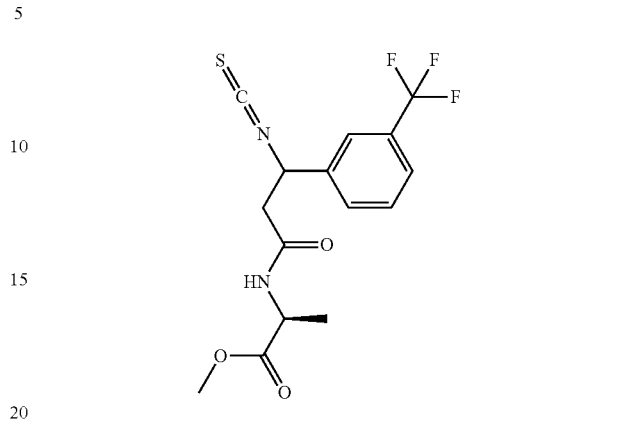

To a solution of methyl (2S)-2-(3-{[(tert-butoxy)carbonyl]amino}-3-[3-(trifluoromethyl)phenyl]propanamido)propanoate (from Step 3), (0.2 g, 0.628 mmol) in dichloromethane (10 mL) at 0° C. was added thiophosgene (0.048 mL, 0.628 mmol) followed by saturated aqueous sodium bicarbonate solution (5 mL). The reaction mixture was allowed to warm to ambient temperature and stirred for 1 h. The reaction mixture was diluted with saturated aqueous sodium bicarbonate solution (50 mL) and extracted with dichloromethane (3×25 mL). The combined organic extracts were dried over anhydrous sodium sulphate and evaporated to afford the title product (0.2 g) as a red gum. This was used in the next step without further purification.

MS: m/z 361.2 (M+1).

Step 5: Preparation of Methyl (2S)-2-(3-{[(2-aminophenyl)carbamothioyl]amino}-3-[3-(trifluoromethyl)phenyl]propanamido)propanoate

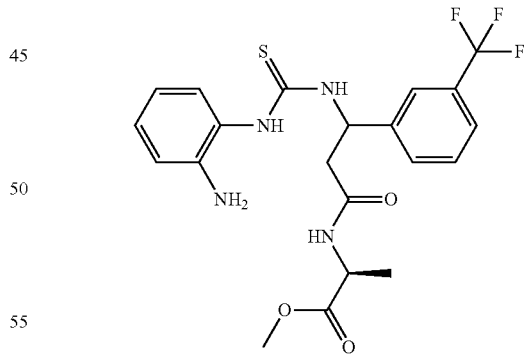

A solution of methyl (2S)-2-{3-isothiocyanato-3-[3-(trifluoromethyl)phenyl]propanamido}propanoate (from Step 4), (0.25 g, 0.694 mmol) and 1,2-phenylene diamine (0.075 g, 0.694 mmol) in dichloromethane (10 mL) was stirred at ambient temperature for 12 h. It was then purified by silica gel (60-120 mesh) column chromatography eluting with 3% methanol in chloroform to afford the title product (0.325 g) as a brown gum.

MS: m/z 469.2 (M+1).

Example 46, Step 6: Methyl (2R)-2-{3-[(1H-1,3-benzodiazol-2-yl)amino]-3-[3-(trifluoromethyl)phenyl]propanamido}propanoate

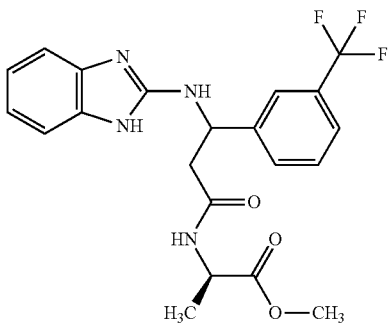 [SMILES: COC(=O)[C@@H](C)NC(=O)CC(Nc1nc2ccccc2[nH]1)c1cccc(C(F)(F)F)c1]

A suspension of methyl (2S)-2-(3-{[(2-aminophenyl)carbamothioyl]amino}-3-[3-(trifluoromethyl)phenyl]propanamido)propanoate (from Step 5), (0.21 g, 448 mmol), mercury(II) oxide (0.194 g, 896 mmol) and sulfur (0.003 g, 89.6 mmol) in methanol (15 mL) was refluxed for 2 h. The reaction mixture was filtered through a celite bed with methanol (3×25 mL). The filtrate was evaporated to afford the crude product which was purified by silica gel (60-120 mesh) column chromatography using 4% methanol in chloroform as eluent to afford the title product (0.195 g) as off-white solid.

$^1$H NMR (400 MHz, MeOH-d$_4$): δ 7.80 (s, 2H), 7.55 (d, 2H, J=7.60 Hz), 7.20 (t, 2H, J=6.00 Hz), 6.98 (dd, 2H, J=3.20, 5.60 Hz), 5.36 (d, 1H, J=12.80 Hz), 4.33 (q, 1H, J=5.6 Hz), 3.64 (s, 1.5H), 3.63 (s, 1.5H) 2.88 (s, 2H), 1.30 (d, 3H, J=7.2 Hz);

MS: m/z 435.2 (M+1).

Example 47: Methyl 2-{3-[(1H-1,3-benzodiazol-2-yl)amino]-N-ethyl-3-[3-(trifluoromethyl)phenyl]propanamido}acetate Prepared by the method described for Example 46 (Steps 2 to 6) but using methyl 2-(ethylamino)acetate in place of methyl (2S)-2-aminopropanoate in Step 2.

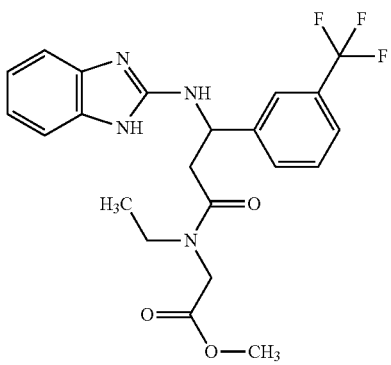 [SMILES: CCN(CC(=O)OC)C(=O)CC(Nc1nc2ccccc2[nH]1)c1cccc(C(F)(F)F)c1]

$^1$H NMR (400 MHz, MeOH-d$_4$) δ 7.81 (d, 1H, J=9.2 Hz), 7.77-7.74 (m, 1H), 7.57-7.54 (m, 2H), 7.21-7.18 (m, 2H), 7.01-6.97 (m, 2H), 5.44 (t, 1H, J=6.00 Hz), 4.04 (s, 1H), 3.75 (s, 1H), 3.65 (s, 2H), 3.46-3.42 (m, 1H), 3.38-3.36 (m, 1H), 3.27-3.20 (m, 1H), 3.08-3.03 (m, 1H), 1.39 (s, 1H), 1.11 (t, 2H, J=7.20 Hz), 1.01 (t, 1H, J=7.20 Hz);

MS: m/z 449.2 (M+1).

Example 48: Ethyl 2-{3-[(1H-1,3-benzodiazol-2-yl)amino]-N-ethyl-3-[3-(trifluoromethyl)phenyl]propanamido}acetate

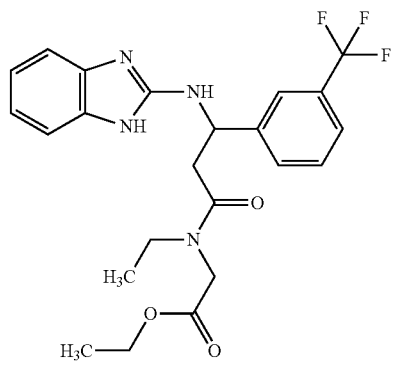 [SMILES: CCOC(=O)CN(CC)C(=O)CC(Nc1nc2ccccc2[nH]1)c1cccc(C(F)(F)F)c1]

To a solution of methyl 2-{3-[(1H-1,3-benzodiazol-2-yl)amino]-N-ethyl-3-[3-(trifluoromethyl)phenyl]propanamido}acetate (from Example 47), (80 mg, 0.18 mmol) in ethanol (5 mL) was added thionyl chloride (21 mg, 0.18 mmol) at 0° C. and the reaction mixture was refluxed for 6 h. The reaction mixture was concentrated, purified by prep. HPLC to afford the desired product as yellow gum (28 mg).

$^1$H NMR (400 MHz, MeOH-d$_4$) δ 7.85 (s, 1H), 7.80-7.78 (m, 1H), 7.68-7.63 (m, 2H), 7.40-7.37 (m, 2H), 7.31-7.28 (m, 2H), 5.45-5.43 (m, 1H), 4.23-4.21 (m, 1H), 4.13-4.01 (m, 3H), 3.49-3.33 (m, 2H), 3.16-3.11 (m, 2H), 1.29-1.07 (m, 6H);

MS: m/z 463.2 (M+1).

Example 49: N-ethyl-N-(2-hydroxyethyl)-3-{[4-(hydroxymethyl)-1H-1,3-benzodiazol-2-yl]amino}-3-[3-(trifluoromethyl)phenyl]propanamide Prepared by the method described for Example 46 (Steps 2 to 6) but using 2-(ethylamino)ethan-1-ol in place of methyl (2S)-2-aminopropanoate in Step 2 and (2,3-diaminophenyl)methanol in place of benzene-1,2-diamine in Step 5.

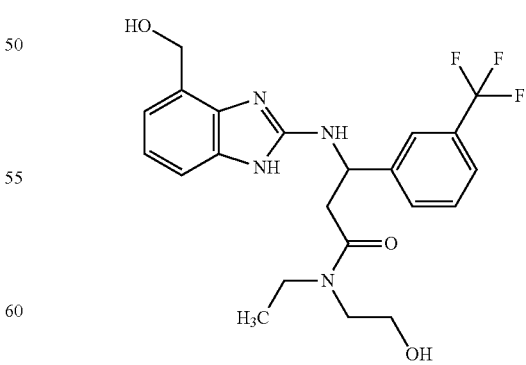

$^1$H NMR (400 MHz, AcOH-d$_4$) δ 7.89 (dd, 2H, J=9.20, 19.6 Hz), 7.66 (d, 1H, J=7.60 Hz), 7.60 (t, 1H, J=8.00 Hz), 7.37 (t, 1H, J=4.00 Hz), 7.25 (dd, 2H, J=7.60, 15.2 Hz), 5.73 (t, 1H, J=11.60 Hz), 4.94 (s, 2H), 3.83 (dd, 1H, J=6.0, 11.6

Hz), 3.74 (t, 1H, J=5.60 Hz), 3.56-3.46 (m, 4H), 3.13 (dd, 2H, J=4.40, 16.4 Hz), 1.15 (t, 3H, J=6.80 Hz);
MS: m/z 451.2 (M+1).

Example 50: N-(cyanomethyl)-3-{[4-(hydroxymethyl)-1H-1,3-benzodiazol-2-yl]amino}-N-methyl-3-[3-(trifluoromethyl)phenyl]propanamide Prepared by the method described for Example 46 (Steps 2 to 6) but using 2-(methylamino)acetonitrile in place of methyl (2S)-2-aminopropanoate in Step 2 and (2,3-diaminophenyl)methanol in place of benzene-1,2-diamine in Step 5.

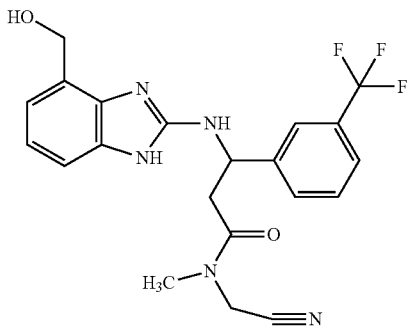 [SMILES: CN(CC#N)C(=O)CC(Nc1nc2c(CO)cccc2[nH]1)c1cccc(C(F)(F)F)c1]

$^1$H NMR (400 MHz, MeOH-d$_4$) δ 7.84 (s, 1H), 7.76 (d, 1H, J=6.80 Hz), 7.58-7.54 (m, 2H), 7.16-7.14 (m, 1H), 7.00-6.96 (m, 2H), 5.51 (t, 1H, J=6.40 Hz), 4.84 (s, 2H), 4.35 (s, 2H), 3.26 (dd, 1H, J=7.20, 16.40 Hz), 3.12 (s, 3H), 3.06 (dd, 1H, J=4.80, 16.00 Hz);
MS: m/z 432.2 (M+1).

Example 51: N-(cyanomethyl)-3-{[4-(2-hydroxyethyl)-1H-1,3-benzodiazol-2-yl]amino}-N-methyl-3-[3-(trifluoromethyl)phenyl]propanamide Prepared by the method described for Example 46 (Steps 2 to 6) but using 2-(methylamino)acetonitrile in place of methyl (2S)-2-aminopropanoate in Step 2 and 2-(2,3-diaminophenyl)ethan-1-ol in place of benzene-1,2-diamine in Step 5.

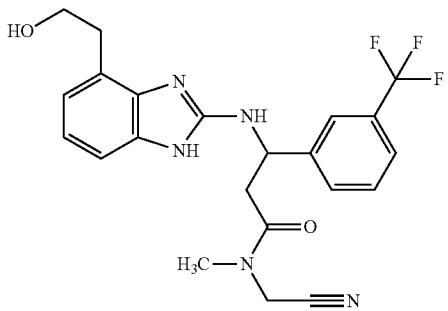 [SMILES: CN(CC#N)C(=O)CC(Nc1nc2c(CCO)cccc2[nH]1)c1cccc(C(F)(F)F)c1]

$^1$H NMR (400 MHz, Acetic Acid-d$_4$): δ 7.91 (s, 1H), 7.85 (d, 1H, J=7.20 Hz), 7.65 (d, 1H, J=7.60 Hz), 7.58 (t, 1H, J=8.0 Hz), 7.29 (d, 1H, J=8.00 Hz), 7.19 (t, 1H, J=8.00 Hz), 7.11 (d, 1H, J=8.00 Hz), 5.63 (dd, 1H, J=4.40, 8.0 Hz), 4.55 (d, 1H, J=17.2 Hz), 4.28 (d, 1H, J=17.60 Hz), 3.96 (t, 2H, J=6.40 Hz), 3.58 (dd, 1H, J=8.0, 16.8 Hz), 3.19-3.05 (m, 6H);
MS: m/z 446.2 (M+1).

Example 52: N-(cyanomethyl)-N-ethyl-3-{[4-(2-hydroxyethyl)-1H-1,3-benzodiazol-2-yl]amino}-3-[3-(trifluoromethyl)phenyl]propanamide Prepared by the method described for Example 46 (Steps 2 to 6) but using 2-(ethylamino)acetonitrile in place of methyl (2S)-2-aminopropanoate in Step 2 and 2-(2,3-diaminophenyl)ethan-1-ol in place of benzene-1,2-diamine in Step 5.

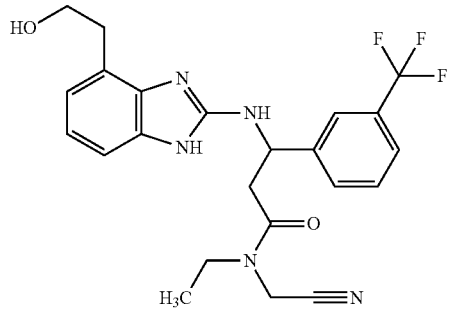 [SMILES: CCN(CC#N)C(=O)CC(Nc1nc2c(CCO)cccc2[nH]1)c1cccc(C(F)(F)F)c1]

$^1$H NMR (400 MHz, AcOH-d$_4$): δ 7.91 (s, 1H), 7.85 (d, 1H, J=7.60 Hz), 7.65 (d, 1H, J=8.00 Hz), 7.58 (t, 1H, J=7.60 Hz), 7.29 (d, 1H, J=8.00 Hz), 7.19 (t, 1H, J=8.00 Hz), 7.11 (d, 1H, J=8.00 Hz), 5.69-5.66 (m, 1H), 4.48 (d, 1H, J=6.80 Hz), 4.23 (d, 1H, J=17.20 Hz), 3.95 (t, 2H, J=6.40 Hz), 3.61-3.55 (m, 3H), 3.20-3.15 (m, 1H), 3.08 (t, 2H, J=6.40 Hz), 1.22 (t, 3H, J=7.20 Hz);
MS: m/z 460.2 (M+1).

Example 53: N-(cyanomethyl)-N-ethyl-3-{[4-(hydroxymethyl)-1H-1,3-benzodiazol-2-yl]amino}-3-[3-(trifluoromethyl)phenyl]propanamide Prepared by the method described for Example 46 (Steps 2 to 6) but using 2-(ethylamino)acetonitrile in place of methyl (2S)-2-aminopropanoate in Step 2 and (2,3-diaminophenyl)methanol in place of benzene-1,2-diamine in Step 5.

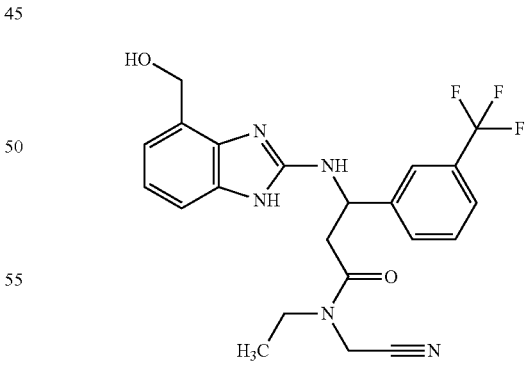

$^1$H NMR (400 MHz, AcOH-d$_4$) δ 7.93 (s, 1H), 7.87 (d, 1H, J=7.6 Hz), 7.65 (d, 1H, J=7.60 Hz), 7.59 (t, 1H, J=7.6 Hz), 7.38 (d, 1H, J=6.8 Hz), 7.22 (q, 2H, J=7.60 Hz), 5.76-5.72 (m, 1H), 4.91 (s, 2H), 4.46 (d, 1H, J=17.60 Hz), 4.23 (d, 1H, J=17.2 Hz), 3.62-3.51 (m, 3H), 3.18 (dd, 1H, J=16.8, 4.8 Hz), 1.22 (t, 3H, J=7.20 Hz);
MS: m/z 446.2 (M+1).

Example 54: N-(carbamoylmethyl)-N-ethyl-3-{[4-(hydroxymethyl)-1H-1,3-benzodiazol-2-yl]amino}-3-[3-(trifluoromethyl)phenyl]propanamide Prepared by the method described for Example 46 (Steps 2 to 6) but using 2-(ethylamino)acetamide in place of methyl (2S)-2-aminopropanoate in Step 2 and (2,3-diaminophenyl)methanol in place of benzene-1,2-diamine in Step 5.

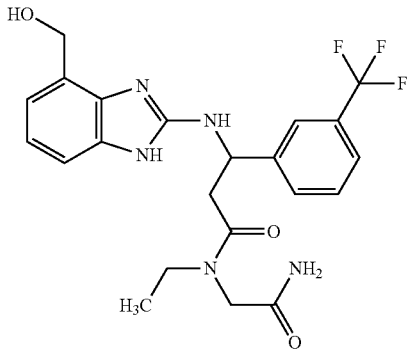 [SMILES: CCN(CC(N)=O)C(=O)CC(Nc1nc2c(CO)cccc2[nH]1)c1cccc(C(F)(F)F)c1]

$^1$H NMR (400 MHz, AcOH-d$_4$) δ 7.90-7.81 (m, 2H), 7.66-7.56 (m, 2H), 7.37 (d, 1H, J=7.2 Hz), 7.25-7.18 (m, 2H), 5.71 (bs, 1H), 4.92 (d, 2H, J=3.6 Hz), 4.34-4.04 (m, 2H), 3.59-3.35 (m, 3H), 3.22-3.06 (m, 1H), 1.17 (t, 1.5H, J=7.20 Hz), 1.04 (t, 1.5H, J=7.20 Hz);
MS: m/z 464.0 (M+1).

Example 55: 3-[(1H-1,3-benzodiazol-2-yl)amino]-N-(cyanomethyl)-N-ethyl-3-[3-(trifluoromethyl)phenyl]propanamide Prepared by the method described for Example 46 (Steps 2 to 6) but using 2-(ethylamino)acetonitrile in place of methyl (2S)-2-aminopropanoate in Step 2.

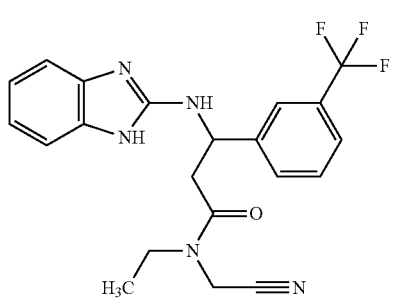 [SMILES: CCN(CC#N)C(=O)CC(Nc1nc2ccccc2[nH]1)c1cccc(C(F)(F)F)c1]

$^1$H NMR (400 MHz, AcOH-d$_4$) δ 7.91 (s, 1H), 7.85 (d, 1H, J=8.0 Hz), 7.65 (d, 1H, J=8.0 Hz), 7.58 (t, 1H, J=7.6 Hz), 7.42-7.39 (m, 2H), 7.26-7.22 (m, 2H), 5.59 (dd, 1H, J=8.4, 4.4 Hz), 4.47 (d, 1H, J=17.6 Hz), 4.22 (d, 1H, J=17.2 Hz), 3.64-3.58 (m, 3H), 3.16 (dd, 1H, J=4.8, 16.8 Hz), 1.24 (t, 3H, J=6.8 Hz);
MS: m/z 416.2 (M+1).

Example 56: 3-[(1H-1,3-benzodiazol-2-yl)amino]-N-(cyanomethyl)-N-methyl-3-[3-(trifluoromethyl)phenyl]propanamide Prepared by the method described for Example 46 (Steps 2 to 6) but using 2-(methylamino)acetonitrile in place of methyl (2S)-2-aminopropanoate in Step 2.

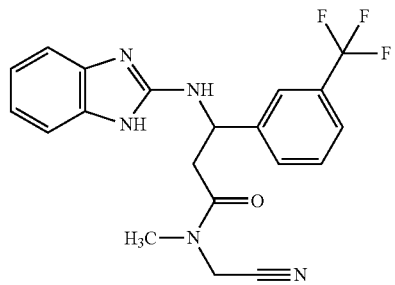 [SMILES: CN(CC#N)C(=O)CC(Nc1nc2ccccc2[nH]1)c1cccc(C(F)(F)F)c1]

$^1$H NMR (400 MHz, CD$_3$OD) δ 7.83 (s, 1H), 7.76 (d, 1H, J=6.8 Hz), 7.58-7.52 (m, 2H), 7.20-7.17 (m, 2H), 6.99-6.95 (m, 2H), 5.46 (t, 1H, J=5.6 Hz), 4.35 (s, 2H), 3.23 (dd, 1H, J=7.2, 16.4 Hz), 3.11 (s, 3H), 3.03 (dd, 1H, J=5.2, 16.0 Hz);
MS: m/z 402.0 (M+1).

The above product was resolved into its two enantiomers by chiral SFC (Column: YMC Cellulose C, mobile phase: 20 mM ammonia in methanol, flow rate: 0.9 mL/min).

Example 56a. (−)3-[(1H-1,3-benzodiazol-2-yl)amino]-N-(cyanomethyl)-N-methyl-3-[3-(trifluoromethyl)phenyl]propanamide The (−) enantiomer was the first to elute off the column.
$^1$H NMR (400 MHz, CD$_3$OD) δ 7.83 (s, 1H), 7.76 (d, 1H, J=6.8 Hz), 7.57-7.51 (m, 2H), 7.20-7.18 (m, 2H), 6.97-6.95 (m, 2H), 5.46 (t, 1H, J=6 Hz), 4.34 (s, 2H), 3.23 (dd, 1H, J=7.2, 16.4 Hz), 3.10 (s, 3H), 3.03 (dd, 1H, J=5.2, 16.0 Hz);
MS: m/z 402.0 (M+1); $[α]_D^{26.1}$=−19.68 (MeOH, c=0.315);

Example 56b. (+)3-[(1H-1,3-benzodiazol-2-yl)amino]-N-(cyanomethyl)-N-methyl-3-[3-(trifluoromethyl)phenyl]propanamide The (+) enantiomer was the second to elute off the column.
$^1$H NMR (400 MHz, CD$_3$OD) δ 7.83 (s, 1H), 7.76 (d, 1H, J=6.8 Hz), 7.57-7.51 (m, 2H), 7.20-7.18 (m, 2H), 6.97-6.95 (m, 2H), 5.46 (t, 1H, J=6 Hz), 4.35 (s, 2H), 3.25-3.20 (m, 1H), 3.11 (s, 3H), 3.03 (dd, 1H, J=5.2, 15.2 Hz);
MS: m/z 402.0 (M+1); $[α]_D^{25}$=+23.42 (MeOH, c=0.38).

Example 57: Methyl 2-{3-[(1H-1,3-benzodiazol-2-yl)amino]-N-methyl-3-[3-(trifluoromethyl)phenyl]propanamido}acetate Prepared by the method described for Example 46 (Steps 2 to 6) but using methyl 2-(methylamino)acetate in place of methyl (2S)-2-aminopropanoate in Step 2.

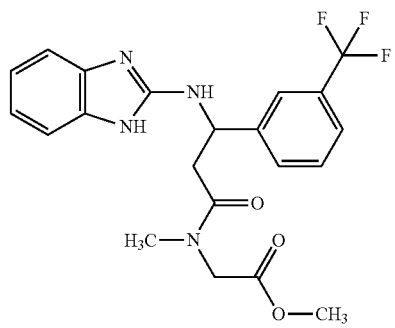 [SMILES: COC(=O)CN(C)C(=O)CC(Nc1nc2ccccc2[nH]1)c1cccc(C(F)(F)F)c1]

¹H NMR (400 MHz, DMSO-d₆) δ 12.77 (bs, 1H, exchangeable), 9.47 (s, 1H, exchangeable), 7.89 (d, 1H, J=12.0 Hz), 7.81 (t, 1H, J=8.0 Hz), 7.71-7.63 (m, 2H), 7.41-7.37 (m, 2H), 7.26-7.23 (m, 2H), 5.42-5.41 (m, 1H), 4.33-4.29 (m, 0.5H), 4.09 (s, 2.0H), 3.58 (s, 3H), 3.31-3.10 (m, 1.5H), 3.05 (s, 3H);
MS: m/z 435.2 [M+1].

The above product was resolved into its two enantiomers by chiral SFC [(column: YMC Cellulose C, mobile phase: 20 mM ammonia in Methanol, flow rate: 0.9 mL/min)].

Example 57a. (−)Methyl 2-{3-[(1H-1,3-benzodiazol-2-yl)amino]-N-methyl-3-[3-(trifluoromethyl)phenyl]propanamido}acetate The (−) enantiomer was the first to elute off the column.
¹H NMR (400 MHz, CD₃OD) δ 7.82 (d, 1H, J=9.6 Hz), 7.76 (t, 1H, J=6.8 Hz), 7.54-7.53 (m, 2H), 7.20-7.17 (m, 2H), 6.98-6.95 (m, 2H), 5.44 (q, 1H, J=5.2 Hz), 4.24 (d, 0.5H, 14.4 Hz), 4.10 (d, 1.5H, J=6 Hz), 3.75 (s, 1H), 3.67 (s, 2H), 3.23 (dd, 1H, J=7.2 Hz), 3.10 (s, 3H), 2.90 (s, 1H);
MS: m/z 435.2 [M+1]; $[\alpha]_D^{24.9}$=−10.85 (MeOH, c=0.175).

Example 57b. (+)Methyl 2-{3-[(1H-1,3-benzodiazol-2-yl)amino]-N-methyl-3-[3-(trifluoromethyl)phenyl]propanamido}acetate The (+) enantiomer was the second to elute off the column.
¹H NMR (400 MHz, CD₃OD) δ 7.81 (d, 1H, J=9.56 Hz), 7.75 (t, 1H, J=6.68 Hz), 7.55-7.50 (m, 2H), 7.18-7.16 (m, 2H), 6.97-6.94 (m, 2H), 5.44 (t, 1H, J=5.56 Hz), 4.19 (q, 0.5H, 18.56 Hz), 4.09 (d, 1.5H, J=6.12 Hz), 3.74 (s, 1H), 3.66 (s, 2H), 3.22 (dd, 1H, J=7.16 Hz), 3.09 (s, 2H), 3.025-3.01 (m, 1H), 2.89 (s, 1H);
MS: m/z 435.2 [M+1]; $[\alpha]_D^{25.9}$=+18.26 (MeOH, c=0.115).

Example 58: N-ethyl-3-{[4-(hydroxymethyl)-1H-1,3-benzodiazol-2-yl]amino}-N-[2-(methylsulfanyl)ethyl]-3-[3-(trifluoromethyl)phenyl]propanamide Prepared by the method described for Example 46 (Steps 2 to 6) but using ethyl[2-(methylsulfanyl)ethyl]amine in place of methyl (2S)-2-aminopropanoate in Step 2 and (2,3-diaminophenyl)methanol in place of benzene-1,2-diamine in Step 5.

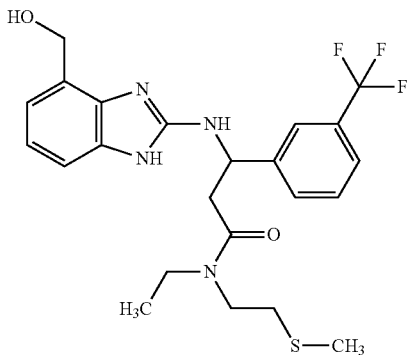 [SMILES: CCN(CCSC)C(=O)CC(Nc1nc2c(CO)cccc2[nH]1)c1cccc(C(F)(F)F)c1]

¹H NMR (400 MHz, AcOH-d₄) δ 7.89 (t, 2H, J=8.4 Hz), 7.66 (d, 1H, J=7.6 Hz), 7.60 (t, 1H, J=7.6 Hz), 7.37 (d, 1H, J=7.6 Hz), 7.26-7.02 (m, 2H), 5.75 (dd, 1H, J=4.4, 8.0 Hz), 4.94 (s, 2H), 3.61-3.39 (m, 5H), 3.19-3.07 (m, 1H), 2.70-2.65 (m, 1H), 2.56-2.52 (m, 1H), 2.11 (s, 1.3H), 2.05 (s, 1.7H), 1.16 (t, 1.5H, J=7.2 Hz), 1.02 (t, 1.5H, J=7.2 Hz);
MS: m/z 481.2 (M+1).

Example 59: Methyl 2-{3-[(1H-1,3-benzodiazol-2-yl)amino]-3-[3-(trifluoromethyl)phenyl]propanamido}acetate Prepared by the method described for Example 46 (Steps 2 to 6) but using methyl 2-aminoacetate in place of methyl (2S)-2-aminopropanoate in Step 2.

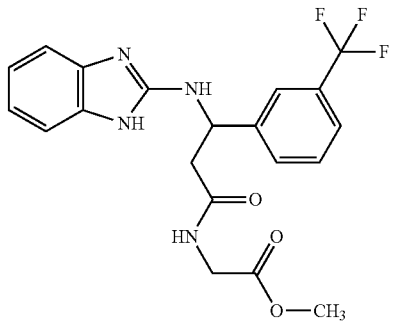 [SMILES: COC(=O)CNC(=O)CC(Nc1nc2ccccc2[nH]1)c1cccc(C(F)(F)F)c1]

A suspension of methyl 2-(3-{[(2-aminophenyl)carbamothioyl]amino}-3-[3-(trifluoromethyl)phenyl]propanamido)acetate (10.0 g, 22.00 mmol), mercury(II) oxide (9.53 g, 44.00 mmol) and sulfur (0.14 g, 4.40 mmol) in methanol (200 mL) was refluxed for 2 h. The reaction mixture was filtered through a celite pad with repeated methanol (4×100 mL) washes. The filtrate was evaporated to afford the crude product (10.2 g) which was purified by silica gel (60-120 mesh) column chromatography using 4% methanol in chloroform as eluent to afford methyl 2-{3-[(1H-1,3-benzodiazol-2-yl)amino]-3-[3-(trifluoromethyl)phenyl]propanamido}acetate (5.5 g) as off-white solid.
¹H NMR (400 MHz, DMSO-d₆) δ 10.84 (s, 1H, exchangeable), 8.43 (t, 1H, J=5.6 Hz, exchangeable), 7.80 (s, 1H, exchangeable), 7.73 (d, 1H, J=6.84 Hz), 7.58-7.51 (m, 2H), 7.37 (d, 1H, J=8.84 Hz), 7.09 (d, 2H, J=7.56 Hz), 6.84 (bs, 2H), 5.38 (q, 1H, J=7.2 Hz), 3.79 (d, 2H, J=5.64 Hz), 3.56 (s, 3H), 2.82 (dd, 1H, J=7.28, 14.4 Hz), 2.72 (dd, 1H, J=6.56, 14.68 Hz);
MS: m/z 421.2 (M+1).

The above product was resolved into its two enantiomers by chiral SFC (column: chiral YMC Cellulose-SB (250×4.6) mm 5 u, mobile phase 'A': 0.1% DEA in Hexane:Ethanol (80:20) Flow: 1.0 mL/min).

Example 59a: (−)Methyl 2-{3-[(1H-1,3-benzodiazol-2-yl)amino]-3-[3-(trifluoromethyl)phenyl]propanamido}acetate The (−) enantiomer was first to elute off the column.
¹H NMR (400 MHz, DMSO-d₆) δ 10.82 (s, 1H, exchangeable), 8.42 (t, 1H, J=5.2 Hz, exchangeable), 7.80 (s, 1H, exchangeable), 7.73 (d, 1H, J=7.2 Hz), 7.58-7.51 (m, 2H), 7.35 (d, 1H, J=8.8 Hz), 7.09 (d, 2H, J=8/.4 Hz), 6.88-6.79 (m, 2H), 5.38 (q, 1H, J=6.8 Hz), 3.79 (d, 2H, J=6.0 Hz), 3.56 (s, 3H), 2.85-2.79 (m, 1H), 2.75-2.70 (m, 1H);
MS: m/z 421.2 (M+1); $[\alpha]_D^{28}$=−37.19 (MeOH, c=0.406).

Example 59b: (+)Methyl 2-{3-[(1H-1,3-benzodiazol-2-yl)amino]-3-[3-(trifluoromethyl)phenyl]propanamido}acetate The (+) enantiomer was second to elute off the column.
¹H NMR (400 MHz, DMSO-d₆) δ 10.83 (s, 1H), 8.42 (t, 1H, J=5.6 Hz), 7.80 (s, 1H), 7.73 (d, 1H, J=6.8 Hz), 7.58-7.51 (m, 2H), 7.35 (d, 1H, J=8.8 Hz), 7.09 (d, 2H, J=8.4 Hz), 6.88-6.80 (m, 2H), 5.38 (q, 1H, J=6.8 Hz), 3.80 (d, 2H, J=5.6 Hz), 3.56 (s, 3H), 2.85-2.79 (m, 1H), 2.75-2.70 (m, 1H);
MS: m/z 421.2 (M+1); [α]$_D^{28}$=+36.96 (MeOH, c=0.376).

Example 60: 3-[(1H-1,3-benzodiazol-2-yl)amino]-N-(carbamoylmethyl)-N-methyl-3-[3-(trifluoromethyl)phenyl]propanamide

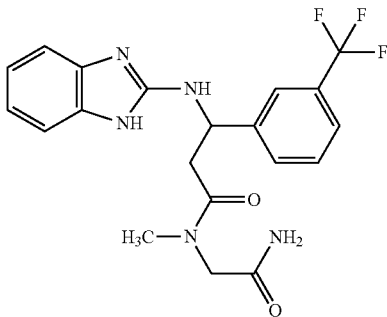 [SMILES: CN(CC(N)=O)C(=O)CC(Nc1nc2ccccc2[nH]1)c1cccc(C(F)(F)F)c1]

To a solution of methyl 2-{3-[(1H-1,3-benzodiazol-2-yl)amino]-N-methyl-3-[3-(trifluoromethyl)phenyl]propanamido}acetate (Example 57 prepared above) (0.2 g, 0.46 mmol) in methanol at 0° C. was added ammonia in methanol (7N, 1.5 mL, 3.75 mmol) and warmed to ambient temperature and stirred for 12 h. The reaction was evaporated to afford the crude product. This was purified by silica gel (60-120 mesh) column chromatography using 5% methanol in chloroform as eluent to afford the title product (0.115 g) as an off-white solid.
¹H NMR (400 MHz, DMSO-d₆) δ 11.15 (bs, 1H), 7.81 (d, 1H, J=7.6 Hz), 7.75 (t, 1H, 7.2 Hz), 7.58-7.42 (m, 3H), 7.23 (d, 1H, J=15.6 Hz), 7.11 (t, 2H, J=4.8 Hz), 7.03 (s, 1H), 6.87 (dd, 2H, J=3.2 Hz, 5.2 Hz), 5.37 (t, 1H, J=7.2 Hz), 4.05-4.01 (m, 0.5H), 3.91-3.75 (m, 1.5H), 3.17-3.11 (m, 1H), 3.05-32.99 (m, 1H), 2.96 (s, 3H);
MS: m/z 420.2 (M+1).

Example 61: Methyl 4-{2-[(1H-1,3-benzodiazol-2-yl)amino]-2-[3-(trifluoromethyl)phenyl]acetyl}piperazine-1-carboxylate

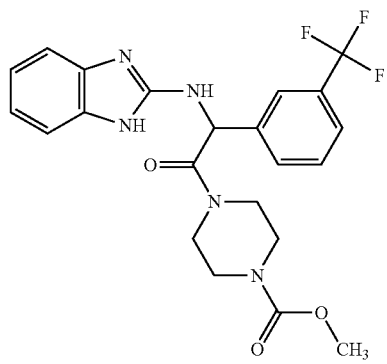 [SMILES: COC(=O)N1CCN(C(=O)C(Nc2nc3ccccc3[nH]2)c2cccc(C(F)(F)F)c2)CC1]

Step 1: Preparation of 2-[(1H-1,3-benzodiazol-2-yl)amino]-2-[3-(trifluoromethyl)phenyl]acetic acid

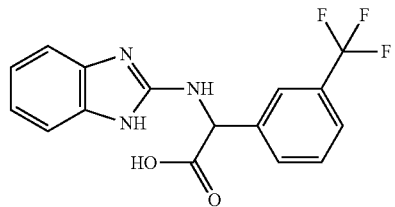 [SMILES: O=C(O)C(Nc1nc2ccccc2[nH]1)c1cccc(C(F)(F)F)c1]

To a solution of methyl 2-[(1H-1,3-benzodiazol-2-yl)amino]-2-[3-(trifluoromethyl)phenyl]acetate (from Example 24, Step 2), (0.3 g, 0.86 mmol) in THF (2 mL) was added a solution of LiOH.5H₂O (43 mg, 1.03 mmol) in water (3 mL) and the reaction mixture was stirred for 2 h. The reaction mixture was concentrated, acidified (pH-5) with 1.5N HCl. The solid formed was filtered and dried. The crude was triturated with dichloromethane:hexane (1:3), filtered, dried to afford the title product as an off-white solid (250 mg).
¹H NMR (400 MHz, DMSO-d₆ and D₂O) δ 7.88 (s, 1H), 7.82 (d, 1H, J=7.76 Hz), 7.71 (d, 1H, J=7.72 Hz), 7.64 (t, 1H, J=7.72 Hz) 7.25 (m, 2H), 7.00 (m, 2H), 5.64 (d, 1H, J=6.32 Hz).

Example 61, Step 2: Preparation of methyl 4-{2-[(1H-1,3-benzodiazol-2-yl)amino]-2-[3-(trifluoromethyl)phenyl]acetyl}piperazine-1-carboxylate

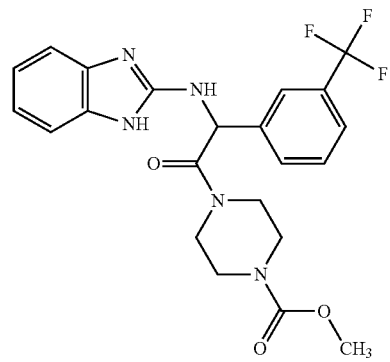 [SMILES: COC(=O)N1CCN(C(=O)C(Nc2nc3ccccc3[nH]2)c2cccc(C(F)(F)F)c2)CC1]

To a solution of 2-[(1H-1,3-benzodiazol-2-yl)amino]-2-[3-(trifluoromethyl)phenyl]acetic acid (from Step 1), (200 mg, 0.6 mmol), in dichloromethane (2 mL) was added triethylamine (91 mg, 0.9 mmol) and the reaction mixture was cooled to 0° C. Then EDC.HCl (126 mg, 0.66 mmol) and HBTU (249 mg, 0.66 mmol) were added and the reaction mixture was stirred for 10 minutes. Methyl piperazine-1-carboxylate (86 mg, 0.6 mmol) was added at 0° C. and the reaction mixture was stirred at ambient temperature for 12 h. The crude was filtered through a pad of celite, purified by preparative HPLC to afford the title product (15 mg) as an off-white solid.
¹H NMR (400 MHz, DMSO-d₆) δ 10.50 (s, 1H), 8.15 (s, 1H), 7.88 (d, 3H, J=10.68 Hz), 7.82 (d, 1H, J=7.48), 7.67 (t, 1H, J=6.56) 7.17 (bs, 1H), 6.89 (bs, 2H), 6.14 (d, 1H, J=8.80), 3.61 (m, 2H), 3.58 (m, 5H), 3.43 (m, 2H), 3.05 (m, 2H);
LCMS: m/z 462.2 (M+1).

Example 62: 3-[(1H-1,3-benzodiazol-2-yl)amino]-N-[2-(2-methoxyacetamido)ethyl]-3-[3-(trifluoromethyl)phenyl]propanamide

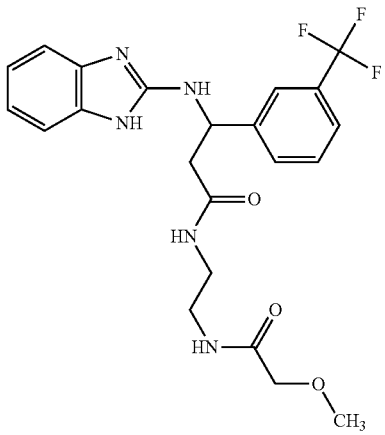 [SMILES: COCC(=O)NCCNC(=O)CC(Nc1nc2ccccc2[nH]1)c1cccc(C(F)(F)F)c1]

Methyl 3-[(1H-1,3-benzodiazol-2-yl)amino]-3-[3-(trifluoromethyl)phenyl]propanoate (from Example 1 Step 5), was converted to 3-[(1H-1,3-benzodiazol-2-yl)amino]-3-[3-(trifluoromethyl)phenyl]propanoic acid by the method described for Example 61 Step 1. To a solution of the resulting 3-[(1H-1,3-benzodiazol-2-yl)amino]-3-[3-(trifluoromethyl)phenyl]propanoic acid, (0.25 g, 0.71 mmol), PyBOP (0.45 g, 0.86 mmol) and triethylamine (0.2 mL, d=0.72 g/mL, 1.4 mmol) in dichloromethane (10 mL) at 0° C. was added ethyl (2-aminoethyl)carbamate (0.095 g, 0.71 mmol) and allowed to warm to ambient temperature and stirred for 12 h. The reaction mixture was diluted with dichloromethane (25 mL), washed with water (15 mL), brine (15 mL), dried over anhydrous sodium sulphate and evaporated to afford the crude product (0.35 g). This was purified by preparative HPLC. The desired product fraction, obtained from prep. HPLC, was concentrated under vacuum to (0.04 g) as colorless gum, as the trifluoroacetic acid salt.

$^1$H NMR (400 MHz, DMSO-$d_6$) δ 12.82 (bs, 2H), 9.63 (s, 1H), 8.12 (bs, 1H), 7.84 (s, 1H), 7.77 (d, 1H, J=7.4 Hz), 7.70-7.62 (m, 2H), 7.40-7.37 (m, 2H), 7.25-7.23 (m, 2H), 7.00 (bs, 1H), 5.35 (t, 1H, J=6.4 Hz), 3.94 (q, 2H, J=6.68 Hz), 3.04-3.01 (m, 2H), 2.93 (d, 2H, J=5.4 Hz), 2.85 (d, 2H, J=6.56 Hz), 1.12 (t, 3H, J=7.04 Hz);

MS: m/z 464.2 (M+1).

Example 63: 2-{3-[(1H-1,3-benzodiazol-2-yl)amino]-3-[3-(trifluoromethyl)phenyl]propanamido}ethyl N-ethylcarbamate

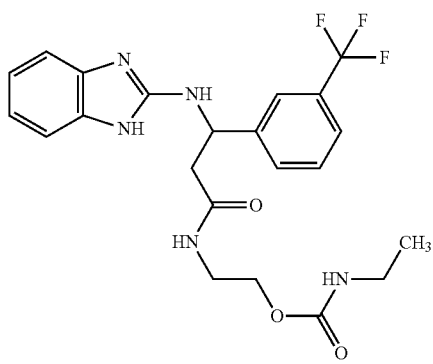 [SMILES: CCNC(=O)OCCNC(=O)CC(Nc1nc2ccccc2[nH]1)c1cccc(C(F)(F)F)c1]

To a solution of 3-[(1H-1,3-benzodiazol-2-yl)amino]-3-[3-(trifluoromethyl)phenyl]propanoic acid (prepared as in Example 62), (0.5 g, 1.4 mmol), PyBOP (0.89 g, 1.7 mmol) and triethylamine (0.8 mL, d=0.72 g/mL, 5.6 mmol) in dichloromethane (15 mL) at 0° C. was added 2-aminoethyl ethylcarbamate 2,2,2-trifluoroacetate and allowed to warm to ambient temperature and stirred for 12 h. The reaction mixture was diluted with dichloromethane (50 mL), washed with water (30 mL), brine (25 mL), dried over anhydrous sodium sulphate and evaporated to afford crude product (0.55 g). This was purified by preparative HPLC. The desired product fraction, obtained from preparative HPLC, was concentrated under vacuum to afford title product as a trifluoroacetic acid salt, (0.07 g) as colorless gum.

$^1$H NMR (400 MHz, DMSO-$d_6$) δ 12.84 (bs, 2H), 9.68 (d, 1H, J=8.4 Hz), 8.20 (t, 1H, J=5.2 Hz), 7.84 (s, 1H), 7.76 (d, 1H, J=7.6 Hz), 7.69-7.61 (m, 2H), 7.39-7.36 (m, 2H), 7.25-7.22 (m, 2H), 7.02 (t, 1H, J=4.8 Hz), 5.38 (t, 1H, J=7.2 Hz), 3.84 (t, 2H, J=6 Hz), 3.21-3.18 (m, 2H), 3.01-2.95 (m, 2H), 2.90-2.82 (m, 2H), 0.99 (t, 3H, J=7.2 Hz);

MS: m/z 464.2 (M+1).

Example 64: 2-[(1H-1,3-benzodiazol-2-yl)amino]-N-ethyl-N-(2-hydroxyethyl)-3-[3-(trifluoromethyl)phenyl]propanamide

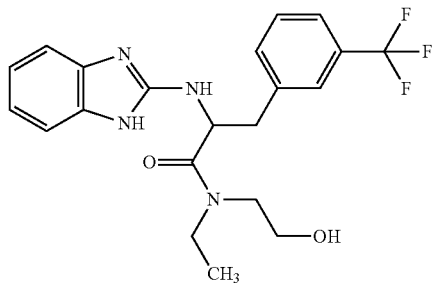 [SMILES: CCN(CCO)C(=O)C(Cc1cccc(C(F)(F)F)c1)Nc1nc2ccccc2[nH]1]

Step 1: Preparation of Methyl 2-amino-3-[3-(trifluoromethyl)phenyl]propanoate hydrochloride

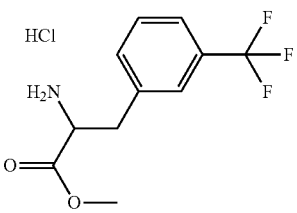 [SMILES: COC(=O)C(N)Cc1cccc(C(F)(F)F)c1 ; Cl]

To a well stirred solution of commercial 2-amino-3-[3-(trifluoromethyl)phenyl]propanoic acid (2.5 g, 11 mmol), in methanol (50 mL) was added thionyl chloride (2.0 mL, 27 mmol) at 0° C. and then refluxed for 20 h. The reaction mixture was concentrated, the residue was washed with diethyl ether (3×20 mL) to afford the title compound as hydrochloride salt as a white solid (2.5 g).

MS: m/z 248 (M+1).

Step 2: Preparation of Methyl 2-isothiocyanato-3-[3-(trifluoromethyl)phenyl]propanoate

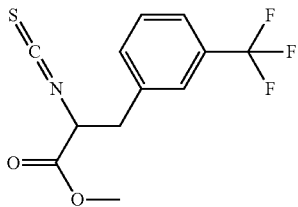 [SMILES: COC(=O)C(Cc1cccc(C(F)(F)F)c1)N=C=S]

To a suspension of methyl 2-amino-3-[3-(trifluoromethyl)phenyl]propanoate hydrochloride (from Step 1), (1.5 g, 0.61 mmol) in dichloromethane (50 mL) was added thiophosgene (0.7 mL, 0.91 mmol) at 0° C. followed by 10% aqueous sodium bicarbonate solution (30 mL) and the reaction mixture was stirred at ambient temperature for 1 h. The reaction mixture was extracted with dichloromethane (3×50 mL). The combined organic extracts were dried over anhydrous sodium sulphate and evaporated to afford methyl 2-isothiocyanato-3-[3-(trifluoromethyl)phenyl]propanoate (1.5 g) as a yellow gum.

MS: m/z 289.9 (M+1).

Step 3: Preparation of Methyl 2-{[(2-aminophenyl)carbamothioyl]amino}-3-[3-(trifluoromethyl)phenyl]propanoate

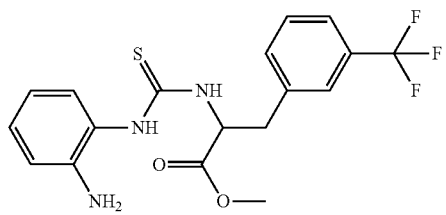 [SMILES: COC(=O)C(Cc1cccc(C(F)(F)F)c1)NC(=S)Nc1ccccc1N]

A mixture of methyl 2-isothiocyanato-3-[3-(trifluoromethyl)phenyl]propanoate (from Step 2), (1.2 g, 4.1 mmol) and 1,2-phenylene diamine (0.56 g, 5.0 mmol) in dichloromethane (50 mL) was stirred at ambient temperature for 12 h. The reaction mixture was concentrated, purified by column chromatography on silica gel (60-120 mesh; 1:0.03 chloroform/methanol) to give the desired product methyl 2-{[(2-aminophenyl)carbamothioyl]amino}-3-[3-(trifluoromethyl)phenyl]propanoate as a yellow gum (1 g).

MS: m/z 398.2 (M+1).

Step 4: Preparation of Methyl 2-[(1H-1,3-benzodiazol-2-yl)amino]-3-[3-(trifluoromethyl)phenyl]propanoate

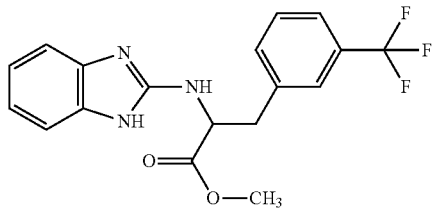 [SMILES: COC(=O)C(Cc1cccc(C(F)(F)F)c1)Nc1nc2ccccc2[nH]1]

To a solution of methyl 2-{[(2-aminophenyl)carbamothioyl]amino}-3-[3-(trifluoromethyl)phenyl]propanoate (from Step 3), (0.3 g, 0.73 mmol) in methanol (10 mL) was added iodoacetic acid (0.14 g, 0.73 mmol) and the reaction mixture was refluxed for 2 h. The reaction mixture was evaporated and the crude was purified by preparative HPLC to give the title product (0.15 g) as an off-white solid.

$^1$H NMR (400 MHz, MeOH-d$_4$) δ 7.63 (s, 1H), 7.61-7.53 (m, 3H), 7.38-7.35 (m, 2H), 7.32-7.29 (m, 2H), 4.76 (dd, 1H, J=5.20, 9.20 Hz), 3.84 (s, 3H), 3.54 (dd, 1H, 5.20, 14.40 Hz), 3.31-3.25 (m, 1H);

MS: m/z 364 (M+1).

Example 64, Step 5: Preparation of 2-[(1H-1,3-benzodiazol-2-yl)amino]-N-ethyl-N-(2-hydroxyethyl)-3-[3-(trifluoromethyl)phenyl]propanamide

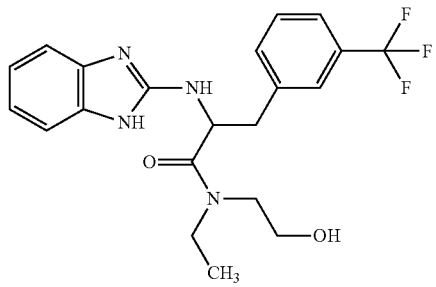 [SMILES: CCN(CCO)C(=O)C(Cc1cccc(C(F)(F)F)c1)Nc1nc2ccccc2[nH]1]

A solution of methyl 2-[(1H-1,3-benzodiazol-2-yl)amino]-3-[3-(trifluoromethyl)phenyl]propanoate (from Step 4), (0.2 g, 0.55 mmol), 2-(ethylamino)ethan-1-ol (0.15 g, 1.7 mmol) in acetonitrile (5 mL) was irradiated in a microwave oven at 120° C. for 3 h. The crude was purified by preparative HPLC to give the title product (65 mg).

$^1$H NMR (400 MHz, MeOH-d$_4$) δ 7.65 (s, 1H), 7.63-7.48 (m, 3H), 7.24-7.20 (m, 2H), 7.02-6.99 (m, 2H), 5.24-5.18 (m, 1H), 3.78-3.72 (m, 1H), 3.67-3.53 (m, 3H), 3.48-3.35 (m, 1H), 3.32-3.14 (m, 3H), 1.08-1.02 (m, 3H);

MS: m/z 421.2 (M+1).

Example 65: 3-[(1H-1,3-benzodiazol-2-yl)amino]-N-ethyl-3-(3-ethyl-4-fluorophenyl)-N-(2-hydroxyethyl)propanamide; Trifluoroacetic Acid

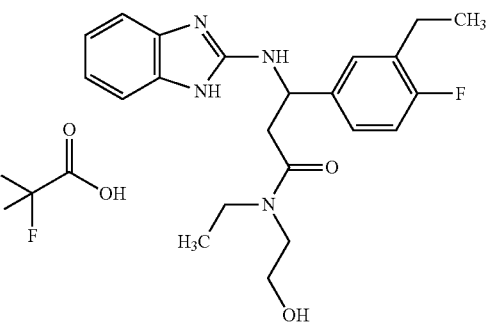

Preparation of
3-amino-3-(3-ethyl-4-fluorophenyl)propanoic acid

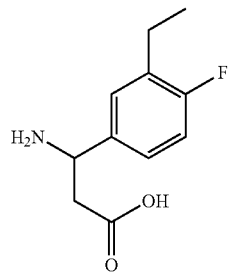

A mixture of malonic acid (8.65 g, 83 mmol), ammonium formate (10.5 g, 166.0 mmol) and 3-ethyl-4-fluoro-benzaldehyde (which can be prepared by the method described in *Journal of Medicinal Chemistry*, 2001, vol. 44, p. 3302-3310), (11.5 g, 76.0 mmol) in ethanol (35 mL) was refluxed for 16 h. The reaction mixture was concentrated to remove the solvent and the residue was diluted with acetone (50 mL) and stirred at room temperature for 1 h. The solid formed was filtered and dried to afford the title product (3.0 g) as white solid.

$^1$H NMR (400 MHz, DMSO-d$_6$): δ 7.37 (d, 1H, J=7.6 Hz), 7.28 (t, 1H, J=6.4 Hz), 7.13 (t, 1H, J=10.0 Hz), 4.25 (q, 1H, J=4.8 Hz), 2.60 (t, 2H, J=7.6 Hz), 2.35 (t, 2H, J=9.6 Hz), 1.17 (t, 3H, J=7.2 Hz);
MS: m/z 212.2 (M+1).

Step 2: Preparation of 3-{[(tert-butoxy)carbonyl]amino}-3-(3-ethyl-4-fluorophenyl)propanoic acid

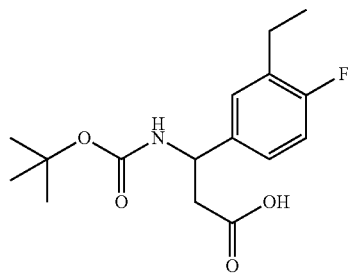 [SMILES: CCc1cc(C(CC(=O)O)NC(=O)OC(C)(C)C)ccc1F]

To a stirred solution of 3-amino-3-(3-ethyl-4-fluorophenyl)propanoic acid (from Step 1), (0.5 g, 2.4 mmol) in t-butanol (10 mL) was added 2N sodium hydroxide solution (2.4 mL, 5.0 mmol) then after 15 min, di-tert-butyl dicarbonate (0.55 mL, 2.6 mmol) was added and it was stirred at ambient temperature for 16 h. The reaction mixture was concentrated to remove the solvent and the residue was acidified with saturated aqueous solution of citric acid (approx. 10 mL, pH: 1-2). The aqueous layer was extracted with ethyl acetate (4×50 mL), the combined extracts were washed with brine (20 mL), dried over anhydrous sodium sulphate, filtered and concentrated to afford the title product (0.5 g) white solid. This was taken to next step without any further purification.

$^1$H NMR (400 MHz, DMSO-d$_6$): δ 12.06 (bs, 1H, —COOH, exchangeable), 7.42 (d, 1H, J=8.4 Hz, —NH, exchangeable), 7.22 (d, 1H, J=6.8 Hz), 7.15 (s, 1H), 7.06 (t, 1H, J=9.6 Hz), 4.85 (d, 1H, J=7.2 Hz), 3.17 (s, 1H), 2.57 (q, 3H, J=8.0 Hz), 1.35 (s, 9H), 1.16 (t, 3H, J=7.6 Hz);
MS: m/z 212.2 (M+1, loss of Boc).

Step 3: Preparation of Tert-Butyl N-{2-[ethyl(2-hydroxyethyl)carbamoyl]-1-(3-ethyl-4-fluorophenyl)ethyl}carbamate

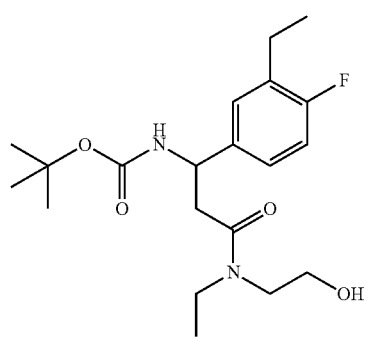 [SMILES: CCc1cc(C(CC(=O)N(CC)CCO)NC(=O)OC(C)(C)C)ccc1F]

To a stirred solution of 3-{[(tert-butoxy)carbonyl]amino}-3-(3-ethyl-4-fluorophenyl)propanoic acid (from Step 2), (1.5 g, 5.0 mmol) in tetrahydrofuran (5 mL) was added di-isopropyl ethyl amine (3.11 g, 24.0 mmol) followed by 2-(ethylamino) ethanol (0.644 g, 7.0 mmol) then BOP reagent (3.2 g, 7.0 mmol) was added and it was stirred at ambient temperature for 16 h. The reaction mixture was diluted with a saturated aqueous solution of sodium bicarbonate (30 mL) and the aqueous layer was extracted with ethyl acetate (4×125 mL). The combined organic layer was washed with brine (20 mL), dried over sodium sulphate, filtered and concentrated to afford crude product (1.9 g,) as a yellow gum. This was purified by flash chromatography (using the Grace Flash Chromatography System and 24.0 g pre-packed flash silica cartridge), the product fraction was eluted using 25-35% ethyl acetate in hexane to afford the titled product (1.5 g) as off-white solid.

$^1$H NMR (400 MHz, DMSO-d$_6$): δ 7.31 (q, 1H, J=8.8 Hz), 7.19 (d, 1H, J=7.2 Hz), 7.12 (t, 1H, J=2.8 Hz), 7.04 (t, 1H, J=9.6 Hz), 4.92 (bs, 1H), 4.81 (bs, 1H), 3.42 (t, 1H, J=5.2 Hz) 3.36 (t, 1H, J=5.6 Hz), 3.29-3.22 (m, 4H) 2.97 (q, 1H, J=5.2 Hz), 2.79-2.70 (m, 1H), 2.59 (q, 2H, J=7.6 Hz) 1.35 (s, 9H), 1.15 (t, 3H, J=7.6 Hz), 0.95 (tt, 3H, J=6.8, 7.2 Hz);
MS: m/z 383.2 (M+1).

Step 4: Preparation of 3-amino-N-ethyl-3-(3-ethyl-4-fluorophenyl)-N-(2-hydroxyethyl)propanamide

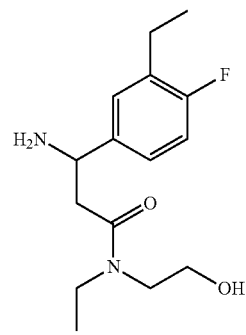 [SMILES: CCc1cc(C(N)CC(=O)N(CC)CCO)ccc1F]

To a stirred solution of tert-butyl N-{2-[ethyl(2-hydroxyethyl)carbamoyl]-1-(3-ethyl-4-fluorophenyl)ethyl}carbamate (from Step 3), (2 g, 5.0 mmol) under a nitrogen atmosphere in dichloromethane (50 mL) was added trifluoroacetic acid (1.8 g, 16.0 mmol) at 0° C. and the mixture was slowly warmed to ambient temperature and stirred for 20 h. The reaction mixture was concentrated to afford the title compound (1.4 g) as yellow gum. This was taken into the next step without further purification.

MS: m/z 283.2 (M+1).

Step 5: Preparation of N-ethyl-3-(3-ethyl-4-fluorophenyl)-N-(2-hydroxyethyl)-3-isothiocyanatopropanamide

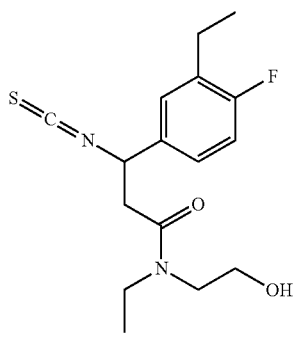 [SMILES: CCc1cc(C(CC(=O)N(CC)CCO)N=C=S)ccc1F]

To a stirred solution of 3-amino-N-ethyl-3-(3-ethyl-4-fluorophenyl)-N-(2-hydroxyethyl)propanamide (from Step 4), (1.4 g, 5.0 mmol) in dichloromethane (50 mL) was added thiophosgene (1.425 g, 12.0 mmol) at 0° C. and then after 30 min, 10% aqueous sodium bicarbonate solution (25 mL) solution was added and it was stirred at ambient temperature. After 4 h, the reaction mixture was diluted with water (25 mL) and it was extracted with dichloromethane (5×125 mL). The combined organic layer was dried over anhydrous sodium sulphate, filtered and concentrated to afford the title compound (1.5 g) as yellow liquid. This could be taken to the next step without any further purification.

$^1$H NMR (400 MHz, CDCl$_3$): δ 7.17 (q, 2H, J=6.8 Hz), 7.02 (q, 1H, J=8.4 Hz), 5.45-5.23 (m, 1H), 4.33 (q, 1H, J=7.2 Hz), 3.67-3.34 (m, 5H), 3.05-2.98 (m, 1H), 2.78 (d, 1H, J=5.2 Hz), 2.69 (q, 2H, J=7.2 Hz), 1.29 (t, 3H, J=4.0 Hz), 1.13 (t, 3H, J=6.8 Hz).

Step 6: Preparation of 3-{[(2-aminophenyl)carbamothioyl]amino}-N-ethyl-3-(3-ethyl-4-fluorophenyl)-N-(2-hydroxyethyl)propanamide

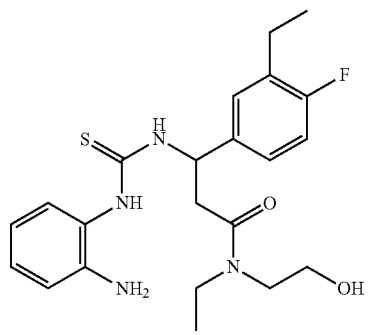 [SMILES: CCc1cc(C(CC(=O)N(CC)CCO)NC(=S)Nc2ccccc2N)ccc1F]

A stirred solution of N-ethyl-3-(3-ethyl-4-fluorophenyl)-N-(2-hydroxyethyl)-3-isothiocyanatopropanamide (from Step 5), (1.5 g, 5.0 mmol) and benzene-1, 2-diamine (0.5 g, 5.0 mmol) under a nitrogen atmosphere in dichloromethane (50 mL) was stirred at ambient temperature for 18 h. The reaction mixture was diluted with 10% aqueous sodium bicarbonate solution (35 mL) and the aqueous layer was extracted with dichloromethane (5×150 mL). The combined organic layer was washed with brine (30 mL), dried over sodium sulphate, filtered and concentrated to afford an off-white solid. It was purified by Grace (using 12.0 g pre-packed flash cartridge), the product fraction was eluted with 90-100% ethyl acetate in hexane to afford the titled product (1.5 g) as an off-white solid.

MS: m/z 433.2 (M+1).

Example 65, Step 7: Preparation 3-[(1H-1,3-benzodiazol-2-yl)amino]-N-ethyl-3-(3-ethyl-4-fluorophenyl)-N-(2-hydroxyethyl)propanamide; trifluoroacetic acid

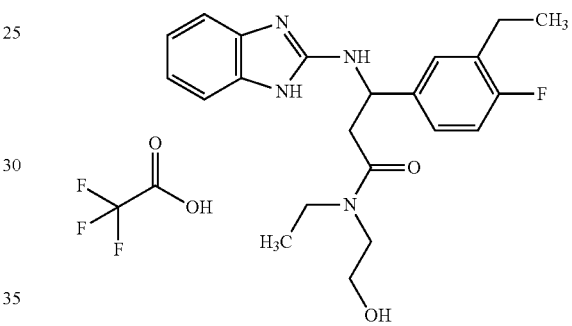

To a stirred solution of 3-{[(2-aminophenyl)carbamothioyl]amino}-N-ethyl-3-(3-ethyl-4-fluorophenyl)-N-(2-hydroxyethyl)propanamide (from Step 6), (1.5 g, 3.47 mmol) in methanol (50 mL) was added iodoacetic acid (0.81 g, 4.35 mmol) and it was heated at 65° C. for 5 h under a nitrogen atmosphere. The reaction mixture was concentrated to afford as yellow gum. It was purified by flash chromatography (using the Grace Flash Chromatography System and 40 g pre-packed flash silica cartridge) eluted using 3-4% methanol in chloroform to afford the title product (1.2 g) as an off-white solid. The above product contains iodoacetic acid, so it was dissolved in dichloromethane (3×100 mL) and washed with saturated solution of sodium hydroxide (30 mL). The organic layer was dried over sodium sulphate, filtered and concentrated to afford desired product (1.0 g) as off-white solid. This was further purified by preparative HPLC-TFA method. After preparative HPLC separation, the product fraction was concentrated to afford desired product (0.370 g) as off-white solid.

$^1$H NMR (400 MHz, AcOH-d$_4$): δ 7.46 (t, 1H, J=7.6 Hz), 7.43-7.36 (m, 3H), 7.24 (q, 2H, J=3.2 Hz), 7.05 (t, 1H, J=9.2 Hz), 5.48 (q, 1H, J=4.0 Hz), 3.83 (d, 1H, J=5.6 Hz), 3.74 (s, 1H), 3.36-3.56 (m, 5H), 3.05-2.98 (m, 1H), 2.68 (q, 2H, J=7.2 Hz), 1.23 (t, 3H, J=7.2 Hz), 1.09 (tt, 3H, J=7.2, 7.2 Hz);

MS: m/z 399.2 (M+1).

The above product was separated into its two enantiomers by SFC Chiral HPLC. Method Information: Column: YMC Cellulose SB, Co-Solvent: 20 mM Ammonia in IPA, Injection Volume: 5 mL, Sample Well: P2: 4B, Column Tem- Example 65a: (−)3-[(1H-1,3-benzodiazol-2-yl)amino]-N-ethyl-3-(3-ethyl-4-fluorophenyl)-N-(2-hydroxyethyl)propanamide; trifluoroacetic acid The (−) enantiomer was the first to elute off the column, as an off-white solid.
$^1$H NMR (400 MHz, AcOH-d$_4$): δ 7.49-7.44 (m, 1H), 7.41-7.35 (m, 3H), 7.25-7.22 (m, 2H), 7.05 (t, 1H, J=9.6), 5.47 (dd, 1H, J=3.9, 8.84 Hz), 3.81 (q, 1H, J=5.64 Hz), 3.73 (t, 1H, J=6.2 Hz), 3.59-3.38 (m, 5H), 3.04-2.97 (m, 1H), 2.69 (q, 2H, J=7.52 Hz), 1.24 (t, 3H, J=7.56 Hz), 1.08 (tt, 3H, J=7.06, 7.12 Hz);
MS: m/z 399.2 (M+1).

Example 65b: (+)Preparation 3-[(1H-1,3-benzodiazol-2-yl)amino]-N-ethyl-3-(3-ethyl-4-fluorophenyl)-N-(2-hydroxyethyl)propanamide; trifluoroacetic acid The (+) enantiomer was the second to elute off the column, as an off-white solid.
$^1$H NMR (400 MHz, AcOH-d$_4$): δ 7.47 (t, 1H, J=7.68), 7.41-7.36 (m, 3H), 7.24-7.23 (m, 2H), 7.05 (t, 1H, J=9.4 Hz), 5.47 (d, 1H, J=5.44 Hz), 3.77 (dd, 2H, J=5.24, 11.36 Hz), 3.39-3.38 (m, 5H), 3.05-2.97 (m, 1H), 2.69 (q, 2H, J=7.48 Hz), 1.24 (t, 3H, J=7.52 Hz), 1.08 (tt, 3H, J=7.08, 7.08 Hz);
MS: m/z 399.2 (M+1).

Example 66: Preparation of Ethyl N-{[2-({2-[ethyl(2-hydroxyethyl)carbamoyl]-1-[3-(trifluoromethyl)phenyl]ethyl}amino)-1H-1,3-benzodiazol-5-yl]methyl}carbamate

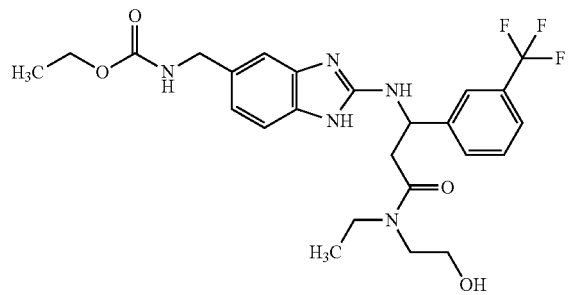 [SMILES: CCOC(=O)NCc1ccc2[nH]c(NC(CC(=O)N(CC)CCO)c3cccc(C(F)(F)F)c3)nc2c1]

Step 1: Preparation of ethyl N-(2,1,3-benzothiadiazol-5-ylmethyl)carbamate

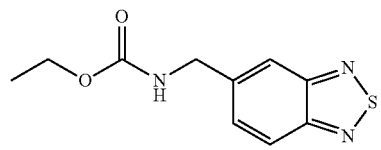 [SMILES: CCOC(=O)NCc1ccc2nsnc2c1]

To an ice cooled (0° C.) solution of 2,1,3-benzothiadiazol-5-ylmethanamine (7.0 g, 42 mmol) (which can be prepared as described in Alantos Pharmaceuticals, Inc., Patent: US2006/173183 A1, Page/Page column 111-112) under nitrogen atmosphere in dry dichloromethane (100 mL) was added triethylamine (14.8 mL, 106.0 mmol). After 15 min, ethylchloroformate (6.0 mL, 64.0 mmol) was added and the reaction mixture was slowly warmed to ambient temperature and stirred for 5 h. The reaction mixture was extracted using dichloromethane (4×200 mL) and the combined organic layer was washed with a saturated solution of aqueous sodium bicarbonate (30 mL), dried over anhydrous sodium sulphate, filtered and concentrated to afford the title product as a white solid. This was used in the next step without further any purification.
$^1$H NMR (400 MHz, DMSO-d$_6$): δ 8.05 (d, 1H, J=8.8 Hz), 7.85 (d, 2H, J=6.0 Hz), 7.63 (q, 1H, J=1.6 Hz), 4.38 (d, 2H, J=6.4 Hz), 4.02 (q, 2H, J=7.2 Hz), 1.18 (t, 3H, J=6.8 Hz);
MS: m/z 238.3 (M+1).

Step 2: Preparation of ethyl N-[(3,4-diaminophenyl)methyl]carbamate

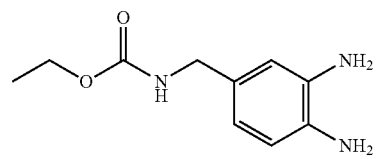

To a stirred solution of ethyl N-(2,1,3-benzothiadiazol-5-ylmethyl)carbamate (from Step 1), (4.0 g, 17 mmol) in dry methanol (500 mL) was added Raney Ni (2.88 g, 34.0 mmol, 100% w/w, after washing five times with methanol) and it was hydrogenated under balloon pressure at ambient temperature for 16 h. The reaction mixture was filtered through a celite pad and was washed with methanol (1000 mL). The combined filtrate was concentrated to afford the title product (3.0 g) as a brown solid.
$^1$H NMR (400 MHz, DMSO-d$_6$): δ 7.35 (bs, 1H), 6.41 (d, 2H, J=7.6 Hz), 6.26 (d, 1H, J=7.6 Hz), 4.41 (s, 2H), 4.32 (s, 2H), 3.98 (t, 2H, J=6.8 Hz, exchangeable), 3.93 (t, 2H, J=8.8 Hz, exchangeable), 1.15 (t, 3H, J=7.2 Hz);
MS: m/z 210.2 (M+1).

Step 3: Preparation of Tert-Butyl N-{2-[ethyl(2-hydroxyethyl)carbamoyl]-1-[3-(trifluoromethyl)phenyl]ethyl}carbamate

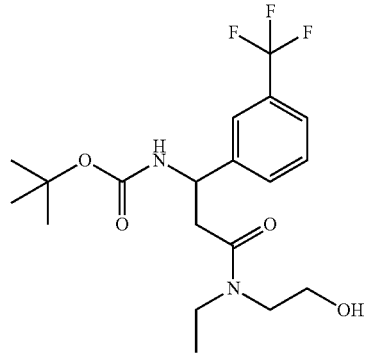 [SMILES: CCN(CCO)C(=O)CC(NC(=O)OC(C)(C)C)c1cccc(C(F)(F)F)c1]

To an ice cooled (0° C.) solution of 3-{[(tert-butoxy)carbonyl]amino}-3-[3-(trifluoromethyl)phenyl]propanoic acid (from Step 2), (1.0 g, 3 mmol) and 2-(ethylamino)ethanol (0.44 mL, 5.0 mmol) under nitrogen atmosphere in dry tetrahydrofuran was added N, N-diisopropyl ethylamine (2.62 mL, 15.0 mmol). After 10 min, BOP reagent (1.73 g, 4 mmol) was added and the resulting reaction mixture was stirred at ambient temperature for 16 h. The reaction mass was concentrated to remove excess solvent, it was diluted with aqueous saturated sodium bicarbonate solution (30 mL) and it was extracted with ethyl acetate (4×125 mL). The combined organic layer was dried over anhydrous sodium sulphate, filtered and concentrated to afford a yellow gum. It was purified by flash chromatography (using the Grace Flash Chromatography System and 24.0 g pre-packed flash silica cartridge), the product was eluted using 75-80% ethyl acetate in hexane to afford the title product (1.2 g) as a colourless gum.

$^1$H NMR (400 MHz, DMSO-$d_6$): δ 7.63-7.51 (m, 4H), 7.44 (t, 1H, J=13.6 Hz), 5.02 (bs, 1H), 4.80 (bs, 1H, —OH exchangeable), 3.34 (q, 2H, J=5.6 Hz), 3.28-3.16 (m, 4H), 2.86-2.77 (m, 1H), 2.73-2.65 (m, 1H), 1.34 (s, 9H), 0.94 (tt, 3H, J=7.2, 6.8 Hz);

MS: m/z 405.2 (M+1).

Step 4: Preparation of 3-amino-N-ethyl-N-(2-hydroxyethyl)-3-[3-(trifluoromethyl)phenyl]propanamide

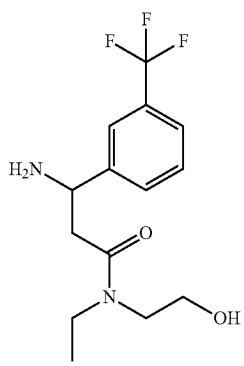 [SMILES: CCN(CCO)C(=O)CC(N)c1cccc(C(F)(F)F)c1]

To an ice cooled (0° C.) solution of tert-butyl N-{2-[ethyl(2-hydroxyethyl)carbamoyl]-1-[3-(trifluoromethyl)phenyl]ethyl}carbamate (from Step 3), (1.0 g, 2.0 mmol) under a nitrogen atmosphere in dichloromethane (30 mL) was add trifluoroacetic acid (0.38 mL, 5.0 mmol). The resulting reaction mixture was slowly warmed to ambient temperature and stirred for 16 h. The reaction mixture was concentrated under high vacuum to afford the title compound (0.7 g, 70.36%) as a white gel. This was used in the next step without further any purification.

MS: m/z 305.2 (M+1).

Step 5: Preparation of N-ethyl-N-(2-hydroxyethyl)-3-isothiocyanato-3-[3-(trifluoromethyl)phenyl]propanamide

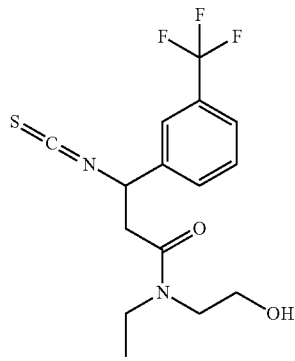 [SMILES: CCN(CCO)C(=O)CC(N=C=S)c1cccc(C(F)(F)F)c1]

To a stirred solution of 3-amino-N-ethyl-N-(2-hydroxyethyl)-3-[3-(trifluoromethyl)phenyl]propanamide (from Step 4), (0.3 g. 1.0 mmol) under nitrogen atmosphere in dichloromethane (15.0 mL) was added thiophosgene (0.283 g, 2.0 mmol) at 0° C. After 20 min, saturated sodium bicarbonate solution (15 mL) was added and the resulting reaction mixture was stirred at room temperature for 16 h. The reaction mass was extracted with dichloromethane (3×100 mL) and the combined organic layer was dried over anhydrous sodium sulphate, filtered and concentrated to afford the title product (0.33 g) as a yellow gum. This was used in the next step without further purification.

$^1$H NMR (400 MHz, CDCl$_3$): δ 7.70-7.47 (m, 4H), 5.52 (tt, 1H, J=3.2, 4.0 Hz), 3.80 (t, 1H, J=4.8 Hz), 3.72-3.68 (m, 1H), 3.57-3.06 (m, 6H), 2.86 (q, 1H, J=4.8 Hz), 1.12 (tt, 3H, J=7.2, 7.2 Hz);

MS: m/z 347.2 (M+1).

Step 6: Preparation of ethyl N-({4-amino-3-[({2-[ethyl(2-hydroxyethyl)carbamoyl]-1-[3-(trifluoromethyl)phenyl]ethyl}carbamothioyl)amino]phenyl}methyl)carbamate and ethyl N-({3-amino-4-[({2-[ethyl(2-hydroxyethyl)carbamoyl]-1-[3-(trifluoromethyl)phenyl]ethyl}carbamothioyl)amino]phenyl}methyl)carbamates

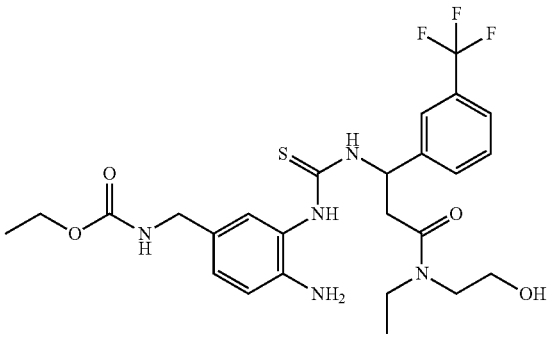

-continued

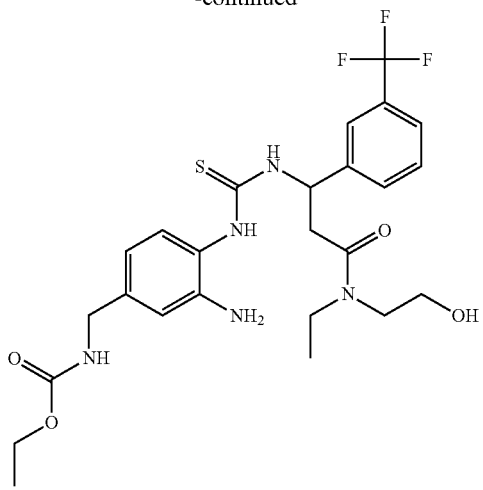

A stirred solution of ethyl N-[(3,4-diaminophenyl)methyl]carbamate (from Step 2), (0.103 g, 5 mmol) and N-ethyl-N-(2-hydroxyethyl)-3-isothiocyanato-3-[3-(trifluoromethyl)phenyl]propanamide (from Step 5), (0.17 g, 5.0 mmol) in dichloromethane (15 mL) was stirred at RT for 16 h under a nitrogen atmosphere. The reaction mixture was concentrated to afford a mixture of the title products (0.27 g, in a ratio of ca. 8:2) as a brown gum. This mixture was used in the next step without further purification.

MS: m/z 556.2 (M+1).

Example 66, Step 7: Preparation of Ethyl N-{[2-({2-[ethyl(2-hydroxyethyl)carbamoyl]-1-[3-(trifluoromethyl)phenyl]ethyl}amino)-1H-1,3-benzodiazol-5-yl]methyl}carbamate

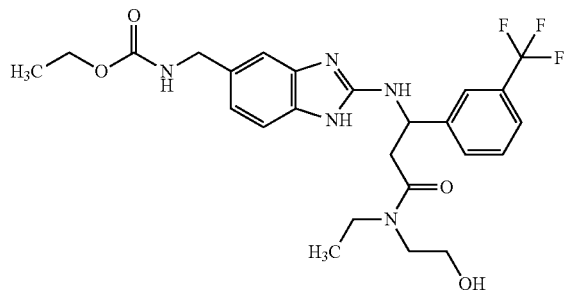 [SMILES: CCOC(=O)NCc1ccc2[nH]c(NC(CC(=O)N(CC)CCO)c3cccc(C(F)(F)F)c3)nc2c1]

To a stirred solution of the mixture of products from Step 6 (0.27 g, 0.49 mmol) under a nitrogen atmosphere in methanol (30 mL) was added iodoacetic acid (0.127 g, 0.7 mmol) and the resultant reaction mixture was heated at 65° C. for 16 h. The reaction mixture was concentrated and the residue was extracted with dichloromethane (4×75 mL). The combined organic layer was washed with saturated sodium hydroxide solution, dried over anhydrous sodium sulphate, filtered and concentrated to afford the crude title product (0.15 g). This was purified by flash chromatography (using the Grace Flash Chromatography System and 24.0 g prepacked flash silica cartridge) eluted with 1:1 ethyl acetate and hexane to afford (0.12 g) as yellow gum. This was further purified by prep-HPLC-TFA method to afford the title compound (0.069 g, 23.62%) as off white solid.

$^1$H NMR (400 MHz, AcOH-d$_4$): δ 7.85 (q, 2H J=8.4 Hz), 7.65 (d, 1H, J=7.6 Hz), 7.58 (t, 1H, J=7.6 Hz), 7.35 (d, 2H, J=8.0 Hz), 7.21 (d, 1H, J=8.4 Hz), 5.60 (q, 1H, J=4.0 Hz), 4.41 (s, 2H), 4.20-4.13 (m, 2H), 3.81 (q, 1H, J=5.6 Hz), 3.73 (t, 1H, J=5.6 Hz), 3.62-3.38 (m, 5H), 3.09 (t, 1H, J=4.4 Hz), 1.24 (t, 3H, J=6.8 Hz), 1.09 (tt, 3H, J=7.2, 7.2 Hz);

MS: m/z 522.2 (M+1).

Example 67: 3-[(1H-1,3-benzodiazol-2-yl)amino]-N-[2-(trifluoromethoxy)ethyl]-3-[3-(trifluoromethyl)phenyl]propanamide

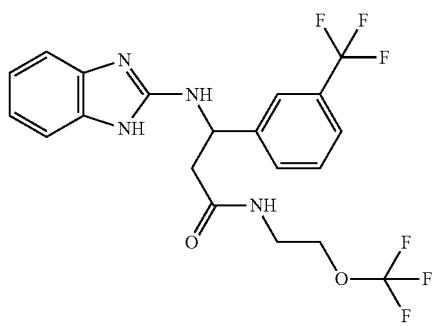 [SMILES: O=C(CC(Nc1nc2ccccc2[nH]1)c1cccc(C(F)(F)F)c1)NCCOC(F)(F)F]

The titled example is prepared by the method described for Example 1 (Step 6) but using 2-(trifluoromethoxy)ethan-1-amine in place of 2-(methylsulfanyl)ethan-1-amine.

$^1$H-NMR (400 MHz, DMSO-d$_6$): δ 10.85 (bs, 1H, exchangeable), 8.25 (t, J=5.60 Hz, 1H, exchangeable), 7.79 (s, 1H), 7.73 (d, J=7.20 Hz, 1H), 7.58-7.51 (m, 2H), 7.40 (d, J=8.40 Hz, 1H, exchangeable), 7.10 (d, J=8.40 Hz, 2H), 6.89-6.82 (m, 2H), 5.38 (q, J=7.20 Hz, 1H), 3.91 (q, J=5.60 Hz, 2H), 3.33-3.27 (m, 2H), 2.79 (dd, J=7.20, 14.40 Hz, 1H), 2.70 (dd, J=6.40, 14.40 Hz, 1H);

MS: m/z 461.2 (M+1).

The enantiomers of the above example were separated by chiral chromatography. Column: YMC Cellulose C; Co-solvent: 20 mM Ammonia in IPA; Co-solvent percentage: 30; Total flow: 3 mL/min; Back pressure: 100 bar.

Example 67a: 3-[(1H-1,3-benzodiazol-2-yl)amino]-N-[2-(trifluoromethoxy)ethyl]-3-[3-(trifluoromethyl)phenyl]propanamide (Isomer 1)

Isomer 1, eluted off the column at 1.31 minutes.

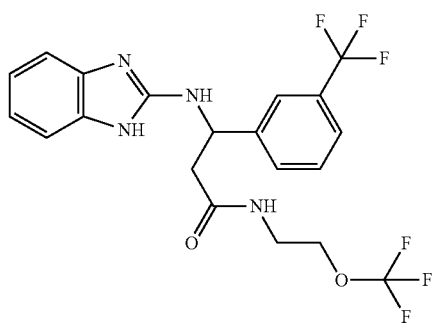 [SMILES: O=C(CC(Nc1nc2ccccc2[nH]1)c1cccc(C(F)(F)F)c1)NCCOC(F)(F)F]

$^1$H-NMR (400 MHz, DMSO-d$_6$): δ 10.85 (s, 1H, exchangeable), 8.25 (t, J=5.60 Hz, 1H, exchangeable), 7.78 (s, 1H), 7.72 (d, J=6.80 Hz, 1H), 7.58-7.53 (m, 2H), 7.40 (d, J=8.80 Hz, 1H, exchangeable), 7.10 (d, J=8.40 Hz, 2H), 6.89-6.82 (m, 2H), 5.38 (d, J=8.40 Hz, 1H), 3.91 (q, J=4.80 Hz, 2H), 3.33-3.27 (m, 2H), 2.79 (dd, J=6.80, 14.40 Hz, 1H), 2.70 (dd, J=3.20, 12.60 Hz, 1H);

MS: m/z 461.2 (M+1).

Example 67b: 3-[(1H-1,3-benzodiazol-2-yl)amino]-N-[2-(trifluoromethoxy)ethyl]-3-[3-(trifluoromethyl)phenyl]propanamide (Isomer 2)

Isomer 2, eluted off the column at 2.92 minutes.

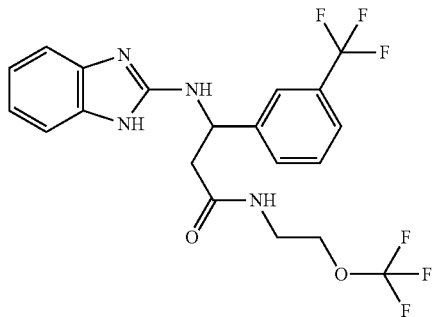 [SMILES: O=C(CC(Nc1nc2ccccc2[nH]1)c1cccc(C(F)(F)F)c1)NCCOC(F)(F)F]

$^1$H-NMR (400 MHz, DMSO-$d_6$): δ 10.84 (s, 1H, exchangeable), 8.25 (t, J=6.00 Hz, 1H, exchangeable), 7.78 (s, 1H), 7.72 (d, J=7.60 Hz, 1H), 7.58-7.51 (m, 2H), 7.39 (d, J=8.80 Hz, 1H, exchangeable), 7.10 (d, J=8.00 Hz, 2H), 6.87-6.80 (m, 2H), 5.38 (d, J=8.80 Hz, 1H), 3.91 (q, J=4.80 Hz, 2H), 3.30-3.27 (m, 2H), 2.79 (dd, J=6.80, 14.40 Hz, 1H), 2.70 (dd, J=2.00, 13.40 Hz, 1H);

MS: m/z 461.2 (M+1).

Example 68: 3-[(1H-1,3-benzodiazol-2-yl)amino]-N-[2-(2,2,2-trifluoroethoxy)ethyl]-3-[3-(trifluoromethyl)phenyl]propanamide The titled example is prepared by the method described for Example 1 (Step 6) but using 2-(2,2,2-trifluoroethoxy)ethan-1-amine in place of 2-(methylsulfanyl)ethan-1-amine.

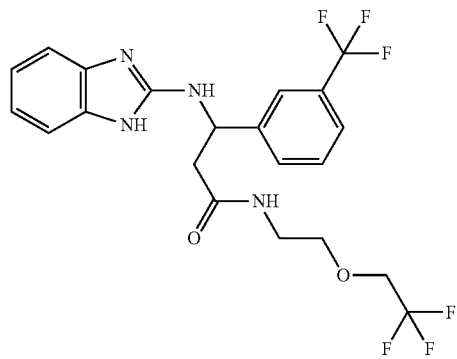 [SMILES: O=C(CC(Nc1nc2ccccc2[nH]1)c1cccc(C(F)(F)F)c1)NCCOCC(F)(F)F]

$^1$H NMR (400 MHz, AcOH-$d_4$): δ 7.87 (s, 1H), 7.82 (d, J=6.88 Hz, 1H), 7.66 (d, J=6.92 Hz, 1H), 7.61 (t, J=7.56 Hz, 1H), 7.42-7.41 (m, 2H), 7.26-7.24 (m, 2H), 5.56 (q, J=4.56 Hz, 1H), 3.88-3.79 (m, 2H), 3.68-3.55 (m, 2H), 3.51-3.40 (m, 2H), 3.24 (dd, J=9.68, 14.58 Hz, 1H), 3.03 (dd, J=5.00, 14.60 Hz, 1H);

MS: m/z 475.1 (M+1).

The enantiomers of the above example were separated by chiral chromatography. Column: YMC Cellulose C; mobile phase: $CO_2$: 20 mM ammonia in IPA (co-solvent); co-solvent percentage: 40; total flow: 4 mL/min; back pressure: 100 bar.

Example 68a: 3-[(1H-1,3-benzodiazol-2-yl)amino]-N-[2-(2,2,2-trifluoroethoxy)ethyl]-3-[3-(trifluoromethyl)phenyl]propanamide (Isomer 1)

Isomer 1, eluted off the column at 0.92 minutes.

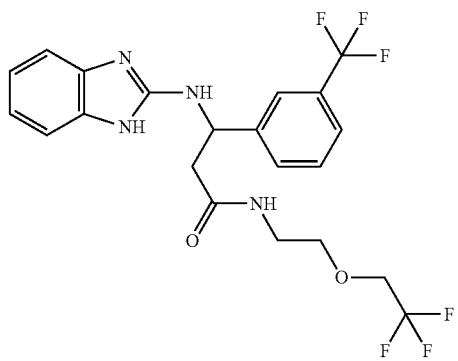 [SMILES: O=C(CC(Nc1nc2ccccc2[nH]1)c1cccc(C(F)(F)F)c1)NCCOCC(F)(F)F]

$^1$H NMR (400 MHz, AcOH-$d_4$): δ 7.85 (s, 1H), 7.80 (d, J=7.60 Hz, 1H), 7.65 (d, J=7.60 Hz, 1H), 7.59 (t, J=7.60 Hz, 1H), 7.41-7.39 (m, 2H), 7.26-7.23 (m, 2H), 5.54 (q, J=5.20 Hz, 1H), 3.86-3.78 (m, 2H), 3.64-3.56 (m, 2H), 3.49-3.37 (m, 2H), 3.19 (dd, J=9.60, 14.60 Hz, 1H), 3.02 (dd, J=5.20, 14.40 Hz, 1H);

MS: m/z 475.1 (M+1).

Example 68b: 3-[(1H-1,3-benzodiazol-2-yl)amino]-N-[2-(2,2,2-trifluoroethoxy)ethyl]-3-[3-(trifluoromethyl)phenyl]propanamide (Isomer 2)

Isomer 2, eluted off the column at 1.42 minutes.

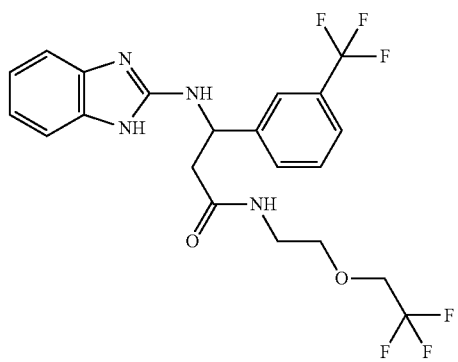 [SMILES: O=C(CC(Nc1nc2ccccc2[nH]1)c1cccc(C(F)(F)F)c1)NCCOCC(F)(F)F]

$^1$H NMR (400 MHz, AcOH-$d_4$): δ 7.85 (s, 1H), 7.80 (d, J=7.60 Hz, 1H), 7.65 (d, J=7.60 Hz, 1H), 7.60 (t, J=8.00 Hz, 1H), 7.41-7.39 (m, 2H), 7.26-7.22 (m, 2H), 5.54 (q, J=5.20 Hz, 1H), 3.87-3.77 (m, 2H), 3.63-3.56 (m, 2H), 3.50-3.37 (m, 2H), 3.19 (dd, J=10.00, 14.60 Hz, 1H), 3.02 (dd, J=5.20, 14.40 Hz, 1H);

MS: m/z 475.1 (M+1).

Example 69: 3-[(1H-1,3-benzodiazol-2-yl)amino]-N-[(1R)-2-methoxy-1-phenylethyl]-3-[3-(trifluoromethyl)phenyl]propanamide The titled example is prepared by the method described for Example 1 (Step 6) but using (1R)-2-methoxy-1-phenylethan-1-amine in place of 2-(methylsulfanyl)ethan-1-amine.

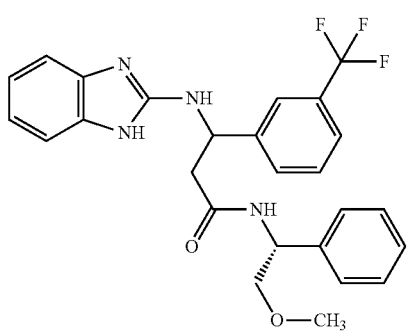 [SMILES: COC[C@H](NC(=O)CC(Nc1nc2ccccc2[nH]1)c1cccc(C(F)(F)F)c1)c1ccccc1]

MS: m/z 483 (M+1).

The enantiomers of the above example were separated by chiral chromatography. Column: YMC Cellulose C, Co-solvent: 20 mM Ammonia in IPA, Co-solvent percentage: 40, Total flow: 4 mL/min, Back pressure: 100 bar.

Example 69a: 3-[(1H-1,3-benzodiazol-2-yl)amino]-N-[(1R)-2-methoxy-1-phenylethyl]-3-[3-(trifluoromethyl)phenyl]propanamide (Isomer 1)

Isomer 1, eluted off the column at 1.08 minutes.

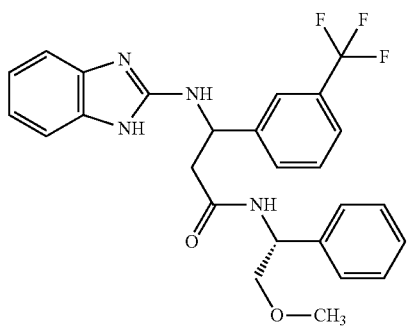 [SMILES: COC[C@H](NC(=O)CC(Nc1nc2ccccc2[nH]1)c1cccc(C(F)(F)F)c1)c1ccccc1]

$^1$H-NMR (400 MHz, AcOH-d$_4$): δ 7.89 (d, J=8.00 Hz, 2H), 7.64 (d, J=8.00 Hz, 1H), 7.56 (t, J=7.60 Hz, 1H), 7.44 (dd, J=3.20, 6.0 Hz, 2H), 7.29-7.24 (m, 2H), 7.21 (s, 5H) 5.60 (dd, J=6.00, 8.8 Hz, 1H), 5.14 (dd, J=4.8, 7.6 Hz, 1H), 3.65 (dd, J=8.0, 10.4, Hz, 1H), 3.56 (dd, J=4.40, 10.4 Hz, 1H), 3.30 (dd, J=9.2, 14.0 Hz, 1H), 3.23 (s, 3H), 3.14 (dd, J=5.60, 14.0 Hz, 1H);

MS: m/z 483 (M+1).

Example 69b: 3-[(1H-1,3-benzodiazol-2-yl)amino]-N-[(1R)-2-methoxy-1-phenylethyl]-3-[3-(trifluoromethyl)phenyl]propanamide (Isomer 2)

Isomer 2, eluted off the column at 2.09 minutes.

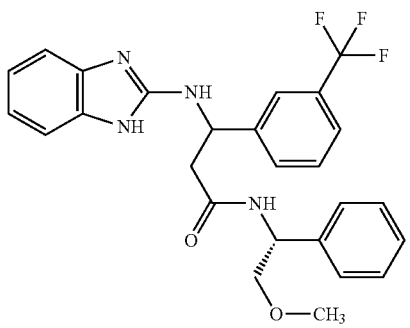 [SMILES: COC[C@H](NC(=O)CC(Nc1nc2ccccc2[nH]1)c1cccc(C(F)(F)F)c1)c1ccccc1]

$^1$H-NMR (400 MHz, AcOH-d$_4$): δ 7.84 (s, 1H), 7.77 (d, J=7.60 Hz, 1H), 7.66 (d, J=7.60 Hz, 1H), 7.59 (t, J=7.60 Hz, 1H), 7.32 (s, 2H), 7.23 (d, J=7.6 Hz, 2H), 7.19 (dd, J=2.8, 5.6 Hz, 2H) 7.10 (t, J=8.00 Hz, 2H), 6.99 (t, J=7.20 Hz, 1H), 5.47 (dd, J=4.40, 10.80 Hz, 1H), 5.10 (dd, J=4.40, 7.6 Hz, 1H), 3.63 (dd, J=8.0, 10.4 Hz, 1H), 3.57 (dd, J=4.8, 10.4 Hz, 1H), 3.34 (s, 3H), 3.25 (dd, J=10.80, 14.4 Hz, 1H), 3.03 (dd, J=4.40, 14.40 Hz, 1H);

MS: m/z 483 (M+1).

Example 70: 3-[(1H-1,3-benzodiazol-2-yl)amino]-N-[(1R)-2-methoxy-1-phenylethyl]-3-{3-[(trifluoromethyl)sulfanyl]phenyl}propanamide

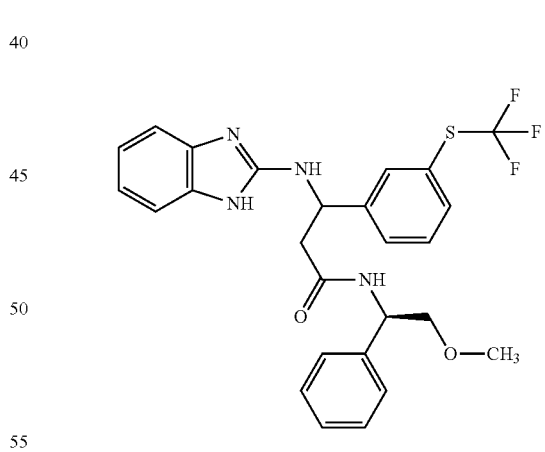

The titled example is prepared by the method described for Example 1 (Steps 1 to 6) but using 3-[(trifluoromethyl)sulfanyl]benzaldehyde in place of 3-(trifluoromethyl)benzaldehyde (Step 1) and (1R)-2-methoxy-1-phenylethan-1-amine in place of 2-(methylsulfanyl)ethan-1-amine (Step 6).

MS: m/z: 515 (M+1).

The enantiomers of the above example were separated by chiral chromatography. Column: YMC Cellulose C, Co-solvent: 20 mM Ammonia in IPA, Co-solvent percentage: 30, Total flow: 3 mL/min, Back pressure: 100 bar.

Example 70a: 3-[(1H-1,3-benzodiazol-2-yl)amino]-N-[(1R)-2-methoxy-1-phenylethyl]-3-{3-[(trifluoromethyl)sulfanyl]phenyl}propanamide (Isomer 1)

Isomer 1, eluted off the column at 1.95 minutes.

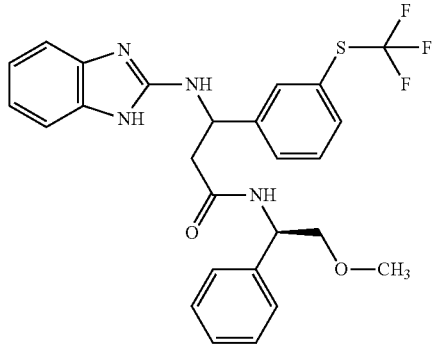 [SMILES: COC[C@H](NC(=O)CC(Nc1nc2ccccc2[nH]1)c1cccc(SC(F)(F)F)c1)c1ccccc1]

¹H-NMR (400 MHz, AcOH-d₄): δ 7.88 (s, 1H), 7.72 (d, J=7.84 Hz, 1H), 7.67 (d, J=7.56 Hz, 1H), 7.49 (t, J=7.68 Hz, 1H), 7.42 (s, 2H), 7.25 (s, 5H), 7.19 (d, J=6.76 Hz, 2H), 5.51 (t, J=8.28 Hz, 1H), 5.14 (t, J=5.76 Hz, 1H), 3.58 (t, J=6.92 Hz, 2H), 3.27 (d, J=12.84 Hz, 1H), 3.23 (s, 3H), 3.12 (dd, J=5.24, 14.20 Hz, 1H);

MS: m/z: 515 (M+1).

Example 70b: 3-[(1H-1,3-benzodiazol-2-yl)amino]-N-[(1R)-2-methoxy-1-phenylethyl]-3-{3-[(trifluoromethyl)sulfanyl]phenyl}propanamide (Isomer 2)

Isomer 2, eluted off the column at 2.63 minutes.

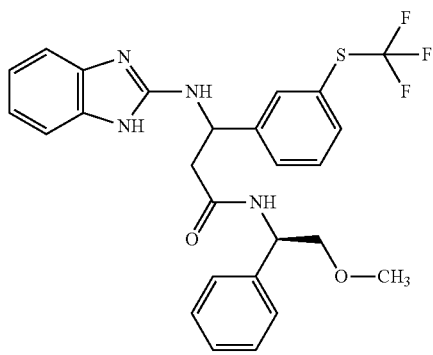 [SMILES: COC[C@H](NC(=O)CC(Nc1nc2ccccc2[nH]1)c1cccc(SC(F)(F)F)c1)c1ccccc1]

MS: m/z: 515 (M+1).

Example 71: 3-[(1H-1,3-benzodiazol-2-yl)amino]-N-(1,2-oxazol-3-ylmethyl)-3-[3-(trifluoromethyl)phenyl]propanamide

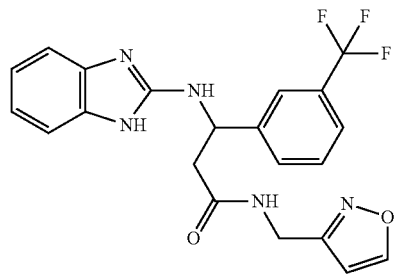 [SMILES: O=C(CC(Nc1nc2ccccc2[nH]1)c1cccc(C(F)(F)F)c1)NCc1ccon1]

The titled example is prepared by the method described for Example 1 (Step 6) but using 1,2-oxazol-3-ylmethanamine in place of 2-(methylsulfanyl)ethan-1-amine.

¹H-NMR (400 MHz, AcOH-d₄): δ 8.33 (d, J=1.60 Hz, 1H), 7.85 (s, 1H), 7.79 (d, J=8.00 Hz, 1H), 7.65 (d, J=7.60 Hz, 1H), 7.58 (t, J=8.00 Hz, 1H), 7.41-7.39 (m, 2H), 7.27-7.23 (m, 2H), 6.24 (d, J=1.60 Hz, 1H), 5.55 (q, J=5.20 Hz, 1H), 4.61 (d, J=15.60 Hz, 1H), 4.46 (d, J=15.60 Hz, 1H), 3.21 (dd, J=9.60, 14.80 Hz, 1H), 3.07 (dd, J=5.20, 14.60 Hz, 1H);

MS: m/z: 430.1 (M+1).

Example 72: 3-[(1H-1,3-benzodiazol-2-yl)amino]-N-(1,3-benzoxazol-2-ylmethyl)-3-[3-(trifluoromethyl)phenyl]propanamide

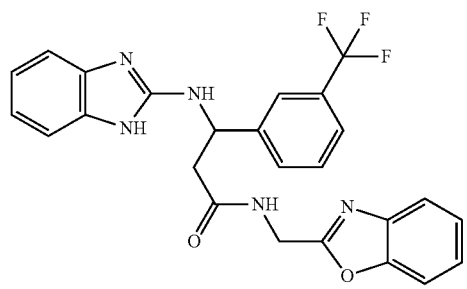 [SMILES: O=C(CC(Nc1nc2ccccc2[nH]1)c1cccc(C(F)(F)F)c1)NCc1nc2ccccc2o1]

The titled example is prepared by the method described for Example 1 (Step 6) but using 1,3-benzoxazol-2-ylmethanamine in place of 2-(methylsulfanyl)ethan-1-amine.

MS: m/z 480.1 (M+1).

Example 73: 3-[(1H-1,3-benzodiazol-2-yl)amino]-N-(1-methoxypropan-2-yl)-3-[3-(trifluoromethyl)phenyl]propanamide

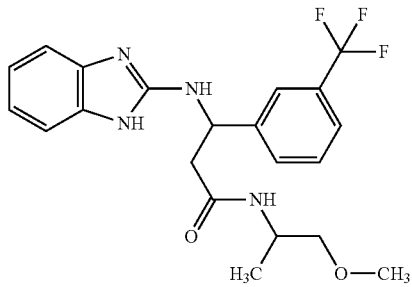 [SMILES: COCC(C)NC(=O)CC(Nc1nc2ccccc2[nH]1)c1cccc(C(F)(F)F)c1]

The titled example is prepared by the method described for Example 1 (Step 6) but using 1-methoxypropan-2-amine in place of 2-(methylsulfanyl)ethan-1-amine.
MS: m/z 421 (M+1).

Example 74: 3-[(1H-1,3-benzodiazol-2-yl)amino]-N-[2-(dimethyl-1,2-oxazol-4-yl)ethyl]-3-[3-(trifluoromethyl)phenyl]propanamide

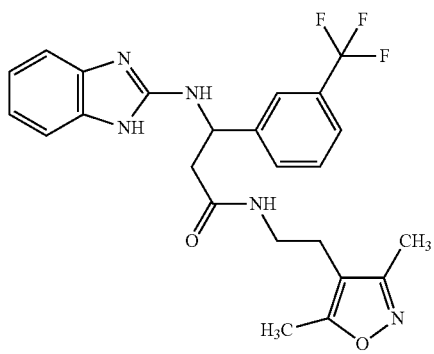 [SMILES: Cc1noc(C)c1CCNC(=O)CC(Nc1nc2ccccc2[nH]1)c1cccc(C(F)(F)F)c1]

The titled example is prepared by the method described for Example 1 (Step 6) but using 2-(dimethyl-1,2-oxazol-4-yl)ethan-1-amine in place of 2-(methylsulfanyl)ethan-1-amine.
MS: m/z: 472.1 (M+1).

Example 75: 3-[(1H-1,3-benzodiazol-2-yl)amino]-N-(1,3-thiazol-2-ylmethyl)-3-[3-(trifluoromethyl)phenyl]propanamide

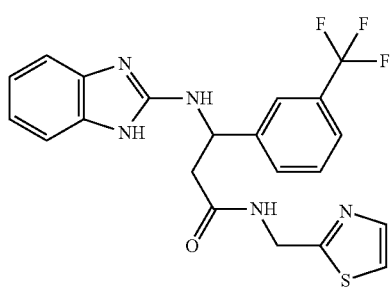 [SMILES: O=C(CC(Nc1nc2ccccc2[nH]1)c1cccc(C(F)(F)F)c1)NCc1nccs1]

The titled example is prepared by the method described for Example 1 (Step 6) but using 1,3-thiazol-2-ylmethanamine in place of 2-(methylsulfanyl)ethan-1-amine.
MS: m/z: 446.1 (M+1).

Example 76: 3-[(1H-1,3-benzodiazol-2-yl)amino]-N-[1-(6-methylpyridin-2-yl)ethyl]-3-[3-(trifluoromethyl)phenyl]propanamide

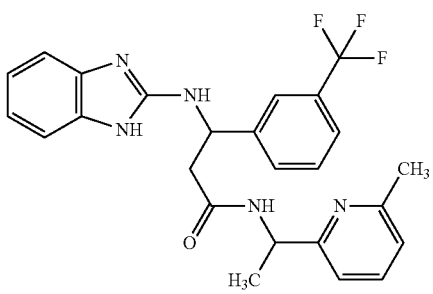 [SMILES: Cc1cccc(C(C)NC(=O)CC(Nc2nc3ccccc3[nH]2)c2cccc(C(F)(F)F)c2)n1]

The titled example is prepared by the method described for Example 1 (Step 6) but using 1-(6-methylpyridin-2-yl)ethan-1-amine in place of 2-(methylsulfanyl)ethan-1-amine.
MS: m/z 468.1 (M+1).

Example 77: 3-[(1H-1,3-benzodiazol-2-yl)amino]-N-[(2-methyl-1,3-thiazol-5-yl)methyl]-3-[3-(trifluoromethyl)phenyl]propanamide

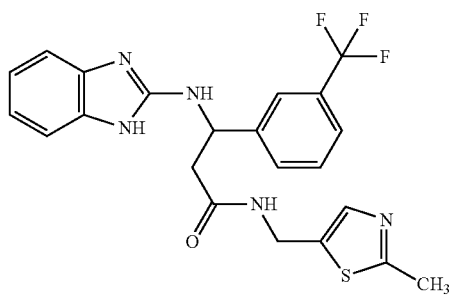 [SMILES: Cc1ncc(CNC(=O)CC(Nc2nc3ccccc3[nH]2)c2cccc(C(F)(F)F)c2)s1]

The titled example is prepared by the method described for Example 1 (Step 6) but using (2-methyl-1,3-thiazol-5-yl)methanamine in place of 2-(methylsulfanyl)ethan-1-amine.
MS: m/z: 460 (M+1).

Example 78: 3-[(1H-1,3-benzodiazol-2-yl)amino]-N-(pyrimidin-5-ylmethyl)-3-[3-(trifluoromethyl)phenyl]propanamide

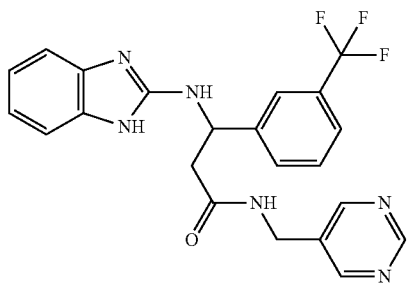 [SMILES: O=C(CC(Nc1nc2ccccc2[nH]1)c1cccc(C(F)(F)F)c1)NCc1cncnc1]

The titled example is prepared by the method described for Example 1 (Step 6) but using pyrimidin-5-ylmethanamine in place of 2-(methylsulfanyl)ethan-1-amine.
MS: m/z 441.2 (M+1).

Example 79: 3-[(1H-1,3-benzodiazol-2-yl)amino]-N-[(2-methylpyridin-4-yl)methyl]-3-[3-(trifluoromethyl)phenyl]propanamide

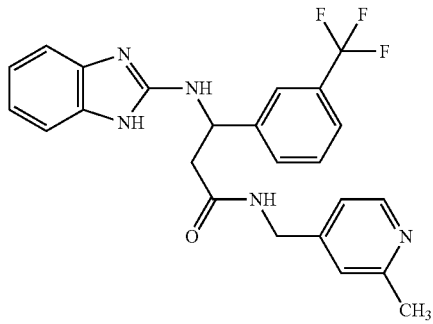 [SMILES: Cc1cc(CNC(=O)CC(Nc2nc3ccccc3[nH]2)c2cccc(C(F)(F)F)c2)ccn1]

The titled example is prepared by the method described for Example 1 (Step 6) but using (2-methylpyridin-4-yl)methanamine in place of 2-(methylsulfanyl)ethan-1-amine.
MS: m/z: 454 (M+1).

Example 80: 3-[(1H-1,3-benzodiazol-2-yl)amino]-3-(4-fluoro-3,5-dimethylphenyl)-N-(2-methoxyethyl)propanamide

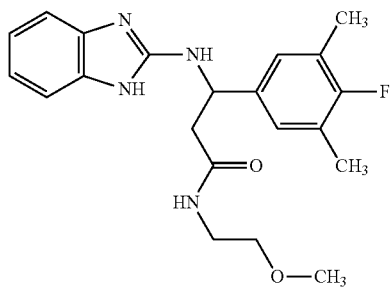 [SMILES: COCCNC(=O)CC(Nc1nc2ccccc2[nH]1)c1cc(C)c(F)c(C)c1]

The titled example is prepared by the method described for Example 1 (Steps 1 to 6) but using 4-fluoro-3,5-dimethylbenzaldehyde in place of 3-(trifluoromethyl)benzaldehyde (Step 1) and 2-methoxyethan-1-amine in place of 2-(methylsulfanyl)ethan-1-amine (Step 6).
$^1$H NMR (400 MHz, AcOH-$d_4$): δ 7.41-7.39 (m, 2H), 7.24 (q, J=2.40 Hz, 2H), 7.18 (d, J=6.80 Hz, 2H), 5.30 (q, J=5.20 Hz, 1H), 3.44-3.34 (m, 4H), 3.25 (s, 3H), 3.09 (dd, J=10.00, 14.40 Hz, 1H), 2.90 (dd, J=5.20, 14.40 Hz, 1H), 2.25 (s, 3H); 2.24 (s, 3H);
MS: m/z 385.2 (M+1).

Example 81: 3-[(1H-1,3-benzodiazol-2-yl)amino]-N-[2-(trifluoromethoxy)ethyl]-3-{3-[(trifluoromethyl)sulfanyl]phenyl}propanamide

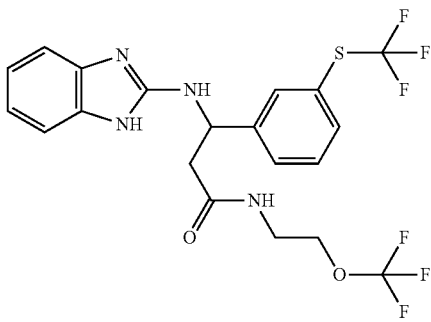 [SMILES: O=C(CC(Nc1nc2ccccc2[nH]1)c1cccc(OC(F)(F)F)c1)NCCOC(F)(F)F]

The titled example is prepared by the method described for Example 1 (Steps 1 to 6) but using 3-[(trifluoromethyl)sulfanyl]benzaldehyde in place of 3-(trifluoromethyl)benzaldehyde (Step 1) and 2-(trifluoromethoxy)ethan-1-amine in place of 2-(methylsulfanyl)ethan-1-amine (Step 6).
$^1$H NMR (400 MHz, AcOH-$d_4$): δ 7.88 (s, 1H), 7.75 (d, J=7.60 Hz, 1H), 7.68 (d, J=8.00 Hz, 1H), 7.53 (t, J=7.60 Hz, 1H), 7.42-7.40 (m, 2H), 7.27-7.23 (m, 2H), 5.52 (q, J=5.60 Hz, 1H), 4.02-3.99 (m, 2H), 3.57-3.53 (m, 2H), 3.22 (dd, J=9.60, 14.80 Hz, 1H), 3.04 (dd, J=5.60, 14.80 Hz, 1H);
MS: m/z 493.1 (M+1).

Example 82: 3-[(1H-1,3-benzodiazol-2-yl)amino]-N-(2-methoxyethyl)-3-{3-[(trifluoromethyl)sulfanyl]phenyl}propanamide

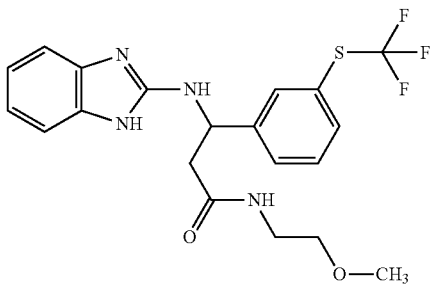 [SMILES: COCCNC(=O)CC(Nc1nc2ccccc2[nH]1)c1cccc(OC(F)(F)F)c1]

The titled example is prepared by the method described for Example 1 (Steps 1 to 6) but using 3-[(trifluoromethyl)sulfanyl]benzaldehyde in place of 3-(trifluoromethyl)benzaldehyde (Step 1) and 2-methoxyethan-1-amine in place of 2-(methylsulfanyl)ethan-1-amine (Step 6).
$^1$H-NMR (400 MHz, AcOH-$d_4$): δ 7.87 (s, 1H), 7.73 (d, J=7.60 Hz, 1H), 7.67 (d, J=8.00 Hz, 1H), 7.53 (t, J=7.60 Hz, 1H), 7.42-7.39 (m, 2H), 7.26-7.22 (m, 2H), 5.51 (q, J=5.20

Hz, 1H), 3.47-3.34 (m, 4H), 3.25 (s, 3H), 3.17 (dd, J=9.60, 14.60 Hz, 1H), 3.00 (dd, J=5.20, 14.80 Hz, 1H);

MS: m/z 439.2 (M+1).

Example 83: 3-[(1H-1,3-benzodiazol-2-yl)amino]-N-[2-(trifluoromethoxy)ethyl]-3-[3-(trifluoromethoxy)phenyl]propanamide

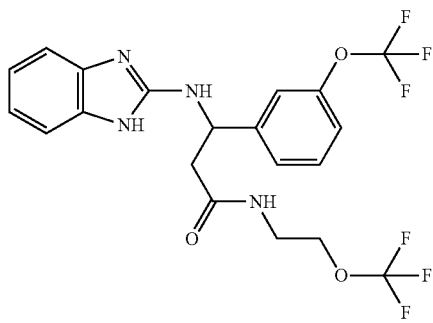

The titled example is prepared by the method described for Example 1 (Steps 1 to 6) but using 3-(trifluoromethoxy)benzaldehyde in place of 3-(trifluoromethyl)benzaldehyde (Step 1) and 2-(trifluoromethoxy)ethan-1-amine in place of 2-(methylsulfanyl)ethan-1-amine (Step 6).

$^1$H NMR (400 MHz, AcOH-d$_4$): δ 8.00 (d, J=7.60 Hz, 1H), 7.97-7.93 (m, 2H), 7.88-7.86 (m, 2H), 7.72-7.69 (m, 3H), 5.97 (q, J=5.20 Hz, 1H), 4.46 (t, J=5.20 Hz, 2H), 4.01 (q, J=5.20 Hz, 2H), 3.66 (dd, J=10.00, 14.60 Hz, 1H), 3.49 (dd, J=5.20, 14.80 Hz, 1H);

MS: m/z 477.1 (M+1).

Example 84: 3-[(1H-1,3-benzodiazol-2-yl)amino]-N-(2-methoxyethyl)-3-[3-(trifluoromethoxy)phenyl]propanamide

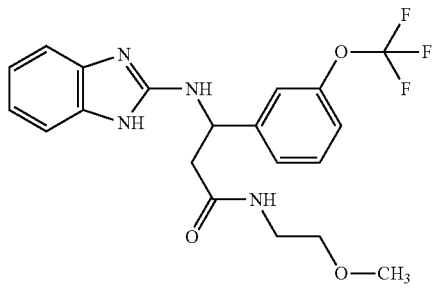

The titled example is prepared by the method described for Example 1 (Steps 1 to 6) but using 3-(trifluoromethoxy)benzaldehyde in place of 3-(trifluoromethyl)benzaldehyde (Step 1) and 2-methoxyethan-1-amine in place of 2-(methylsulfanyl)ethan-1-amine (Step 6).

$^1$H-NMR (400 MHz, AcOH-d$_4$): δ 7.54-7.46 (m, 3H), 7.41 (q, J=3.20 Hz, 2H), 7.26-7.23 (m, 3H), 5.49 (q, J=5.20 Hz, 1H), 3.33-3.47 (m, 4H), 3.25 (s, 3H), 3.15 (dd, J=9.60, 14.60 Hz, 1H), 2.99 (dd, J=4.80, 14.60 Hz, 1H);

MS: m/z 423.2 (M+1).

Example 85: 3-[(1H-1,3-benzodiazol-2-yl)amino]-N-(cyanomethyl)-3-[3-(trifluoromethoxy)phenyl]propanamide

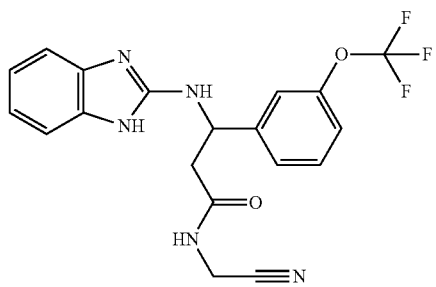 [SMILES: N#CCNC(=O)CC(Nc1nc2ccccc2[nH]1)c1cccc(OC(F)(F)F)c1]

The titled example is prepared by the method described for Example 1 (Steps 1 to 6) but using 3-(trifluoromethoxy)benzaldehyde in place of 3-(trifluoromethyl)benzaldehyde (Step 1) and 2-aminoacetonitrile in place of 2-(methylsulfanyl)ethan-1-amine (Step 6).

$^1$H-NMR (400 MHz, AcOH-d$_4$): δ 7.57-7.48 (m, 3H), 7.41 (dd, J=2.80, 6.0 Hz, 2H), 7.28-7.23 (m, 3H), 5.54 (dd, J=5.20, 9.6 Hz, 1H), 4.25-4.14 (d, J=7.6 Hz, 2H), 3.24 (dd, J=9.60, 15.00 Hz, 1H), 3.06 (dd, J=5.20, 14.80 Hz, 1H);

MS: m/z: 404 (M+1).

Example 86: 3-[(1H-1,3-benzodiazol-2-yl)amino]-N-(cyanomethyl)-3-(4-fluoro-3,5-dimethylphenyl)propanamide

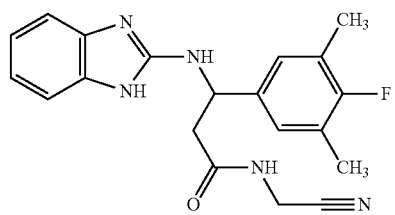 [SMILES: Cc1cc(C(CC(=O)NCC#N)Nc2nc3ccccc3[nH]2)cc(C)c1F]

The titled example is prepared by the method described for Example 1 (Steps 1 to 6) but using 4-fluoro-3,5-dimethylbenzaldehyde in place of 3-(trifluoromethyl)benzaldehyde (Step 1) and 2-aminoacetonitrile in place of 2-(methylsulfanyl)ethan-1-amine (Step 6).

$^1$H-NMR (400 MHz, AcOH-d$_4$): δ 7.40 (dd, J=3.20, 6.00 Hz, 2H), 7.26-7.18 (m, 4H), 5.34 (dd, J=5.20, 9.40 Hz, 1H), 4.18 (q, J=17.60 Hz, 2H), 3.16 (dd, J=9.60, 14.60 Hz, 1H), 2.97 (dd, J=5.60, 14.80 Hz, 1H), 2.25 (s, 3H), 2.24 (s, 3H);

MS: m/z 366.1 (M+1).

Example 87: 3-[(1H-1,3-benzodiazol-2-yl)amino]-3-[3-(cyclobutylsulfanyl)phenyl]-N-(2-methoxyethyl)propanamide

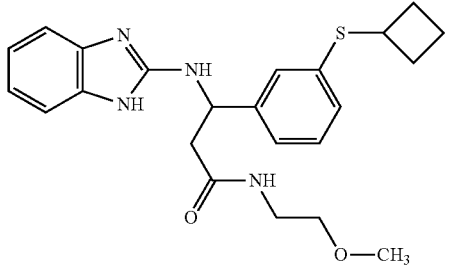 [SMILES: COCCNC(=O)CC(Nc1nc2ccccc2[nH]1)c1cccc(SC2CCC2)c1]

The titled example is prepared by the method described for Example 1 (Steps 1 to 6) but using 3-(cyclobutylsulfanyl)benzaldehyde in place of 3-(trifluoromethyl)benzaldehyde (Step 1) and 2-methoxyethan-1-amine in place of 2-(methylsulfanyl)ethan-1-amine (Step 6).

$^1$H NMR (400 MHz, AcOH-$d_4$) δ 7.42-7.40 (m, 2H), 7.36 (s, 1H), 7.29 (d, 2H, J=4.80 Hz), 7.26-7.23 (m, 2H), 7.20-7.16 (m, 1H), 5.41 (q, 1H, J=10, 4.8 Hz), 3.98 (q, 1H, J=13.2, 6 Hz), 3.48-3.36 (m, 4H), 3.26 (s, 3H), 3.18-3.09 (m, 1H), 2.94 (dd, 1H, J=3.6 Hz), 2.51 (s, 2H), 2.11-1.98 (m, 4H);

MS: m/z 425.10 (M+1).

Example 88: 3-[(1H-1,3-benzodiazol-2-yl)amino]-N-(1,2-oxazol-3-ylmethyl)-3-[3-(trifluoromethoxy)phenyl]propanamide

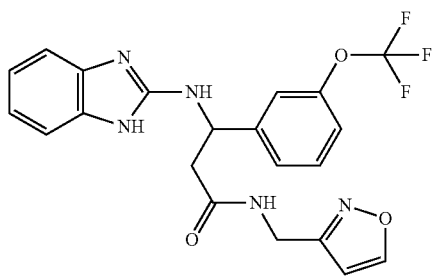 [SMILES: O=C(CC(Nc1nc2ccccc2[nH]1)c1cccc(OC(F)(F)F)c1)NCc1ccon1]

The titled example is prepared by the method described for Example 1 (Steps 1 to 6) but using 3-(trifluoromethoxy)benzaldehyde in place of 3-(trifluoromethyl)benzaldehyde (Step 1) and 1,2-oxazol-3-ylmethanamine in place of 2-(methylsulfanyl)ethan-1-amine (Step 6).

MS: m/z: 446.1 (M+1).

Example 89: 3-[(1H-1,3-benzodiazol-2-yl)amino]-N-(1,3-benzoxazol-2-ylmethyl)-3-{3-[(trifluoromethyl)sulfanyl]phenyl}propanamide

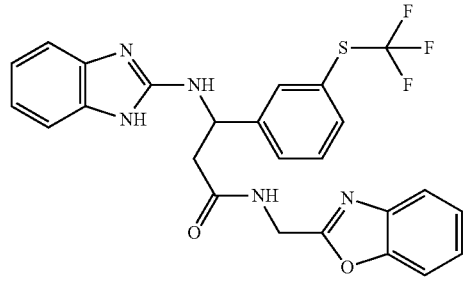 [SMILES: O=C(CC(Nc1nc2ccccc2[nH]1)c1cccc(SC(F)(F)F)c1)NCc1nc2ccccc2o1]

The titled example is prepared by the method described for Example 1 (Steps 1 to 6) but using 3-[(trifluoromethyl)sulfanyl]benzaldehyde in place of 3-(trifluoromethyl)benzaldehyde (Step 1) and 1,3-benzoxazol-2-ylmethanamine in place of 2-(methylsulfanyl)ethan-1-amine (Step 6).

MS: m/z 512.1 (M+1).

Example 90: 3-[(1H-1,3-benzodiazol-2-yl)amino]-N-(1,3-benzoxazol-2-ylmethyl)-3-[3-(trifluoromethoxy)phenyl]propanamide

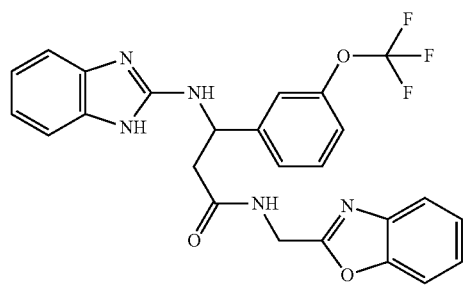 [SMILES: O=C(CC(Nc1nc2ccccc2[nH]1)c1cccc(OC(F)(F)F)c1)NCc1nc2ccccc2o1]

The titled example is prepared by the method described for Example 1 (Steps 1 to 6) but using 3-(trifluoromethoxy)benzaldehyde in place of 3-(trifluoromethyl)benzaldehyde (Step 1) and 1,3-benzoxazol-2-ylmethanamine in place of 2-(methylsulfanyl)ethan-1-amine Step 6).

MS: m/z 496.1 (M+1).

Example 91: 3-[(5-fluoro-1H-1,3-benzodiazol-2-yl)amino]-N-(2-methoxyethyl)-3-[3-(trifluoromethyl)phenyl]butanamide

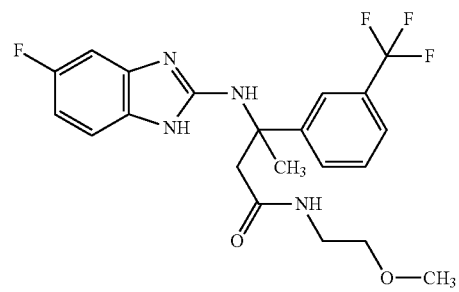 [SMILES: COCCNC(=O)CC(C)(Nc1nc2cc(F)ccc2[nH]1)c1cccc(C(F)(F)F)c1]

The titled example is prepared by the method described for Example 1 (Steps 2 to 6) but using 3-amino-3-[3-(trifluoromethyl)phenyl]butanoic acid in place of 3-amino-3-[3-(trifluoromethyl)phenyl]propanoic acid (Step 2) and 4-fluorobenzene-1,2-diamine in place of benzene-1,2-diamine (Step 4) and 2-methoxyethan-1-amine in place of 2-(methylsulfanyl)ethan-1-amine (Step 6).

$^1$H-NMR (400 MHz, DMSO-d$_6$): δ 8.01 (s, 1H), 7.68 (t, J=4.40 Hz, 2H), 7.58-7.51 (m, 2H), 7.44 (s, 1H exchangeable), 7.06-6.97 (m, 1H), 6.84 (d, J=9.20 Hz, 1H), 6.65 (t, J=8.40 Hz, 1H), 3.32-3.13 (m, 4H), 3.12 (s, 3H), 2.79 (q, J=14.00 Hz, 2H), 1.91 (s, 3H);

MS: m/z 439.1 (M+1).

Example 92: 3-[(1H-1,3-benzodiazol-2-yl)amino]-N-(2-methoxyethyl)-3-[3-(methylsulfanyl)phenyl]propanamide

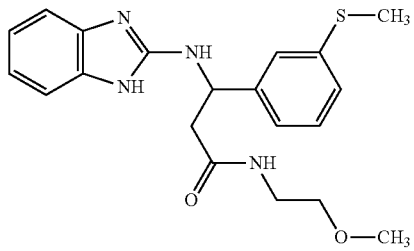 [SMILES: COCCNC(=O)CC(Nc1nc2ccccc2[nH]1)c1cccc(SC)c1]

The titled example is prepared by the method described for Example 65 (Steps 1 to 7) but using 3-(methylsulfanyl)benzaldehyde in place of 3-ethyl-4-fluoro-benzaldehyde (Step 1) and 2-methoxyethan-1-amine in place of 2-(ethylamino)ethanol (Step 3).

$^1$H-NMR (400 MHz, AcOH-d$_4$): δ 7.40 (t, J=5.60 Hz, 3H), 7.30-7.23 (m, 5H), 5.39 (dd, J=5.20, 9.80 Hz, 1H), 3.47-3.39 (m, 2H), 3.36 (t, J=4.80 Hz, 2H), 3.26 (s, 3H), 3.12 (dd, J=10.00, 14.40 Hz, 1H), 2.93 (dd, J=5.20, 14.40 Hz, 1H), 2.49 (s, 3H);

MS: m/z 385.1 (M+1).

Example 93: 3-[(4-methoxy-1H-1,3-benzodiazol-2-yl)amino]-N-(2-methoxyethyl)-3-[3-(trifluoromethyl)phenyl]propanamide

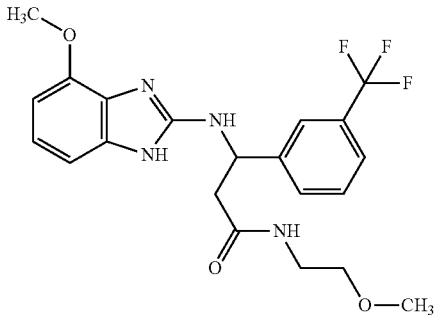 [SMILES: COCCNC(=O)CC(Nc1nc2c(OC)cccc2[nH]1)c1cccc(C(F)(F)F)c1]

The titled example is prepared by the method described for Example 65 (Steps 1 to 7) but using 3-(trifluoromethyl)benzaldehyde in place of 3-ethyl-4-fluoro-benzaldehyde (Step 1) and 2-methoxyethan-1-amine in place of 2-(ethylamino)ethanol (Step 3) and 3-methoxybenzene-1,2-diamine in place of benzene-1,2-diamine (Step 6).

$^1$H-NMR (400 MHz, AcOH-d$_4$): δ 7.85 (s, 1H), 7.80 (d, J=7.60 Hz, 1H), 7.64 (d, J=7.60 Hz, 1H), 7.58 (t, J=7.60 Hz, 1H), 7.18 (t, J=8.40 Hz, 1H), 7.03 (d, J=8.00 Hz, 1H), 6.82 (d, J=8.00 Hz, 1H), 5.62 (dd, J=5.20, 9.6 Hz, 1H), 3.94 (s, 3H), 3.46-3.34 (m, 4H), 3.26 (s, 3H), 3.14 (dd, J=9.60, 14.40 Hz, 1H), 3.00 (dd, J=5.60, 14.60 Hz, 1H);

MS: m/z 437 (M+1).

Example 94: 3-{[4-(hydroxymethyl)-1H-1,3-benzodiazol-2-yl]amino}-N-[2-(trifluoromethoxy)ethyl]-3-[3-(trifluoromethyl)phenyl]propanamide

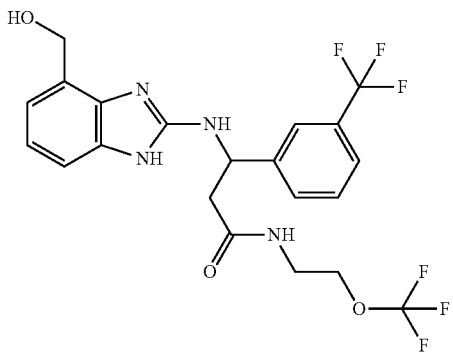 [SMILES: O=C(CC(Nc1nc2c(CO)cccc2[nH]1)c1cccc(C(F)(F)F)c1)NCCOC(F)(F)F]

The titled example is prepared by the method described for Example 65 (Steps 1 to 7) but using 3-(trifluoromethyl)benzaldehyde in place of 3-ethyl-4-fluoro-benzaldehyde (Step 1) and 2-(trifluoromethoxy)ethan-1-amine in place of 2-(ethylamino)ethanol (Step 3) and (2,3-diaminophenyl)methanol in place of benzene-1,2-diamine (Step 6).

MS: m/z: 491.1 (M+1).

Example 95: 3-[(5,6-difluoro-1H-1,3-benzodiazol-2-yl)amino]-N-(2-methoxyethyl)-3-[3-(trifluoromethyl)phenyl]propanamide

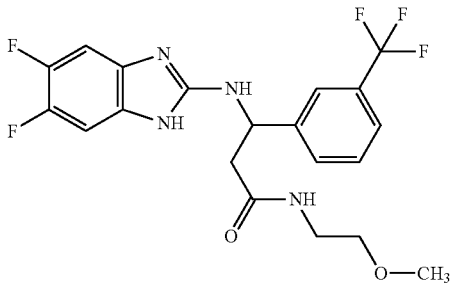 [SMILES: COCCNC(=O)CC(Nc1nc2cc(F)c(F)cc2[nH]1)c1cccc(C(F)(F)F)c1]

The titled example is prepared by the method described for Example 65 (Steps 1 to 7) but using 3-(trifluoromethyl)benzaldehyde in place of 3-ethyl-4-fluoro-benzaldehyde (Step 1) and 2-methoxyethan-1-amine in place of 2-(ethylamino)ethanol (Step 3) and 4,5-difluorobenzene-1,2-diamine in place of benzene-1,2-diamine (Step 6).

$^1$H-NMR (400 MHz, AcOH-d$_4$): δ 7.84 (s, 1H), 7.78 (d, J=8.00 Hz, 1H), 7.66 (d, J=7.60 Hz, 1H), 7.59 (t, J=8.00 Hz, 1H), 7.37 (t, J=8.00 Hz, 2H), 5.51 (q, J=5.20 Hz, 1H), 3.46-3.35 (m, 4H), 3.27 (s, 3H), 3.16 (dd, J=9.60, 14.40 Hz, 1H), 3.00 (dd, J=5.20, 14.60 Hz, 1H);

MS: m/z 443.2 (M+1).

Example 96: 3-[(5-fluoro-4-methyl-1H-1,3-benzodiazol-2-yl)amino]-N-(2-methoxyethyl)-3-[3-(trifluoromethyl)phenyl]propanamide

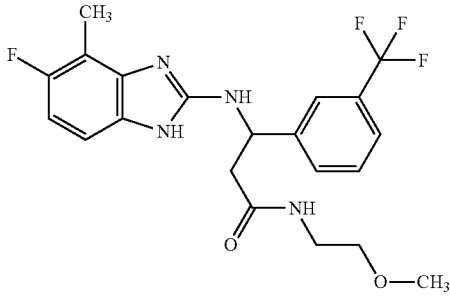 [SMILES: COCCNC(=O)CC(Nc1nc2c(C)c(F)ccc2[nH]1)c1cccc(C(F)(F)F)c1]

The titled example is prepared by the method described for Example 65 (Steps 1 to 7) but using 3-(trifluoromethyl)benzaldehyde in place of 3-ethyl-4-fluoro-benzaldehyde (Step 1) and 2-methoxyethan-1-amine in place of 2-(ethylamino)ethanol (Step 3) and 4-fluoro-3-methylbenzene-1,2-diamine in place of benzene-1,2-diamine (Step 6).

$^1$H NMR (400 MHz, DMSO-$d_6$ and $D_2O$): δ 10.90 (s, 1H, exchangeable), 8.04 (d, J=12.28 Hz, 1H exchangeable), 7.81 (d, J=8.28 Hz, 1H), 7.74 (d, J=5.68 Hz, 1H), 7.57 (s, 2H), 7.54 (s, 1H, exchangeable), 6.86 (dd, J=4.88, 8.28 Hz, 1H), 6.59 (t, J=8.6 Hz, 1H), 5.35-5.30 (m, 1H), 3.48-3.10 (m, 7H), 2.72-2.61 (m, 2H), 2.24 (s, 3H);
MS: m/z 439.1 (M+1).

We claim:

1. A compound of formula (I)

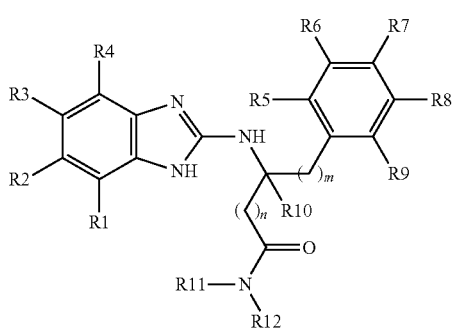

wherein
n is an integer selected from 0, 1, and 2;
m is an integer selected from 0, 1, and 2;
R1-R4 are independently a group selected from H, halogen, CN, $C_{1-6}$ alkyl, $C_{1-6}$ alkylene-OH, $C_{1-6}$ alkoxy, $C_{1-6}$ alkylene-O—$C_{1-6}$ alkyl, $C_{1-6}$ alkylene-S—$C_{1-6}$ alkyl, $C_{3-7}$ cycloalkyl, and $C_{1-6}$ alkylene-NR$^a$R$^b$, wherein R$^a$ and R$^b$ are independently a group selected from H, $C_{1-6}$ alkyl, $C_{1-6}$ alkylene-OH, $C_{1-6}$ alkylene-O—$C_{1-6}$ alkyl, C(═O)—$C_{1-6}$ alkyl, C(═O)—$C_{1-6}$ alkoxy, C(═O)—$C_{1-6}$ alkyl-CN, C(═O)—$C_{1-6}$ alkyl-OH, C(═O)—$C_{1-6}$ alkylene-S—$C_{1-6}$ alkyl, C(═O)—O—$C_{1-6}$ alkylene-O—$C_{1-6}$ alkyl, C(═O)—O—$C_{1-6}$ alkyl-CN, C(═O)—O—$C_{1-6}$ alkyl-OH, C(═O)—O—$C_{1-6}$ alkylene-S—$C_{1-6}$ alkyl, C(═O)—NHC$_{1-6}$ alkyl, C(═O)—NHC$_{1-6}$ alkylene-O—$C_{1-6}$ alkyl, C(═O)—NHC$_{1-6}$ alkylene-S—$C_{1-6}$ alkyl, C(═O)—NHC$_{1-6}$ alkyl-CN, C(═O)—NHC$_{1-6}$ alkyl-OH, C(═O)—N($C_{1-6}$ alkyl)$_2$, SO$_2$—$C_{1-6}$ alkyl, SO$_2$—$C_{1-6}$ alkylene-O—$C_{1-6}$ alkyl, SO$_2$—$C_{1-6}$ alkylene-S—$C_{1-6}$ alkyl, SO$_2$—$C_{1-6}$ alkyl-CN, SO$_2$—$C_{1-6}$ alkyl-OH, and SO$_2$—$C_{1-6}$ alkyl-N($C_{1-6}$ alkyl)$_2$;

R5-R9 are independently a group selected from H, halogen, CH$_2$F, CHF$_2$, CF$_3$, CN, $C_{1-6}$ alkyl, $C_{1-6}$ alkylene-OH, OH, $C_{1-6}$ alkoxy, $C_{1-6}$ alkylene-O—$C_{1-6}$ alkyl, $C_{1-6}$ alkylene-S—$C_{1-6}$ alkyl, $C_{3-7}$ cycloalkyl, C(═O)—O—$C_{1-6}$ alkyl, S—$C_{1-6}$ alkyl, SCF$_3$, OCF$_3$, OCF$_2$H, OCFH$_2$, OC$_{3-7}$ cycloalkyl, SC$_{3-7}$ cycloalkyl;

R10 is a group selected from H and $C_{1-6}$ alkyl, $C_{1-6}$ alkyl substituted with 1 to 3 Fluorine atoms, $C_{3-4}$ cycloalkyl;

R11 is a group selected from $C_{1-6}$ alkylene-OH; $C_{1-6}$ alkylene-O—$C_{1-6}$ alkyl, wherein $C_{1-6}$ alkylene is optionally substituted with a phenyl, and wherein $C_{1-6}$ alkyl is optionally substituted with a halogen; $C_{1-6}$ alkylene-S—$C_{1-6}$ alkyl; $C_{1-6}$ alkylene-CN; $C_{1-6}$ alkylene-C(═O)—O—$C_{1-6}$ alkyl; $C_{1-6}$ alkylene-O—C(═O)—NH—$C_{1-6}$ alkyl; $C_{1-6}$ alkylene-NH—C(═O)—$C_{1-6}$ alkyl; $C_{1-6}$ alkylene-NH—SO$_2$—$C_{1-6}$ alkyl; $C_{1-6}$ alkylene-NH—SO$_2$—$C_{1-6}$ alkylene-phenyl, wherein the phenyl is optionally substituted with a group selected from $C_{1-6}$ alkyl; $C_{1-6}$ alkylene-NR$^c$R$^d$, wherein R$^c$ and R$^d$ are independently a group selected from H and $C_{1-6}$ alkyl; $C_{1-6}$ alkylene-C(═O)—NR$^e$R$^f$, wherein R$^e$ and R$^f$ are independently a group selected from H and $C_{1-6}$ alkyl; a heterocyclyl, optionally substituted with a group selected from $C_{1-6}$ alkyl, OH, and $C_{1-6}$ alkylene-OH; $C_{1-6}$ alkylene-R$^g$, wherein R$^g$ is a heteroaryl, optionally substituted with a group selected from $C_{1-6}$ alkyl, OH, and $C_{1-6}$ alkylene-OH; $C_{1-6}$ alkylene-R$^h$, wherein R$^h$ is a heterocyclyl, optionally substituted with a group selected from $C_{1-6}$ alkyl, OH, and $C_{1-6}$ alkylene-OH; $C_{1-6}$ alkylene-R$^j$, wherein R$^j$ is a $C_{3-7}$ cycloalkyl, optionally substituted with a group selected from $C_{1-6}$ alkyl, OH, and $C_{1-6}$ alkylene-OH; and $C_{1-6}$ alkylene-R$^k$, wherein R$^k$ is a phenyl, optionally substituted with a group selected from $C_{1-6}$ alkyl, OH, and $C_{1-6}$ alkylene-OH; and R12 is a group selected from H, $C_{1-6}$ alkyl, $C_{1-6}$ alkylene-OH, $C_{1-6}$ alkylene-O—$C_{1-6}$ alkyl, $C_{1-6}$ alkylene-S—$C_{1-6}$ alkyl, $C_{1-6}$ alkylene-CN, and $C_{1-6}$ alkylene-CF$_3$; or R11 and R12 together with the nitrogen to which R11 and R12 are linked form a monocyclic or bicyclic 3-10 membered aliphatic heterocycle containing the nitrogen to which R11 and R12 are linked and optionally one or more heteroatoms selected from O, S, and N, wherein the monocyclic or bicyclic heterocycle is optionally substituted with a group selected from $C_{1-6}$ alkyl; oxo; OH; $C_{1-6}$ alkylene-OH; C(═O)—$C_{1-6}$ alkyl; C(═O)—O—$C_{1-6}$ alkyl; SO$_2$—$C_{1-6}$ alkyl; NR$^k$R$^l$, wherein R$^k$ and R$^l$ are independently a group selected from H and $C_{1-6}$ alkyl; and $C_{1-6}$ alkylene-NR$^m$R$^n$, wherein R$^m$ and R$^n$ are independently a group selected from H and $C_{1-6}$ alkyl;

or
a pharmaceutically acceptable salt thereof.

2. The compound of claim 1, wherein m is 0.

3. The compound of claim 1, wherein n is 1.

4. The compound of claim 1, wherein n is 0.

5. The compound of claim 1, wherein R1 is selected from H, $C_{1-6}$ alkyl, $C_{1-6}$ alkoxy and $C_{1-6}$ alkylene-OH.

6. The compound of claim 1, wherein R2 is selected from H, halogen and $C_{1-6}$ alkylene-$NR^aR^b$, wherein $R^a$ and $R^b$ are independently selected from H, $C_{1-6}$ alkyl, $C_{1-6}$ alkylene-OH, $C_{1-6}$ alkoxy, $C(=O)—C_{1-6}$ alkyl, $C(=O)—C_{1-6}$ alkoxy, $C(=O)—O—C_{1-6}$ alkyl, $C(=O)—NHC_{1-6}$ alkyl, $C(=O)—N(C_{1-6}$ alkyl$)_2$, $SO_2—C_{1-6}$ alkyl.

7. The compound of claim 1, wherein R3 is selected from H, halogen and $C_{1-6}$ alkylene-$NR^aR^b$, wherein $R^a$ and $R^b$ are independently selected from H, $C_{1-6}$ alkyl, $C_{1-6}$ alkylene-OH, $C_{1-6}$ alkoxy, $C(=O)—C_{1-6}$ alkyl, $C(=O)—C_{1-6}$ alkoxy, $C(=O)—O—C_{1-6}$ alkyl, $C(=O)—NHC_{1-6}$ alkyl, $C(=O)—N(C_{1-6}$ alkyl$)_2$, $SO_2—C_{1-6}$ alkyl.

8. The compound of claim 1, wherein R4 is selected from H and $C_{1-6}$ alkylene-OH.

9. The compound of claim 1, wherein R5 is selected from H.

10. The compound of claim 1, wherein R6 is selected from H, halogen, $CF_3$, $OCF_3$, $SCF_3$, $SC_{1-6}$ alkyl, $SC_{3-7}$ cycloalkyl and $C_{1-6}$ alkyl.

11. The compound of claim 1, wherein R7 is selected from H, halogen, and $C_{1-6}$ alkyl.

12. The compound of claim 1, wherein R8 is selected from H, halogen, $CF_3$, and $C_{1-6}$ alkyl.

13. The compound of claim 1, wherein R9 is selected from H.

14. The compound of claim 1, wherein R10 is selected from H and $CH_3$.

15. The compound of claim 1, wherein R11 is selected from $C_{1-6}$ alkylene-OH, $C_{1-6}$ alkylene-O—$C_{1-6}$ alkyl, $C_{1-6}$ alkylene-O—$C_{1-6}$ alkyl wherein $C_{1-6}$ alkylene is substituted with a phenyl, $C_{1-6}$ alkylene-O—$C_{1-6}$ alkyl wherein $C_{1-6}$ alkyl is substituted with a halogen, $C_{1-6}$ alkylene-S—$C_{1-6}$ alkyl, $C_{1-6}$ alkylene-CN, $C_{1-6}$ alkylene-C(=O)—O—$C_{1-6}$ alkyl, $C_{1-6}$ alkylene-O—C(=O)—NH—$C_{1-6}$ alkyl, $C_{1-6}$ alkylene-NH—C(=O)—$C_{1-6}$ alkyl-O—$C_{1-6}$ alkyl, $C_{1-6}$ alkylene-NH—$SO_2$—$C_{1-6}$ alkyl, $C_{1-6}$ alkylene-NH—$SO_2$—$C_{1-6}$ alkylene-phenyl; $C_{1-6}$ alkylene-$NR^cR^d$, wherein $R^c$ and $R^d$, are independently selected from H and $C_{1-6}$ alkyl; $C_{1-6}$ alkylene-C(=O)—$NR^eR^f$, wherein $R^e$ and $R^f$ are independently selected from H and $C_{1-6}$ alkyl; a heterocyclyl; $C_{1-6}$ alkylene-$R^g$, wherein $R^g$ is a heteroaryl, optionally substituted with a group selected from $C_{1-6}$ alkyl; $C_{1-6}$ alkylene-$R^h$, wherein $R^h$ is a heterocyclyl.

16. The compound of claim 1, wherein R12 is selected from H and $C_{1-6}$ alkyl.

17. The compound of claim 1, wherein R11 and R12 together with the nitrogen to which R11 and R12 are linked forms a mono or bicyclic 3-7 membered aliphatic heterocycle containing the nitrogen to which R11 and R12 are linked selected from aziridinyl, oxaziridinyl, azetidinyl, diazetidinyl, pyrrolidinyl, imidazolidinyl, pyrazolidinyl, oxazolidinyl, isoxazolidinyl, thiazolidinyl, isothiazolidinyl, morpholinyl, piperidinyl, piperazinyl, and 2-oxa-6-azaspiro[3.3]-heptanyl, optionally substituted with a group selected from $C_{1-6}$ alkyl, oxo, OH, $C_{1-6}$ alkylene-OH, $C(=O)—C_{1-6}$ alkyl, $C(=O)—O—C_{1-6}$ alkyl, $SO_2—C_{1-6}$ alkyl, $NR^kR^l$, wherein $R^k$ and $R^l$ are independently selected from H and $C_{1-6}$ alkyl; $C_{1-6}$ alkylene-$NR^mR^n$, wherein $R^m$ and $R^n$ are independently selected from H and $C_{1-6}$ alkyl.

18. The compound of claim 1, selected from the group consisting of:

3-[(1H-1,3-benzodiazol-2-yl)amino]-N-[2-(methylsulfanyl)ethyl]-3-[3-(trifluoromethyl)phenyl]propanamide,
3-[(1H-1,3-benzodiazol-2-yl)amino]-N-[2-(dimethylamino)ethyl]-N-methyl-3-[3-(trifluoromethyl)phenyl]propanamide,
3-[(1H-1,3-benzodiazol-2-yl)amino]-N-(2-ethanesulfonamidoethyl)-3-[3-(trifluoromethyl)phenyl]propanamide,
3-[(1H-1,3-benzodiazol-2-yl)amino]-N-(2-hydroxy-2-methylpropyl)-3-[3-(trifluoromethyl)phenyl]propanamide,
(−) 3-[(1H-1,3-benzodiazol-2-yl)amino]-N-(2-hydroxy-2-methylpropyl)-3-[3-(trifluoromethyl)phenyl]propanamide,
(+) 3-[(1H-1,3-benzodiazol-2-yl)amino]-N-(2-hydroxy-2-methylpropyl)-3-[3-(trifluoromethyl)phenyl]propanamide,
3-[(1H-1,3-benzodiazol-2-yl)amino]-1-(4-hydroxypiperidin-1-yl)-3-[3-(trifluoromethyl)phenyl]propan-1-one,
3-[(1H-1,3-benzodiazol-2-yl)amino]-1-(3-hydroxyazetidin-1-yl)-3-[3-(trifluoromethyl)phenyl]propan-1-one,
3-[(1H-1,3-benzodiazol-2-yl)amino]-N-(oxetan-3-ylmethyl)-3-[3-(trifluoromethyl)phenyl]propanamide,
3-[(1H-1,3-benzodiazol-2-yl)amino]-N-(oxolan-2-ylmethyl)-3-[3-(trifluoromethyl)phenyl]propanamide,
3-[(1H-1,3-benzodiazol-2-yl)amino]-N-[(3 S)-oxolan-3-yl]-3-[3-(trifluoromethyl)phenyl]propanamide,
3-[(1H-1,3-benzodiazol-2-yl)amino]-N-(oxetan-3-yl)-3-[3-(trifluoromethyl)phenyl]propanamide,
4-{3-[(1H-1,3-benzodiazol-2-yl)amino]-3-[3-(trifluoromethyl)phenyl]propanoyl}-1-methylpiperazin-2-one,
3-[(1H-1,3-benzodiazol-2-yl)amino]-N-[2-(phenylmethanesulfonamido)ethyl]-3-[3-(trifluoromethyl)phenyl]propanamide,
3-[(1H-1,3-benzodiazol-2-yl)amino]-1-[(3R)-3-hydroxypiperidin-1-yl]-3-[3-(trifluoromethyl)phenyl]propan-1-one,
3-[(1H-1,3-benzodiazol-2-yl)amino]-1-[(3R)-3-hydroxypyrrolidin-1-yl]-3-[3-(trifluoromethyl)phenyl]propan-1-one,
3-[(1H-1,3-benzodiazol-2-yl)amino]-1-[(3S)-3-hydroxypyrrolidin-1-yl]-3-[3-(trifluoromethyl)phenyl]propan-1-one,
3-[(1H-1,3-benzodiazol-2-yl)amino]-N-(3-hydroxypropyl)-3-[3-(trifluoromethyl)phenyl]propanamide,
3-[(1H-1,3-benzodiazol-2-yl)amino]-N-(3-hydroxypropyl)-N-methyl-3-[3-(trifluoromethyl)phenyl]propanamide,
(−) 3-[(1H-1,3-benzodiazol-2-yl)amino]-N-(3-hydroxypropyl)-N-methyl-3-[3-(trifluoromethyl)phenyl]propanamide,
(+) 3-[(1H-1,3-benzodiazol-2-yl)amino]-N-(3-hydroxypropyl)-N-methyl-3-[3-(trifluoromethyl)phenyl]propanamide,
3-[(1H-1,3-benzodiazol-2-yl)amino]-N-[(1,3-oxazol-2-yl)methyl]-3-[3-(trifluoromethyl)phenyl]propanamide,
3-[(1H-1,3-benzodiazol-2-yl)amino]-N-[(1-methyl-1H-imidazol-2-yl)methyl]-3-[3-(trifluoromethyl)phenyl]propanamide,
3-[(1H-1,3-benzodiazol-2-yl)amino]-3-(3-chloro-4-methylphenyl)-N-ethyl-N-(2-hydroxyethyl)propanamide,
3-[(1H-1,3-benzodiazol-2-yl)amino]-N-(cyanomethyl)-3-[3-(trifluoromethyl)phenyl]propanamide,
3-[(1H-1,3-benzodiazol-2-yl)amino]-N-[(dimethylcarbamoyl)methyl]-3-[3-(trifluoromethyl)phenyl]propanamide,
Ethyl 2-{3-[(1H-1,3-benzodiazol-2-yl)amino]-3-[3-(trifluoromethyl)phenyl]propanamido}acetate,
N-(2-aminoethyl)-2-[(1H-1,3-benzodiazol-2-yl)amino]-2-[3-(trifluoromethyl)phenyl]acetamide, 2-[(1H-1,3-benzodiazol-2-yl)amino]-N-[2-(dimethyl-amino)ethyl]-N-methyl-2-[3-(trifluoromethyl)phenyl]acetamide,
2-[(1H-1,3-benzodiazol-2-yl)amino]-1-(piperazin-1-yl)-2-[3-(trifluoromethyl)phenyl]ethan-1-one,
2-[(1H-1,3-benzodiazol-2-yl)amino]-1-(4-methylpiperazin-1-yl)-2-[3-(trifluoromethyl)phenyl]ethan-1-one,
(−)2-[(1H-1,3-benzodiazol-2-yl)amino]-1-(4-methylpiperazin-1-yl)-2-[3-(trifluoromethyl)phenyl]ethan-1-one,
(+)2-[(1H-1,3-benzodiazol-2-yl)amino]-1-(4-methylpiperazin-1-yl)-2-[3-(trifluoromethyl)phenyl]ethan-1-one,
2-[(1H-1,3-benzodiazol-2-yl)amino]-1-[3-(dimethyl-amino)azetidin-1-yl]-2-[3-(trifluoromethyl)phenyl]ethan-1-one,
2-[(1H-1,3-benzodiazol-2-yl)amino]-1-(pyrrolidin-1-yl)-2-[3-(trifluoromethyl)phenyl]ethan-1-one,
2-[(1H-1,3-benzodiazol-2-yl)amino]-N-(2-hydroxy-ethyl)-N-methyl-2-[3-(trifluoromethyl)phenyl]acet-amide,
2-[(1H-1,3-benzodiazol-2-yl)amino]-1-(piperidin-1-yl)-2-[3-(trifluoromethyl)phenyl]ethan-1-one,
2-[(1H-1,3-benzodiazol-2-yl)amino]-1-(morpholin-4-yl)-2-[3-(trifluoromethyl)phenyl]ethan-1-one,
2-[(1H-1,3-benzodiazol-2-yl)amino]-1-[4-(propane-2-sulfonyl)piperazin-1-yl]-2-[3-(trifluoromethyl)phenyl]ethan-1-one,
1-(azetidin-1-yl)-2-[(1H-1,3-benzodiazol-2-yl)amino]-2-[3-(trifluoromethyl)phenyl]ethan-1-one,
(+)1-(azetidin-1-yl)-2-[(1H-1,3-benzodiazol-2-yl)amino]-2-[3-(trifluoromethyl)phenyl]ethan-1-one,
1-(azetidin-1-yl)-2-[(1H-1,3-benzodiazol-2-yl)amino]-2-[3-(trifluoromethyl)phenyl]ethan-1-one,
2-[(1H-1,3-benzodiazol-2-yl)amino]-N-(oxetan-3-yl)-2-[3-(trifluoromethyl)phenyl]acetamide,
2-[(1H-1,3-benzodiazol-2-yl)amino]-1-{2-oxa-6-azaspiro[3.3]heptan-6-yl}-2-[3-(trifluoromethyl)phenyl]ethan-1-one,
4-{2-[(1H-1,3-benzodiazol-2-yl)amino]-2-[3-(trifluorom-ethyl)phenyl]acetyl}-1,1-dimethylpiperazin-1-ium,
2-[(1H-1,3-benzodiazol-2-yl)amino]-N-ethyl-N-(2-hy-droxyethyl)-2-[3-(trifluoromethyl)phenyl]acetamide,
(−)2-[(1H-1,3-benzodiazol-2-yl)amino]-N-ethyl-N-(2-hydroxyethyl)-2-[3-(trifluoromethyl)phenyl]acet-amide,
(+)2-[(1H-1,3-benzodiazol-2-yl)amino]-N-ethyl-N-(2-hydroxyethyl)-2-[3-(trifluoromethyl)phenyl]acet-amide,
3-[(1H-1,3-benzodiazol-2-yl)amino]-N-ethyl-3-(4-fluoro-3-methylphenyl)-N-(2-hydroxyethyl)propana-mide,
(−)3-[(1H-1,3-benzodiazol-2-yl)amino]-N-ethyl-3-(4-fluoro-3-methylphenyl)-N-(2-hydroxyethyl)propana-mide,
(+)3-[(1H-1,3-benzodiazol-2-yl)amino]-N-ethyl-3-(4-fluoro-3-methylphenyl)-N-(2-hydroxyethyl)propana-mide,
3-[(1H-1,3-benzodiazol-2-yl)amino]-3-(4-chloro-3-meth-ylphenyl)-N-ethyl-N-(2-hydroxyethyl)propanamide,
(−)3-[(1H-1,3-benzodiazol-2-yl)amino]-3-(4-chloro-3-methylphenyl)-N-ethyl-N-(2-hydroxyethyl)propana-mide,
(+)3-[(1H-1,3-benzodiazol-2-yl)amino]-3-(4-chloro-3-methylphenyl)-N-ethyl-N-(2-hydroxyethyl)propana-mide,
3-[(1H-1,3-benzodiazol-2-yl)amino]-N-ethyl-N-(2-hy-droxyethyl)-3-[3-(trifluoromethyl)phenyl]propana-mide,
(−)3-[(1H-1,3-benzodiazol-2-yl)amino]-N-ethyl-N-(2-hydroxyethyl)-3-[3-(trifluoromethyl)phenyl]propana-mide,
3-[(1H-1,3-benzodiazol-2-yl)amino]-N-ethyl-N-(2-hy-droxyethyl)-3-[3-(trifluoromethyl)phenyl]propana-mide,
3-[(1H-1,3-benzodiazol-2-yl)amino]-N-(2-methoxy-ethyl)-3-[3-(trifluoromethyl)phenyl]propanamide,
(−)3-[(1H-1,3-benzodiazol-2-yl)amino]-N-(2-methoxy-ethyl)-3-[3-(trifluoromethyl)phenyl]propanamide,
(+)3-[(1H-1,3-benzodiazol-2-yl)amino]-N-(2-methoxy-ethyl)-3-[3-(trifluoromethyl)phenyl]propanamide,
3-[(1H-1,3-benzodiazol-2-yl)amino]-N-(2-methoxy-ethyl)-N-methyl-3-[3-(trifluoromethyl)phenyl]pro-panamide,
3-[(1H-1,3-benzodiazol-2-yl)amino]-N-methyl-N-[2-(methylamino)ethyl]-3-[3-(trifluoromethyl)phenyl]propanamide,
3-[(1H-1,3-benzodiazol-2-yl)amino]-N-[2-(dimethyl-amino)ethyl]-N-ethyl-3-[3-(trifluoromethyl)phenyl]propanamide,
Methyl (2R)-2-{3-[(1H-1,3-benzodiazol-2-yl)amino]-3-[3-(trifluoromethyl)phenyl]propanamido}propanoate,
Methyl 2-{3-[(1H-1,3-benzodiazol-2-yl)amino]-N-ethyl-3-[3-(trifluoromethyl)phenyl]propanamido}acetate,
Ethyl 2-{3-[(1H-1,3-benzodiazol-2-yl)amino]-N-ethyl-3-[3-(trifluoromethyl)phenyl]propanamido}acetate,
N-ethyl-N-(2-hydroxyethyl)-3-{[4-(hydroxymethyl)-1H-1,3-benzodiazol-2-yl]amino}-3-[3-(trifluoromethyl)phenyl]propanamide,
N-(cyanomethyl)-3-{[4-(hydroxymethyl)-1H-1,3-benzo-diazol-2-yl]amino}-N-methyl-3-[3-(trifluoromethyl)phenyl]propanamide,
N-(cyanomethyl)-3-{[4-(2-hydroxyethyl)-1H-1,3-benzo-diazol-2-yl]amino}-N-methyl-3-[3-(trifluoromethyl)phenyl]propanamide,
N-(cyanomethyl)-N-ethyl-3-{[4-(2-hydroxyethyl)-1H-1,3-benzodiazol-2-yl]amino}-3-[3-(trifluoromethyl)phe-nyl]propanamide,
N-(cyanomethyl)-N-ethyl-3-{[4-(hydroxymethyl)-1H-1,3-benzodiazol-2-yl]amino}-3-[3-(trifluoromethyl)phe-nyl]propanamide,
N-(carbamoylmethyl)-N-ethyl-3-{[4-(hydroxymethyl)-1H-1,3-benzodiazol-2-yl]amino}-3-[3-(trifluorom-ethyl)phenyl]propanamide,
3-[(1H-1,3-benzodiazol-2-yl)amino]-N-(cyanomethyl)-N-ethyl-3-[3-(trifluoromethyl)phenyl]propanamide,
3-[(1H-1,3-benzodiazol-2-yl)amino]-N-(cyanomethyl)-N-methyl-3-[3-(trifluoromethyl)phenyl]propanamide,
(−)3-[(1H-1,3-benzodiazol-2-yl)amino]-N-(cyanom-ethyl)-N-methyl-3-[3-(trifluoromethyl)phenyl]pro-panamide,
(+)3-[(1H-1,3-benzodiazol-2-yl)amino]-N-(cyanom-ethyl)-N-methyl-3-[3-(trifluoromethyl)phenyl]pro-panamide,
Methyl 2-{3-[(1H-1,3-benzodiazol-2-yl)amino]-N-methyl-3-[3-(trifluoromethyl)phenyl]propanamido}acetate,
(−)Methyl 2-{3-[(1H-1,3-benzodiazol-2-yl)amino]-N-methyl-3-[3-(trifluoromethyl)phenyl]propanamido}acetate,
(+)Methyl 2-{3-[(1H-1,3-benzodiazol-2-yl)amino]-N-methyl-3-[3-(trifluoromethyl)phenyl]propanamido}acetate,
N-ethyl-3-{[4-(hydroxymethyl)-1H-1,3-benzodiazol-2-yl]amino}-N-[2-(methylsulfanyl)ethyl]-3-[3-(trifluo-romethyl)phenyl]propanamide, Methyl 2-{3-[(1H-1,3-benzodiazol-2-yl)amino]-3-[3-(trifluoromethyl)phenyl]propanamido}acetate, (−)Methyl 2-{3-[(1H-1,3-benzodiazol-2-yl)amino]-3-[3-(trifluoromethyl)phenyl]propanamido}acetate, (+)Methyl 2-{3-[(1H-1,3-benzodiazol-2-yl)amino]-3-[3-(trifluoromethyl)phenyl]propanamido}acetate, 3-[(1H-1,3-benzodiazol-2-yl)amino]-N-(carbamoylmethyl)-N-methyl-3-[3-(trifluoromethyl)phenyl]propanamide, Methyl 4-{2-[(1H-1,3-benzodiazol-2-yl)amino]-2-[3-(trifluoromethyl)phenyl]acetyl}piperazine-1-carboxylate, 3-[(1H-1,3-benzodiazol-2-yl)amino]-N-[2-(2-methoxyacetamido)ethyl]-3-[3-(trifluoromethyl)phenyl]propanamide, 2-{3-[(1H-1,3-benzodiazol-2-yl)amino]-3-[3-(trifluoromethyl)phenyl]propanamido}ethyl N-ethylcarbamate, 2-[(1H-1,3-benzodiazol-2-yl)amino]-N-ethyl-N-(2-hydroxyethyl)-3-[3-(trifluoromethyl)phenyl]propanamide, 3-[(1H-1,3-benzodiazol-2-yl)amino]-N-ethyl-3-(3-ethyl-4-fluorophenyl)-N-(2-hydroxyethyl)propanamide, (−)3-[(1H-1,3-benzodiazol-2-yl)amino]-N-ethyl-3-(3-ethyl-4-fluorophenyl)-N-(2-hydroxyethyl)propanamide, (+)3-[(1H-1,3-benzodiazol-2-yl)amino]-N-ethyl-3-(3-ethyl-4-fluorophenyl)-N-(2-hydroxyethyl)propanamide, ethyl N-{[2-({2-[ethyl(2-hydroxyethyl)carbamoyl]-1-[3-(trifluoromethyl)phenyl]ethyl}amino)-1H-1,3-benzodiazol-5-yl]methyl}carbamate, 3-[(1H-1,3-benzodiazol-2-yl)amino]-N-[2-(trifluoromethoxy)ethyl]-3-[3-(trifluoromethyl)phenyl]propanamide, (+)-3-[(1H-1,3-benzodiazol-2-yl)amino]-N-[2-(trifluoromethoxy)ethyl]-3-[3-(trifluoromethyl)phenyl]propanamide, (−)-3-[(1H-1,3-benzodiazol-2-yl)amino]-N-[2-(trifluoromethoxy)ethyl]-3-[3-(trifluoromethyl)phenyl]propanamide, 3-[(1H-1,3-benzodiazol-2-yl)amino]-N-[2-(2,2,2-trifluoroethoxy)ethyl]-3-[3-(trifluoromethyl)phenyl]propanamide, 3-[(1H-1,3-benzodiazol-2-yl)amino]-N-[2-(2,2,2-trifluoroethoxy)ethyl]-3-[3-(trifluoromethyl)phenyl]propanamide (Isomer 1), 3-[(1H-1,3-benzodiazol-2-yl)amino]-N-[2-(2,2,2-trifluoroethoxy)ethyl]-3-[3-(trifluoromethyl)phenyl]propanamide (Isomer 2), 3-[(1H-1,3-benzodiazol-2-yl)amino]-N-[(1R)-2-methoxy-1-phenylethyl]-3-[3-(trifluoromethyl)phenyl]propanamide, (+)-3-[(1H-1,3-benzodiazol-2-yl)amino]-N-[(1R)-2-methoxy-1-phenylethyl]-3-[3-(trifluoromethyl)phenyl]propanamide, (−)-3-[(1H-1,3-benzodiazol-2-yl)amino]-N-[(1R)-2-methoxy-1-phenylethyl]-3-[3-(trifluoromethyl)phenyl]propanamide, 3-[(1H-1,3-benzodiazol-2-yl)amino]-N-[(1R)-2-methoxy-1-phenylethyl]-3-{3-[(trifluoromethyl)sulfanyl]phenyl}propanamide, 3-[(1H-1,3-benzodiazol-2-yl)amino]-N-[(1R)-2-methoxy-1-phenylethyl]-3-{3-[(trifluoromethyl)sulfanyl]phenyl}propanamide (Isomer 1), 3-[(1H-1,3-benzodiazol-2-yl)amino]-N-[(1R)-2-methoxy-1-phenylethyl]-3-{3-[(trifluoromethyl)sulfanyl]phenyl}propanamide (Isomer 2), 3-[(1H-1,3-benzodiazol-2-yl)amino]-N-(1,2-oxazol-3-ylmethyl)-3-[3-(trifluoromethyl)phenyl]propanamide, 3-[(1H-1,3-benzodiazol-2-yl)amino]-N-(1,3-benzoxazol-2-ylmethyl)-3-[3-(trifluoromethyl)phenyl]propanamide, 3-[(1H-1,3-benzodiazol-2-yl)amino]-N-(1-methoxypropan-2-yl)-3-[3-(trifluoromethyl)phenyl]propanamide, 3-[(1H-1,3-benzodiazol-2-yl)amino]-N-[2-(dimethyl-1,2-oxazol-4-yl)ethyl]-3-[3-(trifluoromethyl)phenyl]propanamide, 3-[(1H-1,3-benzodiazol-2-yl)amino]-N-(1,3-thiazol-2-ylmethyl)-3-[3-(trifluoromethyl)phenyl]propanamide, 3-[(1H-1,3-benzodiazol-2-yl)amino]-N-[1-(6-methylpyridin-2-yl)ethyl]-3-[3-(trifluoromethyl)phenyl]propanamide, 3-[(1H-1,3-benzodiazol-2-yl)amino]-N-[(2-methyl-1,3-thiazol-5-yl)methyl]-3-[3-(trifluoromethyl)phenyl]propanamide, 3-[(1H-1,3-benzodiazol-2-yl)amino]-N-(pyrimidin-5-ylmethyl)-3-[3-(trifluoromethyl)phenyl]propanamide, 3-[(1H-1,3-benzodiazol-2-yl)amino]-N-[(2-methylpyridin-4-yl)methyl]-3-[3-(trifluoromethyl)phenyl]propanamide, 3-[(1H-1,3-benzodiazol-2-yl)amino]-3-(4-fluoro-3,5-dimethylphenyl)-N-(2-methoxyethyl)propanamide, 3-[(1H-1,3-benzodiazol-2-yl)amino]-N-[2-(trifluoromethoxy)ethyl]-3-{3-[(trifluoromethyl)sulfanyl]phenyl}propanamide, 3-[(1H-1,3-benzodiazol-2-yl)amino]-N-(2-methoxyethyl)-3-{3-[(trifluoromethyl)sulfanyl]phenyl}propanamide, 3-[(1H-1,3-benzodiazol-2-yl)amino]-N-[2-(trifluoromethoxy)ethyl]-3-[3-(trifluoromethoxy)phenyl]propanamide, 3-[(1H-1,3-benzodiazol-2-yl)amino]-N-(2-methoxyethyl)-3-[3-(trifluoromethoxy)phenyl]propanamide, 3-[(1H-1,3-benzodiazol-2-yl)amino]-N-(cyanomethyl)-3-[3-(trifluoromethoxy)phenyl]propanamide, 3-[(1H-1,3-benzodiazol-2-yl)amino]-N-(cyanomethyl)-3-(4-fluoro-3,5-dimethylphenyl)propanamide, 3-[(1H-1,3-benzodiazol-2-yl)amino]-3-[3-(cyclobutylsulfanyl)phenyl]-N-(2-methoxyethyl)propanamide, 3-[(1H-1,3-benzodiazol-2-yl)amino]-N-(1,2-oxazol-3-ylmethyl)-3-[3-(trifluoromethoxy)phenyl]propanamide, 3-[(1H-1,3-benzodiazol-2-yl)amino]-N-(1,3-benzoxazol-2-ylmethyl)-3-{3-[(trifluoromethyl)sulfanyl]phenyl}propanamide, 3-[(1H-1,3-benzodiazol-2-yl)amino]-N-(1,3-benzoxazol-2-ylmethyl)-3-[3-(trifluoromethoxy)phenyl]propanamide, 3-[(5-fluoro-1H-1,3-benzodiazol-2-yl)amino]-N-(2-methoxyethyl)-3-[3-(trifluoromethyl)phenyl]butanamide, 3-[(1H-1,3-benzodiazol-2-yl)amino]-N-(2-methoxyethyl)-3-[3-(methylsulfanyl)phenyl]propanamide, 3-[(4-methoxy-1H-1,3-benzodiazol-2-yl)amino]-N-(2-methoxyethyl)-3-[3-(trifluoromethyl)phenyl]propanamide, 3-{[4-(hydroxymethyl)-1H-1,3-benzodiazol-2-yl]amino}-N-[2-(trifluoromethoxy)ethyl]-3-[3-(trifluoromethyl)phenyl]propanamide, 3-[(5,6-difluoro-1H-1,3-benzodiazol-2-yl)amino]-N-(2-methoxyethyl)-3-[3-(trifluoromethyl)phenyl]propanamide, and 3-[(5-fluoro-4-methyl-1H-1,3-benzodiazol-2-yl)amino]-N-(2-methoxyethyl)-3-[3-(trifluoromethyl)phenyl]propanamide;

or a pharmaceutically acceptable salt thereof.

19. A method for treatment of a cardiac disease, disorder or condition in a mammal, such as a human, wherein said treatment alleviates or relieves symptoms or complications of the disease, disorder or condition or delays progression of the disease, disorder or condition to alleviate or to relieve the symptoms and complications of the disease, disorder or condition, and wherein a therapeutically effective amount of at least one compound according to claim 1 is administered to a mammal in need of said treatment.

20. The method of claim 19, wherein said cardiac disease, disorder or condition in a mammal is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure.

\* \* \* \* \*